US011220696B2

(12) United States Patent
Wan et al.

(10) Patent No.: US 11,220,696 B2
(45) Date of Patent: Jan. 11, 2022

(54) METHODS AND MEANS OF INCREASING THE WATER USE EFFICIENCY OF PLANTS

(71) Applicant: Performance Plants, Inc., Kingston (CA)

(72) Inventors: Jiangxin Wan, Bath (CA); Yafan Huang, Bath (CA); Shujun Yang, Kingston (CA); Monika Kuzma, Battersea (CA)

(73) Assignee: Performance Plants, Inc., Kingston (CA)

( * ) Notice: Subject to any disclaimer, the term of this patent is extended or adjusted under 35 U.S.C. 154(b) by 0 days.

(21) Appl. No.: 17/385,354

(22) Filed: Jul. 26, 2021

(65) Prior Publication Data

US 2021/0348185 A1 Nov. 11, 2021

Related U.S. Application Data

(63) Continuation of application No. 16/678,306, filed on Nov. 8, 2019, which is a continuation of application No. 16/019,077, filed on Jun. 26, 2018, now Pat. No. 10,508,283, which is a continuation of application No. 15/266,276, filed on Sep. 15, 2016, now Pat. No. 10,036,035, which is a continuation of application No. 12/483,660, filed on Jun. 12, 2009, now Pat. No. 9,453,238.

(60) Provisional application No. 61/132,067, filed on Jun. 13, 2008.

(51) Int. Cl.
*C12N 15/82* (2006.01)
*C12N 9/12* (2006.01)

(52) U.S. Cl.
CPC ....... *C12N 15/8273* (2013.01); *C12N 9/1205* (2013.01); *C12N 15/8218* (2013.01); *C12N 15/8227* (2013.01); *C12N 15/8261* (2013.01); *C12N 15/8271* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 5,240,842 | A | 8/1993 | Mets |
| 5,349,124 | A | 9/1994 | Fischoff et al. |
| 5,683,439 | A | 11/1997 | Jensen |
| 5,985,456 | A | 11/1999 | Zhou et al. |
| 6,809,232 | B1 | 10/2004 | Held et al. |
| 8,420,797 | B2 | 4/2013 | Abbitt |
| 9,115,368 | B2 | 8/2015 | Abad et al. |
| 9,453,238 | B2 | 9/2016 | Wan et al. |
| 10,036,035 | B2 | 7/2018 | Wan et al. |
| 10,508,283 | B2 | 12/2019 | Wan et al. |
| 2006/0075522 | A1 | 4/2006 | Cleveland et al. |
| 2006/0150283 | A1 | 7/2006 | Alexandrov et al. |
| 2006/0162024 | A1 | 7/2006 | Beetham et al. |
| 2007/0214517 | A1 | 9/2007 | Alexandrov et al. |
| 2012/0023627 | A1 | 1/2012 | Gampala et al. |
| 2018/0312862 | A1 | 11/2018 | Wan et al. |
| 2020/0149059 | A1 | 5/2020 | Wan et al. |

FOREIGN PATENT DOCUMENTS

| | | | |
|---|---|---|---|
| WO | WO 96/030530 | A1 | 10/1996 |
| WO | WO 2006/063963 | A1 | 6/2006 |
| WO | WO 2008/0027534 | A2 | 3/2008 |

OTHER PUBLICATIONS

Bedell et al., 2005, PLoS Biology, 3:1-13.*

An et al., "Functional Analysis of the 3' Control Region of the Potato Wound-Inducible Proteinase Inhibitor II Gene", *Plant Cell*, 1(1): 115-122 (1989).

Alonso et al. "Genome-Wide Insertional Mutagenesis of Arabidopsis thaliana", *Science*, vol. 301, No. 5633, pp. 653-657 (2003).

Araus et al., "Plant Breeding and Drought in C3 Cereals: What Should We Breed For?", *Annals of Botany*, 89:925-940 (2002).

Atanassova et al., "A 126 bp Fragment of a Plant Histone Gene Promoter Confers Preferential Expression in Meristems of Transgenic *Arabidopsis", Plant Journal*, 2(3):291-300 (1992).

Baulcombe, D. C., "Gene silencing: RNA makes RNA makes no protein", *Curr. Biol*., 9(16):R599-R601 (1999).

Beetham et al., "A Tool for Functional Plant Genomics: Chimeric RNA/DNA Oligonucleotides Cause in vivo Gene-Specific Mutations", *Proc. Natl. Acad. Sci. USA*, 96:8774-8778 (1999).

Bevan et al., "Structure and Transcription of the Nopaline Synthase Gene Region of T-DNA", *Nucl. Acids Res*., 11:369-385 (1983).

Bevan et al., "The Structure and Transcription Start Site of a Major Potato Tuber Protein Gene", *Nucl. Acids Res*., 14:4625-4636 (1986).

Cheong et al., "Two calcineurin B-like calcium sensors, interacting with protein kinase CIPK23, regulate leaf transpiration and root potassium uptake in Arabidopsis", *Plant J*., 52:223-239 (2007).

Christensen et al., "Maize Polyubiquitin Genes: Structure, Thermal Perturbation of Expression and Transcript Splicing, and Promoter Activity Following Transfer to Protoplasts by Elextroporation", *Plant Mol. Biol*., 18:675-689 (1992).

Condon et al., "Improving Instrinsic Water-Use Efficiency and Crop Yield", *Crop Science*, 42:122-131 (2002).

(Continued)

*Primary Examiner* — Jason Deveau Rosen

(74) *Attorney, Agent, or Firm* — Cooley LLP; Cynthia A. Kozakiewicz; Chen Chen

(57) ABSTRACT

The invention relates to methods of producing a desired phenotype in a plant by manipulation of gene expression within the plant. The method relates to means which inhibit the level of PK220 gene expression or activity, wherein a desired phenotype such as increased water use efficiency relative to a wild type control plant. The invention also relates to nucleic acid sequences and constructs useful such methods and methods of generating and isolating plants having decreased PK220 expression or activity.

7 Claims, No Drawings

Specification includes a Sequence Listing.

(56) References Cited

OTHER PUBLICATIONS

Datla et al., "Modified Binary Plant Transformation Vectors with the Wild-Type Gene Encoding NPTII", *Gene*, 122(2):383-384 (1992).
Davies et al., "Stomatai Control by Chemical Signalling and the Exploitation of this Mechanism to Increase Water Use Efficiency in Agriculture", *New Phytol*., 153:449-460 (2002).
De Loose et al., "The Extensin Signal Peptide Allows Secretion of a Hereologous Protein from Protoplasts", *Gene*, 99:95-100 (1991).
Dong et al., "Oligonucleotide-Directed Gene Repair in Wheat Using a Transient Plasmid Gene Repair Assay System", *Plant Cell Reports*, 25:457-465 (2006).
Dratewka et al., "Polypeptide Structure of Germin as Deduced from cDNA Sequencing", *J. Biol. Chem*., 264:4896-4900 (1989).
Elomaa et al., "A bHLH Transcription Factor Mediates Organ, Region and Flower Type Specific Signals on Dihydroflavonol-4-Reductase (dfr) Gene Expression in the Inflorescence of Gerbera Hybrida (Asteraceae)", *The Plant Journal*, 16(1):93-99 (1998).
Farquhar et al., "Photosynthesis and Carbon Assimilation", *Physiology and Determination of Crop Yield*, Madison, WI: ASA, CSSA, SSSA, pp. 187 (1994).
Fraley et al., "Expression of Bacterial Genes in Plant Cells", *Proc. Natl. Acad. Sci. USA*, 80(15):4803-4807 (1983).
Goldberg, "Regulation of Plant Gene Expression", *Philos. Trans. R. Soc. London Ser. B*, 314:343-353 (1986).
Greene et al., "Spectrum of Chemically Induced Mutations from a Large-Scale Reverse-Genetic Screen in *Arabidopsis", Genetics*, 164(2):731-740 (2003).
Gruber et al., "Vectors for Plant Transformation", *Methods in Plant Molecular Biology and Biotechnology*, Boca Raton, FL, CRC Press, Inc., pp. 89-119 (1993).
Hardie, "Plant Protein Serine/Threonine Kinases: Classification and Functions", *Annu. Rev. Plant Physiol. Plant Mol. Biol*., 50:97-131 (1999).
Horsch et al., "A Simple and General Method for Transferring Genes into Plants", *Science*, 227:1229-1231 (1985).
Huang et al., "ATMPK4, an Arabidopsis Homolog of Mitogen-Activated Protein Kinase, is Activated in vitro by ArMEK1 Through Threonine Phosphorylation", *Plant Physiol*., 122(4):1301-1310 (2000).
Kado, "Molecular Mechanisms of Crown Gall Tumorigenesis", *Crit. Rev. Plant Sci*., 10:1-32 (1991).
Karaba et al., "Improvement of Water Use Efficiency in Rice by Expression of HARDY, an *Arabidopsis* Drought and Salt Tolerance Gene", *Proc. Natl. Acad. Sci. USA*, 104:15270-15275 (2007).
Keil et al., "Primary Structure of a Proteinase Inhibitor II Gene from Potato (*Solanum Tuberosum*)", *Nucl. Acids Res*., 14:5641-5650 (1986).
Kennerdell et al., "Heritable gene silencing in *Drosphila* using a double-stranded RNA", *Nature Biotechnol*., 18(8):896-898 (2000).
Klein et al., "Transformation of Microbes, Plants and Animals by Particle Bombardment", *Biotechnology*, 10:286-291 (1992).
Koh et al., "T-DNA tagged knockout mutation of rice *OsGSK1*, an orthologue of *Arabidopsis* BIN2, with enhanced tolerance to various abiotic stresses", *Plant Mol. Biol*., 65(4):453-466 (2007).
Last et al., "pEmu: An Improved Promotor for Gene Expression in Cereal Cells", *Theor. Appl. Genet*., 81:581-588 (1991).
Lepetit et al., "A Plant Histone Gene Promoter can Direct Both Replication-Dependent and -Independent Gene Expression in Transgenic Plants", *Mol. Gen. Genet*., 231:276-285 (1992).
Lund et al., "A Plant Signal Sequence Enhances The Secretion of Bacterial ChiA in Transgenic Tobacco", *Plant Mol. Biol*., 18:47-53 (1992).
Martin et al., "Restriction Fragment Length Polymorphisms Associated with Water Use Efficiency in Tomato", *Science*, 243(4899): 1725-1728 (1989).
Masle et al., "The ERECTA Gene Regulates Plant Transpiration Efficiency in *Arabidopsis", Nature*, 436:866-870 (2005).
Matsuoka et al., "Propeptide of a Precursor to a Plant Vacuolar Protein Required for Vacuolar Targeting", *Proc. Natl. Acad. Sci. USA*, 88:834-838 (1991).
McElroy et al., "Isolation of an Efficient Actin Promoter for Use in Rice Transformation", *The Plant Cell*, 2:163-171 (1990).
Mian et al., "Molecular Markers Associated with Water Use Efficiency and Leaf Ash in Soybean", *Crop Sci*., 36:1252-1257 (1996).
Mittler et al. "Gain- and loss-of-function mutations in Zatl 0 enhance the tolerance of plants to abiotic stress." *FEBS Letters*. 580.28-29: 6537-6542 (2006).
Mogen et al., "Upstream Sequences Other than AAUAAA are Required for Efficient Messenger RNA 3'-End Formation in Plants", *Plant Cell*, 2:1261-1272 (1990).
Moloney et al., "High Efficiency Transformation of *Brassica napus* using Agrobacterium Vectors", *Plant Cell Reports*, 8:238-242 (1989).
Morillo et al. Functional analysis of receptor-like kinases in monocots and dicots. Curr Opin Plant Biol. 9(5):460-9 (2006).
NCBI EST Accession No. CX709060.1.
NCBI EST Accession No. Os05g0319700.
Needleman et al., "A General Method Applicable to the Search for Similarities in the Amino Acid Sequence of Two Proteins", *J. Mol. Biol*., 48:443-453 (1970).
Odell et al., "Identification of DNA Sequnces Required for Activity of the Cauliflower Mosaic Virus 35S Promoter", *Nature*, 313:810-812 (1985).
Oleykowski et al., "Mutation Detection Using a Novel Plant Endonuclease", *Nucl. Acids Res*., 26(20):4597-4602 (1998).
Price et al., "Linking Drought-Resistance Mechanisms to Drought Avoidance in Upland Rice Using a QTL Approach: Progress and New Opportunities to Integrate Stomatal and Mesophyll Responses", *Journal of Experimental Botany*, 53:989-1004 (2002).
Saijo et al., "Over-expression of a single Ca2+-dependent protein kinase confers both cold and salt/drought tolerance on rice plants", *Plant J*., 23(3):319-327 (2000).
Sanford et al., "Optimizing the Biolistic Process for Different Biological Applications", *Methods Enzymol*., 217:483-509 (1993).
Schwab et al., "Highly Specific Gene Silencing by Artificial MicroRNAs in *Arabidopsis", PlantCell*, 18(5)1121-1133 (2006).
Shiu et al., "Receptor-Like Kinases from *Arabidopsis* Form a Monophyletic Gene Family Related to Animal Receptor Kinases", *Proc. Natl. Acad. Sci. USA*, 98(19): 10763-10768 (2001).
Stockinger et al., "A Linkage Map of Sweet Cherry Based on RAPD Analysis of a Microspore-Derived Callus Culture Population", *J. Heredity*, 87:214-218 (1996).
TAIR Accession No. At2g25220.
TAIR Accession No. At2g44790.
TAIR Accession No. At4g32000.
TAIR Accession No. At5g11020.
TAIR Accession No. TC366835.
TAIR Accession No. TC372789.
TAIR Germplasm/Stock SALK_147838, release date Aug. 15, 2003.
Thomas et al., "Size constraints for targeting post-transcriptional gene silencing and for RNA-directed methylation in Nicotiana benthamiana using a potato virus X vector", *Plant J*., 25:417-425 (2001).
Thumma et al., "Identification of Casual Relationship Among Traits Related to Drought Resistance in *Stylosanthes scabra* Using QTL Analysis", *J. Exp. Botany*, 52:203-214 (2001).
TIGR Accession No. CO439063.
Torii et al., "The *Arabidopsis* ERECTA Gene Encodes a Putative Receptor Protein Kinase with Extracellular Leucine-Rich Repeats", *Plant Cell*., 8(4):735-746 (1996).
Tran et al., "Functional anaylsis of AHK1/ATHK1 and cytokinin receptor histidine kinases in response to abscisic acid, drought, and salt stress in *Arabidopsis", Proc. Natl. Acad. Sci. U.S.A*., 104(51):20623-20628 (2007).
Umezawa et al. "Engineering drought tolerance in plants: discovering and tailoring genes to unlock the future." *Current Opinion in Biotechnology*. 17.2:113-122 (2006).
van der Meer et al., "Promoter Analysis of the Chaicone Synthase (chsA) Gene of Petunia Hybrida: A 67 bp Promoter Region Directs Flower-Specific Expression", *Plant Molecular Biology*, 15(1):95-109 (1990).

(56) References Cited

OTHER PUBLICATIONS

Velten et al., "Isolation of a Dual Plant Promoter Fragment From the Ti Plasmid of Agrobacterium Tumefaciens", *EMBO J.*, 3:2723-2730 (1984).
Verwoert et al., "Developmental Specific Expression and Organelle Targeting of the *Escherichia coli* fabD Gene, Encoding Malonyl Coenzyme A-acyl Carrier Protein Transacylase in Transgenic Rape and Tobacco Seeds", *Plant Mol. Biol.*, 26:189-202 (1994).
Visser et al., "Expression of Chimaeric Granule-Bound Starch Synthase-GUS Gene in Transgenic Potato Plants", *Plant Mol. Biol.*, 17:691-699 (1991).
Walling et al., "Isolation, Characterization and Evolutionary Relatedness of Three Members from the Soybean Multigene Family Encoding Chlorophyll a/b Binding Proteins", *Nucl. Acids Res.*, 16:10477-10492 (1988).
Whisstock J.C et al. "Prediction of protein function from protein sequence and structure", *Q Rev Biophys.* 36(3):307-340 (2003), Review.
Wilkins et al., "Role of Propeptide Glycan in Post-Translational Processing and Transport of Barley Lectin to Vacuoles in Transgenic Tobacco", *Plant Cell*, 2:301-313 (1990).
Yang et al., "Purification, Cloning, and Characterization of the CEL I Nuclease", *Biochemistry*, 39(13):3533-3541 (2000).
Yang Shujun et al. "Narrowing Down the Targets: Towards Successful Genetic Engineering of Drought-Tolerant Crops." *Molecular Plant*. 3.3: 469-490 (2010).
Yang et al. "Ribozyme-mediated high resistance against potato spindle tuber viroid in transgenic", *Proc Natl Acad Sci USA*. 94(10):4861-5 (1997).
Yenofsky et al., "A Mutant Neomyc in Phosphotransferase II Gene Reduces the Resistance of Transformants to Antibiotic Selection Pressure", *Proc. Natl. Acad. Sci. USA*, 87:3435-3439 (1990).

* cited by examiner

METHODS AND MEANS OF INCREASING THE WATER USE EFFICIENCY OF PLANTS

REFERENCE TO RELATED APPLICATIONS

This application is a continuation of U.S. patent application Ser. No. 16/678,306, filed on Nov. 8, 2019, which is a continuation of U.S. patent application Ser. No. 16/019,077, filed on Jun. 26, 2018, now U.S. Pat. No. 10,508,283, which is a continuation of U.S. patent application Ser. No. 15/266,276, filed on Sep. 15, 2016, now U.S. Pat. No. 10,036,035, which is a continuation of U.S. patent application Ser. No. 12/483,660, filed on Jun. 12, 2009, now U.S. Pat. No. 9,453,238, which claims the benefit of U.S. Ser. No. 61/132,067, filed Jun. 13, 2008, the contents of each of which are incorporated herein by reference in their entirety.

INCORPORATION-BY-REFERENCE OF SEQUENCE LISTING

The contents of the text file named "PREP-017_C03US SEQ LISTING.txt", which was created on Nov. 7, 2019 and is 225 KB in size, are hereby incorporated by reference in their entireties.

FIELD OF THE INVENTION

The invention is in the field of plant molecular biology and relates to transgenic plants having novel phenotypes, methods of producing such plants and polynucleotides and polypeptides useful in such methods. More specifically, the invention relates to inhibition of a protein kinase and transgenic plants having inhibited protein kinase activity.

BACKGROUND OF THE INVENTION

Water is essential for plant survival, growth and reproduction. Assimilation of carbon dioxide by photosynthesis is directly linked to water loss through the stomata. Crop productivity which is closely linked to biomass production is dependent on plant water use efficiency (WUE) especially in water limited conditions (Passioura 1994 and Sinclair 1994, in Physiology and Determination of Crop Yield). Water use efficiency over a period of plant's growth can be calculated as the ratio of biomass produced per unit of water transpired (Sinclair 1994). Instantaneous measurements of water use efficiency can also be obtained as the ratio of carbon dioxide assimilation to transpiration using gas exchange measurements (Farquhar and Sharkey 1994, in Physiology and Determination of Crop Yield). Since there is a close correlation between crop productivity and water use efficiency, many attempts have been made to study and understand this relationship and the genetic components involved. To maximize the productivity and yield of a crop, efforts have been made to try to improve the water use efficiency of plants (Condon et al., 2002, Araus et al., 2002, Davies et al., 2002). Higher water use efficiency can be achieved either by increasing the biomass production and carbon dioxide assimilation or by reducing the transpiration water loss. Reduced transpiration, especially under non-limiting water conditions can be associated with reduced growth rate and therefore reduced crop productivity. This poses a dilemma on how to improve crop productivity and yield under water limited conditions but also maintain it under irrigated or non-limited water conditions (Condon et al., 2002).

Improvements to water use efficiency, to date, have used plant breeding methods whereby high water use efficiency varieties were crossed with the more productive but lower water use efficiency varieties in hope of improvements in crop yield under water limited conditions (Condon et al., 2002, Araus et al., 2002). Quantitative trait loci (QTL) approaches to identifying the components of water use efficiency have been the most common methods historically used (Mian et al., 1996, Martin et al., 1989, Thumma et al., 2001, Price et al., 2002), and more recently attempts have been made to engineer improved plants by molecular genetic means.

The first gene associated with water use efficiency was *ERECTA*. The *ERECTA* gene was first identified as a gene functioning in inflorescence development and organ morphogenesis (Torii et al., 1996). It was later found by QTL mapping to be a major contributor to transpiration efficiency, defined as water transpired per carbon dioxide assimilated, an opposite indicator to water use efficiency in *Arabidopsis* (Masle et al., 2005). *ERECTA* encodes a putative leucin-rich repeat receptor-like kinase (LRR-RLK). The regulatory mechanism of LRR-RLK is yet to be understood although it was suggested due to, at least in part, the effects on stomatal density, epidermal cell expansion, mesophyll cell proliferation and cell-cell contact. The normal transpiration efficiency was restored upon complementation using wild type *ERECTA* in mutant exacta. However, it is not known whether overexpression of *ERECTA* in transgenic *Arabidopsis* will result in reduced transpiration efficiency or enhanced water use efficiency. It is the only report showing a plant receptor-like kinase to be involved in transpiration efficiency or water use efficiency.

Another *Arabidopsis* gene implicated in water use efficiency is the HARDY gene, found through the phenotypic screening of an activation tagged mutant collection (Karaba et al., 2007). Overexpression of *HARDY* in rice resulted in improved water use efficiency by enhancing photosynthetic assimilation and reducing transpiration. The transgenic rice with increased expression of *HARDY* exhibited increased shoot biomass under optimal water conditions and increased root biomass under water limited conditions. Overexpression of *HARDY* in *Arabidopsis* resulted in thicker leaves with more mesophyll cells and in rice increased leaf biomass and bundle sheet cells. These modifications contributed to enhanced photosynthetic activity and efficiency (Karaba et al., 2007).

Protein kinases are a large family of enzymes that modify proteins by addition of phosphate groups (phosphorylation). Protein kinases constitute about 2% of all eukaryotic genes, many of which mediate the response of eukaryotic cells to external stimuli. All single subunit protein kinases contain a common catalytic domain near the carboxyl terminus while the amino terminus plays a regulatory role.

Plant receptor-like kinases are serine/threonine protein kinases with a predicted signal peptide at the amino terminus, a single transmembrane region and a cytoplasmic kinase domain. There are more than 610 RLKs potentially encoded in *Arabidopsis* (Shiu and Bleecker 2001). Receptor-like kinases are often part of a signaling cascade. They interpret extracellular signals, through ligand binding, and phosphorylate targets in a signaling cascade which in turn affect downstream cell processes, such as gene expression (Hardie 1999).

Identification of genes that can be manipulated to provide beneficial characteristics is highly desirable. So too are means and methods of utilizing the identified genes to effect the desirable characteristics. The receptor-like kinase identified as At2g25220 in the TAIR database is one serine/threonine kinase, and a member of the large gene family of receptor-like kinases with over 600 members in *Arabidopsis* (Shiu et al., 2001). However, except for annotation of the sequence as a kinase no function or role for the At2g25220 gene has been disclosed. In the present invention a high water use efficiency gene (HWE) has been identified that when its expression or activity is inhibited results in beneficial phenotypes, such as, enhancement of plant biomass accumulation relative to the water used. This occurs under both water limited and non-limited conditions and ensures better growth and therefore greater productivity of the plants.

SUMMARY OF THE INVENTION

This invention is bases upon the discovery of a mutation in the PK220 gene that results in a plant with an altered phenotype such for example, increased water use efficiency, increased drought tolerance, reduced sensitivity to cold temperature and reduced inhibition of seedling growth in low nitrogen conditions compared to plants without the mutation.

More specifically, the invention relates to the identification of a mutant plant that comprises a mutation in the PK220 gene also referred to herein as the HWE gene. The PK220 gene is a receptor-like protein kinase. Inhibition of the expression or activity of the PK220 gene in plants provides beneficial phenotypes such as improved water use efficiency in a plant. The improved water use efficiency phenotype results in plants having improved drought tolerance.

In one aspect the invention provides a method of producing a transgenic plant, by transforming a plant, a plant tissue culture, or a plant cell with a vector containing a nucleic acid construct that inhibits the expression or activity of a PK220 gene to obtain a plant, tissue culture or a plant cell with decreased PK220 expression or activity and growing the plant or regenerating a plant from the plant tissue culture or plant cell. wherein a plant having increased water use efficiency is produced.

Accordingly, the present invention provides a method of producing a plant having an improved property, wherein the method includes inhibiting the expression or activity of an endogenous PK220 gene, wherein a plant is produced having an advantageous phenotype or improved property. In a particular embodiment, the present invention provides a method for producing plants having increased water use efficiency, wherein the method includes include generation of transgenic plants and modification of plants genome using the methods described herein.

Water use efficiency refers to the ratio between the amounts of biomass produced per unit water transpired when measured gravimetrically and the ratio of photosynthetic rate to the rate of transpiration when measured using gas exchange quantification of a leaf or shoot. As used herein, the term "increased water use efficiency" refers to a plant water use efficiency that is 2, 4, 5, 6, 8, 10, 20 or more fold greater as compared to the water use efficiency of a corresponding wild-type plant. For example, a plant having increased water use efficiency as compared to a wild-type plant may have 5%, 10%, 15%, 20%, 25%, 30%, 40%, 50%, 60% 70%, 75% or greater water use efficiency than the corresponding wild-type plant.

The methods of the invention involve inhibiting or reduced the expression or activity of an endogenous gene, such as PK220, wherein a plant is produced having an advantageous phenotype or improved property, such as increased water use efficiency. In one aspect, the invention provides a method of producing a plant having increased water use efficiency relative to a wild-type plant, by introducing into a plant cell a nucleic acid construct that inhibits or reduces the expression or activity of PK220. For example, a plant having increased water use efficiency relative to a wild type plant is produced by a) providing a nucleic acid construct containing a promoter operably linked to a nucleic acid construct that inhibits PK220 activity; b) inserting the nucleic construct into a vector; c) transforming a plant, tissue culture, or a plant cell with the vector to obtain a plant, tissue culture or a plant cell with decreased PK220 activity; d) growing the plant or regenerating a plant from the tissue culture or plant cell, wherein a plant having increased water use efficiency relative to a wild type plant is produced. The construct includes a promoter such as a constitutive promoter, a tissue specific promoter or an inducible promoter. Preferably, the tissue specific promoter is a root promoter. A preferable inducible promoter is a drought inducible promoter.

The term "nucleic acid construct" refers to a full length gene sequence or portion thereof, wherein a portion is preferably at least 19, 20, 21, 22, 23, 24, 25, 30, 40, 50, 60, 70, 75, 80, 90, 100, or 150 nucleotides in length, or the compliment thereof. Alternatively it may be an oligonucleotide, single or double stranded and made up of DNA or RNA or a DNA-RNA duplex. In a particular embodiment, the nucleic acid construct contains the full length PK220 gene sequence, or a portion thereof, wherein the portion of the PK220 sequence is at least 19, 20, 21, 22, 23, 24, 25, 30, 40, 50, 60, 70, 75, 80, 90, 100, or 150 nucleotides in length, or its compliment.

Also provided by the invention is a transgenic plant having an advantageous phenotype or improved property such as increased water use efficiency, produced by the methods described herein.

In another aspect the invention provides a plant having a non-naturally occurring mutation in an PK220 gene, wherein the plant has decreased PK220 expression or activity and the plant has increased water use efficiency relative to a wild-type control. Decreased PK220 expression or activity refers to a 2, 3, 4, 5, 6, 7, 8, 9, 10, 15, 20, 25, 30, 40, 50, 60, or 75-fold reduction or greater, at the DNA, RNA or protein level of an PK220 gene as compared to wild-type PK220, or a 2, 3, 4, 5, 6, 7, 8, 9, 10, 15, 20, 25, 30, 40, 50, 60 or 75 fold reduction of PK220 activity as compared to wild-type PK220 activity. PK220 activity includes but is not limited kinase activity at serine and or threonine amino acid residues of substrate polypeptides, where it participates in phosphorylation reactions.

The invention further provides a transgenic seed produced by the transgenic plant(s) of the invention, wherein the seed produces plant having an advantageous phenotype or improved property such as for example, increased water use efficiency relative to a wild-type plant.

In another embodiment, the invention provides nucleic acids for expression of nucleic acids in a plant cell to produce a transgenic plant having an advantageous phenotype or improved property such as increased water use efficiency.

Exemplary sequences encoding a wild type PK220 gene or portion thereof that find use in aspects of the present invention are described in SEQ ID NO's: 1, 7, 9, 11, 12, 13, 24, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 84, 86, 88, 90, 92, 94, 96, 98, 100, 153, 161 and 193. Exemplary sequences encoding a mutated PK220 gene are described in SEQ ID NO's:3 and 5. Exemplary sequences that are useful for constructs to downregulate PK220 expression or activity are described in SEQ ID NO's: 12, 13, 147, 149, 153, 161, 168 and 174. The invention further provides compositions which contain the nucleic acids of the invention for expression in a plant cell to produce the transgenic plants described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from and are encompassed by the following detailed description and claims.

DETAILED DESCRIPTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

For convenience, before further description of the present invention, certain terms employed in the specification, examples and claims are defined herein. These definitions should be read in light of the remainder of the disclosure and as understood by a person of ordinary skill in the art.

A "promoter sequence", or "promoter", means a nucleic acid sequence capable of inducing transcription of an operably linked gene sequence in a plant cell. Promoters include for example (but not limited to) constitutive promoters, tissue specific promoters such as a root promoter, an inducible promoters such as a drought inducible promoter or an endogenous promoters such as a promoter normally associated with a gene of interest, i.e. a PK220 gene The term "expression cassette" means a vector construct wherein a gene or nucleic acid sequence is transcribed. Additionally, the expressed mRNA may be translated into a polypeptide.

The terms "expression" or "overexpression" are used interchangeably and mean the expression of a gene such that the transgene is expressed. The total level of expression in a cell may be elevated relative to a wild-type cell.

The term "non-naturally occurring mutation" refers to any method that introduces mutations into a plant or plant population. For example, chemical mutagenesis such as ethane methyl sulfonate or methanesulfonic acid ethyl ester, fast neutron mutagenesis, DNA insertional means such as a T-DNA insertion or site directed mutagenesis methods.

The term "drought stress" refers to a condition where plant growth or productivity is inhibited relative to a plant where water is not limiting. The term "water-stress" is used synonymously and interchangeably with the drought water stress.

The term "drought tolerance" refers to the ability of a plant to outperform a wildtype plant under drought stress conditions or water limited conditions or to use less water during grow and development relative to a wildtype plant.

The "term water use efficiency" is an expression of the ratio between the amounts of biomass produced per unit water transpired when measured gravimetrically and the ratio of photosynthetic rate to the rate of transpiration when measured using gas exchange quantification of a leaf or shoot.

The term "dry weight" means plant tissue that has been dried to remove the majority of the cellular water and is used synonymously and interchangeably with the term biomass.

The term "null" is defined as a segregated sibling of a transgenic line that has lost the inserted transgene and is therefore used a control line.

A number of various standard abbreviations have been used throughout the disclosure, such as g, gram; WT, wild-type; DW, dry weight; WUE, water use efficiency; d, day.

The term "hwe116" means a plant having a mutation in a PK220 gene.

The HWE gene is referred to as a PK220 gene sequence and a protein encoded by a PK220 gene is referred to as a PK220 polypeptide or protein. The terms HWE and PK220 are synonymous.

The term "PK220 nucleic acid" refers to at least a portion of a PK220 nucleic acid. Similarly the term "PK220 protein" or "PK220 polypeptide" refers to at least a portion thereof. A portion is of at least 21 nucleotides in length with respect to a nucleic acid and a portion of a protein or polypeptide is at least 7 amino acids. The term "AtPK220" refers to an *Arabidopsis thaliana* PK220 gene, the term "BnPK220" refers to a *Brassica napus* PK220 gene.

The invention is based in part on the discovery of plants having an improved agronomic property, for example, increased water use efficiency, increased drought tolerance, reduced sensitivity to cold temperature and reduced inhibition of seedling growth in low nitrogen conditions relative to a wild type control. The gene responsible for the beneficial phenotype has been determined and shown to be an inhibited PK220 gene.

Methods of producing a plant, including a mutant plant, a transgenic plant or genetically modified plant, having increased water use efficiency are disclosed herein. Specifically the invention identifies a PK220 gene that when expression or activity of the PK220 gene is inhibited, a plant having a beneficial phenotype is obtained.

Determining Homology Between Two or More Sequences

To determine the percent homology between two amino acid sequences or between two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch (1970). Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the coding sequence portion of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Inhibition of Endogenous PK220 Expression and Activity

An aspect of the invention pertains to means and methods of inhibiting or reducing PK220 gene expression and activity, optionally, resulting in an inhibition or reduction of PK220 protein expression and activity. The term "PK220 expression or activity" embraces both these levels of inhibition or reduction. Decreased PK220 expression or activity refers to a 2, 3, 4, 5, 6, 7, 8, 9, 10, 15, 20, 25, 30, 40, 50, 60, or 75-fold reduction or greater, at the DNA, RNA or protein level of an PK220 gene as compared to wild-type PK220, or a 2, 3, 4, 5, 6, 7, 8, 9, 10, 15, 20, 25, 30, 40, 50, 60 or 75 fold reduction of PK220 protein activity as compared to wild-type PK220 activity. PK220 protein activity includes but is not limited kinase activity at serine and or threonine amino acid residues of substrate polypeptides, where it participates in phosphorylation reactions. Methods of measuring serine/threonine kinase activity are known to those in the art.

There are numerous methods known to those skilled in the art of achieving such inhibition that effect a variety of steps in a gene expression pathway, for example transcriptional regulation, post transcriptional and translational regulation. Such methods include, but are not limited to, antisense methods, RNAi constructs, including all hairpin constructs and RNAi constructs useful for inhibition by dsRNA-directed DNA methylation or inhibition by mRNA degradation or inhibition of translation, microRNA (miRNA), including artificial miRNA (amiRNA) (Schwab et al., 2006) technologies, mutagenesis and TILLING methods, in vivo site specific mutagenesis techniques and dominant/negative inhibition approaches.

A preferred method of gene inhibition involves RNA inhibition (RNAi) also known as hairpin constructs. A portion of the gene to inhibit is used and cloned in a sense and antisense direction having a spacer separating the sense and antisense portions. The size of the gene portions should be at least 20 nucleotides in length and the spacer may be a little as 13 nucleotides (Kennerdell and Carthew, 2000) in length and may be an intron sequence, a coding or non-coding sequence.

Antisense is a common approach wherein the target gene, or a portion thereof, is expressed in an antisense orientation resulting in inhibition of the endogenous gene expression and activity. The antisense portions need not be a full length gene nor be 100% identical. Provided that the antisense is at least about 70% or more identical to the endogenous target gene and of least 19, 20, 21, 22, 23, 24, 25, 30, 40, 50, 60, 70, 75, 80, 90, 100, or 150 nucleotides in length. Preferably, 50 nucleotides or greater in length the desired inhibition will be obtained.

Sequences encoding a wild type PK220 gene or portion thereof that are useful in preparing constructs for PK220 inhibition include for example, SEQ ID NO's: 1, 7, 9, 11, 12, 13, 24, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 84, 86, 88, 90, 92, 94, 96, 98, 100, 153, 161 and 193. Exemplary sequences that are useful for constructs to down-regulate PK220 expression or activity are described in SEQ ID NO's: 12, 13, 147, 149, 153, 161, 168 and 174.

When using an antisense strategy of down-regulation, inhibition of endogenous gene activity can be selectively targeted to the gene or genes of choice by proper selection of a fragment or portion for antisense expression. Selection of a sequence that is present in the target gene sequence and not present in related genes (non-target gene) or is less than 70% conserved in the non-target sequences results in specificity of gene inhibition.

Alternatively, amiRNA inhibition can be used to inhibit gene expression and activity in a more specific manner than other RNAi methods. In contrast to siRNA that requires a perfect match between the small RNA and the target mRNA, amiRNA allows up to 5 mismatches with no more than 2 consecutive mismatches. The construction of amiRNA needs to meet certain criteria described in Schawab et al. (2006). This provides a method to down-regulate a target gene expression or activity using a gene portion comprising of at least a 21 nucleotide sequence of PK220.

Dominant/negative inhibition is analogous to competitive inhibition of biochemical reactions. Expression of a modified or mutant polypeptide that lacks full functionality competes with the wild type or endogenous polypeptide thereby reducing the total gene/protein activity. For example an expressed protein may bind to a protein complex or enzyme subunit to produce a non-functional complex. Alternatively the expressed protein may bind substrate but not have activity to perform the native function. Expression of sufficient levels of non active protein will reduce or inhibit the overall function.

Expression of PK220 genes that produce a PK220 protein that is deficient in activity can be used for dominant/negative down-regulation of gene activity. This is analogous to competitive inhibition. A PK220 polypeptide is produced that, for example, may associate with or bind to a target molecule but lacks endogenous activity. An example of such an inactive PK220 is the AtPK220 sequence isolated from the hwe116 mutant and disclosed as SEQ ID NO:3. A target molecule may be an interacting protein of a nucleic acid sequence. In this manner the endogenous PK220 protein is effectively diluted and downstream responses will be attenuated.

In vivo site specific mutagenesis is available whereby one can introduce a mutation into a cells genome to create a specific mutation. The method as essentially described in Dong et al. (2006) or US patent application publication number 20060162024 which refer to the methods of oligonucleotide-directed gene repair. Alternatively one may use chimeric RNA/DNA oligonucleotides essentially as described Beetham (1999). Accordingly, a premature stop codon may be generated in the cells' endogenous gene thereby producing a specific null mutant. Alternatively, the mutation may interfere with splicing of the initial transcript thereby creating a non-translatable mRNA or a mRNA that produces an altered polypeptide which does not possess endogenous activity. Preferable mutations that result loss or reduction of PK220 expression or activity include a C to T conversion at nucleotide position 874 when numbered in accordance with SEQ ID NOs: 1 or 3 or a nucleotide mutation that results in an amino acid change from a Leucine (L) codon (CTT) to a Phenylalanine (F) codon (TTT) at amino acid position 292 when numbered in accordance with SEQ ID NOs: 2 or 4.

TILLING is a method of isolating mutations in a known gene from an EMS-mutagenized population. The population is screened by methods essentially as described in (Greene et al., 2003).

Other strategies of gene inhibition will be apparent to the skilled worker including those not discussed here and those developed in the future.

Identification of AtPK220 Homologues

Homologues of *Arabidopsis thaliana* PK220 (AtPK220) were identified using database sequence search tools, such as the Basic Local Alignment Search Tool (BLAST) (Altschul et al., 1990 and Altschul et al., 1997). The tblastn or blastn sequence analysis programs were employed using the BLOSUM-62 scoring matrix (Henikoff and Henikoff, 1992). The output of a BLAST report provides a score that takes into account the alignment of similar or identical residues and any gaps needed in order to align the sequences. The scoring matrix assigns a score for aligning any possible pair of sequences. The P values reflect how many times one expects to see a score occur by chance. Higher scores are preferred and a low threshold P value threshold is preferred. These are the sequence identity criteria. The tblastn sequence analysis program was used to query a polypeptide sequence against six-way translations of sequences in a nucleotide database. Hits with a P value less than −25, preferably less than −70, and more preferably less than −100, were identified as homologous sequences (exemplary selected sequence criteria). The blastn sequence analysis program was used to query a nucleotide sequence against a nucleotide sequence database. In this case too, higher scores were preferred and a preferred threshold P value was less than −13, preferably less than −50, and more preferably less than −100.

A PK220 gene can be isolated via standard PCR amplification techniques. Use of primers to conserved regions of a PK220 gene and PCR amplification produces a fragment or full length copy of the desired gene. Template may be DNA, genomic or a cDNA library, or RNA or mRNA for use with reverse transcriptase PCR (RtPCR) techniques. Conserved regions can be identified using sequence comparison tools such as BLAST or CLUSTALW for example. Suitable primers have been used and described elsewhere in this application.

Alternatively, a fragment of a sequence from a PK220 gene is $^{32}$P-radiolabeled by random priming (Sambrook et al., 1989) and used to screen a plant genomic library (the exemplary test polynucleotides). As an example, total plant DNA from *Arabidopsis thaliana, Nicotiana tabacum, Lycopersicon pimpinellifolium, Prunus avium, Prunus cerasus, Cucumis sativus*, or *Oryza sativa* are isolated according to Stockinger et al. (Stockinger et al., 1996). Approximately 2 to 10 μg of each DNA sample are restriction digested, transferred to nylon membrane (Micron Separations, Westboro, Mass.) and hybridized. Hybridization conditions are: 42° C. in 50% formamide, 5×SSC, 20 mM phosphate buffer 1×Denhardt's, 10% dextran sulfate, and 100 μg/ml herring sperm DNA. Four low stringency washes at RT in 2×SSC, 0.05% sodium sarcosyl and 0.02% sodium pyrophosphate are performed prior to high stringency washes at 55° C. in 0.2.times.SSC, 0.05% sodium sarcosyl and 0.01% sodium pyrophosphate. High stringency washes are performed until no counts are detected in the washout according to Walling et al. (Walling et al., 1988). Positive isolates are identified, purified and sequenced. Other methods are available for hybridization, for example the ExpressHyb hybridization solution available from Clonetech.

PK220 Recombinant Expression Vectors and Host Cells

Another aspect of the invention pertains to vectors, preferably expression vectors, containing a nucleic acid encoding a PK220 protein, a PK220 gene or genomic sequence or portions thereof and analogs or homologs thereof. As used herein the term expression vector includes vectors which are designed to provide transcription of the nucleic acid sequence. Transcribed sequences may be designed to inhibit the endogenous expression or activity of an endogenous gene activity correlating to the transcribed sequence. Optionally, the transcribed nucleic acid need not be translated but rather inhibits the endogenous gene expression as in antisense or hairpin down-regulation methodology. Alternatively, the transcribed nucleic acid may be translated into a polypeptide or protein product. The polypeptide may be a non-full length, mutant or modified variant of the endogenous protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel (1990). Regulatory sequences include those that direct constitutive expression of a nucleotide sequence in many types of host cell and those that direct expression of the nucleotide sequence only in certain host cells (e.g., tissue-specific regulatory sequences) or inducible promoters (e.g., induced in response to abiotic factors such as environmental conditions, heat, drought, nutrient status or physiological status of the cell or biotic such as pathogen responsive). Examples of suitable promoters include for example constitutive promoters, ABA inducible promoters, tissue specific promoters and abiotic or biotic inducible promoters. It will be appreciated by those skilled in the art that the design of the expression vector can depend on such factors as the choice of the host cell to be transformed, the level of expression of protein desired as well as timing and location of expression, etc. The expression vectors of the invention can be introduced into host cells to thereby produce proteins or peptides, including fusion proteins or peptides, encoded by nucleic acids as described herein (e.g., PK220 proteins, mutant forms of PK220 proteins, fusion proteins, etc.).

The recombinant expression vectors of the invention can be designed for expression of PK220 genes, PK220 proteins, or portions thereof, in prokaryotic or eukaryotic cells. For example, PK220 genes or PK220 proteins can be expressed in bacterial cells such as *Escherichia coli*, insect cells (using baculovirus expression vectors)) yeast cells, plant cells or mammalian cells. Suitable host cells are discussed further in Goeddel (1990). Alternatively, the recombinant expression vector can be transcribed and translated in vitro, for example using T7 promoter regulatory sequences and T7 polymerase.

In one embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CaMV) DNA and vectors such as pBI121.

For expression in plants, the recombinant expression cassette will contain in addition to the PK220 nucleic acids, a promoter region that functions in a plant cell, a transcription initiation site (if the coding sequence to transcribed lacks one), and optionally a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable promoters include promoters from plant viruses such as the 35S promoter from cauliflower mosaic virus (CaMV) (Odell et al., 1985), promoters from genes such as rice actin (McElroy et al., 1990), ubiquitin (Christensen et al., 1992; pEMU (Last et al., 1991), MAS (Velten et al., 1984), maize H3 histone (Lepetit et al., 1992); and Atanassvoa et al., 1992), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as Rsyn7, SCP and UCP promoters, ribulose-1,3-diphosphate carboxylase, fruit-specific promoters, heat shock promoters, seed-specific promoters and other transcription initiation regions from various plant genes, for example, including the various opine initiation regions, such as for example, octopine, mannopine, and nopaline. In some cases a promoter associated with the gene of interest (e.g. PK220) may be used to express a construct targeting the gene of interest, for example the native AtPK220 promoter ($P_{PK}$). Additional regulatory elements that may be connected to a PK220 encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of PK220 gene are known and include, but are not limited to, 3' termination and/or polyadenylation regions such as those of the *Agrobacterium tumefaciens* nopaline synthase (nos) gene (Bevan et al., 1983); the potato proteinase inhibitor II (PINII) gene (Keil et al., 1986) and hereby incorporated by reference); and An et al. (1989); and the CaMV 19S gene (Mogen et al., 1990).

Plant signal sequences, including, but not limited to, signal-peptide encoding DNA/RNA sequences which target proteins to the extracellular matrix of the plant cell (Dratewka-Kos et al., 1989) and the *Nicotiana plumbaginifolia* extension gene (De Loose et al., 1991), or signal peptides which target proteins to the vacuole like the sweet potato sporamin gene (Matsuoka et al., 1991) and the barley lectin gene (Wilkins et al., 1990), or signals which cause proteins to be secreted such as that of PRIb (Lund et al., 1992), or those which target proteins to the plastids such as that of rapeseed enoyl-ACP reductase (Verwoert et al., 1994) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. For example, the promoter associated with a coding sequence identified in the TAIR data base as At2g44790 ($P_{4790}$) is a root specific promoter. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the chalcone synthase-A gene (van der Meer et al., 1990) or the dihydroflavonol-4-reductase (dfr) promoter (Elomaa et al., 1998) direct expression in specific floral tissues. Also available are the patatin class I promoter is transcriptionally activated only in the potato tuber and can be used to target gene expression in the tuber (Bevan, 1986). Another potato-specific promoter is the granule-bound starch synthase (GBSS) promoter (Visser et al., 1991).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, 1986).

The resulting expression system or cassette is ligated into or otherwise constructed to be included in a recombinant vector which is appropriate for plant transformation. The vector may also contain a selectable marker gene by which transformed plant cells can be identified in culture. The marker gene may encode antibiotic resistance. These markers include resistance to G418, hygromycin, bleomycin, kanamycin, and gentamicin. Alternatively the marker gene may encode a herbicide tolerance gene that provides tolerance to glufosinate or glyphosate type herbicides. After transforming the plant cells, those cells having the vector will be identified by their ability to grow on a medium containing the particular antibiotic or herbicide. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms “host cell” and “recombinant host cell” are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms “transformation” and “transfection” are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of cell types may act as suitable host cell for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana, Nicotiana tabacum, Brassica napus, Zea mays, Oryza sativa, Gossypium hirsutum* and *Glycine max.*

Expression of PK220 nucleic acids encoding a PK220 protein that is not fully functional can be useful in a dominant/negative inhibition method. A PK220 variant polypeptide, or portion thereof, is expressed in a plant such that it has partial functionality. The variant polypeptide may for example have the ability to bind other molecules but does not permit proper activity of the complex, resulting in overall inhibition of PK220 activity.

Transformed Plants Cells and Transgenic Plants

The invention includes a protoplast, plants cell, plant tissue and plant (e.g., monocot or dicot) transformed with a PK220 nucleic acid, a vector containing a PK220 nucleic acid or an expression vector containing a PK220 nucleic acid. As used herein, “plant” is meant to include not only a whole plant but also a portion thereof (i.e., cells, and tissues, including for example, leaves, stems, shoots, roots, flowers, fruits and seeds).

The plant can be any plant type including, for example, species from the genera *Arabidopsis, Brassica, Oryza, Zea, Sorghum, Brachypodium, Miscanthus, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Lolium, Avena, Hordeum, Secale, Picea, Caco*, and *Populus.*

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols (See, for example, Miki et al., (1993) “Procedure for Introducing Foreign DNA into Plants”, In: Methods in Plant Molecular Biology and Biotechnology, Glick and Thompson, eds., CRC Press, Inc., Boca Raton, pages 67-88; and Andrew Bent in, Clough S J and Bent A F, (1998) “Floral dipping: a simplified method for *Agrobacterium*-mediated transformation of *Arabidopsis thaliana*”). The methods chosen vary with the host plant, and include chemical transfection methods such as calcium phosphate, polyethylene glycol (PEG) transformation, microorganism-mediated gene transfer such as *Agrobacterium* (Horsch et al., 1985), electroporation, protoplast transformation, micro-injection, flower dipping and biolistic bombardment.

*Agrobacterium*-Mediated Transformation

The most widely utilized method for introducing an expression vector into plants is based on the natural transformation system of *Agrobacterium tumefaciens* and *A. rhizogenes* which are plant pathogenic bacteria which genetically transform plant cells. The Ti and Ri plasmids of *A. tumefaciens* and *A. rhizogenes*, respectfully, carry genes responsible for genetic transformation of plants (See, for example, Kado, 1991). Descriptions of the *Agrobacterium* vector systems and methods for *Agrobacterium*-mediated gene transfer are provided in Gruber et al. (1993). and Moloney et al., (1989).

Transgenic *Arabidopsis* plants can be produced easily by the method of dipping flowering plants into an *Agrobacte-*

*rium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plants are inverted for 1 minute into a solution of *Agrobacterium* culture carrying the appropriate gene construct. Plants are then left horizontal in a tray and kept covered for two days to maintain humidity and then righted and bagged to continue growth and seed development. Mature seed is bulk harvested.

Direct Gene Transfer

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes. (Sanford et al., 1993; Klein et al., 1992).

Plant transformation can also be achieved by the Aerosol Beam Injector (ABI) method described in U.S. Pat. Nos. 5,240,842, 6,809,232. Aerosol beam technology is used to accelerate wet or dry particles to speeds enabling the particles to penetrate living cells. Aerosol beam technology employs the jet expansion of an inert gas as it passes from a region of higher gas pressure to a region of lower gas pressure through a small orifice. The expanding gas accelerates aerosol droplets, containing nucleic acid molecules to be introduced into a cell or tissue. The accelerated particles are positioned to impact a preferred target, for example a plant cell. The particles are constructed as droplets of a sufficiently small size so that the cell survives the penetration. The transformed cell or tissue is grown to produce a plant by standard techniques known to those in the applicable art.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregate and can transmit the PK220 gene construct to its progeny. A more preferred transgenic plant is homozygous for the gene construct, and transmits that gene construct to all offspring on sexual mating. Seed from a transgenic plant may be grown in the field or greenhouse, and resulting sexually mature transgenic plants are self-pollinated to generate true breeding plants. The progeny from these plants become true breeding lines that are evaluated for decreased expression of the PK220 gene.

Method of Producing Transgenic Plants

Also included in the invention are methods of producing a transgenic plant having increased water use efficiency, reduced sensitivity to cold temperature and reduced inhibition of seedling growth in low nitrogen conditions, relative to a wild type plant. The method includes introducing into one or more plant cells a compound that inhibits or reduces PK220 expression or activity in the plant to generate a transgenic plant cell and regenerating a transgenic plant from the transgenic cell. The compound can be, e.g., (i) a PK220 polypeptide; (ii) a PK220 nucleic acid, analog, homologue, orthologue, portion, variant or complement thereof; (iii) a nucleic acid that decreases expression of a PK220 nucleic acid. A nucleic acid that decreases expression of a PK220 nucleic acid may include promoters or enhancer elements. The PK220 nucleic acid can be either endogenous or exogenous, for example an *Arabidoposis* PK220 nucleic acid may be introduced into a *Brassica* or corn species. Preferably, the compound is a PK220 nucleic acid sequence endogenous to the species being transformed. Alternatively, the compound is a PK220 nucleic acid sequence exogenous to the species being transformed and having at least 70%, 75%, 80%, 85%, 90% or greater homology to the endogenous target sequence.

In various aspects the transgenic plant has an altered phenotype as compared to a wild type plant (i.e., untransformed). By altered phenotype is meant that the plant has a one or more characteristic that is different from the wild type plant. For example, when the transgenic plant has been contacted with a compound that decreases the expression or activity of a PK220 nucleic acid, the plant has a phenotype such as increased water use efficiency, reduced sensitivity to cold temperature and reduced inhibition of seedling growth in low nitrogen conditions, relative to a wild type plant.

The plant can be any plant type including, for example, species from the genera *Arabidopsis, Brassica, Oryza, Zea, Sorghum, Brachypodium, Miscanthus, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio,*

*Salpiglossis, Cucumis, Browaalia, Lolium, Avena, Hordeum, Secale, Picea, Caco*, and *Populus*.

EXAMPLES

Identification of High Water Use Efficiency Mutant Hwe116

An *Arabidopsis* EMS mutant (Columbia background) was identified initially as having drought tolerant properties. The mutant was tested for water use efficiency under optimal and drought conditions. The result showed that the drought tolerant nature of this mutant is due to its higher water use efficiency under both water stressed and optimal water conditions. Thus, this mutant is named hwe116.

Map Based Cloning of Hwe116

A F2 population was generated by crossing the hwe116 mutant to the Landsberg *erecta* (Ler) ecotype of *Arabidopsis thaliana* and the resulting population was used for map-based cloning by assaying for drought tolerance and subsequently confirming the presence of the higher water use efficiency trait in the mutant. The water-loss per unit dry weight of the F2 plants was measured over a 5-day drought treatment and the data was normalized for QTL analysis relative to the hwe116 mutant and the two wild type ecotypes, Landsberg *erecta* and Columbia. Leaf tissues were collected from all F2 and control plants used in the phenotyping experiments for genotyping. QTL analysis was conducted using MAPMAKER 3.0 and WinQTLCart 2.5. To further specify the mutations within the QTL peak, celery endonuclease I (CEL I) was used.

Mutation Detection Using CEL I Nuclease

Celery endonuclease I (CEL I), cleaves DNA with high specificity at sites of base-pair substitution that creates a mismatch between wild type and mutant alleles and has been reportedly used for detecting mutations in EMS mutants (Yang et al., 2000; Oleykowski et al., 1998).

DNA fragments of about 5 kb were amplified by optimized PCR using hwe116 or parent Columbia genomic DNA as template. Equal amounts of the amplified products were mixed together and then subjected to a cycle of denaturing and annealing to form heteroduplex DNA. Incubation with CEL I at 42° C. for 20 minutes cleaves the heteroduplex DNA at points of mutation, and DNA fragments were visualized by 1% agarose gel electrophoresis and ethidium bromide staining.

Using this method a 5 kb PCR product was amplified using primers SEQ ID NO:102 and SEQ ID NO:104, and templates: hwe116, and the control Columbia type. The heteroduplexes formed PCR products resulted in smaller fragments (1.4 and 3.6 kb) after CEL I digestion. Overlapping sub-fragments (about 3 kb) were amplified using primers SEQ ID NO:104 and SEQ ID NO:105 to more narrowly define the mutation location. The sub-fragment was sequenced and a C nucleotide was found to have been mutated to T nucleotide in hwe116.

The mutation of interest was identified as a C to T conversion at nucleotide position 874 of SEQ ID NO's:1 and 3 that resulted in an amino acid change from a Leucine (L) codon (CTT) to a Phenylalanine (F) codon (TTT) at amino acid position 292. The gene harboring the mutation was identified as a Serine/Threonine protein kinase (Ser/Thr PK). The wild type gene was identified as being identical to Genbank Accession Number At2g25220. This Ser/Thr protein kinase is referred to as AtPK220 herein, and the mutated form identified in hwe116 is referred to as AtPK220L292F.

Transcriptional Evaluation

Northern analysis and RT-PCR indicate that the expression level and transcript size of the AtPK220 gene in hwe116 is unchanged relative to the wild type control.

Initial Cloning of Partial AtPK220L292F and AtPK220 Sequences

Based on the TAIR annotation, partial sequences of AtPK220L292F (AtPK220L292F(p)) and partial AtPK220 (AtPK220(p)) were amplified by RT-PCRs using the primers SEQ ID NO:106 and SEQ ID NO:107 which included BamHI and PstI restriction sites for cloning and template RNA isolated from hwe116 and the control plant (Columbia), respectively). The resulting partial AtPK220L292F nucleotide sequence is shown as SEQ ID NO:5 and the corresponding amino acid sequence as SEQ ID NO:6. The resulting partial AtPK220 nucleotide sequence is shown as SEQ ID NO:7 and the corresponding amino acid sequence as SEQ ID NO:8.

Kinase Activity Assay of a Partial AtPK220L292F Protein Expressed in *E. coli*

The PCR products were digested with BamHI and PstI, and inserted into the expression vector: pMAL-c2 (New England Biolabs, Beverly, Mass.) to form an in-frame fusion protein with the malE gene for expression of the maltose-binding protein: MBP-AtPK220L292F(p) and MBP-AtPK220(p). The fusion proteins were expressed in *E. coli* and purified using amylose-affinity chromatography as described by the manufacturer (New England Biolabs). Fractions containing the fusion proteins were pooled and concentrated (Centriprep-30 concentrator, Amicon). SDS-PAGE was used to analyze the expression level, size and purity of the fusion proteins.

Activity assays were carried out according to (Huang et al., 2000). The kinase autophosphorylation assay mixtures (30 μl) contained kinase reaction buffer (50 mM Tris, pH 7.5, 10 mM $MgCl_2$, 10 mM $MnCl_2$), 1 μCi [$\gamma$-$^{32}$P] ATP and 10 ng of purified AtPK220L292F(p) or MBP-AtPK220(p). For the trans-phosphorylation assays, myelin basic protein (3 μg) was added to each assay. The reactions were started by the addition of the enzymes. After incubation at room temperature for 30 min, the reactions were terminated by the addition of 30 μl of Laemmli sample buffer (Laemmli, 1970). The samples were heated at 95° C. for 5 min and then loaded on a 15% SDS-polyacrylamide gel. The gels were stained with Coomassie blue R-250, then de-stained and dried. The $^{32}$P-labeled bands were detected using Kodak X-Omat AR film.

The wild type MBP-AtPK220(p) fusion protein was able to phosphorylate the artificial substrate in the in vitro activity assay, indicating that the assay system was effective and the MBP-AtPK220(p) fusion protein was capable of activity. In contrast, the hwe116 mutant form, MBP-AtPK220L292F(p), was unable to catalyse phosphorylation of the model substrate. The single point mutation is sufficient to abolish activity of the AtPK220(p) gene from hwe116.

Isolation of Full-Length cDNA Sequence of AtPK220

The annotation of AtPK220 (At2g25220) in the TAIR database identifies a 5' start codon, termination signal and 3' UTR sequence. Analysis of the 5' portion of the annotated sequence suggested an alternative 5' sequence and start codon location. To determine the AtPK220 genes' 5' region and the likely start codon SMART RACE (Rapid Amplification of cDNA Ends, CloneTech) was performed.

A specific primer, SEQ ID NO:108, was designed for the 5' RACE and yielded a 450 bp PCR product. Sequence data obtained of the 450 bp 5' RACE product indicated that the TAIR annotation of AtPK220 was missing the 5' 186 bp that included 39 bp of 5' UTR sequence and 147 bp of coding sequence. An intron of 324 bp, located 8 bp upstream of the TAIR identified ATG start codon of AtPK220 was also missing from the genomic annotation in TAIR.

Compiling the 5' RACE results and TAIR database annotation yields the full-length cDNA of AtPK220 (SEQ ID NO:9). The sequence was determined to be 1542 bp in length, which included 39 bp of 5' UTR, 204 bp of 3'UTR, and 1299 bp of coding region. The AtPK220 coding region is identified as SEQ ID NO:1 and encodes a protein of 432 amino acids and is identified as SEQ ID NO:2. Comparison of AtPK220 to its closest homolog, At4g32000, shows an additional sequence of 51 bp is present in AtPK220, that includes the sequence of nucleotides 368-418 of SEQ ID NO:9. This sequence provides a target sequence for down-regulation constructs designed to specifically down-regulate the AtPK220 gene but not non-target genes such as At4g32000.

Sequence analysis of AtPK220 indicates that this Ser/Thr PK belongs to a receptor-like protein kinase family, possessing a signal peptide (1-29), an extracellular domain (30-67), a single transmembrane domain (68-88), an ATP-binding domain (152-175 as determined by Prosite) a Ser/Thr protein kinase active-site domain (267-279 as determined by the InterPro method) and an activation loop (289-298, 303-316).

Rescue of the Hwe116 Mutant by AtPK220

Constructs for the expression of wild-type AtPK220 were generated and transformed into the hwe116 mutant. The construct was constitutively expressed from a CaMV 35S promoter and referred to as 35S-AtPK220.

35S-AtPK220

The primer pair SEQ ID NO:109 and SEQ ID NO:110 was used to amplify a fragment comprising the full length open reading frame (ORF) of AtPK220. The primer pair SEQ ID NO:111 and SEQ ID NO:110 was used to amplify a fragment comprising a portion of AtPK220 ORF. The amplified fragments were digested with restriction enzymes SmaI and BamHI and cloned into a pEGAD vector digested with the same restriction enzymes. The fragment comprising the full length open reading frame of AtPK220 resulting from the PCR and subsequent restriction digestion is disclosed as SEQ ID NO:10. The fragment comprising a portion of the AtPK220 ORF resulting from the PCR and subsequent restriction digestion is disclosed as SEQ ID NO:11.

The 35S-AtPK220 construct was transformed into *Arabidopsis* hwe116. The transgenic lines were recovered and advanced to T3 homozygous lines. These lines are tested for their drought tolerance and water use efficiency characteristics. The 35S-AtPK220 construct restores the wild type phenotypes.

T-DNA Knockout Lines and Physiology Assessment

SALK T-DNA knockout lines of AtPK220 and two close homologous genes in which are identified as TAIR Accession numbers AT4G32000 (SEQ ID NO:16) and AT5G11020 (SEQ ID NO:18) were obtained from ABRC and advanced to homozygosity. They are listed as follows;

AtPK220: SALK 147838;

AtPK32000 (AT4G32000): SALK_060167, SALK_029937 and SALK_121979;

AtPK11020 (AT5G11020): SAIL_1260_H05.

Analysis of gene expression levels by either RT-PCR or Northern analysis demonstrated that the target genes in the knockout lines was either significantly reduced or completely abolished. These knockout lines were used for physiological assessment. Only the knockout line of AtPK220 (SALK 147838) showed significant drought tolerance and higher water use efficiency, indicating that AtPK220 is the target gene and responsible for the water use efficiency phenotype of hwe116. The closely related genes AT4G32000 and AT5G11020 are not functionally redundant and inhibition of these genes is insufficient to generate the hwe116 phenotype.

Inhibition of the Protein Activity for PK220 in *Arabidopsis*

Inhibition of gene activity can be achieved by a variety of technical means, for example, antisense expression, RNAi or hairpin constructs, in vivo mutagenesis, dominant negative approaches or generation of a mutant population and selection of appropriate lines by screening means. Provided are examples of said means to produce plants having inhibited PK220 gene expression and or activity.

Down-Regulation of PK220 by RNAi

Constructs were designed for RNAi inhibition of PK220 using hairpin (HP) constructs. The constructs comprised a 288 bp or a 154 bp of AtPK220 cDNA sequence to produce constructs referred to as (270)PK220 and (150)PK220. The 288 bp (270)PK220 fragment comprises 10 bp of intron sequence that was included in the PCR primer during construction of these PCR products. Vector constructs using these fragments can be made to drive expression under the control of a promoter of choice that will be apparent to one of skill in the art. In these examples a constitutive promoter (35S CaMV), or the native AtPK220 promoter ($P_{PK}$) was used. Two fragments, or portions, of the AtPK220 gene were selected, first a 288 bp fragment At(270)PK220 (SEQ ID NO:13) and second a 154 bp fragment At(150)PK220 (SEQ ID NO:12) were selected from a divergent region of AtPK220 as compared to its closest homologue At4g32000.

35S-HP-At(270)PK220 and 35S-HP-At(150)PK220

The hairpin constructs (HP) 35S-HP-At(270)PK220 and 35S-HP-At(150)PK220 constructs were generated as follows. The sense fragments of (270)PK220 and (150)PK220 were amplified by RT-PCR using primer pairs of SEQ ID NO:134/SEQ ID NO:115 and SEQ ID NO:114/SEQ ID NO:115, respectively. The PCR products were digested with SacI, and inserted into a binary vector pBI121tGUS at the SacI site, respectively. The resulting vectors were then used to subclone the antisense fragments of (270)PK220 and (150)PK220 that were derived from RT-PCR products amplified using primer pairs of SEQ ID NO:112/SEQ ID NO:117, and SEQ ID NO:116/SEQ ID NO:117, respectively. Both the vector and PCR products were digested with BamHI and XbaI for subcloning.

$P_{PK}$-HP-At(270)PK220 and $P_{PK}$-HP-At(150)PK220

The $P_{PK}$-HP-At(270)PK220 and $P_{PK}$-HP-At(150)PK220 constructs were made from 35S-HP-At(270)PK220 or 35S-HP-At(150)PK220 respectively by replacing the 35S promoter sequence with AtPK220 promoter sequence (SEQ ID NO:14). The 35S promoter sequence was removed from 35S-HP-At(270)PK220 and 35S-HP-At(150)PK220 by Hind III and Xba I double digestion. The linearized plasmid was then treated with Klenow fragment of DNA polymerase I to generate blunt ends and self-ligated to form a new plasmid, in which XbaI site was restored while Hind III was gone. By using this restored XbaI site, a Nhe I DNA fragment of AtPK220 promoter was cloned upstream of HP-At(270) and HP-At(150) sequence to produce the final plasmids of $P_{PK}$-HP-At(270)PK220 and $P_{PK}$-HP-At(150)PK220. AtPK220 promoter sequence (SEQ ID NO:14) was amplified by PCR from *Arabidopsis* (Columbia) genome using primer pairs of SEQ ID NO:135/SEQ ID NO:136.

$P_{4790}$-HP-At(270)PK220

To specifically down-regulate endogenous AtPK220, a strong root promoter $P_{4790}$ was identified and found to be highly expressed in the roots of *Arabidopsis*, particularly in the endodermis, pericycle, and stele. The $P_{4790}$ promoter is associated with a coding sequence identified as At2g44790 and the expression characteristics of $P_{4790}$ are similar to that of wild type AtPK220 expression. The $P_{4790}$ was used to replace the constitutive 35S promoter in 35S-HP-At(270) PK220. The promoter of At2g44790 was amplified using *Arabidopsis* (Col) genomic DNA as template and primers SEQ ID NO:151 and SEQ ID NO:152. The amplified promoter fragment has the length of 1475 base-pairs right upstream the ATG start codon of At2g44790 according to TAIR annotation. The 1475 bp-$P_{4790}$ fragment is identified a SEQ ID NO:150. Hind III and Xba I restriction sites were introduced to the 5' and 3' end of the promoter fragment by primer design. The promoter sequence was then used to replace the 35S promoter in 35S-HP-At(270)PK plasmids by HindIII/XbaI double digestion, which resulted in the final constructs of pBI-P4790-HP-At(270)PK.

Down-Regulation of BnPK220 in *Brassica* Using RNAi 35S-HP-Bn(340)PK

To down-regulate the AtPK220 homolog in *Brassica* species, a hairpin construct was made using a 338 bp fragment of BnPK220 (SEQ ID NO; 153) as the sense and anti-sense portions, and pBI300tGUS as the vector. Two pairs of primers SEQ ID NO:154 and SEQ ID NO:155; and SEQ ID NO:156 and SEQ ID NO:157 with unique restriction sites were designed according to BnPK220 sequence. A PCR fragment of 338 bp in length was amplified using *Brassica napus* cDNA as the template and the two pairs of primers, respectively. The SacI fragment was then inserted into pBI300tGUS at the SacI site downstream of the tGUS spacer in an antisense orientation. The resulting plasmid was subsequently used for cloning of a XbaI-BamI fragment in a sense orientation at the XbaI and BamHI sites. The vector pBI121tGUS was modified within the NPT II selectable marker gene and named pBI300. The NPT II gene in the vector pBI121 contains a point mutation (G to T at position 3383, amino acid change E182D). To restore the gene with its WT version, the NheI-BstBI fragment (positions 2715-3648) was replaced with the corresponding NheI-BstBI fragment from plasmid pRD400 (PNAS, 87:3435-3439, 1990; Gene, 122:383-384, 1992).

$P_{4790}$-HP-Bn(340)PK

The $P_{4790}$ promoter of At2g44790 was used to control expression of a hairpin construct to down-regulate endogenous BnPK220 in *Brassica*. The plasmid of 35S-HP-Bn (340)PK was digested with HindIII and XbaI to replace the 35S promoter with the $P_{4790}$ promoter.

Down-Regulation of PK220 by Antisense

The construct 35S-antisenseAtPK220 was made to down-regulate expression of AtPK220 via antisense. The antisense fragment was generated using PCR and the primer pair SEQ ID NO:106/SEQ ID NO:113. The synthesised product was digested with BamHI and XbaI to yield a 1177 bp sequence comprising 1160 bp of AtPK220 (SEQ ID NO:11). Included at the 5' end were 10 bp of intron sequence and at the 3'-end, 7 bp of 3' UTR sequence, which were retained from the PCR primers. The 1177 bp fragment was cloned in an antisense orientation to the 35S promoter in pBI121w/oGUS at the BamHI and XbaI.

Down-Regulation of PK220 by AmiRNA

An artificial microRNA (amiRNA) construct was also made to down-regulate the expression of AtPK220 in *Arabidopsis*. An *Arabidopsis* genomic DNA fragment containing microRNA319a gene (SEQ ID NO:148), was amplified by PCR using *Arabidopsis* (Col) genomic DNA as template and primers listed as SEQ ID NO:141 and SEQ ID NO:142. The backbone of miR319a was then used to construct amiRPK220 (SEQ ID NO:149), in which a 21 bp fragment of miRNA319a gene in both antisense and sense orientations was replaced by a 21 bp DNA fragment of AtPK220 using recombinant PCR. Three pairs of primers: SEQ ID NO:141/SEQ ID NO:144; SEQ ID NO:143/SEQ ID NO:146 and SEQ ID NO:145/SEQ ID NO:142 were designed for the construction. The final PCR product was digested with BamHI and XbaI, and subsequently cloned into pBI121w/o GUS for transformation into *Arabidopsis* or other plant species of choice.

Inhibition of PK220 Via Dominant-Negative Strategy 35S-AtPK220L292F

For expression of a non-functional AtPK220 sequence the AtPK220L292F from hwe116 was PCR amplified by RT-PCR using forward and reverse primers SEQ ID NO:118 and SEQ ID NO:110. The PCR product was digested with the restriction enzymes BamHI and XbaI (SEQ ID NO:121) and ligated into the binary vector pBI121w/oGUS. The sequence of SEQ ID NO:121 comprises the AtPK220L292F open reading frame (SEQ ID NO:3) and an additional 3 bp at the 5' end and 7 bp at the 3' end that are derived from UTR sequences (SEQ ID NO:121). The final construct, 35S-AtPK220L292F, was used to generate *Arabidopsis* and *Brassica* transgenic plants that were advanced to homozygosity for physiology assessment. Additionally, the vector is used to transform a plant species of choice and can be a dicot or a monocot.

$P_{4790}$-AtPK220L292F

The HindIII-XbaI fragment of the root promoter $P_{4790}$ was used to replace 35S promoter in pBI300, and then AtPK220L292F sequence was put downstream $P_{4790}$ by XbaI and BamHI digestion to generate the $P_{4790}$-driven dominant-negative construct. The resulting plasmid was then used for *Brassica* transformation. Additionally, the vector is used to transform a plant species of choice and can be a dicot or a monocot.

Down-Regulation of AtPK220 Homologs in a Monocot Species Using RNAi $P_{BdUBQ}$-HP-Bd(272)PK An expression cassette was constructed and inserted into two different vector backbones, the first being into the PacI-AscI sites of pUCAP and the second being into the PacI-AscI sites of pBF012. pBF012 is identical to pBIN-PLUS/ARS except that the potato-Ubi3 driven NPTII cassette has been excised via FseI digestion followed by self-ligation.

*Brachypodium distachyon* PK220 (BdPK220) was amplified using primer combinations SEQ ID NO:158 (bWET XbaI F) plus SEQ ID NO:159 (bWET BamHI R) having XbaI or BamHI sites respectively in the primers and SEQ ID NO:158 (bWET XbaI F) plus SEQ ID NO:160 (bWET ClaI R) having XbaI or ClaI sites respectively in the primers. PCR products were digested with the indicated restriction enzymes giving a 272 bp fragment (SEQ ID NO:161).

The hairpin spacer sequence, BdWx intron 1 (SEQ ID NO:164), was amplified with SEQ ID NO:162 (bWx BamHI F) plus SEQ ID NO:163 (bWx ClaI R) primers having BamHI or ClaI sites respectively in the primers and digested with the indicated restriction enzymes. The *B. distachyon* Wx gene is a homologue of the rice GBSS waxy gene, although the introns show little conservation.

The three fragments were ligated together into the XbaI site of the pUCAP MCS resulting in BdWx intron 1 sequence being flanked by Bd(272)PK220 target sequences in opposite orientations. The *B. distachyon* ubiquitin (BdUBQ) promoter contains an internal BamHI site, so the RNAi cassette was amplified with primers SEQ ID NO:200 (bWET BamHI end1) and SEQ ID NO:165 (bWET BamHI end2) which create BamHI cohesive ends without the need for BamHI digestion. The BamHI RNAi fragment was then ligated into the BamHI site of pUCAP already containing BdUBQ promoter and BdUBQT terminator resulting in the intermediate clone pBF067. The pBF067 complete insert was amplified with SEQ ID NO:166 (BdUBQ PvuI F) and SEQ ID NO:167 (BdUBQT PacI R), digested with PvuI and PacI and subsequently ligated into the PacI site of pUCAP or pBF012 vectors already containing a BdGOS2 driven mutant NPTII selectable marker in the AscI-PacI sites, resulting in pBF108 and pBF109, respectively. This mutant NPTII gene is commonly found in cloning vectors. There is only a single base pair difference from the wild type.

This cassette is in the PacI-AscI sites of pUCAP for the shuttle/bombardment vector pBF108 and in the Pac-AscI sites of pBF012 for the binary vector pBF109.

$P_{BdUBQ}$-HP-Pv(251)PK

An expression cassette was constructed and inserted into two different vector backbones, the first being into the PacI-AscI sites of pUCAP and the second being into the PacI-AscI sites of pBF012. A fragment of *Panicum virgatum* PK220 being 251 bp in length (Pv(251)PK220) and identified as SEQ ID NO:168 was amplified using primer combinations SEQ ID NO:169 (PvWET XbaI F) plus SEQ ID NO:170 (PvWET BamHI R) and SEQ ID NO:169 (PvWET XbaI F) plus SEQ ID NO:171 (PvWET ClaI R). PCR products were digested with the indicated restriction enzymes. No sequence information exists regarding the PvWx intron 1 so the BdWx intron 1 was used as the spacer sequence in this construct. This sequence was amplified with SEQ ID NO:162 (bWx BamHI F) plus SEQ ID NO:163 (bWx ClaI R) primers and digested with the indicated restriction enzymes.

The three fragments were then ligated together into the XbaI site of the pUCAP MCS resulting in BdWx intron 1 sequence being flanked by Pv(251)PK220 target sequences in opposite orientations. No PvUBQ promoter sequence was available so the BdUBQ promoter and terminator are used in this construct. The BdUBQ promoter contains an internal BamHI site, so the RNAi cassette was amplified with primers SEQ ID NO:172 (PvWET BamHI end1) and SEQ ID NO:173 (PvWET BamHI end2) which create BamHI cohesive ends without the need for BamHI digestion. The BamHI RNAi fragment was then ligated into the BamHI site of pUCAP already containing BdUBQ promoter and BdUBQT terminator resulting in the intermediate clone pBF152. The pBF152 complete insert was amplified with SEQ ID NO:166 (BdUBQ PvuI F) and SEQ ID NO:167 (BdUBQT PacI R), digested with PvuI and PacI and subsequently ligated into the PacI site of pUCAP or pBF012 vectors already containing BdGOS2 driven wildtype NPTII in the AscI-PacI sites, resulting in pBF169 and pBF170, respectively.

$P_{SbuBQ}$-HP-Sb(261)PK

An expression cassette was constructed and inserted into two different vector backbones, the first being into the PacI-AscI sites of pUCAP and the second being into the PacI-AscI sites of pBF012. A fragment of *Sorghum bicolor* PK220 (SbPK220) being 261 bp in length (Sb(261)PK220) and identified as SEQ ID NO:174 was amplified using primer combinations SEQ ID NO:175 (SbWET XbaI F) plus SEQ ID NO:176 (SbWET BamHI R) and SEQ ID NO:175 (SbWET XbaI F) plus SEQ ID NO:177 (SbWET ClaI R). PCR products were digested with the indicated restriction enzymes to give a Sb(261)PK220 fragment. The hairpin spacer sequence, SbWx intron 1 (SEQ ID NO:178), was amplified with primers SEQ ID NO:179 (SbWx BamHI) plus SEQ ID NO:180 (SbWx ClaI R) and digested with the indicated restriction enzymes. The three fragments were then ligated together into the XbaI site of the pUCAP MCS resulting in SbWx intron 1 sequence being flanked by SbWET target sequences in opposite orientations. BamHI cohesive ends were added to the RNAi cassette via amplification with primers SEQ ID NO:181 (SbWET BamHI end1) and SEQ ID NO:182 (SbWET BamHI end2). The BamHI RNAi fragment was then ligated into the BamHI site of pUCAP already containing SbUBQ promoter and SbUBQT terminator resulting in the intermediate clone pBF151. The pBF151 complete insert was amplified with SEQ ID NO:192 (SbUBQ PvuI F) and SEQ ID NO:167 (BdUBQT PacI R), digested with PvuI and PacI and subsequently ligated into the PacI site of pUCAP or pBF012 vectors already containing BdGOS2 driven wildtype NPTII in the AscI-PacI sites, resulting in pBF158 and pBF171, respectively.

A SbGOS2 promoter was identified from the *Sorghum* genome sequence was amplified and using the primer pair SEQ ID NO:184 (SbGOS2 HindIII F) and SEQ ID NO:185 (SbGOS2 HindIII R) a 1000 bp fragment of the GOS2 promoter, identified as SEQ ID NO:183, was PCR amplified and cloned using the HindIII restriction sites.

A SbUBQ promoter was identified from the *Sorghum* genome sequence was amplified and using the primer pair SEQ ID NO:187 (SbUBQ PstI F) and SEQ ID NO:188 (SbUBQ PstI R) a 1000 bp fragment of the UBQ promoter, identified as SEQ ID NO:186, was PCR amplified and cloned using the PstI restriction sites.

A SbUBQ terminator was identified from the *Sorghum* genome sequence was amplified and using the primer pair SEQ ID NO:190 (SbUBQT KpnI F) and SEQ ID NO:191 (SbUBQT KpnI R) a 239 bp fragment of the UBQ terminator, identified as SEQ ID NO:189, was PCR amplified and cloned using the KpnI restriction sites.

*Miscanthus giganteus* (MgPK220) RNAi

Expression constructs designed to down regulate via a hairpin strategy can be devised following the same strategy as described above. Resulting in a construct that may comprise the following elements, a BdGOS2-wtNPTII-BdUBQT selectable marker cassette and a BdUBQ-(MgPK220 hairpin-RNAi cassette)-BdUBQT in a vector of choice such as pUCAP and pBF012

AtPK220 Promoter Isolation and Cloning

The AtPK220 promoter was isolated using a PCR approach using *Arabidopsis* (Columbia ecotype) genomic DNA as template. The 5' primer, SEQ ID NO:119, was designed near the adjacent gene and the 3' primer, SEQ ID NO:120, located 25 bp upstream of the ATG start codon of the AtPK220 gene. The amplified product was digested with BamHI and SmaI and cloned into pBI101. The digested fragment, SEQ ID NO:14, was 1510 bp in length. The resulting construct was named $P_{AtPk220}$-GUS.

AtPK220 Promoter Activity Analysis Using GUS Assay $P_{AtPK220}$-GUS was transformed into *Arabidopsis* plants using flower dipping, and the transgenic plants were advanced to T3 homozygorsity. Various tissues including young seedlings and leaves, stems, flowers, siliques, and roots from T3 flowering plants were collected, stained in X-Gluc solution at 37 C overnight, de-stained with ethanol solution, and examined under a microscope. The results showed that the promoter of AtPK220 was expressed mainly in endodermis and pericycle cells of root tissue and was also found in leaf trichomes and seed coat of developing seeds. Of significance was the observation that expression of $P_{AtPK220}$-GUS was suppressed by water stress.

Sub-Cellular Localisation of AtPK220 Proteins in *Arabidopsis*

Expression of a full length wild type AtPK220-GFP fusion protein in transgenic *Arabidopsis* was used to locate the sub-cellular localization of the native protein. The primer pair SEQ ID NO:109 and SEQ ID NO:110 produced a fragment that was digested with SmaI and BamHI to yield a fragment comprising the full length open reading frame of AtPK220 and is disclosed as SEQ ID NO:10 and cloned downstream, in frame with the green fluorescence protein (GFP) in a pEGAD plasmid at the SmaI and BamHI sites. Additionally, the AtPK220 coding sequence was amplified using primer pair SEQ ID NO:198 and SEQ ID NO:199 and inserted upstream and in frame with GFP by AgeI digestion of pEGAD plasmid and the amplified AtPK220 fragment.

The 35S-GFP-AtPK220 and 35S-AtPK220-GFP constructs were transformed into *Arabidopsis* plants and homozygous transgenic plants (root tissues) were used for visual screening of GFP signal under confocal microscope. Green fluorescence was detected along plasma membrane, suggesting that AtPK220 protein was associated with plasma membrane in roots and that AtPK220 possibly functions as receptor kinase to sense or transduce environmental signals.

Isolation of BnPK220 from *Brassica napus* by 5' and 3' RACE

To isolate the homologous gene of AtPK220 from canola, a blast search (BLASTn) of NCBI Nucleotide Collection (nr/nt, est) and TIGR (DFCI) *Brassica napus* EST Database was done using AtPK220 sequence. Based on the sequences with highest similarity, a pair of primers, SEQ ID NO:122 and SEQ ID NO:123 were designed and used to PCR amplify a partial fragment of BnPK220. Both mRNA and genomic DNA isolated from *Brassica* leaves were used as template for these amplifications. A DNA fragment of about 500 bp was obtained by PCR from canola genomic DNA template. Sequence analysis of this PCR product showed that it shares a high identity with AtPK220 in nucleotide sequence as well in the intron organisation.

Based on the partial sequence of BnPK220, 5' and 3' RACE was performed to isolate the full length BnPK220 cDNA. For 3' RACE a forward primer, SEQ ID NO:124 and a nested primer, SEQ ID NO:125, were used. For 5' RACE a reverse primer, SEQ ID NO:126, and its nest primer, SEQ ID NO:127, were designed. RACE-ready cDNA for either 5' RACE or 3' RACE was made from RNA isolated from young *Brassica* leaves.

The 5' RACE yielded an amplified DNA of about 650 bp in length; and 3' RACE yielded a DNA of about 1 kb in size. Sequencing of these two RACE fragments showed high sequence similarity with AtPK220. A full-length mRNA of BnPK220 sequence was assembled by combining 5'RACE, partial BnPK220 fragment and 3' RACE results.

A full length BnPK220 cDNA was amplified by RT-PCR using the PCR primers SEQ ID NO:128 and SEQ ID NO:129. This cDNA comprises an ORF of 1302 nucleotides (SEQ ID NO:25) and encodes a protein of 433 amino acids (SEQ ID NO:26). Another full length BnPK220 cDNA was also amplified by the RT-PCR using cDNA made from *B. napus*. This cDNA (SEQ ID NO: 193) is 98.6% identical to SEQ ID NO:25, and encodes a protein (SEQID NO:194) of 99.3% identical to SEQ ID NO:26.

Isolation of full-length GmPK220 from soybean by 5' RACE

A Blastn search of NCBI EST database, a homolog of AtPK220 was found as a soybean (*Glycine max*) EST, CX709060.1. From this homolog, a unigene cluster of 13 ESTs was retrieved from a soybean EST database. A contig was then assembled from these 13 ESTs, which covers a majority of the gene sequence.

The full-length sequence of GmPK220 (SEQ ID NO:41) was determined by combining the assembled contig, 5' RACE and 3' RACE results. The 5' RACE was performed using the primers of SEQ ID NO:130 for primary RACE PCR and SEQ ID NO:131 for nested RACE PCR. The 3' RACE was performed using the primers of SEQ ID NO:137 for primary RACE PCR and SEQ ID NO:138 for nested RACE PCR. GmPK220 encodes a protein as shown in SEQ ID NO:42.

Isolation of OsPK220 (Rice) Sequence by Database Mining

The rice genome (*Oryza sativa, japonica* cultivar) has been completely sequenced and is publically available. The homolog of AtPK220 in rice was determined by BLAST search of a rice EST database and by BLASTP search of a genomic sequence database. The target having the highest score was identified as Accession number Os05g0319700.

Os05g0319700 is abbreviated as OsPK220, and disclosed as SEQ ID NO:59, which encodes a protein disclosed as SEQ ID NO:60.

Isolation of ZmPK220 (Corn) Sequence

Two candidate homologs were found by BLAST search of the TIGR EST database, one a unigene Accession number TC333547 and the second Accession number CO439063.

Accession number TC333547 is 2125 nucleotides in length and contains an open reading frame of 1377 nucleotides (SEQ ID NO:77) encoding a protein of 458 amino acids (SEQ ID NO:78). This translated protein is full-length and is larger than AtPK220 protein. The C-terminal kinase domain is highly conserved between the *Arabidopsis* and corn protein sequence, however, the N-terminal sequence is more variable.

CO439063 is a short EST sequence and is missing 5' terminal sequence. The missing sequence was obtained by RACE methods. Two 5' RACE primers were designed based on the alignment between AtPK220 and CO439063. The primary 5' RACE primer is SEQ ID NO:132 and the nested 5' RACE primer is SEQ ID NO:133. The 3' RACE was also performed using the primers of SEQ ID NO:139 for primary RACE PCR and SEQ ID NO:140 for nested RACE PCR. The ZmPK220 (SEQ ID NO:79) sequence was assembled based on 5' RACE, 3' RACE results and CO439063 EST sequences. The corresponding protein sequence was listed as SEQ ID NO:80.

Sequence analysis shows that CO439063 has higher sequence similarity with rice OsPK220 than TC333547.

Isolation of BdPK220 Sequence from *Brachipodium distachyon* (Bd)

*Brachipodium* is one of the model monocot plants for functional genomic research. A contig was assembled from public ESTs or GSSs, and it covers a 3'-portion of BdPK220 according to homologue alignment. RACE using Bd81RAR1 primer (SEQ ID NO: 195) and Bd81RAR2 primer (SEQ ID NO: 196) designed from the contig and using *Brachipodium* leaf cDNA produced a unique fragment of about 650 bp. The assembling of the RACE sequence and the contig gave the full length BdPK220 sequence (SEQ ID NO:24), which encodes a protein of 461 amino acids (SEQ ID NO: 197).

Determination of GsPK220 (Cotton) Sequence by Database Mining

A BLAST search of a cotton (*Gossypium*) TIGR-EST database identified a sequence cluster identified as Accession number TC79117, that has high similarity with AtPK220. This cluster has two overlapping ESTs, TC79117 which is referred herein as GsPK220) and consists of an open reading frame of 1086 nucleotides (SEQ ID NO:81). The largest open reading frame encodes a protein of 361 amino acids (SEQ ID NO:82).

Drought Tolerant Phenotype of Hwe116 Mutant Found Under Water Limited Conditions and High Water Use Efficiency Under Both Drought and Optimal Conditions Two groups of plants were grown (5 plants per 3" pot filled with the same amount of soil-less mix) under optimal conditions in a growth chamber (22 C, 18 hr light, 150 uE, 70% relative humidity) until first day of flower (n=6 per entry per treatment). At first flower all plants were supplied with the same amount of water (optimal levels) but one group of plants was used for the optimal treatment and the other for drought treatments. In the optimal treatment the pots were weighed daily to determine daily water loss and then watered back up to optimal levels. In the drought treatment, pots were weighed daily to determine water loss and allowed to dry out. Plants were harvested on days 0, 2 and 4 of drought and optimal treatments for shoot biomass determinations. Lower water loss relative to shoot dry weight (DW) as compared to control, under drought conditions indicates a drought tolerant phenotype. The ratio of shoot dry weight accumulated to water lost during the treatment period provides a measure of water use efficiency (WUE). The hwe116 plants were delayed in flowering by 1 to 2 days. Water loss relative to shoot biomass was significantly lower (by 22%) in hwe116 than parent control under drought conditions. This result indicates that the mutant is drought tolerant. It has also been found that under optimal conditions the water loss relative to shoot DW was also significantly lower in the mutant (by 41%) as compared to the parent control. This result is consistent with higher water use efficiency phenotype. Calculations of water use efficiency showed that under both drought (Table 1) and optimal (Table 2) conditions hwe116 mutant uses water more efficiently because it accumulated more shoot biomass with less water (drought) or the same amount of biomass with less water (optimal).

TABLE 1

Water Use Efficiency (WUE) under drought conditions

| Entry | shoot DW accumulated- day 0 to 4 (g) | water lost- day 0 to 4 (g) | WUE (g shootDW acc/kg water lost) |
|---|---|---|---|
| hwe116 | 0.146 | 56.5 | 2.58 (+13%) |
| Parent | 0.134 | 58.6 | 2.28 |

TABLE 2

Water Use Efficiency (WUE) under optimal conditions

| entry | shoot DW accumulated-day 0 to 4 (g) | water lost- day 0 to 4 (g) | WUE (g shootDW acc/kg water lost) |
|---|---|---|---|
| hwe116 | 0.276 | 92.3 | 2.99 (+22%) |
| Parent | 0.271 | 110.6 | 2.45 |

The final result of enhanced water use efficiency in the mutant is greater shoot DW biomass as shown in Table 3 (harvested on day 4 from 1$^{st}$ flower).

TABLE 3

Final shoot DW biomass

| entry | Drought- shoot DW (g) Mean | S.E. | Optimal- shoot DW (g) Mean | S.E. |
|---|---|---|---|---|
| hwe116 | 0.354 | 0.014 | 0.449 | 0.017 |
| parent | 0.300 | 0.011 | 0.414 | 0.011 |
| hwe116 as % of parent | 118% | | 108% | |

The Hwe116 Mutant Maintains Higher Soil Water Content During Drought Treatment, Reaches Water-Stress Conditions Later and Shows Yield Protection Following Drought Stress During Flowering Relative to Control Plants.

An experiment was set up with 5 plants per 4" pot filled with the same amount of soilless mix. Two groups of plants (optimal and drought) were grown under optimal conditions in a growth chamber (22 C, 18 hr light, 150 uE, 70% relative humidity) until first day of flower (n=9 per entry and per group). At first flower all plants were supplied with the same amount of water and further water was withdrawn for the drought treated group of plants. The optimal group was watered daily as before. Pots in the drought treated group were weighed daily for 6 days of treatment to determine soil water content. After 6 days of drought treatment plants were re-watered and allowed to complete their lifecycle as the optimal group under optimal conditions. At maturity the seeds were harvested from each pot and the seed yield was determined for both optimal and drought treated plants. The results of changes in soil water content during the drought treatments were determined. Soil water content was measured as percentage of initial amount of water in the pot. The results indicate that the mutant was able to retain water in pots longer and therefore it reached the stress level (around 25% soil water content) 1 day later and wilted 1 day later than control. This treatment caused a yield reduction of 17% from optimal levels in the mutant, whereas in control the yield reduction was 41%. Therefore the mutant demonstrated a yield protection of 24% relative to control, following a drought treatment.

The Hwe116 Mutant Seedlings Showed Less Sensitivity to Cold Stress.

Two groups of plants with 8 replicates per entry were grown with 3 plants per 3" pot under optimal conditions of 22° C. and short days to prolong vegetative growth and delay flowering (10 hr light 150 uE, and 14 hr dark), 70% relative humidity in a growth chamber. At 10 days of age (3 days post-transplanting of seedlings into soil from agar plates) the cold treatment group was placed in a chamber at 8° C. for 11 more days of growth while the optimal group was maintained at 22° C. Plants were harvested for shoot dry weight (DW) determinations at 21 days of age. The results are shown in Table 4. The hwe116 mutant had smaller seedlings under optimal conditions than those of controls but after cold exposure the shoot DW was equivalent to that of the parent and as percentage of the optimal DW it was higher than that of both controls by 9 and 15% indicating that the growth of the mutant was not as inhibited by cold as that of controls.

TABLE 4

| shoot dry weight under optimal and cold conditions. | | | | | |
|---|---|---|---|---|---|
| | optimal (22° C.) | | Cold (8° C.) | | |
| | shoot DW (mg) | | shoot DW (mg) | | shoot DW |
| Entry | Mean | S.E. | Mean | S.E. | % of optimal |
| hwe116 | 6.65 | 0.30 | 2.85 | 0.13 | 43% |
| parent | 9.16 | 0.21 | 2.58 | 0.11 | 28% |
| WT | 9.30 | 0.20 | 3.18 | 0.21 | 34% |

The Hwe116 Mutant has Thicker Leaves and Higher Chlorophyll Content Per Leaf Area. The Mutant Showed Delayed Leaf Senescence and Resistance to Oxidative Stress.

Plants were grown 1 per 3" pot under optimal growth conditions in a growth chamber (16 hr light, 300 uE, 22° C., 70% relative humidity). Early into flowering three leaf disks (86.6 um2 each) were taken from three youngest fully developed leaves and placed in petri dishes containing filter paper with 5 uM N,N'-Dimethyl-4,4'-bipyridinium dichloride (paraquat) solution as an oxidizing agent. Plates with leaf disks were placed under continuous light of 150 uE for 25 hours. This resulted in chlorophyll bleaching. The differences between the mutant and controls in the extent of bleaching were quantified by measuring chlorophyll content of the leaf disks. A leaf disk was also removed from leaves that have not been exposed to paraquat treatment and optimal chlorophyll content was determined. These disks were also weighed. The results showed that the mutant had higher total chlorophyll content per leaf surface area (Table 5), however the leaves of this mutant are thicker (leaf disks were 15 to 24% heavier in the mutant compared to those of controls). Chlorophyll content per gram of fresh leaf tissue was, therefore, not different. There were no differences between chlorophyll a to b ratios between the mutant and controls. The hwe116 mutant showed resistance to the oxidative stress as indicated by 5 to 7% higher chlorophyll content following paraquat treatment (Table 5). Leaf senescence was also delayed in the hwe116 mutant (data not shown).

TABLE 5

| Effect of oxidative stress on chlorophyll content of leaves. | | | | | |
|---|---|---|---|---|---|
| | Optimal | | 5 uM paraquat in 24 hr light | | |
| | Chl (a + b)-(mg/m2) | | Chl (a + b)-(mg/m2) | | |
| Entry | Mean | Std Err | Mean | Std Err | % of opt |
| hwe116 | 303.7 | 6.7 | 61.9 | 4.4 | 20% |
| Parent | 259.6 | 4.3 | 39.5 | 5.9 | 15% |
| WT | 250.2 | 5.7 | 32.1 | 2.9 | 13% |

The Growth of Mutant Hwe116 Seedlings Showed Less Inhibition on Low Nitrogen Containing Media.

Twelve seedlings were grown on an agar plate (6 plates per entry) containing ½ MS growth media with optimal (20 mM) or low (0.3 mM) nitrogen content. Plates were placed in a growth room with an 18 hr light period (100 uE) for 6 days in a vertical position, then plates were placed horizontally and seedlings were grown for another 4 days before the shoots were harvested. The average seedling shoot DW after 10 days of growth was calculated per plate. The results are shown in Table 6. The shoot DW of hwe116 mutant grown under optimal conditions was significantly reduced but when grown on low nitrogen there were no differences. The shoot DW on low nitrogen in the mutant was 3 to 7% greater than in controls when compared to the optimal nitrogen levels. This indicates that the mutant may have better nitrogen use efficiency.

TABLE 6

| Effect of nitrogen on seedling shoot DW | | | | | |
|---|---|---|---|---|---|
| | Average seedling shoot DW (mg) | | | | |
| | Optimal nitrogen | | Low nitrogen | | |
| Entry | Mean | S.E. | Mean | S.E. | % Opt |
| hwe116 | 1.03 | 0.03 | 0.23 | 0.01 | 22 |
| Parent | 1.34 | 0.04 | 0.20 | 0.01 | 15 |
| WT | 1.22 | 0.03 | 0.23 | 0.02 | 19 |

Knockout Mutant of PK220 Showed Drought Tolerant Trends and Higher Water Use Efficiency Under Drought Treatment.

Plant lines obtained from the SALK institute that were T-DNA knockouts in the AtPK220 gene (SALK_147838) were grown (5 per 3"pot) under optimal conditions in a growth chamber (18 hr light, 150 uE, 22° C., 60% relative humidity) until first open flower (n=8 per entry and per harvest). The drought treatment was started by watering all plants with the same amount of water and cessation of further watering. Pots were weighed daily and plants were harvested for shoot DW determinations on days 0, 2 and 4 of the drought treatment. The result showed that water lost from pots in 2 days relative to shoot DW on day 2 was significantly lower (by 13%) for the knockout mutant and its shoot DW was also significantly greater (by 24%) on day 2 as compared to control wild-type. This result is consistent with drought tolerant phenotype.

The results showed that the water use efficiency of the knockout mutant was greater than that of the control-WT as the knockout mutant was able to accumulate more shoot biomass in the 2 days of treatment while using the same amount of water as control (Table 7).

TABLE 7

| Water use efficiency under drought treatment | | | |
|---|---|---|---|
| entry | g water lost | g shoot DW gain | WUE (g shoot/kg water) |
| PK220-knockout | 43.1 | 0.059 | 1.37 |
| WT | 42.9 | 0.035 | 0.82 |

Transgenic Lines of 35S-HP-At(270)PK220 Construct in *Arabidopsis* Showed Drought Tolerance.

Plants were grown (5 per 3" pot and 8 pots per entry per harvest) under optimal conditions in a growth chamber (18 hr light, 150 uE, 22° C., 60% relative humidity) until first day of flower. The drought treatment was started by watering all pots with the same amount of water and cessation of further watering. Pots were weighed daily for water loss determinations and plants were harvested for shoot biomass on day 4 of drought treatment. The results (Table 8) showed that 11 out of 13transgenic lines demonstrated a drought tolerant phenotype (having a lower water loss over 2 days relative to shoot biomass on day 4). Four of the lines showed a slight delay in flowering (1 day), as did the hwe116 mutant. The final shoot biomass on day 4 was greater for most of the transgenic lines as compared to control WT. These results are indicative of a drought tolerant phenotype in the transgenic lines down-regulated in PK220 expression. As examples, the reduction in expression level of AtPK220 for the top 3 performing lines: 65-4, 38-5, and 59-3, are 75%, 47% and 58%.

TABLE 8

Drought tolerance and shoot DW (day 4) for 35S-HP-At(270)PK220 transgenic lines relative to wild type (WT) and the hwe116 mutant relative to parent control.

| entry | drought tolerance % of control | shoot DW % of control |
|---|---|---|
| 65-4 | 119% | 132% |
| 38-5 | 116% | 124% |
| 59-3 | 112% | 119% |
| 33-7 | 111% | 114% |
| 54-11 | 108% | 115% |
| 56-3 | 107% | 115% |
| 43-11 | 107% | 113% |
| 23-8 | 106% | 111% |
| 12-2 | 106% | 110% |
| 63-4 | 104% | 110% |
| 32-1 | 104% | 109% |
| 30-3 | 101% | 104% |
| 74-2 | 101% | 107% |
| WT | 100% | 100% |
| hwe116 | 186% | 106% |
| parent | 100% | 100% |

Drought Tolerance of 35S-HP-At(270)PK220 Transgenic Lines in *Arabidopsis* and Enhanced Water Use Efficiency were Confirmed.

The transgenic lines of 35S-HP-At(270)PK220 were grown with 5 per 3" pot under optimal conditions in a growth chamber (18 hr light, 150 uE, 22° C., 60% relative humidity) until first flower (n=8). Drought treatment was started at first flower by watering all the pots with the same amount of water and cessation of further watering. The pots were weighed daily for the 4 days of drought treatment and plants were harvested on days 0, 2 and 4 of treatment. The results confirmed that water lost in 2 days relative to shoot biomass on day 2 was lower in five transgenic lines relative to controls, confirming their drought tolerant phenotype (Table 9). The shoot DW on day 2 was greater in 5 of the transgenic lines.

TABLE 9

Drought tolerance and shoot DW for 35S-HP-At(270)PK220 transgenic lines

| entry | drought tolerance % of WT | shoot DW % of WT |
|---|---|---|
| 59-3 | 110% | 105% |
| 65-4 | 110% | 98% |
| 38-5 | 107% | 109% |
| 33-7 | 103% | 106% |
| 56-3 | 102% | 95% |
| 54-11 | 101% | 103% |
| null (65-1) | 99% | 99% |
| WT | 100% | 100% |

The water use efficiency was greater than that of controls during the 4 days of drought treatment for three transgenic lines and this enhanced water use efficiency was due to greater shoot DW accumulation (Table 10).

TABLE 10

Water use efficiency between day 0 and 4 of the drought treatment in transgenic lines of 35S-HP-At(270)PK220.

| entry | shoot DW accumulated (g) d0-d4 | water lost (g) d0 to d4 | WUE (g shoot/kg water) d0 to d4 |
|---|---|---|---|
| 65-4 | 0.090 | 62.5 | 1.44 (+22 to 33%) |
| 12-2 | 0.079 | 62.2 | 1.27 (+7 to 17%) |
| 56-3 | 0.079 | 62.7 | 1.25 (+6 to 16%) |
| null (65-1) | 0.068 | 62.7 | 1.08 |
| WT | 0.073 | 61.9 | 1.18 |

Transgenic Lines of 35S-HP-At(270)PK220 in *Arabidopsis* had Lower Water Loss Relative to Shoot Biomass and Enhanced WUE Under Optimal Conditions.

Plants of 35S-HP-At(270)PK220 transgenic lines 65-7 and 59-5, WT Columbia, hwe116 mutant and its parent were grown (5 per 3" pot) under optimal conditions in a growth chamber (22° C., 18 hr light—200 uE, 60% relative humidity) until first flower (n=8 per entry, per harvest). At first flower all pots in the water limited group were watered with the same amount of water (to a pot weight of 120 g in first 4 days and to 130 g for last 3 days (as plants grew larger they required more water). Pots were weighed daily to determine daily water loss and plants were harvested on day 0 and day 7 of this treatment. Water use efficiency (WUE) was calculated from the ratio of shoot biomass accumulated to water lost. The results are shown in Table 11.

TABLE 11

Water Use Efficiency under optimal conditions

| entry | shoot DW accumulated (g) d0-d4 | water lost (g) d0 to d4 | WUE (g shoot/kg water) d0 to d4 |
|---|---|---|---|
| 59-5 | 0.514 | 223 | 3.31 (+4%) |
| 65-4 | 0.671 | 276 | 2.43 (+9%) |
| WT | 0.517 | 232 | 2.23 |
| hwe116 | 0.420 | 191 | 2.19 (5%) |
| parent | 0.421 | 202 | 2.08 |

The results show that under optimal water conditions the two transgenic lines and the mutant had enhanced water use efficiency.

Growth Rates of the 35S-HP-At(270)PK220 Transgenic *Arabidopsis* were Greater than Those of Controls During Both Optimal and Water Limited Conditions.

Plants of 35S-HP-At(270)PK220 transgenic line 65-4 and WT Columbia were grown (5 per 3" pot) under optimal conditions in a growth chamber (22° C., 18 hr light—150 uE, 60% relative humidity) until first flower (n=8 per entry, per treatment and per harvest). At first flower all pots in the water limited group were watered with the same amount of water (to a pot weight of 95 g), and further watering was stopped for 2 days. It took 2 days for the water limited group of plants to reach about 30% of initial soil water content (about 55 g total pot weight), referred to as pre-treatment. At that time the water limited treatment was deemed to have started (day 0 of treatment) and plants were watered daily up to a total pot weight of 55 g for 3 days, and up to 65 g in the following 4 days (until day 7 of treatment). The optimal group was maintained under optimal conditions by watering the pots daily up to 100 g total pot weight in the 2 pre-treatment days, the first 3 days of treatment and then up to 130 g in the last 4 days of treatment (as plants grew larger they required more water). The daily water loss from the pots was measured for all the plants and plants in both groups were harvested on days 0, 1, 2, 3, 5, and 7 of treatment for shoot dry weight determinations. The water loss relative to the shoot biomass (drought tolerant phenotype) was calculated over the initial two days before the start of treatment, during the first 3 days of treatment and during the last 4 days of treatment. The results under both optimal (Table 12) and water limited (Table 13) conditions are shown. The transgenic line 65-4 lost less water relative to shoot biomass than WT in both optimal and water limited conditions. Under limited water conditions this is consistent with enhanced drought tolerance phenotype.

TABLE 12

Water loss in g/shoot DW in g under optimal conditions.

| Entry | pre-treatment | d0-d3 | d3-d7 |
|---|---|---|---|
| 65-4 | 231 ± 9 | 162 ± 3 | 237 ± 5 |
| WT | 275 ± 8 | 178 ± 7 | 243 ± 6 |

TABLE 13

Water loss in g/shoot DW in g and Drought tolerance (as percentage of WT) under water limited conditions.

| Entry | pre-treatment (drought toler. in % of WT) | d0-d3 (drought toler. in % of WT) | d3-d7 (drought toler. in % of WT) |
|---|---|---|---|
| 65-4 | 174 ± 2 (108%) | 83 ± 2 (115%) | 153 ± 6 (113%) |
| WT | 189 ± 4 (100%) | 97 ± 4 (100%) | 175 ± 4 (100%) |

Growth rates of the plants were calculated over the seven days of both treatments. The results showed that transgenic line 65-4 had larger plants (up to 24%) than the wild type throughout the treatment under both conditions. The growth rate (shoot dry weight accumulated per day over the 7 days of treatment) was slightly greater for the transgenic line under both optimal and water limited conditions (63.3 and 21.3 mg shoot/day, respectively) than that of WT control (58.3 and 20.4 mg shoot/day, respectively).

The Transgenic Line of 35S-HP-At(270)PK220 *Arabidopsis* and the Hwe116 Mutant Grow Better Under Limited Nitrogen Conditions than Controls.

The 35S-HP-At(270)PK220 transgenic line 65-5, its segregated null control (null 65-1) and wild-type (WT) plus the hwe116 mutant and its parent control were analyzed for growth characteristics of young seedling under optimal and limited nitrogen conditions. Nitrogen content refers to the available nitrogen for plant growth, including nitrate and ammonium sources. Seedlings were grown on agar plates (10 per plate and 5 plates per entry and per treatment) containing either optimal nutrients (including 20 mM nitrogen) or low (limiting to growth) nitrogen (optimal all nutrients except for nitrogen being 0.5 mM). Plates were placed in a growth chamber at 18 hr lights of 200 uE and 22° C. Seedlings were grown for 14 days before being harvested for shoot biomass (8 seedlings) and chlorophyll determinations (2 seedlings). On optimal plates there were no differences in average seedling shoot biomass except for the hwe116 mutant, as shown before had slightly smaller seedling shoot DW (not significant). On low nitrogen the hwe116 mutant had significantly bigger seedling shoot DW and showed 30% less inhibition in growth as compared to its parent. The transgenic line 65-5 showed slightly greater shoot DW than controls and was 5% to 7% less inhibited in growth than the controls (Table 14).

TABLE 14

Effect of nitrogen on seedling shoot DW

| | Average seedling shoot DW (mg) | | | | |
|---|---|---|---|---|---|
| | Optimal N (20 mM) | | Low N (0.5 mM) | | |
| entry | Mean | Std Err | Mean | Std Err | % of opt |
| 65-5 | 5.3 | 0.1 | 2.9 | 0.1 | 56% |
| WT | 5.5 | 0.3 | 2.8 | 0.1 | 51% |
| hwe116 | 4.8 | 0.2 | 3.8 | 0.3 | 80% |
| parent | 5.1 | 0.2 | 2.6 | 0.1 | 50% |

The total chlorophyll content of seedling shoots grown under low N levels reflected the shoot DW results. Chlorophyll content is very closely linked to available N and one of the major symptoms of N-deficiency in plants is leaf chlorosis or bleaching. Table 15 shows that chlorophyll content of the transgenic line 65-5 and the mutant hwe116 was reduced less than that of the controls.

TABLE 15

Effects of nitrogen on seedling shoot total chlorophyll content

| | seedling shoot chlorophyll content (ug/g) | | | | |
|---|---|---|---|---|---|
| | Optimal N (20 mM) | | Low N (0.5 mM) | | |
| entry | Mean | Std Err | Mean | Std Err | % of opt |
| 65-5 | 902 | 35 | 244 | 22 | 27% |
| WT | 854 | 102 | 156 | 17 | 18% |
| hwe116 | 1006 | 51 | 376 | 37 | 37% |
| parent | 836 | 59 | 208 | 47 | 25% |

These results confirmed that the hwe116 mutant grew better on limited nitrogen and the transgenic line showed the same trends. Therefore, down-regulation of the PK220 gene in plants appears to result in increased nitrogen use efficiency (accumulation of more biomass per unit of available nitrogen).

The Transgenic Line of 35S-HP-At(270)PK220 *Arabidopsis* and the Hwe116 Mutant germinate faster and have higher rates of germination in the cold.

Germination under cold (10° C.) conditions was assessed in the transgenic line 65-5 carrying the 35S-HP-At(270) PK220 construct relative to WT-control and that of the hwe116 mutant relative to its parental control on agar plates containing optimal growth media. Four plates per entry with 30 seeds each were prepared and placed in the chamber at 10° C., 18 hr light (200 uE). Germination (emergence of the radicle) scored as a percentage of viable seeds, was noted twice daily for 5 days starting with day 5 from placing of seeds on plates (no germination before day 5). Once no further changes were observed in germination all plates were placed in a chamber at 22° C. to check for viability of the seeds that had not germinated. All entries showed 98 to 100% seed viability, the hwe116 mutant had 94%. viabilty. The results of the germination assessment at 10° C. (Table 16) indicate that the transgenic line 65-5 germinated sooner than it's WT-control. The hwe116 mutant had higher rates of germination in the cold than its parent control. These data, together with the evidence that the mutant grows better under cold conditions are indicative of a greater seed and seedling vigor under cold stress

TABLE 16 percentage germination of viable seeds at 10° C.

| entry | # reps | Hours @ 10° C. 114.5 | 121 | 139 | 145 | 163 | 169 | 188.5 | 212.5 | 235 | 241 | % Viable Seed |
|---|---|---|---|---|---|---|---|---|---|---|---|---|
| 65-5 | 4 | 15.1 | 32.8 | 75.7 | 80.7 | 90.0 | 90.8 | 90.8 | 92.5 | 93.3 | 94.2 | 99.2 |
| WT | 4 | 5.9 | 16.0 | 55.4 | 62.9 | 78.1 | 79.0 | 80.7 | 80.7 | 81.5 | 81.5 | 98.4 |
| hwe116 | 4 | 15.9 | 28.4 | 67.5 | 81.4 | 94.2 | 98.0 | 99.0 | 99.0 | 100.0 | 100.0 | 94.0 |
| Parent | 4 | 6.7 | 26.7 | 72.5 | 77.5 | 85.0 | 85.0 | 85.9 | 85.9 | 85.9 | 85.9 | 100.0 |

Gas Exchange Measurements Support Higher WUE in Transgenic 35S-HP-At(270)PK220 *Arabidopsis* Under Optimal Conditions Plants of two transgenic lines and WT were grown in four inch diameter pots (one per pot) under optimal conditions in a growth chamber at 18 hr light (200 uE), 22° C., 60% RH. Eight days from first open flower gas exchange measurements were made on the youngest, fully developed leaf of 10 to 11 replicates per entry. Photosynthesis and transpiration rates were measured inside the growth chamber at the ambient growth light and temperature conditions and 400 ppm carbon dioxide using Li-6400 and *Arabidopsis* leaf cuvette. From the ratio of photosynthesis to transpiration instantaneous water use efficiency (WUE) was calculated. The results are shown in Table 17. The WUE in the transgenic lines was 11 and 18% greater than that of the WT. This data is consistent with the WUE measurements over a period of few days using the ratio of biomass accumulated to water lost in transpiration.

TABLE17

Photosynthesis (umol carbon dioxide/m2/s), transpiration (mmol H2O/m2/s) and WUE measured under optimal growth conditions.

| entry | Phots. (umol/m2/s) | Photos. (% WT) | Trans. (mmol/m2/s) | Trans. (% WT) | WUE (Photos/Trans) | WUE (% WT) |
|---|---|---|---|---|---|---|
| 59-6 | 3.9 ± 0.2 | 105% | 4.2 ± 0.5 | 95% | 1.03 ± 0.11 | 118% |
| 65-5 | 3.6 ± 0.2 | 97% | 3.8 ± 0.4 | 86% | 0.97 ± 0.13 | 111% |
| WT | 3.7 ± 0.2 | | 4.4 ± 0.2 | | 0.87 ± 0.05 | |

Drought Tolerance of 35S-HP-At(270)PK220 Transgenic *Arabidopsis* Results in Seed Yield and Biomass Protection Following Drought Stress.

Plants of two transgenic lines and the WT were grown (5 per 3 inch pot containing equal amount of soil) under optimal conditions in a growth chamber (22 C, 18 hr light of 200 uE, 60% RH) until first open flower. At first flower the drought treatment was applied to half of the plants while the other half was maintained under optimal conditions until maturity. The drought treatment consisted of watering all the plants to the same saturated water level. Plants were then weighed daily to monitor water loss from the pots and their water content was equalized daily by watering all pots to the level of the heaviest pot. As a result the soil water content was declining and reached stress levels with plants wilting on day 4. Plants were maintained at that stress level for another 2 days and on day 6 all plants were re-watered and maintained under optimal conditions for the rest of their life cycle. At maturity both optimal and drought plants were harvested for seed and shoot biomass. The impact of drought stress on both seed yield and shoot biomass was determined by comparing the optimal and drought treated plants. The results are shown in Table 18. Under optimal conditions the seed yield and the final shoot biomass of the transgenic lines was 7 to 10% higher than that of the WT. Following the drought stress during flowering the reduction in seed yield and the shoot biomass were not as great in transgenic plants as in the WT, resulting in seed yield protection of 5-7% and shoot biomass protection of 4%. The protection was calculated as the difference between the transgenics and WT in seed yield or shoot biomass a percentage of optimal.

TABLE 18

| Seed yield and final shoot biomass from optimal and drought stressed plants, n = 10 | | | | | | |
|---|---|---|---|---|---|---|
| entry | Seed yield-opt (g) | Shoot DW-opt (g) | Seed yield-drought (g) | % of opt | Shoot DW-drought (g) | % of opt |
| 59-6 | 1.29 ± 0.05 | 2.96 ± 0.13 | 1.06 ± 0.03 | 82% | 2.37 ± 0.07 | 80% |
| 65-5 | 1.27 ± 0.03 | 2.89 ± 0.08 | 1.01 ± 0.02 | 80% | 2.32 ± 0.06 | 80% |
| WT | 1.18 ± 0.04 | 2.69 ± 0.10 | 0.89 ± 0.02 | 75% | 2.04 ± 0.05 | 76% |

Over-Expression of Wild Type AtPK220 in Hwe116.2 Background can Restore the WT phenotype Transgenic plants of 35S-AtPK220 (in hwe116.2) were grown (5 per 3 inch pot) under optimal conditions in a growth chamber as described above until the first open flower. Drought treatment was applied by watering all plants to the same saturated level. Further watering was withheld. Plants were weighed daily to determine the daily water loss and all plants were harvested on day 4 of treatment by which time all plants showed wilting. The water loss relative to final shoot biomass was used to calculate drought tolerance where that of WT was assumed at 100%. The data are shown in Table 19. Three transgenic lines showed a reduction in drought tolerance from the mutant levels as indicated by increased water loss relative to shoot biomass. The three transgenic lines also flowered earlier than the mutant line and similar to the time that the WT lines flowered. These results support the conclusion that the AtPK220 gene mutation in hwe116.2 is responsible for the altered phenotypes observed and expression of a WT gene restore the WT characteristics of a mutant plant.

TABLE 19

| Water loss relative to shoot biomass and drought tolerance, n = 8 | | | |
|---|---|---|---|
| entry | Days to flower | Water lost in 3d/shoot DW d4 | Drought tolerance (% of WT) |
| 28-4 | 20.9 ± 0.1 | 155.1 ± 3.1 | 111% |
| 2-4 | 21.8 ± 0.1 | 164.7 ± 2.4 | 105% |
| 7-11 | 21.6 ± 0.1 | 177.9 ± 4.4 | 97% |
| hwe116.2 | 23.1 ± 0.2 | 134.9 ± 3.6 | 117% |
| WT | 20.8 ± 0.2 | 173.4 ± 5.1 | 100% |

Down Regulation of AtPK220 with the AtPK220-Promoter ($P_{PK}$) in *Arabidopsis* Results in Enhanced Drought Tolerance of Plants

*Arabidopsis* plants of $P_{PK}$-HP-At(270)PK220 were grown (5 per 3 inch pot) under optimal conditions in a growth chamber as mentioned above until the first open flower. Drought treatment was applied then by watering all plants to the same saturated level. Further water was withheld. Plants were weighed daily to determine the daily water loss and all plants were harvested on day 4 of treatment (all plants were wilted). The water loss relative to final shoot biomass was used to calculate drought tolerance where that of WT was assumed at 100%. The results of this study are shown in Table 20.

TABLE 20

| Water loss relative to shoot biomass and drought tolerance, n = 8 | | | |
|---|---|---|---|
| entry | Days to flower | Water lost in 3d/shootDW d4 | Drought tolerance (% WT) |
| 14-04 | 22 | 158 ± 5 | 116% |
| 15-06 | 20 | 183 ± 8 | 104% |
| 45-3 | 20 | 185 ± 9 | 103% |
| WT | 20 | 190 ± 9 | 100% |

One of the transgenic lines, 14-04, showed significantly greater drought tolerance than the wild type control as indicated by lower water loss relative to shoot biomass. This result is supported by data from line 14-04 that showed nearly complete inhibition of PK220 gene expression. The expression of AtPK220 was reduced by nearly 96% in the roots compared to WT. These results indicate that down regulation of PK220 in the roots is sufficient to achieve significant drought tolerance phenotype and presumably enhanced water use efficiency.

Overexpression of *Brassica napus* PK220 in the *Arabidopsis* Hwe116 Mutant can Restore the WT Phenotype Transgenic plants of 35S-BnPK220 (in hwe116) plus two null controls (segregated siblings of the transgenic lines without the transgene, therefore hwe116 mutant) were grown (5 per 3 inch pot) under optimal conditions in a growth chamber as mentioned above until the first open flower. Drought treatment was applied then by watering all plants to the same saturated level. Further water was withheld. Plants were weighed daily to determine the daily water loss and all plants were harvested on day 4 of treatment (all plants were wilted). The water loss relative to final shoot biomass was used to calculate drought tolerance where that of WT was assumed at 100%. The results of this study are shown in Table 21. The results indicate that 6 lines had a reduction of 8% or more in drought tolerance as compared to the nulls (the hwe116 mutant background) and therefore restoration towards the WT phenotype. This indicates that BnPK220 is functional and can work in the *Arabidopsis*.

TABLE 21

| Water loss relative to shoot DW and drought tolerance, n = 8 | | |
|---|---|---|
| entry | Water lost in 3d/shoot DW d4 | Drought tolerance (% of null) |
| 106-11 | 148 ± 6 | 98% |
| 67-6 | 150 ± 4 | 97% |
| 51-6 | 152 ± 4 | 96% |
| 5-1 | 152 ± 2 | 95% |

TABLE 21-continued

| Water loss relative to shoot DW and drought tolerance, n = 8 | | |
|---|---|---|
| entry | Water lost in 3d/shoot DW d4 | Drought tolerance (% of null) |
| 74-12 | 157 ± 5 | 92% |
| 38-7 | 160 ± 5 | 90% |
| 70-2 | 161 ± 2 | 89% |
| 97-3 | 164 ± 5 | 87% |
| 31-6 | 165 ± 4 | 87% |
| 93-8 | 172 ± 4 | 82% |
| Null 38-10 | 146 ± 3 | 100% |
| Null 90-7 | 135 ± 5 | 107% |

Transgenic *Brassica* Lines Having a 35S-AtPK220L292F Construct Showed Drought Tolerance and Higher Water Use Efficiency Down regulation of endogenous PK220 activity was demonstrated using a dominant negative strategy by expression of the mutant allele of the AtPK220 gene in *Brassica napus*. Three *Brassica napus* transgenic lines having the *Arabidopsis* mutant AtPK220L292F. gene and one null control line (a segregated sibling of the transgenic line lacking the transgene) per line were grown in 4.5 inch diameter pots containing equal amounts of soilless mix (Sunshine Professional Organic Mix #7) under optimal conditions of 16 hr light (400 uE) and 22 C day/18 C night temperature. At the four leaf stage, two treatments were applied. In the optimal treatment plants were watered to saturation and pots were covered with plastic bags to prevent any water loss from the pots due to evaporation. These plants were weighed daily for 7 days to determine the water loss from the pots due to transpiration and the same amount of water was added back daily to each pot to maintain the plants under optimal water conditions. In the drought treatment all plants were watered to saturation levels. Pots were covered with plastic and were weighed daily. However, these pots were watered daily to the level of the heaviest pots. This treatment went for 7 days with the soil water content gradually reaching stress levels. Plants started to wilt by day 5. At the end of the 7 days both groups of plants were harvested for shoot biomass determinations.

Gas exchange measurements were done on drought treated plants of two transgenic lines plus their nulls on days 3 and 4 of the treatment. Photosynthesis and transpiration were measured on leaf 3 under steady state growth conditions of 400 uE light, 400 ppm carbon dioxide and 22 C using Li-6400. From the ratio of photosynthesis to transpiration, water use efficiency (WUE) was calculated. The drought treated plants were used to calculate the drought tolerance (as percentage of their nulls). This was done using the ratio of cumulative daily transpirational water loss between days 3 and 7, relative to the final shoot dry weight and normalizing it to the nulls (set at 100%).

The results in Table 22 indicate that transgenic lines had strong trends toward greater drought tolerance. This was a result of lower water loss relative to shoot dry weight, a phenotype present also under optimal conditions.

The gas exchange data (Table 23) showed that on both days 3 and 4 of the drought treatment the transgenic plants had slightly higher WUE than controls (4 to 16%).

Water use efficiency calculated from the ratio of photosynthesis to transpiration provides only a single point, instantaneous measurement rather than cumulative measurement over the period of treatment and as a result may be of lesser magnitude.

In conclusion, the data with transgenic 35S-AtPK220L292F *Brassica* plants indicate that water use efficiency technology is transferable to *Brassica* when using a AtPK220L292F gene from a heterologous species.

TABLE 22

| Water loss between days 3 and 7 relative to final shoot dry weight under optimal and drought treatment. Drought tolerance (% of the appropriate null), n = 8 | | | |
|---|---|---|---|
| entry | optimal-g water lost d3-7/g shootDW d7 | drought-g water lost d3-7/g shootDW d7 | Drought tolerance (% of null) |
| Tr-05 | 172 ± 6 | 121 ± 5 | 109% |
| Null-05 | 190 ± 4 | 133 ± 7 | 100% |
| Tr-27 | 194 ± 6 | 134 ± 7 | 113% |
| Null-27 | 205 ± 8 | 155 ± 11 | 100% |
| Tr-09 | 171 ± 10 | 129 ± 3 | 113% |
| Null-09 | 178 ± 17 | 149 ± 13 | 100% |

TABLE 23

| Photosynthesis (umol carbon dioxide/m2/s), Transpiration (mmol H2O/m2/s) and WUE (Photos/Trans) on days 3 and 4 of drought treatment. n = 8 | | | | | | |
|---|---|---|---|---|---|---|
| entry | Photos D3 | Trans. D3 | WUE D3 | Photos. D4 | Trans. D4 | WUE D4 |
| Tr-05 | 13.4 ± 1.2 | 2.1 ± 0.2 | 6.6 ± 0.2 (116% of null) | 11.6 ± 1.3 | 1.9 ± 0.2 (104% of null) | 6.1 ± 0.4 |
| Null-05 | 14.4 ± 1.1 | 2.5 ± 0.2 | 5.7 ± 0.2 | 12.6 ± 1.2 | 2.2 ± 0.2 | 5.9 ± 0.3 |
| Tr-27 | 14.1 ± 0.7 | 2.4 ± 0.2 | 5.9 ± 0.3 (105% of null) | 11.4 ± 1.6 | 1.9 ± 0.3 (108% of null) | 6.2 ± 0.5 |
| Null-27 | 14.1 ± 1.3 | 2.5 ± 0.1 | 5.6 ± 0.5 | 13.7 ± 1.0 | 2.4 ± 0.1 | 5.7 ± 0.4 |

| SEQUENCE ID REFERENCE CHART | | | | |
|---|---|---|---|---|
| SPECIES | SEQ ID NO: | REFERENCE | | |
| *ARABIDOPSIS THALIANA* | SEQ ID NO: 1 | AtPK220 | NT | 1299 |
| *ARABIDOPSIS THALIANA* | SEQ ID NO: 2 | AtPK220 | AA | 432 |
| *ARABIDOPSIS THALIANA* | SEQ ID NO: 3 | AtPK220L292F | NT | 1299 |

-continued

| SEQUENCE ID REFERENCE CHART | | | | |
|---|---|---|---|---|
| SPECIES | SEQ ID NO: | REFERENCE | | |
| *ARABIDOPSIS THALIANA* | SEQ ID NO: 4 | AtPK220L292F | AA | 432 |
| *ARABIDOPSIS THALIANA* | SEQ ID NO: 5 | AtPK220L292F_partial | NT | 1160 |
| *ARABIDOPSIS THALIANA* | SEQ ID NO: 6 | AtPK220L292F_partial_orf | AA | 383 |
| *ARABIDOPSIS THALIANA* | SEQ ID NO: 7 | AtPK220_partial | NT | 1160 |
| *ARABIDOPSIS THALIANA* | SEQ ID NO: 8 | AtPK220_partial_orf | AA | 383 |
| *ARABIDOPSIS THALIANA* | SEQ ID NO: 9 | AtPK220_with_UTR | NT | 1542 |
| *ARABIDOPSIS THALIANA* | SEQ ID NO: 10 | AtPK220_for_35s-AtPK220 | NT | 1309 |
| *ARABIDOPSIS THALIANA* | SEQ ID NO: 11 | AtPK220_partial | NT | 1177 |
| *ARABIDOPSIS THALIANA* | SEQ ID NO: 12 | At(150)PK | NT | 154 |
| *ARABIDOPSIS THALIANA* | SEQ ID NO: 13 | At(270)PK | NT | 288 |
| *ARABIDOPSIS THALIANA* | SEQ ID NO: 14 | AtPK220_promoter | NT | 1510 |
| *ARABIDOPSIS THALIANA* | SEQ ID NO: 15 | At4g32000_UTR | NT | 157 |
| *ARABIDOPSIS THALIANA* | SEQ ID NO: 16 | At4g32000 | NT | 1257 |
| *ARABIDOPSIS THALIANA* | SEQ ID NO: 17 | At4g32000 | AA | 418 |
| *ARABIDOPSIS THALIANA* | SEQ ID NO: 18 | At5g11020 | NT | 1302 |
| *ARABIDOPSIS THALIANA* | SEQ ID NO: 19 | At5g11020 | AA | 433 |
| *ARABIDOPSIS THALIANA* | SEQ ID NO: 20 | At2g25440 | NT | 2016 |
| *ARABIDOPSIS THALIANA* | SEQ ID NO: 21 | At2g25440 | AA | 671 |
| *ARABIDOPSIS THALIANA* | SEQ ID NO: 22 | At2g23890 | NT | 1662 |
| *ARABIDOPSIS THALIANA* | SEQ ID NO: 23 | At2g23890 | AA | 553 |
| *BRACHYPODIUM DISTACHYON* | SEQ ID NO: 24 | BdPK220 | NT | 1386 |
| *BRASSICA NAPUS* | SEQ ID NO: 25 | BnPK220 | NT | 1302 |
| *BRASSICA NAPUS* | SEQ ID NO: 26 | BnPK220 | AA | 433 |
| *CICHORIUM ENDIVIA* | SEQ ID NO: 27 | EL362007.1 | NT | 657 |
| *CICHORIUM ENDIVIA* | SEQ ID NO: 28 | EL362007.1_ORF | AA | 218 |
| *CITRUS CLEMENTINA* | SEQ ID NO: 29 | CX290402.1 | NT | 474 |
| *CITRUS CLEMENTINA* | SEQ ID NO: 30 | CX290402.1_ORF | AA | 157 |
| *CITRUS SINENSIS* | SEQ ID NO: 31 | CK934154.1 | NT | 770 |
| *CITRUS SINENSIS* | SEQ ID NO: 32 | CK934154.1_ORF | AA | 257 |
| *COFFEA CANEPHORA* | SEQ ID NO: 33 | DV708241.1 | NT | 621 |
| *COFFEA CANEPHORA* | SEQ ID NO: 34 | DV708241.1_ORF | AA | 206 |
| *EUCALYPTUS GUNNII* | SEQ ID NO: 35 | CT986101.1 | NT | 411 |
| *EUCALYPTUS GUNNII* | SEQ ID NO: 36 | CT986101.1_ORF | AA | 136 |
| *FESTUCA ARUNDINACEA* | SEQ ID NO: 37 | DT714073 | NT | 522 |
| *FESTUCA ARUNDINACEA* | SEQ ID NO: 38 | DT714073_ORF | AA | 173 |
| *GINKGO BILOBA* | SEQ ID NO: 39 | EX942240.1 | NT | 740 |
| *GINKGO BILOBA* | SEQ ID NO: 40 | EX942240.1_ORF | AA | 247 |
| *GLYCINE MAX* | SEQ ID NO: 41 | GmPK220 | NT | 1254 |

-continued

SEQUENCE ID REFERENCE CHART

| SPECIES | SEQ ID NO: | REFERENCE | | |
|---|---|---|---|---|
| *GLYCINE MAX* | SEQ ID NO: 42 | GmPK220 | AA | 418 |
| *HELIANTHUS ARGOPHYLLUS* | SEQ ID NO: 43 | EE622910.1 | NT | 702 |
| *HELIANTHUS ARGOPHYLLUS* | SEQ ID NO: 44 | EE622910.1_ORF | AA | 233 |
| *HELIANTHUS CILIARIS* | SEQ ID NO: 45 | EL429543.1 | NT | 752 |
| *HELIANTHUS CILIARIS* | SEQ ID NO: 46 | EL429543.1_ORF | AA | 251 |
| *HELIANTHUS EXILIS* | SEQ ID NO: 47 | EE654885.1 | NT | 630 |
| *HELIANTHUS EXILIS* | SEQ ID NO: 48 | EE654885.1_ORF | AA | 209 |
| *HORDEUM VULGARE* | SEQ ID NO: 49 | TC151622 | NT | 780 |
| *HORDEUM VULGARE* | SEQ ID NO: 50 | TC151622_ORF | AA | 259 |
| *IPOMOEA BATATAS* | SEQ ID NO: 51 | EE883089.1 | NT | 816 |
| *IPOMOEA BATATAS* | SEQ ID NO: 52 | EE883089.1_ORF | AA | 272 |
| *LACTUCA SATIVA* | SEQ ID NO: 53 | DW125133.1 | NT | 867 |
| *LACTUCA SATIVA* | SEQ ID NO: 54 | DW125133.1_ORF | AA | 288 |
| *MEDICAGO TRUNCATULA* | SEQ ID NO: 55 | Contig | NT | 804 |
| *MEDICAGO TRUNCATULA* | SEQ ID NO: 56 | Contig | AA | 267 |
| *NICOTIANA TABACUM* | SEQ ID NO: 57 | BP131484.1 | NT | 636 |
| *NICOTIANA TABACUM* | SEQ ID NO: 58 | BP131484.1 | AA | 211 |
| *ORYZA SATIVA* | SEQ ID NO: 59 | NM_001061720.1 | NT | 1437 |
| *ORYZA SATIVA* | SEQ ID NO: 60 | NP_001055185.1 | AA | 478 |
| *PHYSCOMITRELLA* | SEQ ID NO: 61 | EDQ75046.1_cds | NT | 891 |
| *PHYSCOMITRELLA* | SEQ ID NO: 62 | EDQ75046.1 | AA | 297 |
| *PICEA* | SEQ ID NO: 63 | TC12392 | NT | 1065 |
| *PICEA* | SEQ ID NO: 64 | TC12392_orf | AA | 354 |
| *PINUS* | SEQ ID NO: 65 | CT578985.1 | NT | 596 |
| *PINUS* | SEQ ID NO: 66 | CT578985.1_ORF | AA | 199 |
| *POPULUS* | SEQ ID NO: 67 | TC76879 | NT | 1377 |
| *POPULUS* | SEQ ID NO: 68 | TC76879_ORF | AA | 459 |
| *SACCHARUM OFFICINARUM* | SEQ ID NO: 69 | TC46535 | NT | 693 |
| *SACCHARUM OFFICINARUM* | SEQ ID NO: 70 | TC46535_ORF | AA | 230 |
| *TRIPHYSARIA VERSICOLOR* | SEQ ID NO: 71 | DR169688.1 | NT | 414 |
| *TRIPHYSARIA VERSICOLOR* | SEQ ID NO: 72 | DR169688.1_ORF | AA | 137 |
| *TRITICUM AESTIVUM* | SEQ ID NO: 73 | TC254793 | NT | 1140 |
| *TRITICUM AESTIVUM* | SEQ ID NO: 74 | TC254793_ORF | AA | 380 |
| *VITIS VINIFERA* | SEQ ID NO: 75 | CAO44295.1_cds | NT | 978 |
| *VITIS VINIFERA* | SEQ ID NO: 76 | CAO44295.1 | AA | 325 |
| *ZEA MAYS* | SEQ ID NO: 77 | TC333547 | NT | 1377 |
| *ZEA MAYS* | SEQ ID NO: 78 | TC333547_ORF | AA | 458 |

-continued

SEQUENCE ID REFERENCE CHART

| SPECIES | SEQ ID NO: | REFERENCE | | |
|---|---|---|---|---|
| *ZEA MAYS* | SEQ ID NO: 79 | ZmPK220 | NT | 1188 |
| *ZEA MAYS* | SEQ ID NO: 80 | ZmPK220 | AA | 396 |
| *GOSSYPIUM* | SEQ ID NO: 81 | TC79117 | NT | 1086 |
| *GOSSYPIUM* | SEQ ID NO: 82 | TC79117_ORF | AA | 361 |
| *SOLANUM LYCOPERSICUM* | SEQ ID NO: 83 | Contig3 | NT | 1089 |
| *AQUILEGIA* | SEQ ID NO: 84 | DR918821 | NT | 875 |
| *AQUILEGIA* | SEQ ID NO: 85 | DR918821_ORF | AA | 292 |
| *CENTAUREA MACULOSA* | SEQ ID NO: 86 | EL933228.1 | NT | 696 |
| CENTAUREA MACULOSA | SEQ ID NO: 87 | EL933228.1_ORF | AA | 231 |
| *CICHORIUM INTYBUS* | SEQ ID NO: 88 | EH693146.1 | NT | 842 |
| *CICHORIUM INTYBUS* | SEQ ID NO: 89 | EH693146.1_ORF | AA | 281 |
| *CUCUMIS MELO* | SEQ ID NO: 90 | AM742189.1 | NT | 495 |
| *CUCUMIS MELO* | SEQ ID NO: 91 | AM742189.1_ORF | AA | 164 |
| *ERAGROSTIS CURVULA* | SEQ ID NO: 92 | EH186232.1 | NT | 375 |
| *ERAGROSTIS CURVULA* | SEQ ID NO: 93 | EH186232.1_ORF | AA | 124 |
| *GERBERA HYBRID* | SEQ ID NO: 94 | AJ753651.1 | NT | 414 |
| *GERBERA HYBRID* | SEQ ID NO: 95 | AJ753651.1_ORF | AA | 137 |
| *HELIANTHUS PARADOXUS* | SEQ ID NO: 96 | EL488199.1 | NT | 498 |
| *HELIANTHUS PARADOXUS* | SEQ ID NO: 97 | EL488199.1_ORF | AA | 165 |
| *IPOMOEA NIL* | SEQ ID NO: 98 | BJ566706.1 | NT | 612 |
| *IPOMOEA NIL* | SEQ ID NO: 99 | BJ566706.1_ORF | AA | 203 |
| *NUPHAR ADVENA* | SEQ ID NO: 100 | DT603238.1 | NT | 708 |
| *NUPHAR ADVENA* | SEQ ID NO: 101 | DT603238.1_ORF | AA | 235 |
| SYNTHETIC PRIMER | SEQ ID NO: 102 | 747F | NT | 30 |
| SYNTHETIC PRIMER | SEQ ID NO: 103 | 747R | NT | 34 |
| SYNTHETIC PRIMER | SEQ ID NO: 104 | C747F2 | NT | 32 |
| SYNTHETIC PRIMER | SEQ ID NO: 105 | C747R2 | NT | 31 |
| SYNTHETIC PRIMER | SEQ ID NO: 106 | A220BamF1 | NT | 42 |
| SYNTHETIC PRIMER | SEQ ID NO: 107 | A220PstR | NT | 40 |
| SYNTHETIC PRIMER | SEQ ID NO: 108 | K188R | NT | 30 |
| SYNTHETIC PRIMER | SEQ ID NO: 109 | A220A1SmaF2 | NT | 53 |
| SYNTHETIC PRIMER | SEQ ID NO: 110 | A220BamR | NT | 38 |
| SYNTHETIC PRIMER | SEQ ID NO: 111 | A220SmaF | NT | 41 |
| SYNTHETIC PRIMER | SEQ ID NO: 112 | A220BamF2 | NT | 41 |
| SYNTHETIC PRIMER | SEQ ID NO: 113 | A220XbaR | NT | 39 |
| SYNTHETIC PRIMER | SEQ ID NO: 114 | K116SacF | NT | 35 |
| SYNTHETIC PRIMER | SEQ ID NO: 115 | K270SacR | NT | 37 |
| SYNTHETIC PRIMER | SEQ ID NO: 116 | K116BamF | NT | 37 |

-continued

| SEQUENCE ID REFERENCE CHART | | | | |
|---|---|---|---|---|
| SPECIES | SEQ ID NO: | REFERENCE | | |
| SYNTHETIC PRIMER | SEQ ID NO: 117 | K270XbaR | NT | 40 |
| SYNTHETIC PRIMER | SEQ ID NO: 118 | PK81A1XbaF | NT | 52 |
| SYNTHETIC PRIMER | SEQ ID NO: 119 | K81PmBamF | NT | 47 |
| SYNTHETIC PRIMER | SEQ ID NO: 120 | Pm81SmaR2 | NT | 41 |
| *ARABIDOPSIS THALIANA* | SEQ ID NO: 121 | AtPK220L292F_with_UTR | NT | 1309 |
| SYNTHETIC PRIMER | SEQ ID NO: 122 | Bn81F | NT | 25 |
| SYNTHETIC PRIMER | SEQ ID NO: 123 | Bn81R | NT | 32 |
| SYNTHETIC PRIMER | SEQ ID NO: 124 | Bn81RAF1 | NT | 32 |
| SYNTHETIC PRIMER | SEQ ID NO: 125 | Bn81RAF2 | NT | 32 |
| SYNTHETIC PRIMER | SEQ ID NO: 126 | Bn81RAR1 | NT | 31 |
| SYNTHETIC PRIMER | SEQ ID NO: 127 | Bn81RAR2 | NT | 37 |
| SYNTHETIC PRIMER | SEQ ID NO: 128 | Bn81F1 | NT | 28 |
| SYNTHETIC PRIMER | SEQ ID NO: 129 | Bn81R1 | NT | 27 |
| SYNTHETIC PRIMER | SEQ ID NO: 130 | Gm81RAR1 | NT | 27 |
| SYNTHETIC PRIMER | SEQ ID NO: 131 | Gm81RAR2 | NT | 29 |
| SYNTHETIC PRIMER | SEQ ID NO: 132 | Cn81RAR1 | NT | 29 |
| SYNTHETIC PRIMER | SEQ ID NO: 133 | Cn81RAR2 | NT | 28 |
| SYNTHETIC PRIMER | SEQ ID NO: 134 | A220SacF | NT | 41 |
| SYNTHETIC PRIMER | SEQ ID NO: 135 | Pm81NheF | NT | 47 |
| SYNTHETIC PRIMER | SEQ ID NO: 136 | Pm81NheR | NT | 43 |
| SYNTHETIC PRIMER | SEQ ID NO: 137 | Gm81RAF1 | NT | 29 |
| SYNTHETIC PRIMER | SEQ ID NO: 138 | Gm81RAF2 | NT | 31 |
| SYNTHETIC PRIMER | SEQ ID NO: 139 | Zm81RAF1 | NT | 31 |
| SYNTHETIC PRIMER | SEQ ID NO: 140 | Zm81RAF2 | NT | 27 |
| SYNTHETIC PRIMER | SEQ ID NO: 141 | MiR319XbaF | NT | 31 |
| SYNTHETIC PRIMER | SEQ ID NO: 142 | MiR319BamR | NT | 33 |
| SYNTHETIC PRIMER | SEQ ID NO: 143 | MiPK220F1 | NT | 40 |
| SYNTHETIC PRIMER | SEQ ID NO: 144 | MiPK220R1 | NT | 35 |
| SYNTHETIC PRIMER | SEQ ID NO: 145 | MiPK220F2 | NT | 35 |
| SYNTHETIC PRIMER | SEQ ID NO: 146 | MiPK220R2 | NT | 42 |
| ARTIFICIAL SEQUENCE | SEQ ID NO: 147 | Synthesized_gene_fragment | NT | 21 |
| *ARABIDOPSIS THALIANA* | SEQ ID NO: 148 | At4g23713_w_genomic | NT | 399 |
| ARTIFICIAL SEQUENCE | SEQ ID NO: 149 | Artificial_micro_RNA_construct | NT | 399 |
| *ARABIDOPSIS THALIANA* | SEQ ID NO: 150 | Promoter At2g44790 | NT | 1475 |
| SYNTHETIC PRIMER | SEQ ID NO: 151 | P790-H3-F | NT | 31 |
| SYNTHETIC PRIMER | SEQ ID NO: 152 | P790-Xb-R | NT | 31 |
| *BRASSICA NAPUS* | SEQ ID NO: 153 | BnPK220 | NT | 338 |

-continued

SEQUENCE ID REFERENCE CHART

| SPECIES | SEQ ID NO: | REFERENCE | | |
|---|---|---|---|---|
| SYNTHETIC PRIMER | SEQ ID NO: 154 | Bn340BamF | NT | 38 |
| SYNTHETIC PRIMER | SEQ ID NO: 155 | Bn340XbaR | NT | 37 |
| SYNTHETIC PRIMER | SEQ ID NO: 156 | Bn340SacF | NT | 38 |
| SYNTHETIC PRIMER | SEQ ID NO: 157 | Bn340SacR | NT | 37 |
| SYNTHETIC PRIMER | SEQ ID NO: 158 | bVVET XbaI F | NT | 24 |
| SYNTHETIC PRIMER | SEQ ID NO: 159 | bVVET BamHI R | NT | 28 |
| SYNTHETIC PRIMER | SEQ ID NO: 160 | bVVET ClaI R | NT | 28 |
| *BRACHYPODIUM DISTACHYON* | SEQ ID NO: 161 | BdPK220 | NT | 272 |
| SYNTHETIC PRIMER | SEQ ID NO: 162 | bWx BamHI F | NT | 31 |
| SYNTHETIC PRIMER | SEQ ID NO: 163 | bWx ClaI R | NT | 30 |
| *BRACHYPODIUM DISTACHYON* | SEQ ID NO: 164 | BdWx intron 1 | NT | 1174 |
| SYNTHETIC PRIMER | SEQ ID NO: 165 | bWET BamHI end2 | NT | 22 |
| SYNTHETIC PRIMER | SEQ ID NO: 166 | BdUBQ PvuI F | NT | 30 |
| SYNTHETIC PRIMER | SEQ ID NO: 167 | BdUBQT PacI R | NT | 28 |
| *PANICUM VIRGATUM* | SEQ ID NO: 168 | Pv(251)PK220 | NT | 251 |
| SYNTHETIC PRIMER | SEQ ID NO: 169 | PvWET XbaI F | NT | 27 |
| SYNTHETIC PRIMER | SEQ ID NO: 170 | PvWET BamHI R | NT | 27 |
| SYNTHETIC PRIMER | SEQ ID NO: 171 | PvWET ClaI R | NT | 27 |
| SYNTHETIC PRIMER | SEQ ID NO: 172 | PvWET BamHI end1 | NT | 25 |
| SYNTHETIC PRIMER | SEQ ID NO: 173 | PvWET BamHI end2 | NT | 21 |
| SORGHUN BICOLOR | SEQ ID NO: 174 | Sb(261)PK220 | NT | 261 |
| SYNTHETIC PRIMER | SEQ ID NO: 175 | SbWET XbaI F | NT | 26 |
| SYNTHETIC PRIMER | SEQ ID NO: 176 | SbWET BamHI R | NT | 28 |
| SYNTHETIC PRIMER | SEQ ID NO: 177 | SbWET ClaI R | NT | 28 |
| SORGHUN BICOLOR | SEQ ID NO: 178 | SbWx intron 1 | NT | 273 |
| SYNTHETIC PRIMER | SEQ ID NO: 179 | SbWx BamHI | NT | 30 |
| SYNTHETIC PRIMER | SEQ ID NO: 180 | SbWx ClaI R | NT | 34 |
| SYNTHETIC PRIMER | SEQ ID NO: 181 | SbWET BamHI end1 | NT | 24 |
| SYNTHETIC PRIMER | SEQ ID NO: 182 | SbWET BamHI end2 | NT | 21 |
| SORGHUN BICOLOR | SEQ ID NO: 183 | SbGOS2 promoter | NT | 1000 |
| SYNTHETIC PRIMER | SEQ ID NO: 184 | SbGOS2 HindIII F | NT | 28 |
| SYNTHETIC PRIMER | SEQ ID NO: 185 | SbGOS2 HindIII R | NT | 30 |
| SORGHUN BICOLOR | SEQ ID NO: 186 | SbUBQ promoter | NT | 1000 |
| SYNTHETIC PRIMER | SEQ ID NO: 187 | SbUBQ PstI F | NT | 26 |
| SYNTHETIC PRIMER | SEQ ID NO: 188 | SbUBQ PstI R | NT | 28 |
| SORGHUN BICOLOR | SEQ ID NO: 189 | SbUBQ terminator | NT | 239 |
| SYNTHETIC PRIMER | SEQ ID NO: 190 | SbUBQT KpnI F | NT | 27 |
| SYNTHETIC PRIMER | SEQ ID NO: 191 | SbUBQT KpnI R | NT | 27 |

-continued

SEQUENCE ID REFERENCE CHART

| SPECIES | SEQ ID NO: | REFERENCE | | |
|---|---|---|---|---|
| SYNTHETIC PRIMER | SEQ ID NO: 192 | SbUBQ PvuI F | NT | 34 |
| *BRASSICA NAPUS* | SEQ ID NO: 193 | BnPK220 | NT | 1302 |
| *BRASSICA NAPUS* | SEQ ID NO: 194 | BnPK220 | AA | 433 |
| SYNTHETIC PRIMER | SEQ ID NO: 195 | Bd81RAR1 | NT | 31 |
| SYNTHETIC PRIMER | SEQ ID NO: 196 | Bd81RAR2 | NT | 32 |
| *BRACHYPODIUM DISTACHYON* | SEQ ID NO: 197 | BdPK220 | AA | 461 |
| SYNTHETIC PRIMER | SEQ ID NO: 198 | A200A1AgeF | NT | 53 |
| SYNTHETIC PRIMER | SEQ ID NO: 199 | A220AgeR | NT | 39 |
| SYNTHETIC PRIMER | SEQ ID NO: 200 | bWET BamHI end1 | NT | 18 |

Sequences

>SEQ ID NO: 1
ATGAGAGAGCTTCTTCTTCTTCTTCTTCTTCATTTTCAGTCTCTAATTCTTTTGATGATCTTCATCACTGTCTCTGCTTCTTCTGCTTCA
AATCCTTCTTTAGCTCCTGTTTACTCTTCCATGGCTACATTCTCTCCTCGAATCCAAATGGGAAGTGGTGAAGAAGATAGATTTGATGCT
CATAAGAAACTTCTGATTGGTCTCATAATCAGTTTCTCTTCTCTTGGCCTTATAATCTTGTTCTGTTTTGGCTTTTGGGTTTATCGCAAG
AACCAATCTCCAAAATCCATCAACAACTCAGATTCTGAGAGTGGGAATTCATTTTCCTTGTTAATGAGACGACTTGGCTCGATTAAAACT
CAGAGAAGAACTTCTATCCAAAAGGGTTACGTGCAATTTTTCGATATCAAGACCCTCGAGAAAGCGACAGGCGGTTTTAAAGAAAGTAGT
GTAATCGGACAAGGCGGTTTCGGATGCGTTTACAAGGGTTGTTTGGACAATAACGTTAAAGCAGCGGTCAAGAAGATCGAGAACGTTAGC
CAAGAAGCAAAACGAGAATTTCAGAATGAAGTTGACTTGTTGAGCAAGATCCATCACTCGAACGTTATATCATTGTTGGGCTCTGCAAGC
GAAATCAACTCGAGTTTCATCGTTTATGAGCTTATGGAGAAAGGATCATTAGATGAACAGTTACATGGGCCTTCTCGTGGATCAGCTCTA
ACATGGCACATGCGTATGAAGATTGCTCTTGATACAGCTAGAGGACTAGAGTATCTCCATGAGCATTGTCGTCCACCAGTTATCCACAGA
GATTTGAAATCTTCGAATATTCTTCTTGATTCTTCCTTCAACGCCAAGATTTCAGATTTCGGTCTTGCTGTATCGCTGGATGAACATGGC
AAGAACAACATTAAACTCTCTGGGACACTTGGTTATGTTGCCCCGGAATACCTCCTTGACGGAAAACTGACGGATAAGAGTGATGTTTAT
GCATTTGGGGTAGTTCTGCTTGAACTCTTGTTGGGTAGACGACCAGTTGAAAAATTAACTCCAGCTCAATGCCAATCTCTTGTAACTTGG
GCAATGCCACAACTTACCGATAGATCCAAGCTTCCAAACATTGTGGATGCCGTTATAAAAGATACAATGGATCTCAAACACTTATACCAG
GTAGCAGCCATGGCTGTGTTGTGCGTGCAGCCAGAACCAAGTTACCGGCCGTTGATAACCGATGTTCTTCACTCACTTGTTCCACTGGTT
CCGGTAGAGCTAGGAGGGACTCTCCGGTTAACAAGATGA

>SEQ ID NO: 2
MRELLLLLLLLHFQSLILLMIFITVSASSASNPSLAPVYSSMATFSPRIQMGSGEEDRFDAHKKLLIGLIISFSSLGLIILFCFGFWVYRK
NQSPKSINNSDSESGNSFSLLMRRLGSIKTQRRTSIQKGYVQFFDIKTLEKATGGFKESSVIGQGGFGCVYKGCLDNNVKAAVKKIENVS
QEAKREFQNEVDLLSKIHHSNVISLLGSASEINSSFIVYELMEKGSLDEQLHGPSRGSALTWHMRMKIALDTARGLEYLHEHCRPPVIHR
DLKSSNILLDSSFNAKISDFGLAVSLDEHGKNNIKLSGTLGYVAPEYLLDGKLTDKSDVYAFGVVLLELLLGRRPVEKLTPAQCQSLVTW
AMPQLTDRSKLPNIVDAVIKDTMDLKHLYQVAAMAVLCVQPEPSYRPLITDVLHSLVPLVPVELGGTLRLTR

>SEQ ID NO: 3
ATGAGAGAGCTTCTTCTTCTTCTTCTTCTTCATTTTCAGTCTCTAATTCTTTTGATGATCTTCATCACTGTCTCTGCTTCTTCTGCTTCA
AATCCTTCTTTAGCTCCTGTTTACTCTTCCATGGCTACATTCTCTCCTCGAATCCAAATGGGAAGTGGTGAAGAAGATAGATTTGATGCT
CATAAGAAACTTCTGATTGGTCTCATAATCAGTTTCTCTTCTCTTGGCCTTATAATCTTGTTCTGTTTTGGCTTTTGGGTTTATCGCAAG
AACCAATCTCCAAAATCCATCAACAACTCAGATTCTGAGAGTGGGAATTCATTTTCCTTGTTAATGAGACGACTTGGCTCGATTAAAACT
CAGAGAAGAACTTCTATCCAAAAGGGTTACGTGCAATTTTTCGATATCAAGACCCTCGAGAAAGCGACAGGCGGTTTTAAAGAAAGTAGT
GTAATCGGACAAGGCGGTTTCGGATGCGTTTACAAGGGTTGTTTGGACAATAACGTTAAAGCAGCGGTCAAGAAGATCGAGAACGTTAGC
CAAGAAGCAAAACGAGAATTTCAGAATGAAGTTGACTTGTTGAGCAAGATCCATCACTCGAACGTTATATCATTGTTGGGCTCTGCAAGC
GAAATCAACTCGAGTTTCATCGTTTATGAGCTTATGGAGAAAGGATCATTAGATGAACAGTTACATGGGCCTTCTCGTGGATCAGCTCTA
ACATGGCACATGCGTATGAAGATTGCTCTTGATACAGCTAGAGGACTAGAGTATCTCCATGAGCATTGTCGTCCACCAGTTATCCACAGA
GATTTGAAATCTTCGAATATTCTTCTTGATTCTTCCTTCAACGCCAAGATTTCAGATTTCGGTTTTGCTGTATCGCTGGATGAACATGGC
AAGAACAACATTAAACTCTCTGGGACACTTGGTTATGTTGCCCCGGAATACCTCCTTGACGGAAAACTGACGGATAAGAGTGATGTTTAT
GCATTTGGGGTAGTTCTGCTTGAACTCTTGTTGGGTAGACGACCAGTTGAAAAATTAACTCCAGCTCAATGCCAATCTCTTGTAACTTGG
GCAATGCCACAACTTACCGATAGATCCAAGCTTCCAAACATTGTGGATGCCGTTATAAAAGATACAATGGATCTCAAACACTTATACCAG
GTAGCAGCCATGGCTGTGTTGTGCGTGCAGCCAGAACCAAGTTACCGGCCGTTGATAACCGATGTTCTTCACTCACTTGTTCCACTGGTT
CCGGTAGAGCTAGGAGGGACTCTCCGGTTAACAAGATGA

>SEQ ID NO: 4
MRELLLLLLLLHFQSLILLMIFITVSASSASNPSLAPVYSSMATFSPRIQMGSGEEDRFDAHKKLLIGLIISFSSLGLIILFCFGFWVYRK
NQSPKSINNSDSESGNSFSLLMRRLGSIKTQRRTSIQKGYVQFFDIKTLEKATGGFKESSVIGQGGFGCVYKGCLDNNVKAAVKKIENVS
QEAKREFQNEVDLLSKIHHSNVISLLGSASEINSSFIVYELMEKGSLDEQLHGPSRGSALTWHMRMKIALDTARGLEYLHEHCRPPVIHR
DLKSSNILLDSSFNAKISDFGFAVSLDEHGKNNIKLSGTLGYVAPEYLLDGKLTDKSDVYAFGVVLLELLLGRRPVEKLTPAQCQSLVTW
AMPQLTDRSKLPNIVDAVIKDTMDLKHLYQVAAMAVLCVQPEPSYRPLITDVLHSLVPLVPVELGGTLRLTR

>SEQ ID NO: 5
ATGGGAAGTGGTGAAGAAGATAGATTTGATGCTCATAAGAAACTTCTGATTGGTCTCATAATCAGTTTCTCTTCTCTTGGCCTTATAATC
TTGTTCTGTTTTGGCTTTTGGGTTTATCGCAAGAACCAATCTCCAAAATCCATCAACAACTCAGATTCTGAGAGTGGGAATTCATTTTCC

Sequences

TTGTTAATGAGACGACTTGGCTCGATTAAAACTCAGAGAAGAACTTCTATCCAAAAGGGTTACGTGCAATTTTTCGATATCAAGACCCTC
GAGAAAGCGACAGGCGGTTTTAAAGAAAGTAGTGTAATCGGACAAGGCGGTTTCGGATGCGTTTACAAGGGTTGTTTGGACAATAACGTT
AAAGCAGCGGTCAAGAAGATCGAGAACGTTAGCCAAGAAGCAAAACGAGAATTTCAGAATGAAGTTGACTTGTTGAGCAAGATCCATCAC
TCGAACGTTATATCATTGTTGGGCTCTGCAAGCGAAATCAACTCGAGTTTCATCGTTTATGAGCTTATGGAGAAAGGATCATTAGATGAA
CAGTTACATGGGCCTTCTCGTGGATCAGCTCTAACATGGCACATGCGTATGAAGATTGCTCTTGATACAGCTAGAGGACTAGAGTATCTC
CATGAGCATTGTCGTCCACCAGTTATCCACAGAGATTTGAAATCTTCGAATATTCTTCTTGATTCTTCCTTCAACGCCAAGATTTCAGAT
TTCGGTTTTGCTGTATCGCTGGATGAACATGGCAAGAACAACATTAAACTCTCTGGGACACTTGGTTATGTTGCCCCGGAATACCTCCTT
GACGGAAAACTGACGGATAAGAGTGATGTTTATGCATTTGGGGTAGTTCTGCTTGAACTCTTGTTGGGTAGACGACCAGTTGAAAAATTA
ACTCCAGCTCAATGCCAATCTCTTGTAACTTGGGCAATGCCACAACTTACCGATAGATCCAAGCTTCCAAACATTGTGGATGCCGTTATA
AAAGATACAATGGATCTCAAACACTTATACCAGGTAGCAGCCATGGCTGTGTTGTGCGTGCAGCCAGAACCAAGTTACCGGCCGTTGATA
ACCGATGTTCTTCACTCACTTGTTCCACTGGTTCCGGTAGAGCTAGGAGGGACTCTCCGGTTAACAAGATGATTCACAGA

>SEQ ID NO: 6
MGSGEEDRFDAHKKLLIGLIISFSSLGLIIILFCFGFWVYRKNQSPKSINNSDSESGNSFSLLMRRLGSIKTQRRTSIQKGYVQFFDIKTL
EKATGGFKESSVIGQGGFGCVYKGCLDNNVKAAVKKIENVSQEAKREFQNEVDLLSKIHHSNVISLLGSASEINSSFIVYELMEKGSLDE
QLHGPSRGSALTWHMRMKIALDTARGLEYLHEHCRPPVIHRDLKSSNILLDSSFNAKISDFGFAVSLDEHGKNNIKLSGTLGYVAPEYLL
DGKLTDKSDVYAFGVVLLELLLGRRPVEKLTPAQCQSLVTWAMPQLTDRSKLPNIVDAVIKDTMDLKHLYQVAAMAVLCVQPEPSYRPLI
TDVLHSLVPLVPVELGGTLRLTR

>SEQ ID NO: 7
ATGGGAAGTGGTGAAGAAGATAGATTTGATGCTCATAAGAAACTTCTGATTGGTCTCATAATCAGTTTCTCTTCTCTTGGCCTTATAATC
TTGTTCTGTTTTGGCTTTTGGGTTTATCGCAAGAACCAATCTCCAAAATCCATCAACAACTCAGATTCTGAGAGTGGGAATTCATTTTCC
TTGTTAATGAGACGACTTGGCTCGATTAAAACTCAGAGAAGAACTTCTATCCAAAAGGGTTACGTGCAATTTTTCGATATCAAGACCCTC
GAGAAAGCGACAGGCGGTTTTAAAGAAAGTAGTGTAATCGGACAAGGCGGTTTCGGATGCGTTTACAAGGGTTGTTTGGACAATAACGTT
AAAGCAGCGGTCAAGAAGATCGAGAACGTTAGCCAAGAAGCAAAACGAGAATTTCAGAATGAAGTTGACTTGTTGAGCAAGATCCATCAC
TCGAACGTTATATCATTGTTGGGCTCTGCAAGCGAAATCAACTCGAGTTTCATCGTTTATGAGCTTATGGAGAAAGGATCATTAGATGAA
CAGTTACATGGGCCTTCTCGTGGATCAGCTCTAACATGGCACATGCGTATGAAGATTGCTCTTGATACAGCTAGAGGACTAGAGTATCTC
CATGAGCATTGTCGTCCACCAGTTATCCACAGAGATTTGAAATCTTCGAATATTCTTCTTGATTCTTCCTTCAACGCCAAGATTTCAGAT
TTCGGTCTTGCTGTATCGCTGGATGAACATGGCAAGAACAACATTAAACTCTCTGGGACACTTGGTTATGTTGCCCCGGAATACCTCCTT
GACGGAAAACTGACGGATAAGAGTGATGTTTATGCATTTGGGGTAGTTCTGCTTGAACTCTTGTTGGGTAGACGACCAGTTGAAAAATTA
ACTCCAGCTCAATGCCAATCTCTTGTAACTTGGGCAATGCCACAACTTACCGATAGATCCAAGCTTCCAAACATTGTGGATGCCGTTATA
AAAGATACAATGGATCTCAAACACTTATACCAGGTAGCAGCCATGGCTGTGTTGTGCGTGCAGCCAGAACCAAGTTACCGGCCGTTGATA
ACCGATGTTCTTCACTCACTTGTTCCACTGGTTCCGGTAGAGCTAGGAGGGACTCTCCGGTTAACAAGATGATTCACAGA

>SEQ ID NO: 8
MGSGEEDRFDAHKKLLIGLIISFSSLGLIIILFCFGFWVYRKNQSPKSINNSDSESGNSFSLLMRRLGSIKTQRRTSIQKGYVQFFDIKTL
EKATGGFKESSVIGQGGFGCVYKGCLDNNVKAAVKKIENVSQEAKREFQNEVDLLSKIHHSNVISLLGSASEINSSFIVYELMEKGSLDE
QLHGPSRGSALTWHMRMKIALDTARGLEYLHEHCRPPVIHRDLKSSNILLDSSFNAKISDFGLAVSLDEHGKNNIKLSGTLGYVAPEYLL
DGKLTDKSDVYAFGVVLLELLLGRRPVEKLTPAQCQSLVTWAMPQLTDRSKLPNIVDAVIKDTMDLKHLYQVAAMAVLCVQPEPSYRPLI
TDVLHSLVPLVPVELGGTLRLTR

>SEQ ID NO: 9
ATCAAAAACTTTTCTTTTCTTAGCAAAAAAAACAAAAAAATGAGAGAGCTTCTTCTTCTTCTTCTTCTTCATTTTCAGTCTCTAATTCTT
TTGATGATCTTCATCACTGTCTCTGCTTCTTCTGCTTCAAATCCTTCTTTAGCTCCTGTTTACTCTTCCATGGCTACATTCTCTCCTCGA
ATCCAAATGGGAAGTGGTGAAGAAGATAGATTTGATGCTCATAAGAAACTTCTGATTGGTCTCATAATCAGTTTCTCTTCTCTTGGCCTT
ATAATCTTGTTCTGTTTTGGCTTTTGGGTTTATCGCAAGAACCAATCTCCAAAATCCATCAACAACTCAGATTCTGAGAGTGGGAATTCA
TTTTCCTTGTTAATGAGACGACTTGGCTCGATTAAAACTCAGAGAAGAACTTCTATCCAAAAGGGTTACGTGCAATTTTTCGATATCAAG
ACCCTCGAGAAAGCGACAGGCGGTTTTAAAGAAAGTAGTGTAATCGGACAAGGCGGTTTCGGATGCGTTTACAAGGGTTGTTTGGACAAT
AACGTTAAAGCAGCGGTCAAGAAGATCGAGAACGTTAGCCAAGAAGCAAAACGAGAATTTCAGAATGAAGTTGACTTGTTGAGCAAGATC
CATCACTCGAACGTTATATCATTGTTGGGCTCTGCAAGCGAAATCAACTCGAGTTTCATCGTTTATGAGCTTATGGAGAAAGGATCATTA
GATGAACAGTTACATGGGCCTTCTCGTGGATCAGCTCTAACATGGCACATGCGTATGAAGATTGCTCTTGATACAGCTAGAGGACTAGAG
TATCTCCATGAGCATTGTCGTCCACCAGTTATCCACAGAGATTTGAAATCTTCGAATATTCTTCTTGATTCTTCCTTCAACGCCAAGATT
TCAGATTTCGGTCTTGCTGTATCGCTGGATGAACATGGCAAGAACAACATTAAACTCTCTGGGACACTTGGTTATGTTGCCCCGGAATAC
CTCCTTGACGGAAAACTGACGGATAAGAGTGATGTTTATGCATTTGGGGTAGTTCTGCTTGAACTCTTGTTGGGTAGACGACCAGTTGAA
AAATTAACTCCAGCTCAATGCCAATCTCTTGTAACTTGGGCAATGCCACAACTTACCGATAGATCCAAGCTTCCAAACATTGTGGATGCC
GTTATAAAAGATACAATGGATCTCAAACACTTATACCAGGTAGCAGCCATGGCTGTGTTGTGCGTGCAGCCAGAACCAAGTTACCGGCCG
TTGATAACCGATGTTCTTCACTCACTTGTTCCACTGGTTCCGGTAGAGCTAGGAGGGACTCTCCGGTTAACAAGATGATTCACAGAAACA
CGCCAAAAGAAATCCAAAGCCATTTAGATGATTTCTTTTATCCTTTGCCTTTATATTTTTTTGTATAGGGTTATGATCCACTCATCTGA
AAGTTTGGGGGTAAGAATGTGAGAATATAAGTTTTCAGGGTTGTTGAGTTCTATATAATTATATTTGTTTCTTTTTATTGTCAAATATAA
TTATATTTTTGT

>SEQ ID NO: 10
AAAATGAGAGAGCTTCTTCTTCTTCTTCTTCTTCATTTTCAGTCTCTAATTCTTTTGATGATCTTCATCACTGTCTCTGCTTCTTCTGCT
TCAAATCCTTCTTTAGCTCCTGTTTACTCTTCCATGGCTACATTCTCTCCTCGAATCCAAATGGGAAGTGGTGAAGAAGATAGATTTGAT
GCTCATAAGAAACTTCTGATTGGTCTCATAATCAGTTTCTCTTCTCTTGGCCTTATAATCTTGTTCTGTTTTGGCTTTTGGGTTTATCGC
AAGAACCAATCTCCAAAATCCATCAACAACTCAGATTCTGAGAGTGGGAATTCATTTTCCTTGTTAATGAGACGACTTGGCTCGATTAAA
ACTCAGAGAAGAACTTCTATCCAAAAGGGTTACGTGCAATTTTTCGATATCAAGACCCTCGAGAAAGCGACAGGCGGTTTTAAAGAAAGT
AGTGTAATCGGACAAGGCGGTTTCGGATGCGTTTACAAGGGTTGTTTGGACAATAACGTTAAAGCAGCGGTCAAGAAGATCGAGAACGTT
AGCCAAGAAGCAAAACGAGAATTTCAGAATGAAGTTGACTTGTTGAGCAAGATCCATCACTCGAACGTTATATCATTGTTGGGCTCTGCA
AGCGAAATCAACTCGAGTTTCATCGTTTATGAGCTTATGGAGAAAGGATCATTAGATGAACAGTTACATGGGCCTTCTCGTGGATCAGCT
CTAACATGGCACATGCGTATGAAGATTGCTCTTGATACAGCTAGAGGACTAGAGTATCTCCATGAGCATTGTCGTCCACCAGTTATCCAC
AGAGATTTGAAATCTTCGAATATTCTTCTTGATTCTTCCTTCAACGCCAAGATTTCAGATTTCGGTCTTGCTGTATCGCTGGATGAACAT
GGCAAGAACAACATTAAACTCTCTGGGACACTTGGTTATGTTGCCCCGGAATACCTCCTTGACGGAAAACTGACGGATAAGAGTGATGTT
TATGCATTTGGGGTAGTTCTGCTTGAACTCTTGTTGGGTAGACGACCAGTTGAAAAATTAACTCCAGCTCAATGCCAATCTCTTGTAACT
TGGGCAATGCCACAACTTACCGATAGATCCAAGCTTCCAAACATTGTGGATGCCGTTATAAAAGATACAATGGATCTCAAACACTTATAC
CAGGTAGCAGCCATGGCTGTGTTGTGCGTGCAGCCAGAACCAAGTTACCGGCCGTTGATAACCGATGTTCTTCACTCACTTGTTCCACTG
GTTCCGGTAGAGCTAGGAGGGACTCTCCGGTTAACAAGATGATTCACAG

-continued

| Sequences |
|---|

>SEQ ID NO: 11
TCTGTGTCAGGAATCCAAATGGGAAGTGGTGAAGAAGATAGATTTGATGCTCATAAGAAACTTCTGATTGGTCTCATAATCAGTTTCTCT
TCTCTTGGCCTTATAATCTTGTTCTGTTTTGGCTTTTGGGTTTATCGCAAGAACCAATCTCCAAAATCCATCAACAACTCAGATTCTGAG
AGTGGGAATTCATTTTCCTTGTTAATGAGACGACTTGGCTCGATTAAAACTCAGAGAAGAACTTCTATCCAAAAGGGTTACGTGCAATTT
TTCGATATCAAGACCCTCGAGAAAGCGACAGGCGGTTTTAAAGAAAGTAGTGTAATCGGACAAGGCGGTTTCGGATGCGTTTACAAGGGT
TGTTTGGACAATAACGTTAAAGCAGCGGTCAAGAAGATCGAGAACGTTAGCCAAGAAGCAAAACGAGAATTTCAGAATGAAGTTGACTTG
TTGAGCAAGATCCATCACTCGAACGTTATATCATTGTTGGGCTCTGCAAGCGAAATCAACTCGAGTTTCATCGTTTATGAGCTTATGGAG
AAAGGATCATTAGATGAACAGTTACATGGGCCTTCTCGTGGATCAGCTCTAACATGGCACATGCGTATGAAGATTGCTCTTGATACAGCT
AGAGGACTAGAGTATCTCCATGAGCATTGTCGTCCACCAGTTATCCACAGAGATTTGAAATCTTCGAATATTCTTCTTGATTCTTCCTTC
AACGCCAAGATTTCAGATTTCGGTCTTGCTGTATCGCTGGATGAACATGGCAAGAACAACATTAAACTCTCTGGGACACTTGGTTATGTT
GCCCCGGAATACCTCCTTGACGGAAAACTGACGGATAAGAGTGATGTTTATGCATTTGGGGTAGTTCTGCTTGAACTCTTGTTGGGTAGA
CGACCAGTTGAAAAATTAACTCCAGCTCAATGCCAATCTCTTGTAACTTGGGCAATGCCACAACTTACCGATAGATCCAAGCTTCCAAAC
ATTGTGGATGCCGTTATAAAAGATACAATGGATCTCAAACACTTATACCAGGTAGCAGCCATGGCTGTGTTGTGCGTGCAGCCAGAACCA
AGTTACCGGCCGTTGATAACCGATGTTCTTCACTCACTTGTTCCACTGGTTCCGGTAGAGCTAGGAGGGACTCTCCGGTTAACAAGATGA
TTCACAG

>SEQ ID NO: 12
TCGCAAGAACCAATCTCCAAAATCCATCAACAACTCAGATTCTGAGAGTGGGAATTCATTTTCCTTGTTAATGAGACGACTTGGCTCGAT
TAAAACTCAGAGAAGAACTTCTATCCAAAAGGGTTACGTGCAATTTTTCGATATCAAGACCCTC

>SEQ ID NO: 13
TCTGTGTCAGGAATCCAAATGGGAAGTGGTGAAGAAGATAGATTTGATGCTCATAAGAAACTTCTGATTGGTCTCATAATCAGTTTCTCT
TCTCTTGGCCTTATAATCTTGTTCTGTTTTGGCTTTTGGGTTTATCGCAAGAACCAATCTCCAAAATCCATCAACAACTCAGATTCTGAG
AGTGGGAATTCATTTTCCTTGTTAATGAGACGACTTGGCTCGATTAAAACTCAGAGAAGAACTTCTATCCAAAAGGGTTACGTGCAATTT
TTCGATATCAAGACCCTC

>SEQ ID NO: 14
TGTTAAAAGCGATTTATAATTTACACCGTTTTGGTGTATATTTCTATCTATCCTTTTACAAGACCTATATATGTTATGTTATGGTGGTGT
ACTATTTTAAGTGAGCGACATAGTATTTTCTTCATATAGCTAATTAATCAACAACAATTTCCCAACTTACAACTATTTGCGTACTTTAAA
CTTATATTGAAAGAGAACTACAAATTATTTTTTTGTACAAGAGAATTATGGTCTTCGGATCAATAATTTCTCTAGATATAATATGTAAA
GCCAACCCTATAATTTGTAAAATCCATGATTTGATATAATTTTCTTTTAAAATTGTGAATTGGCAGACAAAAACAACATTACATTTTGAT
TTAAATTCATAACTTTGACTTGCTAAGGAAACACCATGATTCATTTTTTGTCATTTGTTACATCATCACTAGAAATATTTGATCTAACTT
TATTATGATAATAGACTACATACTACATATGCAGTTACGATTTTAAATACTACATATTTAAGCGTGTTTAAACTGTAACCATATCATATA
AAATGACATATCTAAAAGTGATTTTCAATATTTTGATATGATATGTGTTGTAGCACGGATAATGATCTAATTTTTAAGTAATAAGCTTGT
TCATTACAAAAGAGAAGAAAGTAGTATTGGGCCATGATTATGTAAGGACAAAATAGGAAGATGTGGAAGAAGCCATTCGAGGGTTTTATT
ACAAAAACAGAGTATATAATTGGTCATAATGTTTTATTCACTTAATTTAACATTATTGCATTATATTTTCATGAACACATATTTCTTTAA
CTAAAAATATACACATATTTCTTATTGTAGATGAAGTGAAAAGAACAATATTTGGGTTCACATCTATGGGTGAATCCTTTTAATCACCCC
CTAAAATAAAAAAGGTGCCATATTTCTATTTTTAGAGAAAGATATAGAGCACCATTGGAGTGGTTTTGCTCCAAATATAGAGTTTAGAGA
AATATATAATACACCATTGGAGATGCTCTAAAATGAATTTATTTATTTATTTAGATGGAAGATTCTAATTGGTTAGAAAAAGAGGAAGTG
AATAATAGGATTCACCTATAAGAGTGAACCCAAGTATTTTTAAGAGATAATGTGTAAAGTAAATAGATGGTCATTGTGTGAATTATGAAT
AGAACCATGGTTTTCCATTTTTAATTGCTTAACATAGGGTAATCAACAATGGGGTTTAATATGTCAATAGACAATAGTAAAGAAAGTATT
TGATCTATCCCAAATCTTTCTTCGTTCGTTAGTTCATCACTTTCTTTCTTTTTGGTTATATTAATGGTAGAGAACTAAAAATTCAACTTT
TTATTCAAAAGCTCCCTTTCTCTTTCCCTCCTTTATTTGCCATAAAAGTGATTTCAAGAAGACAGCGAGAGAGAAAGTGATAGTTCGTTC
ACTCTTCGCTTTCTCAAGAATTTCAAAACACCAAAAAAGTCTTTAGATTGAATTTCATCAAAAACTTTTC

>SEQ ID NO: 15
AGACAAGAAAAAAGGAAACAAAATTTTATGAAAGAGATCTCCATTAGAGAAAGAGAGAGCGAGAGAGAGAGATTAATCTTGGAAGAGCAATC
TCACATTCTCACACTGCTCTTAGAAAATCTCTCTTTCACCATTAAAAATCCCAAAGAGTCTGGAGAA

>SEQ ID NO: 16
ATGGGAAAGATTCTTCATCTTCTTCTTCTTCTTCTTAAGGTCTCTGTTCTTGAATTCATCATTAGTGTTTCTGCTTTTACTTCACCTGCT
TCACAGCCTTCTCTTTCTCCTGTTTACACTTCCATGGCTTCCTTTTCTCCAGGGATCCACATGGGCAAAGGCCAAGAACACAAGTTAGAT
GCACACAAGAAACTTCTAATCGCTCTCATAATCACCTCATCTTCTCTAGGACTAATACTTGTATCTTGTTTATGCTTTTGGGTTTATTGG
TCTAAGAAATCTCCCAAAAACACCAAGAACTCAGGTGAGAGTAGGATTTCATTATCCAAGAAGGGCTTTGTGCAGTCCTTCGATTACAAG
ACACTAGAGAAAGCAACAGGCGGTTTCAAAGACGGTAATCTTATAGGACGAGGCGGGTTCGGAGATGTTTACAAGGCCTGTTTAGGCAAC
AACACTCTAGCAGCAGTCAAAAAGATCGAAAACGTTAGTCAAGAAGCAAAACGAGAATTTCAGAATGAAGTTGATTTGTTGAGCAAGATT
CACCACCCGAACATCATCTCATTGTTTGGATATGGAAATGAACTCAGTTCGAGTTTTATCGTCTACGAGCTGATGGAAAGCGGATCATTG
GATACACAGTTACACGGACCTTCTCGGGGATCGGCTTTAACATGGCACATGCGGATGAAGATTGCTCTTGATACAGCAAGAGCTGTTGAG
TATCTCCACGAGCGTTGTCGTCCTCCGGTTATCCACAGAGATCTTAAATCGTCAAATATTCTCCTTGATTCTTCCTTCAACGCCAAGATT
TCGGATTTTGGTCTTGCGGTAATGGTGGGGGCTCACGGCAAAAACAACATTAAACTATCAGGAACACTTGGTTATGTTGCTCCAGAATAT
CTCCTAGATGGAAAATTGACGGATAAGAGTGATGTTTATGCGTTTGGTGTGGTTTTACTTGAACTCTTGTTAGGAAGACGGCCGGTTGAG
AAATTGAGTTCGGTTCAGTGTCAATCTCTTGTCACTTGGGCAATGCCCCAACTTACGGATAGATCAAAGCTTCCGAAAATCGTGGATCCG
GTTATCAAAGATACAATGGATCATAAGCACTTATACCAGGTGGCAGCCGTGGCAGTGCTTTGTGTACAACCAGAACCGAGTTATCGACCG
TTGATAACCGATGTTCTTCACTCACTAGTTCCATTGGTTCCGGTAGAGCTAGGAGGGACTCTCCGGTTAATACCATCATCGTCTTGA

>SEQ ID NO: 17
MGKILHLLLLLLKVSVLEFIISVSAFTSPASQPSLSPVYTSMASFSPGIHMGKGQEHKLDAHKKLLIALIITSSSLGLILVSCLCFWVYW
SKKSPKNTKNSGESRISLSKKGFVQSFDYKTLEKATGGFKDGNLIGRGGFGDVYKACLGNNTLAAVKKIENVSQEAKREFQNEVDLLSKI
HHPNIISLFGYGNELSSSFIVYELMESGSLDTQLHGPSRGSALTWHMRMKIALDTARAVEYLHERCRPPVIHRDLKSSNILLDSSFNAKI
SDFGLAVMVGAHGKNNIKLSGTLGYVAPEYLLDGKLTDKSDVYAFGVVLLELLLGRRPVEKLSSVQCQSLVTWAMPQLTDRSKLPKIVDP
VIKDTMDHKHLYQVAAVAVLCVQPEPSYRPLITDVLHSLVPLVPVELGGTLRLIPSSS

>SEQ ID NO: 18
ATGAAGCAAATTGTTATAACAGCTCTTGTTTTACTACAAGCTTATGTTCTTCATCAATCCACATGTGTTATGTCCCTTACTACACAAGAA
TCTCCTTCTCCTCAACCTTCTGCTTTCACTCCCGCCTTATCTCCTGATTATCAACAGAGAGAGAAGGAATTGCATAAACAAGAGAGTAAC
AACATGAGACTGGTTATTTCACTAGCAGCTACATTTTCCTTAGTTGGTATAATCTTACTTTGCTCTCTGCTTTATTGGTTTTGCCATAGG

-continued

| Sequences |
|---|
| AGAAGAAACCTCAAGAGCTCAGGTTGTGGGTGTAGTGGAATCACATTCTTGAATCGGTTTAGTCGCTCAAAAACATTAGACAAGAGAACT ACAAAGCAGGGAACAGTGTCATTGATCGATTACAATATACTAGAAGAAGGAACTAGTGGTTTCAAGGAGAGTAACATTTTGGGTCAAGGT GGATTTGGATGTGTATATTCTGCCACATTAGAGAACAACATTTCAGCTGCGGTTAAGAAGCTAGACTGTGCCAATGAAGATGCAGCAAAG GAATTTAAGAGTGAGGTTGAGATATTGAGTAAGCTCCAGCACCCGAATATAATATCCCTTTTGGGTTATAGCACGAATGATACTGCGAGA TTCATTGTCTATGAGCTGATGCCAAACGTTTCTCTGGAATCTCATTTACACGGATCTTCTCAGGGTTCGGCGATCACATGGCCTATGAGG ATGAAGATTGCTCTTGATGTAACAAGGGGATTAGAATATTTGCATGAACATTGTCATCCAGCAATCATTCACAGGGACTTGAAATCATCC AACATCTTATTAGATAGCAATTTCAATGCTAAGATTTCAGATTTTGGTCTAGCTGTTGTTGATGGGCCAAAGAACAAGAACCATAAACTT TCCGGGACAGTTGGCTACGTTGCACCAGAGTATCTTCTCAACGGCCAATTGACAGAAAAGAGCGACGTGTATGCTTTTGGAGTAGTGTTA TTAGAGCTTTTACTCGGGAAAAAACCTGTGGAGAAACTAGCTCCCGGTGAATGCCAATCCATCATCACTTGGGCAATGCCTTATCTCACT GATAGAACCAAGTTACCAAGCGTCATAGATCCTGCGATTAAAGATACGATGGACTTGAAACACCTTTACCAGGTAGCGGCAGTGGCGATT TTGTGCGTGCAGCCAGAACCGAGTTATAGACCGTTGATTACAGACGTCTTGCATTCTCTTATACCTTTGGTTCCAATGGAACTTGGTGGA ACCTTAAAAACCATCAAATGTGCTTCAATGGATCACTGTTAA |
| >SEQ ID NO: 19 MKQIVITALVLLQAYVLHQSTCVMSLTTQESPSPQPSAFTPALSPDYQQREKELHKQESNNMRLVISLAATFSLVGIILLCSLLYWFCHR RRNLKSSGCGCSGITFLNRFSRSKTLDKRTTKQGTVSLIDYNILEEGTSGFKESNILGQGGFGCVYSATLENNISAAVKKLDCANEDAAK EFKSEVEILSKLQHPNIISLLGYSTNDTARFIVYELMPNVSLESHLHGSSQGSAITWPMRMKIALDVTRGLEYLHEHCHPAIIHRDLKSS NILLDSNFNAKISDFGLAVVDGPKNKNHKLSGTVGYVAPEYLLNGQLTEKSDVYAFGVVLLELLLGKKPVEKLAPGECQSIITWAMPYLT DRTKLPSVIDPAIKDTMDLKHLYQVAAVAILCVQPEPSYRPLITDVLHSLIPLVPMELGGTLKTIKCASMDHC |
| >SEQ ID NO: 20 ATGAAGACTATGTCCAAATCGTCTTTGCGTTTGCATTTTCTCTCGCTACTCTTACTTGTTGTGTCTCCCCTTCAAGCTTTGTCATTATA AGATTCATTACACATAATCATTTTGATGGTCTAGTACGTTGTCATCCCCACAAGTTTCAAGCCCTTACGCAGTTCAAGAACGAGTTTGAT ACCCGCCGTTGCAACCACAGTAACTACTTTAATGGAATCTGGTGTGATAACTCCAAGGTGCGGTCACAAAGCTACGACTACGGGACTGTC TCAGTGGAACTCTCAAATCAAACAGTAGCCTCTTCCAGTTTCATCATCTTCGCTACCTTGATCTCTCTCACAACAACTTCACCTCCTCTT CCCTCCCTTCCGAGTTTGTTTCCCACTTTGCGGAATCTAACCAAGCTCACAGTTTTAGACCTTTCTCATAATCACTTCTCCGGAACTTTG AAGCCCAACAATAGCCTCTTTGAGTTACACCACCTTCGTTACCTTAATCTCGAGGTCAACAACTTCAGTTCCTCACTCCCTTCCGAGTTT GGCTATCTCAACAATTTACAGCACTGTGGCCTCAAAGAGTTCCCAAACATATTCAAGACCCTTAAAAAAATGGAGGCTATAGACGTATCC AACAATAGAATCAACGGGAAAATCCCTGAGTGGTTATGGAGCCTTCCTCTTCATTTAGTGAATATTTTAAATAATTCTTTTGACGGT TTCGAAGGATCAACGGAAGTTTTAGTAAATTCATCGGTTCGGATATTACTTTTGGAGTCAAACAACTTTGAAGGAGCACTTCCTAGTCTA CCACACTCTATCAACGCCTTCTCCGCGGGTCATAACAATTTCACTGGAGAGATACCTCTTTCAATCTGCACCAGAACCTCACTTGGTGTC CTTGATCTAAACTACAACAACCTCATTGGTCCGGTTTCTCAATGTTTGAGTAATGTCACGTTTGTAAATCTCCGGAAAAACAATTTGGAA GGAACTATTCCTGAGACTTTCATTGTCGGTTCCTCGATAAGGACACTTGATGTTGGATACAATCGACTAACGGGAAAGCTTCCAAGGTCT CTTTTGAACTGCTCATCTCTAGAGTTTCTAAGCGTTGACAACAACAGAATCAAAGACACATTTCCTTTCTGGCTCAAGGCTTTACCAAAG TTACAAGTCCTTACCCTAAGTTCAAACAAGTTTTATGGTCCTATATCTCCTCCTCATCAAGGTCCTCTCGGGTTTCCAGAGCTGAGAATA CTTGAGATATCTGATAATAAGTTTACTGGAAGCTTGTCGTCAAGATACTTTGAGAATTGGAAAGCATCGTCCGCCATGATGAATGAATAT GTGGGTTTATATATGGTTTACGAGAAGAATCCTTATGGTGTAGTTGTCTATACCTTTTTGGATCGTATAGATTTGAAATACAAAGGTCTA AACATGGAGCAAGCGAGGGTTCTCACTTCCTACAGCGCCATTGATTTTTCTAGAAATCTACTTGAAGGAAATATTCCTGAATCCATTGGA CTTTTAAAGGCATTGATTGCACTAAACTTATCGAACAACGCTTTTACAGGCCATATTCCTCAGTCTTTGGCAAATCTTAAGGAGCTCCAG TCACTAGACATGTCTAGGAACCAACTCTCAGGGACTATTCCTAATGGACTCAAGCAACTCTCGTTTTTGGCTTACATAAGTGTGTCTCAT AACCAACTCAAGGGTGAAATACCACAAGGAACACAAATTACTGGGCAATTGAAATCTTCCTTTGAAGGGAATGTAGGACTTTGTGGTCTT CCTCTCGAGGAAAGGTGCTTCGACAATAGTGCATCTCCAACGCAGCACCACAAGCAAGACGAAGAAGAAGAAGAAGAACAAGTGTTACAC TGGAAAGCGGTGGCAATGGGGTATGGACCTGGATTGTTGGTTGGATTTGCAATTGCATATGTCATTGCTTCATACAAGCCGGAGTGGCTA ACCAAGATAATTGGTCCGAATAAGCGCAGAAACTAG |
| >SEQ ID NO: 21 MKTMSKSSLRLHFLSLLLLCCVSPSSFVIIRFITHNHFDGLVRCHPHKFQALTQFKNEFDTRRCNHSNYFNGIWCDNSKVRSQSYDYGTV SVELSNQTVASSSFIIFATLISLTTTSPPLPSLPSLFPTLRNLTKLTVLDLSHNHFSGTLKPNNSLFELHHLRYLNLEVNNFSSSLPSEF GYLNNLQHCGLKEFPNIFKTLKKMEAIDVSNNRINGKIPEWLWSLPLLHLVNILNNSFDGFEGSTEVLVNSSVRILLLESNNFEGALPSL PHSINAFSAGHNNFTGEIPLSICTRTSLGVLDLNYNNLIGPVSQCLSNVTFVNLRKNNLEGTIPETFIVGSSIRTLDVGYNRLTGKLPRS LLNCSSLEFLSVDNNRIKDTFPFWLKALPKLQVLTLSSNKFYGPISPPHQGPLGFPELRILEISDNKFTGSLSSRYFENWKASSAMMNEY VGLYMVYEKNPYGVVVYTFLDRIDLKYKGLNMEQARVLTSYSAIDFSRNLLEGNIPESIGLLKALIALNLSNNAFTGHIPQSLANLKELQ SLDMSRNQLSGTIPNGLKQLSFLAYISVSHNQLKGEIPQGTQITGQLKSSFEGNVGLCGLPLEERCFDNSASPTQHHKQDEEEEEEQVLH WKAVAMGYGPGLLVGFAIAYVIASYKPEWLTKIIGPNKRRN |
| >SEQ ID NO: 22 ATGACTTCCTCTCGCCGTCTTCTTCTTCCTCTCGGAGCATCGCTCACTAGAGGAAGATTTTCTTCCGATCAAATCCGAAATGGATTTCTA AGAAACTTCCGTGGATTCGCCACCGTAACTTCGTCGGAACCGGCCTTAGCCAATCTGGAAGCGAAATATGCCGTAGCGTTGCCAGAATGT TCAACAGTAGAGGACGAGATCACGAAGATCCGTCATGAATTCGAGTTAGCGAAACAGAGGTTTCTTAATATCCCTGAAGCTATTAATAGT ATGCCGAAGATGAATCCTCAAGGGATATATGTGAATAAGAATCTGAGATTGGATAATATACAAGTTTATGGATTTGATTATGATTACACT TTGGCACATTACTCTTCTCACTTACAGAGTTTGATCTATGATCTTGCCAAGAAACATATGGTTAATGAGTTTAGATATCCTGATGTTTGC ACTCAGTTTGAGTATGATCCTACTTTTCCAATCCGTGGGTTGTACTATGATAAACTAAAAGGATGCCTCATGAAATTGGATTTCTTCGGT TCAATCGAGCCAGATGGGTGTTATTTTGGTCGTCGTAAGCTTAGTAGGAAGGAAATAGAAAGCATGTATGGAACGCGGCACATAGGTCGT GATCAAGCGAGAGGTTTGGTGGGATTGATGGATTTCTTCTGTTTTAGCGAGGCGTGTCTTATAGCAGACATGGTGCAATATTTTGTTGAC GCCAAACTTGAGTTTGATGCCTCTAACATCTACAATGATGTCAATCGTGCTATTCAACATGTCCATAGAAGTGGATTGGTTCATAGAGGA ATTCTTGCTGATCCCAACAGATATTTGCTAAAAAATGGTCAGCTTCTACGTTTCCTGAGAATGCTAAAAGATAAAGGAAAGAAGCTTTTT TTGCTGACCAACTCTCCGTATAATTTTGTTGATGGCGGAATGCGCTTTCTAATGGAGGAATCTTTTGGCTTCGGAGATTCCTGGCGAGAA CTCTTTGATGTTGTGATTGCTAAAGCAAATAAACCAGAATTTTACACATCTGAGCACCCTTTCCGTTGTTATGATTCGGAGAGGGATAAT TTGGCATTTACAAAAGTGGATGCATTTGACCCAAAGAAAGTTTATTATCATGGTTGTCTTAAATCCTTCCTTGAAATCACAAAGTGGCAT GGCCCTGAGGTGATTTATTTCGGAGATCACTTATTTAGTGATCTAAGAGGGCCTTCAAAAGCTGGTTGGCGAACTGCTGCCATAATTCAT GAGCTCGAGCGAGAGATACAGATACAAAATGATGATAGCTACCGGTTTGAGCAGGCCAAGTTCCATATTATCCAAGAGTTACTCGGTAGA TTTCACGCGACTGTATCAAACAATCAGAGAAGTGAAGCATGCCAATCACTTTTGGATGAGCTGAACAATGCGAGGCAGAGAGCAAGAGAC ACGATGAAACAAATGTTCAACAGATCGTTTGGAGCTACATTTGTCACAGACACTGGTCAAGAATCAGCATTCTCTTATCACATCCACCAA TACGCAGACGTTTATACCAGTAAACCTGAGAACTTTCTGTTATACCGACCTGAAGCCTGGCTTCACGTTCCTTACGATATCAAGATCATG CCACATCATGTCAAGGTTGCTTCAACCCTTTTCAAAACCTGA |

-continued

| Sequences |
|---|

>SEQ ID NO: 23
MTSSRRLLLPLGASLTRGRFSSDQIRNGFLRNFRGFATVTSSEPALANLEAKYAVALPECSTVEDEITKIRHEFELAKQRFLNIPEAINS
MPKMNPQGIYVNKNLRLDNIQVYGFDYDYTLAHYSSHLQSLIYDLAKKHMVNEFRYPDVCTQFEYDPTFPIRGLYYDKLKGCLMKLDFFG
SIEPDGCYFGRRKLSRKEIESMYGTRHIGRDQARGLVGLMDFFCFSEACLIADMVQYFVDAKLEFDASNIYNDVNRAIQHVHRSGLVHRG
ILADPNRYLLKNGQLLRFLRMLKDKGKKLFLLTNSPYNFVDGGMRFLMEESFGFGDSWRELFDVVIAKANKPEFYTSEHPFRCYDSERDN
LAFTKVDAFDPKKVYYHGCLKSFLEITKWHGPEVIYFGDHLFSDLRGPSKAGWRTAAIIHELEREIQIQNDDSYRFEQAKFHIIQELLGR
FHATVSNNQRSEACQSLLDELNNARQRARDTMKQMFNRSFGATFVTDTGQESAFSYHIHQYADVYTSKPENFLLYRPEAWLHVPYDIKIM
PHHVKVASTLFKT

>SEQ ID NO: 24
ATGGAGATTCCGGCGGCGCCGCCGCCTCCATTGCCGGTGCTGTGCTCGTACGTCGTCTTCTTGCTGCTGCTGTCTTCGTGCTCACTGGCC
AGAGGGAGGATCGCGGTTTCTTCCCCGGGCCCGTCGCCTGTGGCCGCCGCCGTTACAGCCAATGAGACCGCTTCATCCTCTTCTTCTCCG
GTGTTTCCGGCCGCTCCTCCCGTCGTGATCACAGTGGTGAGGCACCACCATTACCACCGGGAGCTGGTCATCTCCGCTGTCCTCGCCTGC
GTCGCCACCGCCATGATCCTCCTCTCCACACTCTACGCCTGGACGATGTGGCGGCGGTCTCGCCGGACCCCCCACGGCGGCAAGGGCCGC
GGCCGGAGATCAGGGATCACACTGGTGCCAATCCTGAGCAAGTTCAATTCAGTGAAGATGAGCAGGAAGGGGGGCCTTGTGACGATGATC
GAGTACCCGTCGCTGGAGGCGGCGACAGGCAAGTTCGGCGAGAGCAATGTGCTCGGTGTCGGCGGCTTCGGTTGCGTTTATAAGGCGGCG
TTTGATGGCGGTGCCACCGCCGCCGTGAAGAGGCTTGAAGGCGGCGGGCCGGATTGCGAGAAGGAATTCGAGAATGAGCTGGATTTGCTT
GGCAGGATCAGGCACCCAAACATAGTGTCTCTCCTGGGCTTCTGTGTCCATGGTGGCAATCACTACATTGTTTATGAGCTCATGGAGAAG
GGATCATTGGAGACACAGCTGCATGGGTCTTCACATGGATCTGCTCTGAGCTGGCACGTTCGGATGAAGATCGCGCTCGATACGGCGAGG
GGATTAGAGTATCTTCATGAGCACTGCAATCCACCTGTGATCCATAGGGATCTGAAACCTTCTAATATACTTTTAGATTCAGACTTCAAT
GCTAAGATTGCAGATTTTGGCCTTGCGGTCACCGGTGGGAATCTCAACAAAGGGAACCTGAAGCTTTCCGGGACCTTGGGTTATGTAGCC
CCTGAGTACTTATTAGATGGGAAGTTGACTGAGAAGAGCGATGTATACGCATTTGGAGTAGTGCTTCTAGAGCTCCTGATGGGAAGGAAG
CCTGTTGAGAAAATGTCACCATCTCAGTGCCAATCAATTGTGTCATGGGCTATGCCTCAGCTGACCGACAGATCGAAGCTCCCCAACATA
ATTGACCTGGTGATCAAGGACACCATGGACCCAAAACACTTGTACCAAGTTGCAGCAGTGGCTGTTCTATGTGTGCAGCCCGAACCGAGC
TACAGACCACTGATAACAGATGTTCTCCACTCTCTTGTTCCTCTAGTGCCTGCGGAGCTCGGAGGAACACTCAGGGTTGCAGAGCCACCT
TCACCTTCTCCAGACCAAAGACATTATCCTTGTTGA

>SEQ ID NO: 25
ATGAAGAAACTGGTTCATCTTCAGTTTTTGTTTCTTGTCAAGATCTTTGCTACTCAATTCCTCACTCCTTCTTCATCATCTTTTGCTGCT
TCAAATCCTTCTATAGCTCCTGTTTACACCTCCATGACTACTTTCTCTCCAGGAATTCAAATGGGAAGTGGTGAAGAACACAGATTAGAT
GCACATAAGAAACTCCTGATTGGTCTTATAATCAGTTCCTCTTCTCTTGGTATCATAATCTTGATTTGCTTTGGCTTCTGGATGTACTGT
CGCAAGAAAGCTCCCAAACCCATCAAGATTCCGGATGCCGAGAGTGGGACTTCATCATTTTCAATGTTTGTGAGGCGGCTAAGCTCAATT
AAAACTCACAGAACATCTAGCAATCAGGGTTATGTGCAGCGTTTCGATTCCAAGACGCTAGAGAAAGCGACAGGCGGTTTCAAAGACAGT
AATGTAATCGGACAGGGCGGTTTCGGATGCGTTTACAAGGCTTCTTTGGACAGCAACACTAAAGCAGCGGTTAAAAAGATCGAAAACGTT
ACCCAAGAAGCAAAACGAGAATTTCAGAATGAAGTTGAGCTGTTGAGCAAGATCCAGCACTCCAATATTATATCATTGTTGGGCTCTGCA
AGTGAAATCAACTCGAGTTTCGTCGTTTATGAGTTGATGGAGAAAGGATCCTTAGATGATCAGTTACATGGACCTTCGTGTGGATCCGCT
CTAACATGGCATATGCGTATGAAGATTGCTCTAGATACAGCTAGAGGACTAGAGTATCTCCATGAACATTGTCGTCCACCAGTTATCCAC
AGGGACCTGAAATCGTCTAATATTCTTCTTGATTCTTCCTTCAATGCCAAGATTTCAGATTTTGGTCTGGCTGTATCGGTTGGAGTGCAT
GGGAGTAACAACATTAAACTCTCTGGGACACTTGGTTATGTTGCCCCGGAATATCTCCTAGACGGAAAGTTGACGGATAAGAGTGATGTC
TATGCATTTGGGGTGGTTCTTCTTGAACTTTTGTTGGGTAGGCGGCCGGTTGAGAAATTGAGTCCATCTCAGTGTCAATCTCTTGTGACT
TGGGCAATGCCACAACTTACCGATAGATCGAAACTCCCAAACATCGTGGATCCGGTTATAAAAGATACAATGGATCTTAAGCACTTATAC
CAAGTAGCAGCCATGGCTGTGCTGTGCGTACAGCCAGAACCGAGTTACCGGCCGCTGATAACCGATGTTCTTCATTCACTTGTTCCATTG
GTTCCGGTAGAGCTAGGAGGGACTCTCCGGTTAACCCGATGA

>SEQ ID NO: 26
MKKLVHLQFLFLVKIFATQFLTPSSSSFAASNPSIAPVYTSMTTFSPGIQMGSGEEHRLDAHKKLLIGLIISSSSLGIIILICFGFWMYC
RKKAPKPIKIPDAESGTSSFSMFVRRLSSIKTHRTSSNQGYVQRFDSKTLEKATGGFKDSNVIGQGGFGCVYKASLDSNTKAAVKKIENV
TQEAKREFQNEVELLSKIQHSNIISLLGSASEINSSFVVYELMEKGSLDDQLHGPSCGSALTWHMRMKIALDTARGLEYLHEHCRPPVIH
RDLKSSNILLDSSFNAKISDFGLAVSVGVHGSNNIKLSGTLGYVAPEYLLDGKLTDKSDVYAFGVVLLELLLGRRPVEKLSPSQCQSLVT
WAMPQLTDRSKLPNIVDPVIKDTMDLKHLYQVAAMAVLCVQPEPSYRPLITDVLHSLVPLVPVELGGTLRLTR

>SEQ ID NO: 27
ATTTTTGGTGTTGAAATGATGCACAACGGATCTTTGGAATCCCAATTGCATGGTCCGTCTCATGGAACTGGCTTAAGCTGGCAGCATCGA
ATGAAAATTGCACTTGATATTGCACGAGGACTAGAGTATCTTCACGAGCGCTGTACCCCGCCTGTGATTCATAGAGATCTGAAATCGTCC
AACATTCTTCTAGGTTCGAACTACAATGCTAAACTTTCTGATTTCGGGCTCGCGATTACTGGTGGGATTCAGGGCAAGAACAACGTAAAG
CTTTCGGGAACATTAGGTTATGTAGCTCCAGAATACCTCTTAGATGGTAAACTTACTGATAAAAGTGATGTTTATGCGTTTGGAGTTGTA
CTTCTTGAACTTTTGATAGGTAGAAAACCAGTGGAGAAAATGTCACCATCTCAATGCCAATCTATCGTTACATGGGCAATGCCTCAACTA
ACCGACCGATCAAAGCTTCCTAACATCGTTGATCCCGTGATTAGAGATACAATGGACTTGAAGCACTTGTATCAAGTTGCTGCGGTTGCT
GTGCTATGTGTACAACCGGAACCGAGTTACAGGCCATTGATAACAGATGTTTTGCATTCGTTCATCCCACTTGTACCTGTTGAGCTTGGA
GGGTCGCTAAGAGTTACCGAATCTTGA

>SEQ ID NO: 28
IFGVEMMHNGSLESQLHGPSHGTGLSWQHRMKIALDIARGLEYLHERCTPPVIHRDLKSSNILLGSNYNAKLSDFGLAITGGIQGKNNVK
LSGTLGYVAPEYLLDGKLTDKSDVYAFGVVLLELLIGRKPVEKMSPSQCQSIVTWAMPQLTDRSKLPNIVDPVIRDTMDLKHLYQVAAVA
VLCVQPEPSYRPLITDVLHSFIPLVPVELGGSLRVTES

>SEQ ID NO: 29
AATTCGGCACGAGGGCTGGATTCCAGTTTTAATGCAAAGCTTTCAGATTTTGGCCTTTCTGTGACTGCTGGAACCCAGAGTAGGAATGTT
AAGATCTCTGGAACTCTGGGTTATGTTGCCCCGGAGTACCTATTAGAAGGAAAACTAACTGATAAAAGTGATGTATATGCTTTCGGAGTT
GTATTGCTGGAACTTTTGATGGGGAGAAGGCCTGTGGAAAAGATGTCACCAACTCAATGTCAATCAATGGTCACATGGGCCATGCCTCAG
CTCACCGATAGATCAAAGCTTCCAAACATTGTGGATCCAGTAATTAGAGACACAATGGATTTAAAGCACTTATACCAGGTAGCCGCTGTG
GCAGTGCTATGTATACAACCTGAACCAAGTTATAGGCCATTGATAACCGACGTTCTGCATTCCCTCATTCCTCTTGTACCTACCGACCTT
GGAGGGTCACTCCGAGTGACCTAA

-continued

| Sequences |
| --- |

>SEQ ID NO: 30
NSARGLDSSFNAKLSDFGLSVTAGTQSRNVKISGTLGYVAPEYLLEGKLTDKSDVYAFGVVLLELLMGRRPVEKMSPTQCQSMVTWAMPQ
LTDRSKLPNIVDPVIRDTMDLKHLYQVAAVAVLCIQPEPSYRPLITDVLHSLIPLVPTDLGGSLRVT

>SEQ ID NO: 31
GGATTGTGTTTGTGGCTTTATCATTTGAAGTACTCCTTCAAATCCAGTAACAAGAATGCAAAGAGCAAAGATTCTGAGAATGGAGTTGTG
TTATCATCATTTTTGGGCAAATTCACTTCTGTGAGGATGGTTAGTAAGAAGGGATCTGCTATTTCATTTATTGAGTATAAGCTGTTAGAG
AAAGCCACCGACAGTTTTCATGAGAGTAATATATTGGGTGAGGGTGGATTTGGATGTGTTTACAAGGCTAAATTGGATGATAACTTGCAC
GTCGCTGTCAAAAAATTAGATTGTGCAACACAAGATGCCGGCAGAGAATTTGAGAATGAGGTGGATTTGCTGAGTAATATTCACCACCCA
AATGTTGTTTGTCTGTTGGGTTATAGTGCTCATGATGACACAAGGTTTATTGTTTATGAATTGATGGAAAATCGGTCCCTTGATATTCAA
TTGCATGGTCCTTCTCATGGATCAGCATTGACTTGGCATATGCGAATGAAAATTGCTCTTGATACCGCTAGAGGATTAGAATATTTACAT
GAGCACTGCAACCCTGCAGTCATTCATAGAGATCTGAAATCCTCCAATATACTTCTAGATTCCAAGTTTAATGCTAAGCTCTCAGATTTT
GGTCTTGCCATAACCGATGGATCCCAAAACAAGAACAATCTTAAGCTTTCGGGCACTTTGGGATATGTGGCTCCCGAGTATCTTTTAGAT
GGTAAATTGACAGACAAGAGTGATGTCTATGCTTTTGGAGTTGTGCTTCT

>SEQ ID NO: 32
GLCLWLYHLKYSFKSSNKNAKSKDSENGVVLSSFLGKFTSVRMVSKKGSAISFIEYKLLEKATDSFHESNILGEGGFGCVYKAKLDDNLH
VAVKKLDCATQDAGREFENEVDLLSNIHHPNVVCLLGYSAHDDTRFIVYELMENRSLDIQLHGPSHGSALTWHMRMKIALDTARGLEYLH
EHCNPAVIHRDLKSSNILLDSKFNAKLSDFGLAITDGSQNKNNLKLSGTLGYVAPEYLLDGKLTDKSDVYAFGVVLL

>SEQ ID NO: 33
GCATTGACATGGCATCTTAGGATGAAAATTGCCCTTGATGTAGCTAGAGGATTAGAATTTTTGCATGAGCACTGCCACCCAGCAGTGATC
CATAGAGATCTGAAATCATCTAATATCCTTCTGGATTCAAATCTCAATGCTAAGCTATCTGATTTTGGTCTTGCCATTCTTGATGGGGCT
CAAAATAAGAACAACATCAAGCTTTCTGGAACCTTGGGCTATGTAGCTCCAGAGTACCTCTTAGATGGTAAATTGACTGACAAGAGTGAT
GTTTATGCTTTTGGAGTGGTGCTTTTGGAGCTTCTCCTGAGAAGAAAGCCTGTGGAGAAGCTGGCACCAGCTCAATGCCAATCTATAGTC
ACATGGGCTATGCCTCAGCTGACAGATAGATCAAAGCTTCCAAACATCGTGGATCCTGTGATTAGAAATGCTATGGATATAAAGCACTTA
TTCCAGGTTGCTGCAGTCGCTGTGCTATGCGTGCAGCCTGAACCAAGCTATCGACCACTGATAACAGATGTGTTGCATTCCCTTGTTCCC
CTTGTTCCTATGGAGCTTGGCGGGACGCTCAGAGTTGAACGACCTGCTTCTGTGACCTCTCTGTTGATTGATTCTACCTGA

>SEQ ID NO: 34
ALTWHLRMKIALDVARGLEFLHEHCHPAVIHRDLKSSNILLDSNLNAKLSDFGLAILDGAQNKNNIKLSGTLGYVAPEYLLDGKLTDKSD
VYAFGVVLLELLLRRKPVEKLAPAQCQSIVTWAMPQLTDRSKLPNIVDPVIRNAMDIKHLFQVAAVAVLCVQPEPSYRPLITDVLHSLVP
LVPMELGGTLRVERPASVTSLLIDST

>SEQ ID NO: 35
ACTGAGGTGACCCGGAAGAAAAACAGGGTAAAGCTATCGGGCACTTTGGGTTATGTAGCCCCAGAATATGTCTTGGATGGTAAATTGACT
GATAAGAGTGATGTCTATGCCTTTGGAGTTGTGCTTTTGGAGCTCCTTTTGAGAAGAAGGCCTCTTGAGATAGTAGCACCCACTCAGTGC
CAGTCTATTGTTACATGGGCCATGCCTCAGCTGACCGACCGAACTAAGCTTCCAGATATTGTGGATCCTGTAATTAGAGATGCGATGGAT
GTCAAGCACTTATACCAGGCAGCTGCTGTTGCTGTTTTGTGTCTGCAACCAGAACCGATCTACCGGCCACTGATAACGGATGTACTCCAC
TCTCTCATTCCACTTGTACCCGTTGAACTTGGGGGAACGCTGAAGACCTAG

>SEQ ID NO: 36
TEVTRKKNRVKLSGTLGYVAPEYVLDGKLTDKSDVYAFGVVLLELLLRRRPLEIVAPTQCQSIVTWAMPQLTDRTKLPDIVDPVIRDAMD
VKHLYQAAAVAVLCLQPEPIYRPLITDVLHSLIPLVPVELGGTLKT

>SEQ ID NO: 37
ACGAGGCCTCGTGCCATACTTTTGGATTCAGATTTCAATGCCAAGATTTCGGATTTCGGTCTTGCAGTGTCAAGTGGAAATCGCACCAAA
GGTAATCTGAAGCTTTCCGGAACTTTGGGCTATGTTGCTCCTGAGTACTTATTAGACGGGAAGTTGACAGAGAAGAGTGATGTATATGCG
TTCGGAGTAGTACTTCTTGAGCTTTTGTTAGGAAGGAGGCCAATTGAGAAGATGGCCCCATCTCAATGCCAATCAATTGTTACATGGGCC
ATGCCTCAGCTAATTGACAGATCAAAGCTCCCAACCATAATTGACCCCGTGATCAGGAACACGATGGACCTGAAGCACTTGTACCAAGTT
GCTGCAGTGGCTGTGCTCTGTGTGCAGCCAGAACCAAGTTATAGGCCACTAATCACAGATGTGCTCCACTCTCTGATTCCCCTGGTGCCC
ATGGAGCTCGGAGGGTCACTGAGGGCTACCTTGGAATCGCCTCGCGTATCACAACATCGTTCTCCCTGCTGA

>SEQ ID NO: 38
TRPRAILLDSDFNAKISDFGLAVSSGNRTKGNLKLSGTLGYVAPEYLLDGKLIEKSDVYAFGVVLLELLLGRRPIEKMAPSQCQSIVTWA
MPQLIDRSKLPTIIDPVIRNTMDLKHLYQVAAVAVLCVQPEPSYRPLITDVLHSLIPLVPMELGGSLRATLESPRVSQHRSPC

>SEQ ID NO: 39
CCTTTATTGAATAGATTGAACTCCTTCCGTGGTTCTAGGAGAAAGGGATGTGCATATATAATTGAATATTCTCTGCTGCAAGCAGCCACA
AATAATTTTAGTACAAGTGACATCCTTGGAGAGGGTGGTTTTGGGTGTGTATACAGAGCTAGGTTAGATGATGATTTCTTTGCTGCTGTG
AAGAAGTTAGATGAGGGCAGCAAGCAGGCTGAGTATGAATTTCAGAATGAAGTTGAACTAATGAGCAAAATCAGACATCCAAATCTTGTT
TCTTTGCTGGGGTTCTGCATTCATGGGAAGACTCGGTTGCTAGTCTACGAGCTCATGCAAAATGGTTCTTTGGAAGACCAATTACATGGG
CCATCTCATGGATCCGCACTTACATGGTACCTGCGCATGAAAATAGCCCTTGATTCAGCAAGGGGTCTAGAACACTTGCACGAGCACTGC
AATCCTGCTGTGATTCATCGTGATTTCAAATCATCAAATATCCTTCTGGATGCAAGCTTCAATGCCAAGCTTTCAGATTTTGGTCTTGCA
GTAACAGCTGCAGGAGGTATTGGTAATGCTAATGTCGAGCTACTGGGCACTTTGGGATATGTAGCTCCAGAATACCTGCTTGATGGCAAG
TTGACGGAGAAAAGTGATGTCTATGGATTTGGAGTTGTTCTTTTGGAGCTAATTATGGGAAGAAAGCCAGTTGATAAATCTGTGGCAACT
GAAAGTCAATCGCTAGTTTC

>SEQ ID NO: 40
PLLNRLNSFRGSRRKGCAYIIEYSLLQAATNNFSTSDILGEGGFGCVYRARLDDDFFAAVKKLDEGSKQAEYEFQNEVELMSKIRHPNLV
SLLGFCIHGKTRLLVYELMQNGSLEDQLHGPSHGSALTWYLRMKIALDSARGLEHLHEHCNPAVIHRDFKSSNILLDASFNAKLSDFGLA
VTAAGGIGNANVELLGTLGYVAPEYLLDGKLIEKSDVYGFGVVLLELIMGRKPVDKSVATESQSLVS

>SEQ ID NO: 41
ATGAAAATGAAGCTTCTCCTCATGCTTCTTCTTCTTGTTCTTCTTCTTCACCAACCCATTTGGGCTGCAGACCCTCCTGCTTCTTCTCCT
GCTTTATCTCCAGGGGAGGAGCAGCATCACCGGAATAATAAAGTGGTAATAGCTATCGTCGTAGCCACCACTGCACTTGCTGCACTCATT

| Sequences |
|---|
| TTCAGTTTCTTATGCTTCTGGGTTTATCATCATACCAAGTATCCAACAAAATCCAAATTCAAATCCAAAAATTTTCGAAGTCCAGATGCA GAGAAGGGGATCACCTTAGCACCGTTTGTGAGTAAATTCAGTTCCATCAAGATTGTTGGCATGGACGGGTATGTTCCAATAATTGACTAT AAGCAAATAGAAAAAACGACCAATAATTTTCAAGAAAGTAACATCTTGGGTGAGGGCGGTTTTGGACGTGTTTACAAGGCTTGTTTGGAT CATAACTTGGATGTTGCAGTCAAAAAACTACATTGTGAGACTCAACATGCTGAGAGAGAATTTGAGAACGAGGTGAATATGTTAAGCAAA ATTCAGCATCCGAATATAATATCTTTACTGGGTTGTAGCATGGATGGTTACACGAGGCTCGTTGTCTATGAGCTGATGCATAATGGATCA TTGGAAGCTCAGTTACATGGACCTTCTCATGGCTCGGCATTGACTTGGCACATGAGGATGAAGATTGCTCTTGACACAGCAAGAGGATTA GAATATCTGCACGAGCACTGTCACCCTGCAGTGATCCATAGGGATATGAAATCTTCTAATATTCTCTTAGATGCAAACTTCAATGCCAAG CTGTCTGATTTTGGTCTTGCCTTAACTGATGGGTCCCAAAGCAAGAAGAACATTAAACTATCGGGTACCTTGGGATACGTAGCACCGGAG TATCTTCTAGATGGTAAATTAAGTGATAAAAGTGATGTCTATGCTTTTGGGGTTGTGCTATTGGAGCTCCTACTAGGAAGGAAGCCAGTA GAAAAACTGGTACCAGCTCAATGCCAATCTATTGTCACATGGGCCATGCCACACCTCACGGACAGATCCAAGCTTCCAAGCATTGTGGAT CCAGTGATTAAGAATACAATGGATCCCAAGCACTTGTACCAGGTTGCTGCTGTAGCTGTGCTGTGCGTGCAACCAGAACCTAGTTACCGT CCACTGATCATTGATGTTCTTCACTCACTCATCCCTCTTGTTCCCATTGAGCTTGGAGGAACACTAAGAGTTTCACAAGTAATT |
| >SEQ ID NO: 42<br>MKNIKLLLMLLLLVLLLHQPIWAADPPASSPALSPGEEQHHRNNKVVIAIVVATTALAALIFSFLCFWVYHHTKYPTKSKFKSKNFRSPD AEKGITLAPFVSKFSSIKIVGMDGYVPIIDYKQIEKTTNNFQESNILGEGGFGRVYKACLDHNLDVAVKKLHCETQHAEREFENEVNMLS KIQHPNIISLLGCSMDGYTRLVVYELMHNGSLEAQLHGPSHGSALTWHMRNIKIALDTARGLEYLHEHCHPAVIHRDMKSSNILLDANFN AKLSDFGLALTDGSQSKKNIKLSGTLGYVAPEYLLDGKLSDKSDVYAFGVVLLELLLGRKPVEKLVPAQCQSIVTWAMPHLTDRSKLPSI VDPVIKNTMDPKHLYQVAAVAVLCVQPEPSYRPLIIDVLHSLIPLVPIELGGTLRVSQVI |
| >SEQ ID NO: 43<br>ACTCAAGCATCAAAATATTGTAAATCTTTTGGGTATTGTGTTCATGATGACACAAGGTTTTTGGTCTATGAAATGATGCATCAAGGCTCT TTGGACTCACAATTGCATGGACCAACTCATGGAACCGCATTAACCTGGCATCGAAGAATGAAAGTCGCACTTGATATTGCTCGAGGATTA GAGTATCTTCATGAACGATGCAACCCGCCTGTGATTCATAGAGATCTTAAGTCATCGAACATTTTGCTAGATTCCAATTTCAATGCTAAA ATTTCGAATTTTGCACTTGCTACCACTGAGCTCCATGCGAAGAACAAAGTTAAGCTTTCGGCTACTTCTGGTTATTTGGCTCCGGAATAC CTATCAGAAGGTAAACTTACCGATAAAAGCGACGTATATGCATTCGGAGTAGTACTTCTTGGGCTTTTAATCGGTAGAAAACCAGTGGAG AAAATGTCACCATCTTTATTTCAATCTATTGTCACATGGGCAATGCCTCAGTTAACAGACCGGTCAAAGCTTCCAAACATCGTTGACCCT GTGATTAGAGATACAATGGACCTGAAGCACTTATATCAAGTTGCTGCTGTAGCCGTACTTTGCGTGCAACCCGAACCAAGTTACAGACCG TTGATTACAGACGTACTACACTCATTCATTCCACTCGTACCCGTTGATCTTGGAGGGTCATTAAGAGCTTAA |
| >SEQ ID NO: 44<br>TQASKYCKSFGYCVHDDTRFLVYEMMHQGSLDSQLHGPTHGTALTWHRRNIKVALDIARGLEYLHERCNPPVIHRDLKSSNILLDSNFNA KISNFALATTELHAKNKVKLSATSGYLAPEYLSEGKLTDKSDVYAFGVVLLGLLIGRKPVEKMSPSLFQSIVTWAMPQLTDRSKLPNIVD PVIRDTMDLKHLYQVAAVAVLCVQPEPSYRPLITDVLHSFIPLVPVDLGGSLRA |
| >SEQ ID NO: 45<br>CGATCATTTCGTTGCGGCTGTAAAAAACTCCATGGTCCAGAACCAGATGCCCAAAAAGGGTTTGAGAATGAAGTAGATTGGTTAGGTAAA CTCAAGCATCAAAATATTGTAAATTTTTTGGGTTATTGTGTTCATGATGACACAAGGTTTTTGGTCTATGAAATGATGCATCAAGGCTCT TTGGACTCACAATTGCATGGACCAACTCATGGAACCGCATTAACCTGGCATCGAAGAATGAAAGTCGCACTTGATATTGCTCGAGGATTA GAGTATCTTCATGAACGATGCAACCCGCCTGTGATTCATAGAGATCTCAAGTCATCGAACATTTTGCTAGATTCCAATTTCAATGCTAAA ATTTCGAATTTTGCACTTGCTACCACTGAGCTCCATGCGAAGAACAAAGTTAAGCTTTCGGGTACTTCTGGTTATTTGGCTCCGGAATAC CTATCCGAAGGTAAACTTACCGATAAAAGTGATGTATATGCATTCGGAGTAGTACTTCTTGAGCTTTTAATCGGTAGAAAACCAGTGGAG AAAATGTCACCATCTTTATTTCAATCTATTGTCACATGGGCAATGCCTCAGCTAACAGACCGGTCAAAGCTTCCAAACATTGTTGACCCT GTGATTAGAGATACAATGGACCTGAAGCACTTGTATCAAGTTGCTGCTGTAGCCGTACTTTGCGTGCAACCCGAACCAAGTTACAGACCG TTGATTACAGACGTACTACACTCATTCATTCC |
| >SEQ ID NO: 46<br>RSFRCGCKKLHGPEPDAQKGFENEVDWLGKLKHQNIVNFLGYCVHDDTRFLVYEMMHQGSLDSQLHGPTHGTALTWHRRNIKVALDIARG LEYLHERCNPPVIHRDLKSSNILLDSNFNAKISNFALATTELHAKNKVKLSGTSGYLAPEYLSEGKLTDKSDVYAFGVVLLELLIGRKPV EKMSPSLFQSIVTWAMPQLTDRSKLPNIVDPVIRDTMDLKHLYQVAAVAVLCVQPEPSYRPLITDVLHSFIP |
| >SEQ ID NO: 47<br>ATGATGCATCAAGACTCTTTGGACTCACAATTGCATGGACCAACTCATGGAACCGCATTAACCTGGCATCGAAGAATGAAAGTCGCACTT GATATTGCTCGAGGATTAGAGTATCTTCATGAACGATGCAACCCGCCTGTGATTCATAGAGATCTCAAGTCATCGAACATTTTGCTAGAT TCCAATTTCAATGCTAAAATTTCGAATTTTGCACTTGCTACCACTGAGCTCCATGCGAAGAACAAAGTTAAGCTTTCGGGTACTTCTGGT TATTTGGCTCCGGAATACCTATCCGAAGGTAAACTTACCGATAAAAGTGATGTATATGCATTCGGAGTAGTACTTCTTGAGCTTTTAATC GGTAGAAAACCAGTGGAGAAAATGTCACCATCTTTATTTCAATCTATTGTCACATGGGCAATGCCTCAGCTAACAGACCGGTCAAAGCTT CCAAACATTGTTGACCCTGTGATTAGAGATACAATGGACCTGAAGCACTTGTATCAAGTTGCTGCTGTAGCCGTACTTTGCGTGCAACCC GAACCAAGTTACAGACCGTTGATTACAGACGTACTACACTCATTCATTCCACTCGTACCCGTTGATCTTGGAGGGTCATTAAGAGCTTAA |
| >SEQ ID NO: 48<br>MMHQDSLDSQLHGPTHGTALTWHRRNIKVALDIARGLEYLHERCNPPVIHRDLKSSNILLDSNFNAKISNFALATIELHAKNKVKLSGTS GYLAPEYLSEGKLTDKSDVYAFGVVLLELLIGRKPVEKMSPSLFQSIVTWAMPQLTDRSKLPNIVDPVIRDTMDLKHLYQVAAVAVLCVQ PEPSYRPLITDVLHSFIPLVPVDLGGSLRA |
| >SEQ ID NO: 49<br>AATTTGAGAGGTGAGCTGGATTTGCTTCAGAGGATTCAGCATTCGAATATAGTGTCCCTTGTGGGCTTCTGCATTCATGAGGAGAACCGC TTCATTGTTTATGAGCTGATGGTGAATGGATCACTTGAAACACAGCTTCATGGGCCATCACATGGATCAGCTCTGAGTTGGCACATTCGG ATGAAGATTGCTCTTGATACAGCAAGGGGATTGGAGTATCTTCACGAGCACTGCAATCCACCAATCATCCATAGGGATCTGAAGTCGTCT AACATACTTTTGAATTCAGACTTTAATGCAAAGATTTCAGATTTTGGCCTTGCAGTGACAAGTGGAAATCGCAGCAAAGGGAATCTGAAG CTTTCCGGTACTTTGGGTTATGTTGCCCCTGAGTACTTACTAGATGGGAAGTTGACTGAGAAGAGCGATGTATATGCATTTGGAGTAGTA CTTCTTGAGCTTCTTTTGGGAAGGAGGCCAGTTGAGAAGATGGCACCATCTCAGTGTCAATCAATTGTTACATGGGCCATGCCCCAGCTA ATTGACAGATCCAAGCTCCCTACCATAATCGACCCCGTGATCAGGGACACGATGGATCGGAAGCACTTGTACCAAGTTGCTGCAGTGGCT GTGCTCTGCGTGCAGCCAGAACCAAGCTACAGGCCACTGATCACAGATGTCCTCCACTCTCTGATTCCCCTGGTGCCCATGGACCTTGGA GGGACGCTGAGGATCAACCCGGAATCGCCTTGCACGACACGAAATCAATCTCCCTGCTGA |

-continued

Sequences

>SEQ ID NO: 50
NLRGELDLLQRIQHSNIVSLVGFCIHEENRFIVYELMVNGSLETQLHGPSHGSALSWHIRMKIALDTARGLEYLHEHCNPPIIHRDLKSS
NILLNSDFNAKISDFGLAVTSGNRSKGNLKLSGTLGYVAPEYLLDGKLTEKSDVYAFGVVLLELLLGRRPVEKMAPSQCQSIVTWAMPQL
IDRSKLPTIIDPVIRDTMDRKHLYQVAAVAVLCVQPEPSYRPLITDVLHSLIPLVPMDLGGTLRINPESPCTTRNQSPC

>SEQ ID NO: 51
CGGGGGCTCTTATCACTCATTGCTGCTGCTACTGCACTGGGTACAAGCTTATTGCTCATGGGTTGCTTCTGGATTTATCATAGAAAGAAA
ATCCACAAATCTCATGACATTATTCATAGCCCAGATGTAGTTAAAGGTCTTGCATTATCCTCATATATTAGCAAATACAACTCCTTCAAG
TCGAATTGTGTGAAACGACATGTCTCGTTGTGGGAGTACAATACACTCGAGTCGGCCACAAATAGTTTTCAAGAAAGCGAGATCTTGGGT
GGAGGGGGGTTCGGGCTTGTGTACAAGGGAAAACTAGAAGACAACTTGTATGTAGCTGTGAAGAGGCTGGAAGTTGGAAGACAAAACGCA
ATTAAAGAATTCGAGGCTGAAATAGAGGTATTGGGCACGATTCAGCACCCGAATATAATTTCGTTGTTGGGATATAGCATTCATGCTGAC
ACGAGGCTGCTAGTTTATGAACTGATGCAGAATGGATCTCTGGAGTATCAACTACATGGACCTTCCCATGGATCAGCATTAGCGTGGCAT
AATAGATTGAAAATCGCACTTGATACAGCAAGGGGATTAGAATATTTACATGAACATTGCAAACCACCAGTTATCCATAGAGATCTGAAA
TCCTCCAATATTCTTCTAGATGCCAACTTCAATGCCAAGATCTCAGATTTTGGTCTTGCTGTGCGCGATGGGGCTCAAAACAAAAATAAC
ATTAAGCTCTCGGGAACCGTTGGCTATGTAGCTCCAGAATACCTATTAGATGGAATACTAACAGATAAAAGTGATGTTTATGGCTTCCGA
GTTGTA

>SEQ ID NO: 52
RGLLSLIAAATALGTSLLLMGCFWIYHRKKIHKSHDIIHSPDVVKGLALSSYISKYNSFKSNCVKRHVSLWEYNTLESATNSFQESEILG
GGGFGLVYKGKLEDNLYVAVKRLEVGRQNAIKEFEAEIEVLGTIQHPNIISLLGYSIHADTRLLVYELMQNGSLEYQLHGPSHGSALAWH
NRLKIALDTARGLEYLHEHCKPPVIHRDLKSSNILLDANFNAKISDFGLAVRDGAQNKNNIKLSGTVGYVAPEYLLDGILTDKSDVYGFR
VV

>SEQ ID NO: 53
GGGGATATACGTGTAGAATCAGCAACAAATAACTTCGGTGAAAGCGAGATATTAGGCGTAGGTGGATTTGGATGCGTGTATAAAGCTCGA
CTCGATGATAATTTGCATGTAGCTGTTAAAAGATTAGATGGTATTAGTCAAGACGCCATTAAAGAATTCCAGACGGAGGTGGATCTATTG
AGTAAAATTCATCATCCGAATATCATCACCTTATTGGGATATTGTGTTAATGATGAAACCAAGCTTCTTGTTTATGAACTGATGCATAAT
GGATCTTTAGAAACTCAATTACATGGGCCTTCCAGTGGATCCAATTTAACATGGCATTGCAGGATGAAGATTGCTCTAGATACAGCAAGA
GGATTAGAATATTTGCATGAGAACTGCAAACCATCGGTGATTCATAGAGATCTGAAATCATCTAATATCCTTCTGGATTCCAGCTTCAAT
GCTAAGCTTTCAGATTTTGGTCTTGCTATAATGGATGGGGCCCAGAACAAAAACAACATTAAGCTTTCAGGGACATTGGGTTATGTAGCT
CCCGAGTATCTTTTAGATGGAAAATTGACGGATAAAAGTGACGTGTATGCGTTTGGAGTTGTGCTTTTAGAGCTTTTACTTGGAAGGCGA
CCTGTAGAAAAATTAGCAGAGTCGCAATGCCAATCTATTGTCACTTGGGCTATGCCACAATTAACAGACAGATCAAAGCTTCCGAATATT
GTAGATCCCGTGATCAGATACACAATGGATCTCAAGCACCTGTACCAAGTTGCTGCGGTGGCTGTGTTATGTGTACAACCCGGACCAAGC
TACCGGCCATTTATAAACCGACGTCTTGCATTCTCTGATCCCTCTTGTTCCCCGTGA

>SEQ ID NO: 54
GDIRVESATNNFGESEILGVGGFGCVYKARLDDNLHVAVKRLDGISQDAIKEFQTEVDLLSKIHHPNIITLLGYCVNDETKLLVYELMHN
GSLETQLHGPSSGSNLTWHCRNIKIALDTARGLEYLHENCKPSVIHRDLKSSNILLDSSFNAKLSDFGLAIMDGAQNKNNIKLSGTLGYV
APEYLLDGKLTDKSDVYAFGVVLLELLLGRRPVEKLAESQCQSIVTWAMPQLTDRSKLPNIVDPVIRYTMDLKHLYQVAAVAVLCVQPGP
SYRPFINRRLAFSDPSCSP

>SEQ ID NO: 55
AAGTTGAACTGTGAATGTCAATATGCTGAGAGAGAATTTGAGAATGAGGTGGATTTGTTAAGTAAAATTCAACATCCAAATGTAATTTCT
CTACTGGGCTGTAGCAGTAATGAGGATTCAAGGTTTATTGTCTATGAGTTGATGCAAAATGGATCATTGGAAACTCAATTACATGGACCA
TCTCATGGCTCAGCATTGACTTGGCATATGAGGATGAAGATTGCTCTTGACACAGCTAGAGGTTTAAAATATCTGCATGAGCACTGCTAC
CCTGCAGTGATCCATAGAGATCTGAAATCTTCTAATATTCTTTTAGATGCAAACTTCAATGCCAAGCTTTCTGATTTTGGTCTTGCAATA
ACTGATGGGTCCCAAAACAAGAATAACATCAAGCTTTCAGGCACATTGGGGTATGTTGCCCCGGAGTATCTTTTAGATGGTAAATTGACA
GATAAAAGTGATGTGTATGCTTTTGGAGTTGTGCTTCTTGAGCTTCTATTAGGAAGAAAGCCTGTGGAAAAACTTACACCATCTCAATGC
CAGTCTATTGTCACATGGGCCATGCCACAGCTCACAGACAGATCCAAGCTTCCAAACATTGTGGATAATGTGATTAAGAATACAATGGAT
CCTAAGCACTTATACCAGGTTGCTGCTGTGGCTGTATTATGTGTGCAACCAGAGCCGTGCTACCGCCCTTTGATTGCAGATGTTCTACAC
TCCCTCATCCCTCTTGTACCTGTTGAGCTTGGAGGAACACTCAGAGTTGCACAAGTGACGCAGCAACCTAAGAATTCTAGTTAA

>SEQ ID NO: 56
KLNCECQYAEREFENEVDLLSKIQHPNVISLLGCSSNEDSRFIVYELMQNGSLETQLHGPSHGSALTWHMRMKIALDTARGLKYLHEHCY
PAVIHRDLKSSNILLDANFNAKLSDFGLAITDGSQNKNNIKLSGTLGYVAPEYLLDGKLTDKSDVYAFGVVLLELLLGRKPVEKLTPSQC
QSIVTWAMPQLTDRSKLPNIVDNVIKNTMDPKHLYQVAAVAVLCVQPEPCYRPLIADVLHSLIPLVPVELGGTLRVAQVTQQPKNSS

>SEQ ID NO: 57
CAGTTGCATGGACCTCCTCGTGGATCAGCTTTGAATTGGCATCTTCGCATGGAAATTGCATTGGATGTGGCTAGGGGACTAGAATACCTC
CATGAGCGCTGTAACCCCCCTGTAATCCATAGAGATCTCAAATCGTCTAATGTTCTATTGGATTCCTACTTCAATGCAAAGCTTTCTGAC
TTTTGGCCTAGCTATAGCTGGATGGAACTTAAACAAGAGCACCGTAAAGTCTTTCGGGAACTCTGGGATATGTGGCTCCAGAGTTACCTC
TTAGATGGGAAATTAACTGATAAGAGTGATGTCTATGCTTTCGGCATTATACTTCTGGAGCTTCTAATGGGGAGAAGACCATTGGAGAAA
CTAGCAGGAGCTCAGTGCCAATCTATCGTCACATGGGCAATGCCACAGCTTACTGACAGGTCAAAGCTCCCAAATATTGTTGATCCTGTC
ATCAGAAACGGAATGGGCCTCAAGCACTTGTATCAAGTTGCTGCTGTAGCCGTGCTATGTGTACAACCAGAACCAAGTTACCGACCACTG
ATAACAGATGTCCTGCACTCCTTCATTCCCCTTGTACCAATTGAGCTTGGTGGGTCCTTGAGAGTTGTGGATTCTGCATTATCTGTTAAC
GCATAA

>SEQ ID NO: 58
QLHGPPRGSALNWHLRMEIALDVARGLEYLHERCNPPVIHRDLKSSNVLLDSYFNAKLSDFWPSYSWMELKQEHRKVFRELWDMWLQSYL
LDGKLTDKSDVYAFGIILLELLMGRRPLEKLAGAQCQSIVTWAMPQLTDRSKLPNIVDPVIRNGMGLKHLYQVAAVAVLCVQPEPSYRPL
ITDVLHSFIPLVPIELGGSLRVVDSALSVNA

>SEQ ID NO: 59
ATGGAGATGGCGCTAACTCCATTGCCGCTCCTGTGTTCGTCCGTCTTGTTCTTGGTGCTATCTTCGTGCTCGTTGGCCAATGGGAGGGAT
ACGCCTTCTTCTTCTTCTTCTTCTTCTTCTTCTTCTTCTTCTTCTTCTTCTTCTTCTTCTTCTTCTTCTTCTTCTCCGGCGACGTCTACTGTG
GCCACCGGCATTTCCGCCGCCGCCGCCGCCGCCGCCAATGGACGGCCGCCTTGTCTTCGGCAGTTCCGGCGCCTCCGCCTGTTGTGATC

-continued

Sequences

GTAGTGCACCACCATTTCCACCGCGAGCTGGTCATCGCCGCCGTCCTCGCCTGCATCGCCACCGTCACGATCTTCCTTTCCACGCTCTAC
GCTTGGACACTATGGCGGCGATCTCGCCGGAGCACCGGCGGCAAGGTCACCAGGAGCTCAGACGCAGCGAAGGGGATCAAGCTGGTGCCG
ATCTTGAGCAGGTTCAACTCGGTGAAGATGAGCAGGAAGAGGCTGGTTGGGATGTTCGAGTACCCGTCGCTGGAGGCAGCGACAGAGAAG
TTCAGCGAGAGCAACATGCTCGGTGTCGGCGGGTTTGGCCGCGTCTACAAGGCGGCGTTCGACGCCGGAGTTACCGCGGCGGTGAAGCGG
CTCGACGGCGGCGGGCCCGACTGCGAGAAGGAATTCGAGAATGAGCTGGATTTGCTTGGCAGGATCAGGCACCCCAACATTGTGTCCCTC
TTGGGCTTCTGTATCCATGAGGGGAATCACTACATTGTTTATGAGCTGATGGAGAAGGGATCACTGGAAACACAGCTTCATGGGTCTTCA
CATGGATCAACTCTGAGCTGGCACATCCGGATGAAGATCGCCCTTGACACGGCCAGGGGATTAGAGTACCTTCATGAGCACTGCAGTCCA
CCAGTGATCCATAGGGATCTGAAATCGTCTAACATACTTTTGGATTCAGACTTCAATGCTAAGATTGCAGATTTTGGTCTTGCTGTGTCT
AGTGGGAGTGTCAACAAAGGGAGTGTGAAGCTCTCCGGGACCTTGGGTTATGTAGCTCCTGAGTACTTGTTGGATGGGAAGTTGACTGAA
AAGAGCGATGTATACGCGTTCGGAGTAGTGCTTCTAGAGCTCCTTATGGGGAGGAAGCCTGTTGAGAAGATGTCACCATCTCAGTGCCAA
TCAATTGTGACATGGGCAATGCCACAGTTGACCGACAGATCGAAGCTCCCCAGCATAGTTGACCCAGTGATCAAGGACACCATGGATCCA
AAACACCTGTACCAAGTTGCAGCAGTGGCTGTTCTATGCGTGCAGGCTGAACCAAGCTACAGGCCACTGATCACAGATGTGCTCCACTCT
CTTGTTCCTCTAGTGCCGACGGAGCTCGGAGGAACACTAAGAGCTGGAGAGCCACCTTCCCCGAACCTGAGGAATTCTCCATGCTGA

>SEQ ID NO: 60
MEMALTPLPLLCSSVLFLVLSSCSLANGRDTPSSSSSSSSSSSSSSSSSSSSSSPATSTVATGISAAAAAAANGTAALSSAVPAPPPVVI
VVHHHFHRELVIAAVLACIATVTIFLSTLYAWTLWRRSRRSTGGKVTRSSDAAKGIKLVPILSRFNSVKMSRKRLVGMFEYPSLEAAIEK
FSESNMLGVGGFGRVYKAAFDAGVTAAVKRLDGGGPDCEKEFENELDLLGRIRHPNIVSLLGFCIHEGNHYIVYELMEKGSLETQLHGSS
HGSTLSWHIRMKIALDTARGLEYLHEHCSPPVIHRDLKSSNILLDSDFNAKIADFGLAVSSGSVNKGSVKLSGTLGYVAPEYLLDGKLTE
KSDVYAFGVVLLELLMGRKPVEKMSPSQCQSIVTWAMPQLTDRSKLPSIVDPVIKDTMDPKHLYQVAAVAVLCVQAEPSYRPLITDVLHS
LVPLVPTELGGTLRAGEPPSPNLRNSPC

>SEQ ID NO: 61
TACTCTCTTTTACAAACTGCTACGAACAACTTCAGCTCCTCCAATTTGCTGGGCGAGGGAAGTTTCGGGCATGTGTATAAAGCGAGACTC
GATTATGATGTCTATGCCGCTGTAAAGAGACTTACCAGCGTAGGAAAACAGCCCCAAAAAGAACTCCAGGGAGAGGTGGATCTGATGTGC
AAGATAAGACATCCCAACTTGGTGGCTCTCCTGGGCTATTCAAATGACGGCCCAGAGCCCTTGGTTGTGTACGAGCTCATGCAGAATGGT
TCACTTCATGATCAGCTTCATGGCCCCTCATGCGGGAGTGCACTCACCTGGTACCTACGACTAAAGATTGCTCTTGAAGCTGCCAGCAGA
GGACTGGAGCACCTGCATGAAAGCTGCAAGCCTGCAATAATCCACAGAGACTTCAAGGCATCCAACATCCTCTTGGACGCCAGCTTCAAT
GCGAAGGTGTCCGACTTTGGTATAGCGGTAGCTCTGGAGGAAGGTGGCGTGGTGAAAGACGACGTACAAGTGCAAGGCACCTTCGGGTAC
ATTGCTCCTGAGTACCTGATGGACGGGACATTGACAGAGAAGAGTGATGTTTACGGATTTGGAGTAGTATTGCTTGAGCTGCTGACAGGC
AGACTGCCCATTGATACGTCCTTACCACTCGGATCGCAATCTCTAGTGACATGGGTAACACCCATACTAACTAACCGAGCAAAGCTGATG
GAAGTTATCGACCCCACCCTTCAAGATACGCTGAACGTGAAGCAACTTCACCAGGTGGCCGCAGTGGCAGTCCTTTGCGTCCAAGCGGAA
CCCAGCTACCGCCCTCTCATCGCCGACGTGGTTCAGTCACTGGCTCCGCTGGTGCCTCAAGAGCTCGGCGGCGCATTGCGA

>SEQ ID NO: 62
YSLLQTATNNFSSSNLLGEGSFGHVYKARLDYDVYAAVKRLTSVGKQPQKELQGEVDLMCKIRHPNLVALLGYSNDGPEPLVVYELMQNG
SLHDQLHGPSCGSALTWYLRLKIALEAASRGLEHLHESCKPAIIHRDFKASNILLDASFNAKVSDFGIAVALEEGGVVKDDVQVQGTFGY
IAPEYLMDGTLTEKSDVYGFGVVLLELLTGRLPIDTSLPLGSQSLVTWVTPILTNRAKLMEVIDPTLQDTLNVKQLHQVAAVAVLCVQAE
PSYRPLIADVVQSLAPLVPQELGGALR

>SEQ ID NO: 63
ACCTCAGATGCCTATAGGGGTATTCCACTCATGCCTCTCCTGAATCGTTTGAACTCCCGTATTTCCAAGAAGAAGGGATGTGCAACTGCA
ATTGAATATTCTAAGCTGCAAGCAGCTACAAATAACTTCAGCAGCAATAACATTCTTGGAGAGGGTGGATTTGCGTGTGTATACAAGGCC
ATGTTTGATGATGATTCCTTTGCTGCTGTGAAGAAGCTAGATGAGGGTAGCAGACAGGCTGAGCATGAATTTCAGAATGAAGTGGAGCTG
ATGAGCAAAATCCGACATCCAAACCTTGTTTCTTTGCTTGGGTTCTGCTCTCATGAAAATACACGGTTCTTAGTATATGATCTGATGCAG
AATGGCTCTTTGGAAGACCAATTACATGGGCCATCTCACGGATCTGCACTTACATGGTTTTTGCGCATAAAGATAGCACTTGATTCAGCA
AGGGGTCTAGAACACTTGCATGAGCACTGCAACCCTGCAGTGATTCATCGAGATTTCAAATCATCAAATATTCTTCTTGATGCAAGCTTC
AACGCCAAGCTTTCAGATTTTGGTCTTGCAGTAACAAGTGCAGGATGTGCTGGCAATACAAATATTGATCTAGTAGGGACATTGGGATAT
GTAGCTCCAGAATACCTACTTGATGGTAAATTGACAGAGAAAAGTGATGTCTATGCATATGGAGTTGTTTTGTTGGAGCTACTTTTTGGA
AGAAAGCCAATTGATAAATCTCTACCAAGTGAATGCCAATCTCTCATTTCTTGGGCAATGCCACAGCTAACAGATAGAGAAAAGCTCCCA
ACTATAGTAGACCCCATGATCAAAGGCACAATGAACTTGAAACACCTATATCAAGTAGCAGCTGTTGCAATGCTATGTGTGCAGCCAGAA
CCCAGTTACAGGCCATTAATAGCTGACGTTGTGCACTCTCTCATTCCTCTCGTACCAATAGAACTCGGGGGAACTTTAAAGCTCTCTAAT
GCACGACCCACTGAGATGAAGTTATTTACTTCTTCCCAATGCAGTGTTGAGATTGCTTCCAACCCAAAATTGTGA

>SEQ ID NO: 64
TSDAYRGIPLMPLLNRLNSRISKKKGCATAIEYSKLQAATNNFSSNNILGEGGFACVYKAMFDDDSFAAVKKLDEGSRQAEHEFQNEVEL
MSKIRHPNLVSLLGFCSHENTRFLVYDLMQNGSLEDQLHGPSHGSALTWFLRIKIALDSARGLEHLHEHCNPAVIHRDFKSSNILLDASF
NAKLSDFGLAVTSAGCAGNTNIDLVGTLGYVAPEYLLDGKLTEKSDVYAYGVVLLELLFGRKPIDKSLPSECQSLISWAMPQLTDREKLP
TIVDPMIKGTMNLKHLYQVAAVAMLCVQPEPSYRPLIADVVHSLIPLVPIELGGTLKLSNARPIEMKLFTSSQCSVEIASNPKL

>SEQ ID NO: 65
AATTCGGCACGAGGAGAACACTTGCACGAGCACTGCAACCCTGCAGTGATTCACCGAGATTTCAAATCATCAAATATTCTTCTTGATGCA
AGCTTCAACGCCAAGCTTTCAGATTTTGGTCTTGCAGTAAAAAGTGCAGGATGTGCTGGTAACACAAATATTGATCTAGTAGGGACATTG
GGATATGTAGCTCCAGAATACATGCTTGATGGTAAATTGACAGAGAAAAGTGATGTCTATGCATATGGAGTTGTTTTGTTAGAGCTACTT
TTTGGAAGAAAGCCAATTGATAAATCTCTACCAAGTGAATGCCAATCTCTCATTTCTTGGGCAATGCCACAGCTAACAGATAGAGAAAAG
CTCCCGACTATAATAGATCCCATGATCAAAGGCGCAATGAACTTGAAACACCTATATCAAGTGGCAGCTGTTGCAGTGCTATGTGTGCAG
CCAGAACCCAGTTACAGGCCATTAATAGCTGACGTTGTGCACTCTCTCATTCCTCTCGTACCAGTAGAACTTGGGGGAACATTAAAGTCA
TCACCCACTGAGATGAAGTCATTTGCTTCTTCCCAATGCAGTGCCCACGTTGCTTC

>SEQ ID NO: 66
NSARGEHLHEHCNPAVIHRDFKSSNILLDASFNAKLSDFGLAVKSAGCAGNTNIDLVGTLGYVAPEYMLDGKLTEKSDVYAYGVVLLELL
FGRKPIDKSLPSECQSLISWAMPQLTDREKLPTIIDPMIKGAMNLKHLYQVAAVAVLCVQPEPSYRPLIADVVHSLIPLVPVELGGTLKS
SPTEMKSFASSQCSAHVAS

>SEQ ID NO: 67
ATGTTCTTGTTTCCTAAAACAGTTCCTATTTGGTTTTTTCATCTGTGTCTAGTAGCAGTTCATGCCATACAAGAAGACCCACCTGTCCCT
TCACCATCTCCCTCTCTCATTTCTCCTATTTCAACTTCAATGGCTGCCTTCTCTCCAGGGGTTGAATCGGAAATGGGAATCAAAGACCAC

Sequences

CCCCAGCATGATGACCTCCACAGGAAAATAATCTTGTTGCTCACTGTTGCTTGTTGCATACTTGTTATCATCCTTCTTTCTTTGTGTTCT
TGTTTCATTTACTATAAGAAGTCCTCACAAAAGAAAAAAGCTACTCGGTGTTCAGATGTGGAGAAAGGGCTTTCATTGGCACCATTTTTG
GGCAAATTCAGTTCCTTGAAAATGGTTAGTAATAGGGGATCTGTTTCATTAATTGAGTATAAGATACTAGAGAAAGGAACAAACAATTTT
GGCGATGATAAATTGTTGGGAAAGGGAGGATTTGGACGTGTATATAAGGCTGTAATGGAAGATGACTCAAGTGCTGCAGTCAAGAAACTA
GACTGCGCAACTGATGATGCGCAGAGAGAATTTGAGAATGAGGTGGATTTGTTAAGCAAATTTCACCATCCAAATATAATTTCTATTGTG
GGTTTTAGTGTTCATGAGGAGATGGGGTTCATTATTTATGAGTTAATGCCAAATGGGTGCCTTGAAGATCTACTGCATGGACCTTCTCGT
GGATCTTCACTAAATTGGCATTTAAGGTTGAAAATTGCTCTTGATACAGCAAGAGGATTAGAATATCTGCATGAATTCTGCAAGCCAGCA
GTGATCCATAGAGATCTGAAATCATCGAATATTCTTTTGGACGCCAACTTCAATGCCAAGCTGTCAGATTTTGGTCTTGCTGTAGCTGAT
AGCTCTCATAACAAGAAAAAGCTCAAGCTTTCAGGCACTGTGGGTTATGTAGCCCCAGAGTATATGTTAGATGGTGAATTGACGGATAAG
AGTGATGTCTATGCTTTTGGAGTTGTGCTTCTAGAGCTTCTATTAGGAAGAAGGCCTGTAGAAAAACTGACACCAGCTCATTGCCAATCT
ATAGTAACATGGGCCATGCCTCAGCTCACTAACAGAGCTGTGCTTCCAACCCTTGTGGATCCTGTGATCAGAGATTCAGTAGATGAGAAG
TACTTGTTCCAGGTTGCAGCAGTAGCCGTGTTGTGTATTCAACCAGAGCCAAGTTACCGCCCTCTCATAACAGATGTTGTGCACTCTCTC
GTCCCATTAGTTCCTCTTGAGCTTGGAGGGACACTAAGAGTTCCACAGCCTACAACTCCCAGAGGTCAACGACAAGGCCCATCAAAGAAA
CTGTTTTTGGATGGTGCTGCCTCTGCT

>SEQ ID NO: 68
MFLFPKTVPIWFFHLCLVAVHAIQEDPPVPSPSPSLISPISTSMAAFSPGVESEMGIKDHPQHDDLHRKIILLLTVACCILVIILLSLCS
CFIYYKKSSQKKKATRCSDVEKGLSLAPFLGKFSSLKMVSNRGSVSLIEYKILEKGTNNFGDDKLLGKGGFGRVYKAVMEDDSSAAVKKL
DCATDDAQREFENEVDLLSKFHHPNIISIVGFSVHEEMGFIIYELMPNGCLEDLLHGPSRGSSLNWHLRLKIALDTARGLEYLHEFCKPA
VIHRDLKSSNILLDANFNAKLSDFGLAVADSSHNKKKLKLSGTVGYVAPEYMLDGELTDKSDVYAFGVVLLELLLGRRPVEKLTPAHCQS
IVTWAMPQLTNRAVLPTLVDPVIRDSVDEKYLFQVAAVAVLCIQPEPSYRPLITDVVHSLVPLVPLELGGTLRVPQPTTPRGQRQGPSKK
LFLDGAASA

>SEQ ID NO: 69
GCTGCTGCGGTGAAGAGATTGGATGGTGGGGCTGGGGCACATGATTGCGAGAAGGAATTCGAGAATGAGTTAGATTTGCTTGGAAAGATT
CGGCATCCGAACATTGTGTCCCTTGTGGGCTTCTGTATTCATGAGGAGAACCGTTTCATTGTTTATGAGCTGATAGAGAATGGGTCGTTG
GATTCACAACTTCATGGGCCATCACATGGTTCAGCTCTGAGCTGGCATATTCGGATGAAGATTGCTCTTGACACGGCAAGGGGATTAGAG
TACCTGCATGAGCACTGCAACCCACCAGTTATCCATAGGGATCTGAAGTCATCTAACATACTTTTAGATTCAGACTTCAGTGCTAAGATT
TCAGATTTTGGCCTTGCGGTGATTAGTGGGAATCACAGCAAAGGGAATTTAAAGCTTTCTGGGACTATGGGCTATGTGGCCCCTGAGTAC
TTATTGGATGGGAAGTTGACTGAGAAGAGCGATGTATATGCGTTTGGGGTGGTACTTCTAGAACTTCTACTGGGAAGGAAACCTGTTGAG
AAGATGGCACAATCTCAATGCCAATCAATTGTTACATGGGCCATGCCTCAGCTAACTGATAGATCCAAACTCCCTAACATAATTGATCCC
ATGATCAAGAACACAATGGATCTGAAACACTTGTACCAAGTTGCTGCAATGGCTGTGCTCTGA

>SEQ ID NO: 70
AAAVKRLDGGAGAHDCEKEFENELDLLGKIRHPNIVSLVGFCIHEENRFIVYELIENGSLDSQLHGPSHGSALSWHIRNIKIALDTARGL
EYLHEHCNPPVIHRDLKSSNILLDSDFSAKISDFGLAVISGNHSKGNLKLSGTMGYVAPEYLLDGKLIEKSDVYAFGVVLLELLLGRKPV
EKMAQSQCQSIVTWAMPQLTDRSKLPNIIDPMIKNTMDLKHLYQVAAMAVL

>SEQ ID NO: 71
ACCCTCGGTTATGTAGCTCCTGAGTATCTGTTAGATGGTAAGTTAACAGAGAAAAGCGATGTGTATGGGTTTGGAGTAGTGTTACTCGAG
CTTCTGCTTGGGAAGAAGCCTATGGAGAAAGTGGCAACAACAGCAACTCAGTGCCAGATGATAGTCACATGGACCATGCCTCAGCTCACT
GACAGAACGAAACTTCCGAATATCGTGGATCCGGTGATCAGAAACTCCATGGATTTAAAGCACTTGTACCAGGTTGCTGCTGTGGCAGTA
TTGTGTGTGCAGCCAGAACCGAGTTATCGGCCATTGATAACTGATATTTTGCATTCTCTTGTGCCCCTTGTCCCTGTTGAGCTTGGTGGG
ACGCTCAGGAACTCGATAACAATGGCTACAACAACAATATCTCCTGAAAGCTAA

>SEQ ID NO: 72
TLGYVAPEYLLDGKLIEKSDVYGFGVVLLELLLGKKPMEKVATTATQCQMIVTWTMPQLTDRTKLPNIVDPVIRNSMDLKHLYQVAAVAV
LCVQPEPSYRPLITDILHSLVPLVPVELGGTLRNSITMATTTISPES

>SEQ ID NO: 73
CGGCACGAGGGGCTGGTGGCCATGATCGAGTACCCGTCGCTGGAGGCGGCGACGGGCAAGTTCAGCGAGAGCAACGTGCTCGGCGTCGGC
GGGTTCGGCTGCGTCTACAAGGCGGCGTTCGACGGCGGCGCCACCGCCGCCGTGAAGAGGCTCGAAGGCGGCGAGCCGGACTGCGAGAAG
GAGTTCGAGAATGAGCTGGACTTGCTTGGCAGGATCAGGCACCCAAACATAGTGTCCCTCCTGGGCTTCTGCGTCCATGGTGGCAATCAC
TACATTGTTTATGAGCTCATGGAGAAGGGATCATTGGAGACACAACTGCATGGGCCTTCACATGGATCGGCTATGAGCTGGCACGTCCGG
ATGAAGATCGCGCTCGACACGGCGAGGGGATTAGAGTATCTTCATGAGCACTGCAATCCACCAGTCATCCATAGGGATCTGAAATCGTCT
AATATACTCTTGGATTCAGACTTCAATGCTAAGATTGCAGATTTTGGCCTTGCAGTGACAAGTGGGAATCTTGACAAAGGGAACCTGAAG
ATCTCTGGGACCTTGGGATATGTAGCTCCCGAGTACTTATTAGATGGGAAGTTGACCGAGAAGAGCGACGTCTACGCGTTTGGAGTAGTG
CTTCTAGAGCTCCTGATGGGGAGGAAGCCTGTTGAGAAGATGTCACCATCTCAGTGCCAATCAATTGTGTCATGGGCCATGCCTCAGCTA
ACCGACAGATCGAAGCTACCCAACATCATCGACCCGGTGATCAAGGACACAATGGACCCAAAGCATTTATACCAAGTTGCGGCGGTGGCC
GTTCTATGCGTGCAGCCCGAACCGAGTTACAGACCGCTGATAACAGACGTTCTCCACTCCCTTGTTCCTCTGGTACCCGCGGATCTCGGG
GGAACGCTCAGAGTTACAGAGCCGCATTCTCCACACCAAATGTACCATCCCTCTTGAGAAGTGATCCTACAAGTTTCGTCGAAGCGGGG
AAAGCGAATNTATACGGTCCAGCGGTAGATGGCTGTTATTTTGGTACTTATATCTCACCCTGTCCTGCTGCTTATCTTAGGATGAGTGAN
GAGCTCCNACCTGCTGCTTTTGCTGGTTGGGCAGAGAGAATACAGTTCTGGTTAGGATTG

>SEQ ID NO: 74
RHEGLVAMIEYPSLEAATGKFSESNVLGVGGFGCVYKAAFDGGATAAVKRLEGGEPDCEKEFENELDLLGRIRHPNIVSLLGFCVHGGNH
YIVYELMEKGSLETQLHGPSHGSAMSWHVRMKIALDTARGLEYLHEHCNPPVIHRDLKSSNILLDSDFNAKIADFGLAVTSGNLDKGNLK
ISGTLGYVAPEYLLDGKLTEKSDVYAFGVVLLELLMGRKPVEKMSPSQCQSIVSWAMPQLTDRSKLPNIIDPVIKDTMDPKHLYQVAAVA
VLCVQPEPSYRPLITDVLHSLVPLVPADLGGNAQSYRAAFSTPNVPSLLRSDPTSFVEAGKANXYGPAVDGCYFGTYISPCPAAYLRMSX
ELXPAAFAGWAERIQFWLGL

>SEQ ID NO: 75
ATGAAAGTGATTGGGAGAAAGGGTTATGTCTCTTTTATTGATTATAAGGTACTAGAAACTGCAACAAACAATTTTCAGGAAAGTAATATC
CTGGGTGAGGGCGGGTTTGGTTGCGTCTACAAGGCGCGGTTGGATGATAACTCCCATGTGGCTGTGAAGAAGATAGATGGTAGAGGCCAG
GATGCTGAGAGAGAATTTGAGAATGAGGTGGATTTGTTGACTAAAATTCAGCACCCAAATATAATTTCTCTCCTGGGTTACAGCAGTCAT
GAGGAGTCAAAGTTTCTTGTCTATGAGCTGATGCAGAATGGATCTCTGGAAACTGAATTGCACGGACCTTCTCATGGATCATCTCTAACT
TGGCATATTCGAATGAAAATCGCTCTGGATGCAGCAAGAGGATTAGAGTATCTACATGAGCACTGCAACCCACCAGTCATCCATAGAGAT

| Sequences |
|---|
| CTTAAATCATCTAATATTCTTCTGGATTCAAACTTCAATGCCAAGCTTTCGGATTTTGGTCTAGCTGTAATTGATGGGCCTCAAAACAAG AACAACTTGAAGCTTTCAGGCACCCTGGGTTATCTAGCTCCTGAGTATCTTTTAGATGGTAAACTGACTGATAAGAGTGATGTGTATGCA TTTGGAGTGGTGCTTCTAGAGCTACTACTGGGAAGAAAGCCTGTGGAAAAACTGGCACCAGCTCAATGCCAGTCCATTGTCACATGGGCC ATGCCACAGCTGACTGACAGATCAAAGCTCCCAGGCATCGTTGACCCTGTGGTCAGAGACACGATGGATCTAAAGCATTTATACCAAGTT GCTGCTGTAGCTGTGCTATGTGTGCAACCAGAACCAAGTTACCGGCCATTGATAACAGATGTTCTGCACTCCCTCATCCCACTCGTTCCA GTTGAGTTGGGAGGGATGCTAAAAGTTACCCAGCAAGCGCCGCCTATCAACACCACTGCACCTTCTGCTGGAGGTTGA |
| >SEQ ID NO: 76<br>MKVIGRKGYVSFIDYKVLETATNNFQESNILGEGGFGCVYKARLDDNSHVAVKKIDGRGQDAEREFENEVDLLTKIQHPNIISLLGYSSH EESKFLVYELMQNGSLEIELHGPSHGSSLTWHIRNIKIALDAARGLEYLHEHCNPPVIHRDLKSSNILLDSNFNAKLSDFGLAVIDGPQN KNNLKLSGTLGYLAPEYLLDGKLTDKSDVYAFGVVLLELLLGRKPVEKLAPAQCQSIVTWAMPQLTDRSKLPGIVDPVVRDTMDLKHLYQ VAAVAVLCVQPEPSYRPLITDVLHSLIPLVPVELGGMLKVTQQAPPINTTAPSAGG |
| >SEQ ID NO: 77<br>ATGCCGCCGCCATCGCCGCTCCTCCGTTCCTCCGCCTTCGTCGTCTTGCTGCTCCTGGTGTGTCGCCCGTTGTTGGTCGCCAATGGGAGG GCCACGCCGCCTTCTCCGGGATGGCCACCGGCGGCTCAGCCCGCGCTGCAGCCTGCACCCACCGCCAGCGGCGGCGTGGCCTCCGTGCTT CCTTCGGCCGTGGCGCCTCCTCCCTTAGGTGTGGTTGTGGCGGAGAGGCACCACCACCTCAGCAGGGAGCTCGTCGCTGCCATTATCCTC TCATCCGTCGCCAGCGTCGTGATCCCCATTGCCGCGCTGTATGCCTTCTTGCTGTGGCGACGATCACGGCGAGCCCTGGTGGATTCCAAG GACACCCAGAGCATAGATACCGCAAGGATTGCTTTTGCGCCGATGTTGAACAGCTTTGGCTCGTACAAGACTACCAAGAAGAGTGCCGCG GCGATGATGGATTACACATCTTTGGAGGCAGCGACAGAAAACTTCAGTGAGAGCAATGTCCTTGGATTTGGTGGGTTTGGGTCTGTGTAC AAAGCCAATTTTGATGGGAGGTTTGCTGCTGCGGTGAAGAGACTGGATGGTGGGGCACATGATTGCAAGAAGGAATTCGAGAATGAGCTA GACTTGCTTGGGAAGATTCGACATCCGAACATCGTGTCCCTTGTGGGCTTCTGCATTCATGAGGAGAACCGTTTCGTTGTTTATGAGCTG ATGGAGAGTGGGTCGTTGGATTCGCAACTTCATGGGCCATCACATGGTTCAGCTCTGAGCTGGCATATTCGGATGAAGATTGCTCTCGAC ACAGCAAGGGGATTAGAGTACCTGCATGAGCACTGCAACCCACCGGTTATCCATAGGGATCTTAAGTCATCTAACATACTTTTAGATTCA GACTTCAGCGCTAAGATTTCAGACTTTGGCCTGGCAGTGACTAGTGGGAATCACAGCAAAGGGAATTTAAAGCTTTCTGGGACTATGGGC TATGTGGCTCCTGAGTACTTATTAGATGGGAAGCTGACTGAGAAGAGCGATGTATACGCGTTTGGGGTAGTACTTCTAGAACTCCTGCTG GGAAGGAAACCTGTCGAGAAGATGGCACAATCTCAGTGCCGATCAATCGTTACATGGGCCATGCCTCAGCTAACTGATAGATCCAAGCTC CCGAACATAATTGATCCCATGATCAAGAACACAATGGATCTGAAACACTTGTACCAAGTTGCTGCAGTGGCCGTGCTCTGCGTGCAGCCA GAGCCGAGTTACAGGCCACTGATCACCGACGTGCTTCACTCACTGGTACCTCTAGTGCCCACGGAGCTTGGAGGAACGCTGAGGATCGGC CCGGAATCGCCCTACCTACGCTACTAA |
| >SEQ ID NO: 78<br>MPPPSPLLRSSAFVVLLLLVCRPLLVANGRATPPSPGWPPAAQPALQPAPTASGGVASVLPSAVAPPPLGVVVAERHHHLSRELVAAIIL SSVASVVIPIAALYAFLLWRRSRRALVDSKDTQSIDTARIAFAPMLNSFGSYKTTKKSAAAMMDYTSLEAATENFSESNVLGFGGFGSVY KANFDGRFAAAVKRLDGGAHDCKKEFENELDLLGKIRHPNIVSLVGFCIHEENRFVVYELMESGSLDSQLHGPSHGSALSWHIRNIKIAL DTARGLEYLHEHCNPPVIHRDLKSSNILLDSDFSAKISDFGLAVTSGNHSKGNLKLSGTMGYVAPEYLLDGKLTEKSDVYAFGVVLLELL LGRKPVEKMAQSQCRSIVTWAMPQLTDRSKLPNIIDPMIKNTMDLKHLYQVAAVAVLCVQPEPSYRPLITDVLHSLVPLVPIELGGTLRI GPESPYLRY |
| >SEQ ID NO: 79<br>ATGTTGCTCGCGTGTCCTGCAGTGATCATCGTGGAGCGCCACCGTCATTTCCACCGTGAGCTAGTCATCGCCTCCATCCTCGCCTCAATC GCCATGGTCGCGATTATCCTCTCCACGCTGTACGCGTGGATCCCGCGCAGGCGGTCCCGCCGGCTGCCCCGCGGCATGAGCGCAGACACC GCGAGGGGGATCATGCTGGCGCCGATCCTGAGCAAGTTCAACTCGCTCAAGACGAGCAGGAAGGGGCTCGTGGCGATGATCGAGTACCCG TCGCTGGAGGCAGCGACAGGGGGGTTCAGTGAGAGCAACGTGCTCGGCGTAGGCGGCTTCGGTTGCGTCTACAAGGCAGTCTTCGATGGC GGCGTTACCGCGGCGGTCAAGAGGCTGGAGGGAGGTGGCCCTGAGTGCGAGAAGGAATTCGAGAATGAGCTGGATCTGCTTGGCAGGATT CGGCACCCCAACATCGTGTCCCTGCTGGGCTTTTGTGTTCACGAGGGGAATCACTACATTGTTTATGAGCTCATGGAGAAGGGATCCCTG GACACACAGCTGCATGGGGCCTCACATGGATCAGCGCTGACCTGGCATATCCGGATGAAGATCGCACTCGACATGGCCAGGGGATTAGAA TACCTCCATGAGCACTGCAGTCCACCAGTGATCCATAGGGATCTGAAGTCATCTAACATACTTTTAGATTCTGACTTCAATGCTAAGATT TCAGATTTTGGTCTTGCAGTGACCAGTGGGAACATTGACAAGGGAAGCATGAAGCTTTCTGGGACCTTGGGTTATGTGGCCCCTGAGTAC CTATTAGATGGGAAGCTGACTGAAAAGAGTGACGTATATGCATTTGGAGTGGTGCTTCTTGAGCTACTAATGGGAAGGAAGCCTGTCGAG AAGATGAGTCAAACTCAGTGCCAATCAATTGTGACGTGGGCCATGCCGCAGCTGACTGACAGAACAAAACTTCCCAACATAGTTGACCCA GTGATCAGGGACACCATGGATCCAAAGCATTTGTACCAAGTGGCAGCAGTGGCAGTTCTATGTGTGCAACCAGAACCAAGTTACAGACCG CTGATTACTGATGTTCTCCACTCTCTTGTCCCTCTAGTCCCTGTGGAGCTCGGAGGGACACTGAGGGTTGTAGAGCCACCTTCCCCAAAC CTAAAACATTCTCCTTGT |
| >SEQ ID NO: 80<br>MLLACPAVIIVERHRHFHRELVIASILASIAMVAIILSTLYAWIPRRRSRRLPRGMSADTARGIMLAPILSKFNSLKTSRKGLVAMIEYP SLEAATGGFSESNVLGVGGFGCVYKAVFDGGVTAAVKRLEGGGPECEKEFENELDLLGRIRHPNIVSLLGFCVHEGNHYIVYELMEKGSL DTQLHGASHGSALTWHIRMKIALDMARGLEYLHEHCSPPVIHRDLKSSNILLDSDFNAKISDFGLAVTSGNIDKGSMKLSGTLGYVAPEY LLDGKLTEKSDVYAFGVVLLELLMGRKPVEKMSQTQCQSIVTWAMPQLTDRTKLPNIVDPVIRDTMDPKHLYQVAAVAVLCVQPEPSYRP LITDVLHSLVPLVPVELGGTLRVVEPPSPNLKHSPC |
| >SEQ ID NO: 81<br>ATGAAGAAGAAGCTTGTGCTGCATCTGCTTCTTTTCCTTGTTTGTGCTCTTGAAAACATTGTTTTGGCCGTACAAGGCCCTGCTTCATCA CCCATTTCTACTCCCATCTCTGCTTCAATGGCTGCCTTCTCTCCAGCTGGGATTCAACTTGGAGGTGAGGAGCACAAGAAAATGGATCCA ACCAAGAAAATGTTATTAGCTCTCATTCTTGCTTGCTCTTCATTGGGTGCAATTATCTCTTCCTTGTTCTGTTTATGGATTTATTACAGG AAGAATTCAAGCAAATCCTCTAAAAATGGCGCTAAGAGCTCAGATGGTGAAAAAGGGAATGGTTTGGCACCATATTTGGGTAAATTCAAG TCTATGAGGACGGTTTCCAAAGAGGGTTATGCTTCGTTTATGGACTATAAGATACTTGAAAAAGCTACAAACAAGTTCCATCATGGTAAC ATTCTGGGTGAGGGTGGATTTGGATGTGTTTACAAGGCTCAATTCAATGATGGTTCTTATGCTGCTGTTAAGAAGTTGGACTGTGCAAGC CAAGATGCTGAAAAAGAATATGAGAATGAGGTGGGTTTGCTATGTAGATTTAAGCATTCCAATATAATTTCACTGTTGGGTTATAGCAGT GATAACGATACAAGGTTTATTGTTTATGAGTTGATGGAAAATGGTTCTTTGGAAACTCAATTACATGGACCTTCTCATGGTTCATCATTA ACTTGGCATAGGAGGATGAAAATTGCTTTGGATACAGCAAGAGGATTAGAATATCTACATGAGCATTGCAATCCACCAGTCATCCATAGA GATCTGAAATCATCTAATATACTTTTGGATTTGGACTTCAATGCAAAGCTTTCAGATTTTGGTCTTGCAGTAACTGATGCGGCAACAAAC AAGAATAACTTGAAGCTTTCGGGTACTTTAGGTTATCTAGCTCCAGAATACCTTTTAGATGGTAAATTAACAGATAAGAGTGATGTTTAT GCATTCGGTGTTGTGCTGCTCGAACTTCTATTGGGACGAAAGGCTGTTGAAAAATTATCACAACTCAGTGCCAATCTTAGGTCCATTTGG GCATAG |

-continued

| Sequences |
| --- |

>SEQ ID NO: 82
MKKKLVLHLLLFLVCALENIVLAVQGPASSPISTPISASMAAFSPAGIQLGGEEHKKMDPTKKMLLALILACSSLGAIISSLFCLWIYYR
KNSSKSSKNGAKSSDGEKGNGLAPYLGKFKSMRTVSKEGYASFMDYKILEKATNKFHHGNILGEGGFGCVYKAQFNDGSYAAVKKLDCAS
QDAEKEYENEVGLLCRFKHSNIISLLGYSSDNDTRFIVYELMENGSLETQLHGPSHGSSLTWHRRNIKIALDTARGLEYLHEHCNPPVIH
RDLKSSNILLDLDFNAKLSDFGLAVTDAATNKNNLKLSGTLGYLAPEYLLDGKLTDKSDVYAFGVVLLELLLGRKAVEKLSQLSANLRSI
WA

>SEQ ID NO: 83
GGAGTGGGAATTGAGAAGCAGCCACCCACCCACCCACCCTATGGATAAAAATAGAAGGCTGTTGATAGCACTCATTGTAGCTTCTACTGC
ATTAGGACTAATCTTTATCTTCATCATTTTATTCTGGATTTTTCACAAAAGATTTCACACCTCAGATGTTGTGAAGGGAATGAGTAGGAA
AACATTGGTTTCTTTAATGGACTACAACATACTTGAATCAGCCACCAACAAATTTAAAGAAACTGAGATTTTAGGTGAGGGGGGTTTTGG
ATGTGTGTACAAAGCTAAATTGGAAGACAATTTTTATGTAGCTGTCAAGAAACTAACCCAAAATTCCATTAAAGAATTTGAGACTGAGTT
AGAGTTGTTGAGTCAAATGCAACATCCCAATATTATTTCATTGTTGGGATATTGCATCCACAGTGAAACAAGATTGCTTGTCTATGAACT
CATGCAAAATGGATCACTAGAAACTCAATTACATGGGCCTTCCCGTGGATCAGCATTAACTTGGCATCGCAGGATAAAAATTGCCCTTGA
TGCAGCAAGAGGAATAGAATATTTACATGAGCAGCGCCATCCCCCTGTAATTCATAGAGATCTGAAATCATCTAATATTCTTTTAGATTC
CAACTTCAATGCAAAGGTAAAACTTTTTATGTAGAAATTATACTAGGACTAGTTTTCCCTCTATTAATCTTGTGTTGTGATTAATTTTAG
CTGTCAGATTTTGGTCTTGCTGTGTTGAGTGGGGCTCAAAACAAAAACAATATCAAGCTTTCTGGAACTATAGGTTATGTAGCGCCTGAA
TACATGTTAGATGGAAAATTAAGTGATAAAAGTGATGTTTATGGTTTTGGAGTAGTACTTTTGGAGCTGTTATTGGGAAGGCGGCCTGTA
GAAAAGGAGGCAGCCACTGAATGTCAGTCTATAGTGACATGGGCCATGCCTCAGCTGACAGATAGATCAAAGCTTCCAAACATTGTTGAT
CCTGTCATACAAAACACAATGGATTTAAAGCATNTGTATCAGGTTGCTGCAGGTGCTCTATTATGTGTTCAGCCAGAGCCAAGCTATCGT
CCCGTATAA

>SEQ ID NO: 84
GAGTATCAGTTATTGGAAGCTGCAACTGACAATTTTAGTGAGAGTAATATTTTGGGAGAAGGTGGATTTGGATGTGTTTACAAAGCATGT
TTTGATAACAACTTTCTCGCTGCTGTCAAGAGAATGGATGTTGGTGGGCAAGATGCAGAAAGAGAATTTGAGAAAGAAGTAGATTTGTTG
AATAGAATTCAGCATCCGGATATAATTTCCCTGTTGGGTTATTGTATTCATGATGAGACAAGGTTCATCATTTATGAACTAATGCAGAAC
GGATCTTTGGAAAGACAATTACATGGACCTTCTCATGGATCGGCTTTAACTTGGCATATCCGGATGAAAATTGCACTTGATACAGCAAGA
GCATTAGAATATCTCCATGAGAATTGCAACCCTCCTGTGATCCACAGAGATCTGAAATCATCCAATATACTTTTGGATTCTAATTTCAAG
GCCAAGATTTCAGATTTGGTCTTGCTGTAATTTCTGGGAGTCAAAACAAGAACAACATTAAGCTTTCAGGCACTCTTGGTTATGTTGCT
CCAGAATATCTGTTAGATGGTAAATTGACTGACAAAAGTGATGTCTATGCTTTGGGGTTATCCTTCTAGAACTCCTAATGGGAAGAAAA
CCTGTAGAGAAAATGACACGAACTCAGTGTCAATCTATCGTTACATGGGCCATGCCTCAACTCACTGATAGATCAAAGCTACCAAACATT
GTTGATCCTGTGATTAAAAACACAATGGATTTGAAGCATTTGTTCCAAGTTGCTGCTGTAGCTGTACTGTGTGTACAACCAGAACCAAGT
TACCGGCCATTAATCACAGATGTCCTTCACTCCCTCGTACCCCTTGTTCCTGTCGATCTTGGAGG

>SEQ ID NO: 85
EYQLLEAATDNFSESNILGEGGFGCVYKACFDNNFLAAVKRMDVGGQDAEREFEKEVDLLNRIQHPDIISLLGYCIHDETRFIIYELMQN
GSLERQLHGPSHGSALTWHIRMKIALDTARALEYLHENCNPPVIHRDLKSSNILLDSNFKAKISDFGLAVISGSQNKNNIKLSGTLGYVA
PEYLLDGKLTDKSDVYAFGVILLELLMGRKPVEKMTRTQCQSIVTWAMPQLTDRSKLPNIVDPVIKNTMDLKHLFQVAAVAVLCVQPEPS
YRPLITDVLHSLVPLVPVDLGG

>SEQ ID NO: 86
TGTGCTCATGATGAGACCAAACTACTTGTTTACGAACTTATGCACAATGGTTCGTTAGAAACTCAATTACACGGTCCTTCTTGTGGATCC
AATTTAACATGGCATTGTCGGATGAAAATTGCGCTAGATATAGCGAGAGGATTGGAATATTTACATGAACACTGCAAACCATCTGTGATT
CATAGAGATTTGAAGTCATCTAACATCCTTTTGGATTCAAAATTCAATGCCAAGCTTTCGGATTTCGGTCTTGCTGTGATGAACGGTGCC
AATACCAAAAACATTAAGCTTTCGGGGACGTTGGGTTACGTAGCTCCCGAGTATCTTTTAAATGGGAAATTGACCGATAAAAGTGACGTC
TACGCATTCGGAGTTGTACTTTTAGAGCTTCTACTCAAAAGGCGGCCTGTCGAAAAACTAGCACCATCCGAGTGCCAGTCCATCGTCACT
TGGGCTATGCCGCAACTAACAGACAGAACAAAGCTTCCGAGTGTTATAGATCCCGTGATCAGGGACACGATGGATCTTAAACACTTGTAT
CAAGTGGCGGCTGTGGCTGTGTTGTGTGTTCAACCGGAACCGGGATACCGGCCGTTGATAACCGACGTCTTGCATTCTCTGGTTCCTCTC
GTGCCGGTTGAACTCGGAGGGACTCTACGAGTTGCGGAAACAGGTTGCGGCACAGTTGACTTATGA

>SEQ ID NO: 87
CAHDETKLLVYELMHNGSLETQLHGPSCGSNLTWHCRMKIALDIARGLEYLHEHCKPSVIHRDLKSSNILLDSKFNAKLSDFGLAVMNGA
NTKNIKLSGTLGYVAPEYLLNGKLTDKSDVYAFGVVLLELLLKRRPVEKLAPSECQSIVTWAMPQLTDRTKLPSVIDPVIRDTMDLKHLY
QVAAVAVLCVQPEPGYRPLITDVLHSLVPLVPVELGGTLRVAETGCGTVDL

>SEQ ID NO: 88
TGGATTTGGATGCGTTTAAAAGCTCAACTCAATGATAACTTATTAGTTGCGGTCAAACGACTAGACAATAAAAGTCAAAATTCCATCAAA
GAATTCCAGACGGAAGTGAATATTTTGAGTAAAATTCAACATCCAAATATAATTAGTTTGTTGGGATATTGCGATCATGATGAAAGCAAG
CTACTTGTTTACGAATTGATGCAAAATGGTTCTTTAGAAACTCAGTTACATGGGCCTTCTTGTGGATCCAATTTAACATGGTATTGCCGG
ATGAAAATTGCCCTAGATATAGCAAGAGGATTGGAATATTTACATGAACACTCCAAACCATCTGTGATTCATAGAGATCTCAAATCATCT
AATATACTTCTTGATTCAAATTTCAATGCAAAGCTTTCGGATTTTGGTCTTGCGGTGATGGAAGGTGCAAATAGCAAAAACATTAAACTT
TCGGGGACATTGGGATACGTAGCACCCGAATATCTTTTAGATGGGAAATTAACCGATAAAAGTGACGTGTATGCATTTGGAGTCGTACTT
TTTGAGCTTTTACTCAGAAGACGACACGTTGAAAAACTAGAATCATCACAATCCCGCCAATCTATTGTCACTTGGGCGATGCCACTACTA
ATGGACAGATCGAAGCTTCCGAGTGTGATAGATCCTGTGATTAGGGATACAATGGATCTTAAACATCTTTATCAAGTGGCTGCGGTGGCG
GTGTTGTGTGTTCAATCGGAACCGAGTTACCGTCCGTTGATAACCGATGTTTTACATTCTCTTGTTCCTCTTGTCCCGGTTGAACTTGGA
GGGACACTTAGAGTTGTAGAAAAGAGTGTTGT

>SEQ ID NO: 89
WIWMRLKAQLNDNLLVAVKRLDNKSQNSIKEFQTEVNILSKIQHPNIISLLGYCDHDESKLLVYELMQNGSLETQLHGPSCGSNLTWYCR
NIKIALDIARGLEYLHEHSKPSVIHRDLKSSNILLDSNFNAKLSDFGLAVMEGANSKNIKLSGTLGYVAPEYLLDGKLTDKSDVYAFGVV
LFELLLRRRHVEKLESSQSRQSIVTWAMPLLMDRSKLPSVIDPVIRDTMDLKHLYQVAAVAVLCVQSEPSYRPLITDVLHSLVPLVPVEL
GGTLRVVEKSVV

>SEQ ID NO: 90
ATTCTTTTAGATGCAAACTTCAATGCCAAGCTTTCTGATTTTGGCTTGTCTGTCATTGTTGGAGCACAAAACAAGAATGATATAAAGCTT
TCCGGAACGATGGGTTATGTTGCTCCTGAATATCTTTTAGATGGTAAATTGACTGATAAAAGTGATGTCTATGCTTTTGGAGTTGTGCTT
TTGGAGCTTCTTTTAGGAAGAAGGCCTGTTGAAAAACTGGCACCATCTCAATGTCAATCCATTGTCACATGGGCTATGCCTCAACTCACT

-continued

| Sequences |
|---|
| GATAGATCAAAGTTACCCGATATCGTTGATCCGGTGATCAGACACACAATGGACCCTAAACATTTATTTCAGGTTGCTGCTGTCGCCGTG CTGTGTGTGCAACCAGAACCGAGCTATCGTCCCCTAATAACAGATCTTTTGCACTCTCTTATTCCTCTTGTTCCTGTTGAGCTAGGAGGT ACTCACAGATCATCAACATCACAAGCTCCTGTGGCTCCAGCTTAG |
| >SEQ ID NO: 91 ILLDANFNAKLSDFGLSVIVGAQNKNDIKLSGTMGYVAPEYLLDGKLTDKSDVYAFGVVLLELLLGRRPVEKLAPSQCQSIVTWAMPQLT DRSKLPDIVDPVIRHTMDPKHLFQVAAVAVLCVQPEPSYRPLITDLLHSLIPLVPVELGGTHRSSTSQAPVAPA |
| >SEQ ID NO: 92 GATGGGAAGCTCACCGAGAAAAGCGACGTGTACGCGTTTGGCATAGTGCTTCTTGAGCTGCTAATGGGAAGGAAGCCTGTTGAGAAGTTG AGTCAATCTCAGTGCCAATCAATTGTGACTTGGGCCATGCCCCAACTGACAGACAGATCAAAACTTCCCAACATAATTGACCCAGTGATC AGGGACACAATGGATCCAAAGCACTTGTATCAGGTTGCAGCAGTGGCTGTTCTATGCGTGCAACCAGAACCGAGTTACAGACCACTGATA ACGGATGTTCTCCACTCTTTAGTTCCTCTAGTGCCTGTGGAGCTTGGTGGGACACTAAGGGTTGCAGAGCCACCGTCCCCAAACCAAAAT CATTCTCCTCGTTGA |
| >SEQ ID NO: 93 DGKL IEKSDVYAFGIVLLELLMGRKPVEKLSQSQCQSIVTWAMPQLTDRSKLPNIIDPVIRDTMDPKHLYQVAAVAVLCVQPEPSYRPL ITDVLHSLVPLVPVELGGTLRVAEPPSPNQNHSPR |
| >SEQ ID NO: 94 GGGGTTCATGGCAAGAACAATATAAAACTTTCAGGAACTTTAGGATATGTCGCGCCGGAATACCTTTTAGATGGTAAACTTACTGATAAA AGTGACGTTTATGCGTTTGGAGTTGTGCTTCTCGAGCTTTTGATAGGACGAAAACCCGTGGAGAAAATGTCACCATTTCAATGCCAATTT ATCGTTACATGGGCAATGCCTCAGCTAACGGACAGATCGAAGCTTCCTAATCTTGTGGATCCTGTGATTAGAGATACTATGGACTTGAAG CCCTTATATCAAGTTGCGGCTGTAACTGTGTTATGTGTACAACCCGAACCAAGTTACCGCCCATTAATAACGGATGTTTTGCATTCGTTC ATCCCACTTGTACCTGCTGATCTTGGAGGGTCGTTAAAAGTTGTCGACTTTTAA |
| >SEQ ID NO: 95 GVHGKNNIKLSGTLGYVAPEYLLDGKLTDKSDVYAFGVVLLELLIGRKPVEKMSPFQCQFIVTWAMPQLTDRSKLPNLVDPVIRDTMDLK PLYQVAAVTVLCVQPEPSYRPLITDVLHSFIPLVPADLGGSLKVVDF |
| >SEQ ID NO: 96 ATCGTGTTCCATTTTGGTTGTTGTCTAAAGCTTTCAGATTTTGGTCTTGCTGTAATGGATGGAGCCCAGAACAAAAACAACATCAAGCTT TCAGGGACATTGGGTTATGTAGCTCCAGAGTATCTTTTAGATGGAAAACTGACCGACAAAAGTGATGTATATGCATTTGGAGTTGTACTT TTAGAGCTTCTACTTGGAAGACGGCCTGTAGAAAAACTGGCCGCATCTCAATGCCAATCTATCGTCACTTGGGCCATGCCACAGCTAACA GACAGATCAAAGCTCCCAAATATTGTCGATCCTGTAATCAGATATACGATGGATCTCAAACACTTGTACCAAGTTGCTGCCGTGGCAGTG CTGTGTGTGCAACCAGAGCCAAGTTACCGGCCATTAATAACCGATGTTTTGCATTCTCTTATCCCTCTTGTTCCGGTGGAGCTCGGGGGA ACTCTAAAAGCTCCACAAACAAGGTCTTCGGTAACAAATGACCCGTGA |
| >SEQ ID NO: 97 IVFHFGCCLKLSDFGLAVMDGAQNKNNIKLSGTLGYVAPEYLLDGKLTDKSDVYAFGVVLLELLLGRRPVEKLAASQCQSIVTWAMPQLT DRSKLPNIVDPVIRYTMDLKHLYQVAAVAVLCVQPEPSYRPLITDVLHSLIPLVPVELGGTLKAPQTRSSVTNDP |
| >SEQ ID NO: 98 CGTGGATCAACTTTAAGTTGGCCTCTCCGAATGAAAATTGCTTTGGATATTGCAAGAGGATTAGAATACCTTCACGAGCGTTGCAACCCC CCTGTGATCCATAGGCATCTCAAATCGTCTAATATTCTTCTTGATTCCAGCTTCAACGCAAAGATTTCTGATTTTGGCCTTTCTGTAACT GGCGGAAACCTAAGCAAGAACATAACCAAGATTTCGGGATCACTGGGTTATCTTGCTCCAGAGTATCTCTTAGACGGTAAACTAACTGAT AAGAGTGATGTGTATGGTTTTGGCATTATTCTTCTAGAGCTTTTGATGGGTAAAAGGCCAGTGGAGAAAGTGGGAGAAACTAAGTGCCAA TCAATAGTTACATGGGCTATGCCCCAGCTTACGGACCGATCAAAGCTTCCGAATATTGTTGACCCTACGATCAGGAACACAATGGATGTT AAGCATTTATATCAGGTTGCGGCTGTAGCTGTGTTATGTGTGCAACCGGAGCCAAGCTATAGGCCATTGATAACTGATGTACTACACTCC TTCATTCCACTTGTACCAAATGAACTCGGGGGGTCGCTTAGGGTAGTGGATTCTACTCCCCATTGCTCATAG |
| >SEQ ID NO: 99 RGSTLSWPLRMKIALDIARGLEYLHERCNPPVIHRHLKSSNILLDSSFNAKISDFGLSVTGGNLSKNITKISGSLGYLAPEYLLDGKLTD KSDVYGFGIILLELLMGKRPVEKVGETKCQSIVTWAMPQLTDRSKLPNIVDPTIRNTMDVKHLYQVAAVAVLCVQPEPSYRPLITDVLHS FIPLVPNELGGSLRVVDSTPHCS |
| >SEQ ID NO: 100 TTAGATAATGGCGGACCCGATTGTCAACGAGAATTCGAGAATGAGGTTGATTTGATGAGTAGAATTAGGCATCCAAATGTGGTTTCTTTA TTGGGTTATTGCATTCATGGAGAAACCAGGCTTCTTGTCTATGAAATGATGCAAAACGGGACGTTGGAATCGCTATTGCATGGACCATCA CATGGATCCTCACTAACTTGGCACATTCGTATGAAGATCGCCCTCGACACAGCAAGAGGCCTCGAGTATCTGCATGAACACTGCGACCCC TCTGTGATCCACCGTGACCTGAAGCCTTCTAACATTCTTTTGGATTCCAACTACAATTCCAAGCTCTCAGACTTTGGTCTTGCAGTCACT GTTGGAAGCCAGAATCAAACCAACATTAAGATTCTAGGGACACTGGGTTACCTTGCACCAGAGTACGTTTTGAATGGCAAATTGACAGAG AAAAGTGATGTGTTTGCTTTTGGAGTTGTCCTGTTGGAGCTTCTCATGGGCAAGAAACCAGTGGAGAAGATGGCATCCCCTCCATGCCAA TCCATTGTCACATGGGCGATGCCTCATCTTACTGACAGAATTAAGCTTCCAAATATCATTGATCCTGTTATTAGAAACACCATGGATCTG AAACACTTGTACCAGGTTGCAGCTGTTGCTGTTCTCTGCGTACAACCAGAGCCCCAGTTATCGTCCTCTGATAACTGA |
| >SEQ ID NO: 101 LDNGGPDCQREFENEVDLMSRIRHPNVVSLLGYCIHGETRLLVYEMMQNGTLESLLHGPSHGSSLTWHIRMKIALDTARGLEYLHEHCDP SVIHRDLKPSNILLDSNYNSKLSDFGLAVTVGSQNQTNIKILGTLGYLAPEYVLNGKLIEKSDVFAFGVVLLELLMGKKPVEKMASPPCQ SIVTWAMPHLTDRIKLPNIIDPVIRNTMDLKHLYQVAAVAVLCVQPEPQLSSSDN |
| >SEQ ID NO: 102 TCGGCTCGGCCCAGAACAAGATCGCAAGAC |
| >SEQ ID NO: 103 CTACATTCTCTCCTCGTATTATTCCTCGTTGACT |

-continued

| Sequences |
|---|
| >SEQ ID NO: 104<br>ACTTTCAGATGAGTGGATCATAACCCTATACA |
| >SEQ ID NO: 105<br>AGATACAATGGATCTCAAACACTTATACCAG |
| >SEQ ID NO: 106<br>AAAGGATCCATGGGAAGTGGTGAAGAAGATAGATTTGATGCT |
| >SEQ ID NO: 107<br>TTTCTGCAGTCTGTGAATCATCTTGTTAACCGGAGAGTCC |
| >SEQ ID NO: 108<br>TCTGAGTTTTAATCGAGCCAAGTCGTCTCA |
| >SEQ ID NO: 109<br>TATCCCGGGAAAATGAGAGAGCTTCTTCTTCTTCTTCTTCTTCATTTTCAGTC |
| >SEQ ID NO: 110<br>TTTGGATCCTGTGAATCATCTTGTTAACCGGAGAGTCC |
| >SEQ ID NO: 111<br>ATACCCGGGTCTGTGTCAGGAATCCAAATGGGAAGTGGTGA |
| >SEQ ID NO: 112<br>AAAGGATCCTCTGTGTCAGGAATCCAAATGGGAAGTGGTGA |
| >SEQ ID NO: 113<br>AAATCTAGACTGTGAATCATCTTGTTAACCGGAGAGTCC |
| >SEQ ID NO: 114<br>ATAGAGCTCGCAAGAACCAATCTCCAAAATCCATC |
| >SEQ ID NO: 115<br>ATAGAGCTCGAGGGTCTTGATATCGAAAAATTGCACG |
| >SEQ ID NO: 116<br>ATAGGATCCTCGCAAGAACCAATCTCCAAAATCCATC |
| >SEQ ID NO: 117<br>ATATCTAGACTCGAGGGTCTTGATATCGAAAAATTGCACG |
| >SEQ ID NO: 118<br>ATATCTAGAAAATGAGAGAGCTTCTTCTTCTTCTTCTTCTTCATTTTCAGTC |
| >SEQ ID NO: 119<br>ATAGGATCCTGTTAAAAGCGATTTATAATTTACACCGTTTTGGTGTA |
| >SEQ ID NO: 120<br>ATACCCGGGAAAAGTTTTTGATGAAATTCAATCTAAAGACT |
| >SEQ ID NO: 121<br>AAAATGAGAGAGCTTCTTCTTCTTCTTCTTCTTCATTTTCAGTCTCTAATTCTTTTGATGATCTTCATCACTGTCTCTGCTTCTTCTGCT<br>TCAAATCCTTCTTTAGCTCCTGTTTACTCTTCCATGGCTACATTCTCTCCTCGAATCCAAATGGGAAGTGGTGAAGAAGATAGATTTGAT<br>GCTCATAAGAAACTTCTGATTGGTCTCATAATCAGTTTCTCTTCTCTTGGCCTTATAATCTTGTTCTGTTTTGGCTTTTGGGTTTATCGC<br>AAGAACCAATCTCCAAAATCCATCAACAACTCAGATTCTGAGAGTGGGAATTCATTTTCCTTGTTAATGAGACGACTTGGCTCGATTAAA<br>ACTCAGAGAAGAACTTCTATCCAAAAGGGTTACGTGCAATTTTTCGATATCAAGACCCTCGAGAAAGCGACAGGCGGTTTTAAAGAAAGT<br>AGTGTAATCGGACAAGGCGGTTTCGGATGCGTTTACAAGGGTTGTTTGGACAATAACGTTAAAGCAGCGGTCAAGAAGATCGAGAACGTT<br>AGCCAAGAAGCAAAACGAGAATTTCAGAATGAAGTTGACTTGTTGAGCAAGATCCATCACTCGAACGTTATATCATTGTTGGGCTCTGCA<br>AGCGAAATCAACTCGAGTTTCATCGTTTATGAGCTTATGGAGAAAGGATCATTAGATGAACAGTTACATGGGCCTTCTCGTGGATCAGCT<br>CTAACATGGCACATGCGTATGAAGATTGCTCTTGATACAGCTAGAGGACTAGAGTATCTCCATGAGCATTGTCGTCCACCAGTTATCCAC<br>AGAGATTTGAAATCTTCGAATATTCTTCTTGATTCTTCCTTCAACGCCAAGATTTCAGATTTCGGTTTTGCTGTATCGCTGGATGAACAT<br>GGCAAGAACAACATTAAACTCTCTGGGACACTTGGTTATGTTGCCCCGGAATACCTCCTTGACGGAAAACTGACGGATAAGAGTGATGTT<br>TATGCATTTGGGGTAGTTCTGCTTGAACTCTTGTTGGGTAGACGACCAGTTGAAAAATTAACTCCAGCTCAATGCCAATCTCTTGTAACT<br>TGGGCAATGCCACAACTTACCGATAGATCCAAGCTTCCAAACATTGTGGATGCCGTTATAAAAGATACAATGGATCTCAAACACTTATAC<br>CAGGTAGCAGCCATGGCTGTGTTGTGCGTGCAGCCAGAACCAAGTTACCGGCCGTTGATAACCGATGTTCTTCACTCACTTGTTCCACTG<br>GTTCCGGTAGAGCTAGGAGGGACTCTCCGGTTAACAAGATGATTCACAG |
| >SEQ ID NO: 122<br>TCGGACAAGGCGGTTTCGGATGCGT |
| >SEQ ID NO: 123<br>TAGTCCTCTAGCTGTATCAAGAGCAATCTTCA |
| >SEQ ID NO: 124<br>TATCATTGTTGGGCTCTGCAAGTGAAATCAAC |

-continued

| Sequences |
|---|
| >SEQ ID NO: 125<br>TGGAGAAAGGATCCTTAGATGATCAGTTACAT |
| >SEQ ID NO: 126<br>TCCATGTAACTGATCATCTAAGGATCCTTTC |
| >SEQ ID NO: 127<br>ATAAACGACGAAACTCGAGTTGATTTCACTTGCAGAG |
| >SEQ ID NO: 128<br>AAAATGAAGAAACTGGTTCATCTTCAGT |
| >SEQ ID NO: 129<br>TAGACTTCTATTCTCACATTCTTACAC |
| >SEQ ID NO: 130<br>TCCAATGATCCATTATGCATCAGCTCA |
| >SEQ ID NO: 131<br>TCGTTCTCAAATTCTCTCTCAGCATGTTG |
| >SEQ ID NO: 132<br>TCCGGATATGCCAGGTCAGCGCTGATCCA |
| >SEQ ID NO: 133<br>TCCAGGGATCCCTTCTCCATGAGCTCAT |
| >SEQ ID NO: 134<br>AAAGAGCTCTCTGTGTCAGGAATCCAAATGGGAAGTGGTGA |
| >SEQ ID NO: 135<br>ATAGCTAGCTGTTAAAAGCGATTTATAATTTACACCGTTTTGGTGTA |
| >SEQ ID NO: 136<br>ATAGCTAGCAGAAAAGTTTTTGATGAAATTCAATCTAAAGACT |
| >SEQ ID NO: 137<br>TCTGGGTTTATCATCATACCAAGTATCCA |
| >SEQ ID NO: 138<br>ATTCAGTTCCATCAAGATTGTTGGCATGGAC |
| >SEQ ID NO: 139<br>TGGAGGGAGGTGGCCCTGAGTGCGAGAAGGA |
| >SEQ ID NO: 140<br>GCTGGATCTGCTTGGCAGGATTCGGCA |
| >SEQ ID NO: 141<br>ATATCTAGATGCTAGGTTATAGATCCATGCA |
| >SEQ ID NO: 142<br>ATAGGATCCACCAGAACTATATATACGAAGGCA |
| >SEQ ID NO: 143<br>AGGACGACTTGGCTCGATTAAAATCACAGGTCGTGATATG |
| >SEQ ID NO: 144<br>TAATCGAGCCAAGTCGTCCTACATATATATTCCTA |
| >SEQ ID NO: 145<br>TAATCGAGCCAAGTCGTCCTCTCTTTTGTATTCCA |
| >SEQ ID NO: 146<br>AGGACGACTTGGCTCGATTAAAATCAAAGAGAATCAATGATC |
| >SEQ ID NO: 147<br>GACGACTTGGCTCGATTAAAA |
| >SEQ ID NO: 148<br>TGCTAGGTTATAGATCCATGCAAATATGGAGTAGATGTACAAACACACGCTCGGACGCATATTACACATGTTCATACACTTAATACTCGC<br>TGTTTTGAATTGATGTTTTAGGAATATATATGTAGAGAGAGCTTCCTTGAGTCCATTCACAGGTCGTGATATGATTCAATTAGCTTCCGA<br>CTCATTCATCCAAATACCGAGTCGCCAAAATTCAAACTAGACTCGTTAAATGAATGAATGATGCGGTAGACAAATTGGATCATTGATTCT<br>CTTTGATTGGACTGAAGGGAGCTCCCTCTCTCTTTTGTATTCCAATTTTCTTGATTAATCTTTCCTGCACAAAAACATGCTTGATCCACT<br>AAGTGACATATATGCTGCCTTCGTATATATAGTTCTGGT |

-continued

| Sequences |
|---|

>SEQ ID NO: 149
TGCTAGGTTATAGATCCATGCAAATATGGAGTAGATGTACAAACACACGCTCGGACGCATATTACACATGTTCATACACTTAATACTCGC
TGTTTTGAATTGATGTTTTAGGAATATATATGTAGGACGACTTGGCTCGATTAAAATCACAGGTCGTGATATGATTCAATTAGCTTCCGA
CTCATTCATCCAAATACCGAGTCGCCAAAATTCAAACTAGACTCGTTAAATGAATGAATGATGCGGTAGACAAATTGGATCATTGATTCT
CTTTGATTTTAATCGAGCCAAGTCGTCCTCTCTTTTGTATTCCAATTTTCTTGATTAATCTTTCCTGCACAAAAACATGCTTGATCCACT
AAGTGACATATATGCTGCCTTCGTATATATAGTTCTGGT

>SEQ ID NO: 150
CTTAGCCAATGGATGAGGATGACACGATAATGATAATCAAAGATCAACATGGCACGCTCAAGACCGCCTTTAGAAGTCCTCTCTAAATTC
TTTCTTCCGATCTCCTAAATATGTTTTGTTTTGGTCAAATAAATTGATAGGTAATACTTAGTGATTATACTATTTGGTTTTTGTTTTATC
ATTGACTATTTCACTTTTATAAATCAAATACTTATCAAAATTGTTCTTTCCGTATGTATTCATATTTTCTAATATTGTAAAGATTTGTTT
CACCTAACATCTGTACCCATCTTTGATCATTGACAAAATATATATTAGAATGGCCTTAGAACGTGTTAGGCATCTTCCTACTATTATCAT
ATTACCTAATCCCCAATTTTATTACATTTTTTAATTTCTAAAAGAGCTTGAATATAATGTCATTTCGAATATCTCTGTTCATCTTTTTTT
TTTTCTGTGCGACTTCTGACCCAAAGCCTTCGACGATTTTTTCCAATCTGAAAACTTTTGAATAAGGAACTTAGTCAATGGTCAACACCT
TGCTAATTAAACAAAGTTCCATTGATACAATAATGAGATTTTTGTACATTAACGCTTTCATATAGTTTTTGCGATTCAACAGATAATCTT
AAAATTAAGGAGTCCTATTGATAAAGTCTTGTTCAAACGTACAAACTCAATCCACACAAAACCTTCATAAAATACGATATAGGAAATAAA
GATTGTTTTTGCGTGAGAAAATACTATATGAACTCAAAAGATTTTAAAACAATTTGTATTAATACATAAACAATTGTTGTGATACACCCG
TGTAAAATTTTAAGATTGTTTTTTTCTGAAATTCTTCAAGGAAACTTATAGCTTAAAATCTACACTTCAAATACTCTGTTTTAAAGGCAT
TAAAAATAACTGCGTTTCAGAAAAATATTGAAATTTTAGCTGATCTTTTGCTACAAATTTAAGGAATCTTGGCACCTGCAGAATCTATAA
CATGTTCATTAAGTAATGCAATAGTTATACAATTATACATTATTTGCATCATACTTATATTATAGTGATATTAACAAACCCATGTTCTCA
GCACACTTTTACGTAGAAAAACATAAAAACCCAAATAGGAAGAAGCCACTCATAAGGATAATGGGTTTATATAATTCACAGCAAAGAAAG
CCATCGAACTATTCGATTAATTATCCATTCTTTTTTTTTTTAGTTTGAATGTATAAGAACAAAGAGTTGTTACGCATCATGACAATGTCT
TAGAAAACAAAAGAAATGAATAAAAAAGTAAAACGAAAAATAAAAAGTGAGGATGAAGTTGTTGAATGAGTTGGCGAGGCGGCGACTTTT
TCATACATTCCATTTACTTAATTCCTAAAGTCCTTCTCACATCTCTTTGTTATATAATGACACCATAACCATTTCTTCTCTTCACAATCT
TTACAAGAATATCTCTCTTCTACAGTAAACAAAAA

>SEQ ID NO: 151
ACGTAAGCTTCTTAGCCAATGGATGAGGATG

>SEQ ID NO: 152
ACGTTCTAGATTTTTGTTTACTGTAGAAGAG

>SEQ ID NO: 153
TGCTGCTTCAAATCCTTCTATAGCTCCTGTTTATACCACCATGACTACTTTCTCTCCAGGAATTCAAATGGGAAGTGGTGAAGAACACAG
ATTAGATGCACATAAGAAACTCCTGATTGGTCTTATAATCAGTTCCTCTTCTCTTGGTATCGTAATCTTGATTTGCTTTGGCTTCTGGAT
GTACTGTCGCAAGAAAGCTCCCAAACCCATCAAGATTCCGGATGCTGAGAGTGGGACTTCATCATTTCAATGTTTGTGAGGCGGCTAAG
CTCAATCAAAACTCAGAGAACATCTAGCAATCAGGGTTATGTGCAGCGTTTCGATTCCAAGACGCTAG

>SEQ ID NO: 154
TATGGATCCTGCTGCTTCAAATCCTTCTATAGCTCCTG

>SEQ ID NO: 155
TATTCTAGACTAGCGTCTTGGAATCGAAACGCTGCAC

>SEQ ID NO: 156
TATGAGCTCTGCTGCTTCAAATCCTTCTATAGCTCCTG

>SEQ ID NO: 157
TATGAGCTCCTAGCGTCTTGGAATCGAAACGCTGCAC

>SEQ ID NO: 158
GCAGATCGCTCCTCCCGTCGTGAT

>SEQ ID NO: 159
CGCCTAGG AGCGACGGGTACTCGATCAT

>SEQ ID NO: 160
CCTAGCTA AGCGACGGGTACTCGATCAT

>SEQ ID NO: 161
GCTCCTCCCGTCGTGATCACAGTGGTGAGGCACCACCATTACCACCGGGAGCTGGTCATCTCCGCTGTCCTCGCCTGCGTCGCCACCGCC
ATGATCCTCCTCTCCACACTCTACGCCTGGACGATGTGGCGGCGGTCTCGCCGGACCCCCCACGGCGGCAAGGGCCGCGGCCGGAGATCA
GGGATCACACTGGTGCCAATCCTGAGCAAGTTCAATTCAGTGAAGATGAGCAGGAAGGGGGGCCTTGTGACGATGATCGAGTACCCGTCG
CT

>SEQ ID NO: 162
CGGGATCCCGGCATAACAAACTCGTGCATCC

>SEQ ID NO: 163
CCATCGATGGCGCCAAACACAATA GCT CAA

>SEQ ID NO: 164
GTAAGTAATTTCAAGTTTAAGTTTCATAAGCATAACAAACTCGTGCATCCAATTTGAACCATTTTACTGTCCTGGCATCCTCTAAATATT
TCCTTGATTATCAGCTTATCTTCATCCCATTGAATCAGAAAATTACCAACCCTTGTTTTAGCTTTAATCATTGTTATTTGTTGTCTGAGG
GGCTACACTGTTTCTTTATATTGGTGAAGGAGTTACCAGGCAAAAATTCCCACCTCCTGATATTAGCAGAGACCCCCTTTTTTGTGCCTG
TATGCATACTAACAAATAATACAGATGGAAATATGTATATTTGTTATATCATGGATTGATGCTTTATGTTTAGCAAGTCCATGCAATGGT

-continued

Sequences

AGTCAAAAGATGTAAACTTTTGAATGATATATTGGGGCTTTAGATTAGCCATTTTTACCCTCACTTGAAAATGACAATTTTGCCCTTCCG
ATCTACTTTCTCTTGTCACCTCAGGCAGGCTCTTGAAAGTTCTTATCCCTGAATTCCGTGGAAGTTTATTATTCTAATGTTATAGTTTAC
TTAAAGTGTCGCATAATCTACTAGAGCCTAATGGAAGTACTGATGGACTTTGTTTTGCTACAATCACTGCTTGCAAGAATGACTACTTTG
GGGCATTTCTAATATATTATTGATATTTCTATGATGTATTGTTGTCCATGTACTTCAGTCCTTACAGCGACTAGTCCTATTTCTGCATTG
ATAAATTGTTCACTGTCAGACCATCTTGAGTGGCAAGAATGAGTATAACATGTCTTGTTTTTCTGTGATTTCAAGGTAAGCGCACATGCG
CACAGTGTACACCGTCACCACATGTGAGTACACCCCCTAGTACACATGTAAAAAAAGCACAGTCCAGTTATTAAATGGACCATTGGCATT
GATTGTCGTGTTTATAGGAGTAAAGATACATGTAAACACTAATTCATTGGGAGATATAAATTTATACTACCATTGAATGTGACATAGGCT
CTAAGGTTTTTAGTTCAGCATTTCGAAAGAGCTTTGTTTGGTTGGCTTGGGATGGAATCAGGTGACAACATTTTTGGGTTGCAGCAAATT
TAATATTGATTGAGGAGGCATACAACGAAATCATTGAGCTATTGTGTTTGGCGTTACATCTATGGAATTTCTTCTAATCTGATTATTGTT
TGTA

>SEQ ID NO: 165
GATCCGCTCCTCCCGTCGTGAT

>SEQ ID NO: 166
AACGCGATCGCTTGCATGCCTGCAGTAGAC

>SEQ ID NO: 167
GACTTAATTAAGAATTCGAGCTCGGGTA

>SEQ ID NO: 168
TCGTAGTGCACCACCATTTCCACCGCGAGCTGGTCATCGCCGCCGTCCTCGCCTGCATCGCCACCGTCACGATCTTCCTTTCCACGCTCT
ACGCTTGGACACTATGGCGGCGATCTCGCCGGAGCACCGGCGGCAAGGTCACCAGGAGCTCAGACGCAGCGAAGGGGATCAAGCTGGTGC
CGATCTTGAGCAGGTTCAACTCGGTGAAGATGAGCAGGAAGAGGCTGGTTGGGATGTTCGAGTACCCGTCG

>SEQ ID NO: 169
GCAGATCTCGTAGTGCACCACCATTTC

>SEQ ID NO: 170
CGCCTAGGCGACGGGTACTCGAACATC

>SEQ ID NO: 171
CCTAGCTACGACGGGTACTCGAACATC

>SEQ ID NO: 172
GATCCTCGTAGTGCACCACCATTTC

>SEQ ID NO: 173
CTCGTAGTGCACCACCATTTC

>SEQ ID NO: 174
AATGGGACCGCCTCCGTTGCTCCGGCGGTGCCGGCGCCGCCTCCCGTCGTGATCATCGTGGAGCGGCGCCATCATTTCCACCGCGAGCTA
GTCATCGCCTCCGTTCTCGCCTCCATCGCCATCGTCGCGATTATCCTCTCCACGCTCTATGCGTGGATCCTGTGGCGGCGGTCTCGCCGG
CTGCCCAGCGGCAAGGGCGCCAGGAGCGCAGACACCGCGAGGGGAATCATGCTGGTGCCGATCCTGAGCAAGTTCCACTCA

>SEQ ID NO: 175
GCAGATCAATGGGACCGCCTCCGTTG

>SEQ ID NO: 176
CGCCTAGGTGAGTGGAACTTGCTCAGGA

>SEQ ID NO: 177
CCTAGCTATGAGTGGAACTTGCTCAGGA

>SEQ ID NO: 178
GTAAGTATTCTTGCAACACATTACTATTTTCAATAACCACAAGTTTAAAAGCTTGAGTCCATTTCGCAAACCAGTTGTTCATAACCAAAT
TCTTAGGTAATTAGGTCCAATTGAGAAAATCTGATCATTGAACACTAGCAGGAAATAACTCAGACATAGTTTCTGCATACTATAATGATG
CTTAATATATTTGTTCTCTTTTGAGATTGTATTGCATAGACATTTCTGTGTAAAATAATGTTTTACATCATGTATATATATATCACTTTTTA
TAG

>SEQ ID NO: 179
CGGGATCCTTCTTGCAACACATTACTATTT

>SEQ ID NO: 180
CCATCGATGAAATGTCTATGCAATACAATCTCAA

> SEQ ID NO: 181
GATCCAATGGGACCGCCTCCGTTG

>SEQ ID NO: 182
CAATGGGACCGCCTCCGTTGA

>SEQ ID NO: 183
GGCCCCGGCCGCGCGCGTCTCCGTGTCCTCCGCGACTGTGCACGTTTCGTCGGGAGCGGCGTGCCCACGCCCACCCCCCGTCCACCAGCC
AGCAACCGACGGCACTGGTGACACGCGGCTGGTCCGCTCGGTCCGCCCCGCGGCTCCAGATCACGGCAAGCGCGCCCGCCGCCCGCTGCT
GCGCTGCGCTGCACGTCCCGCCCTGACGCCACGCCACGCCAAGCGCGACACGACACGACACGACACGACCCGACCCCCGCCAACGAAACG
CCGAAACGCGGCAACGCGTGACGGGCGCGCATGGTCGATGCTCTACCCGCGCGTCCGCCCCACGCCAATCTCCCGGCGGGTCCCTCGTGG

Sequences

GACGGGGAACGCGATGCGGCTGCAGGCTGCGACCGCGACCGCGACCGCGACCGCGCCCACGTGAAGGCAGGCAGGCAGCCCCGGAGCGGG
CGCGGCGGTGGGCCAACGACGCGTTGCCGTCGCGAATCTTCTTCTGGCCACGGCCAAGGGCCAATCGCCCGCTCCGCTCCGCTCCGCACT
CCGCCTCCGCTAGGGAATATGGAACCCGATCCCACGGCCCTCTGGGTCTGGTCGACGGGTCCTCTCGCCGTGGCAGCTGCTTCCCGGACC
GGAGGATCGCTGAGCGCGGACGCCACTGCCATTGCCGTCCGACTATAGTTGTTAATTACCATAAAATAATTTGTTAACGATAAAACCCGT
GTCAGGCACCGTCGTCTGGACGCTGCTATGGGATAACCATTCGCGTACGTCGGTTGTATGGGTGGGATCCTCTGCGGCACGCCATTCTGG
TGCTGCTAGTGGAATAGACAAAAAAAGGGCCGACGGTGTTTGCTCGTGGCAGGCCACACAGAGTGACAACCAGAGTGGTTGCCGCAAAAA
CAACCAATCACACAAAAAGTGTTGTACCGGTGGAGGACAGCCATTAATCAGCAGGCCGGCTTCGCGGCCAAAAGAAACGGAGAAGAGGAA
AAAGGGGGGC

>SEQ ID NO: 184
TCCCAAGCTTGCGCGTCTCCGTGTCCTC

>SEQ ID NO: 185
AGTAAAGCTTCCCCCTTTTTCCTCTTCTCC

>SEQ ID NO: 186
TAATGGTCGAGTGAGGCCCGTATAGATGTAGTTAAATAGCTAAAATTTTTGGAGAAATAAGCATTTTTTTGGAAGAATATATTTAAACAT
GGGCTTGTAAAACTTGGCTGTAAAGATTTGGAATTTAGGATCTTGGAGCCCCAAAACTGTATAAACTTGCTTAGGGACCCGTGTCTTGTG
TGTTGCAGACCAAAAAATTTAGAAAGCATCTAAACACCTATTTGAATGTAAAGTTTACAGCCAAAAGTTTTAGGATGTAAAGATTTGGGA
TCTAAAAGTAGTCATTAGGAAATAACACGTTAGAGAGAGAGAGTAGATCTTCTTATTGGTTTCTCATGCACTAATCGAACCAATCACTGG
ACCACTTGAACCAAACTTTATCACATTGAACTTTGTCAGTTCAGTTCGAACGCAGGACTGGAGCTGCCCTTAAGGCCAATTGCTCAAGAT
TCATTCAACAATTGAAACATCTCCCATGATTAAATCAGTATAAGGTTGCTATGGTCTTGCTTGACAAAGTTTTTTTTTGAGGGAATTTC
AACTAAATTTTTGAGTGAAACTATCAAATACTGATTTTAAAAATTTTTTATAAAAGGAAGCGCAGAGATAAAAGGCCATCTATGCTACAA
AAGTACCCAAAAATGTAATCCTAAAGTATGAATTGCATTTTTTTTGTTTGGACGAAAGGAAAGGAGTATTACCACAAGAATGATATCATC
TTCATATTTAGATCTTTTTTGGGTAAAGCTTGAGATTCTCTAAATATAGAGAAATCAGAAGAAAAAAAAACCGTGTTTTGGTGGTTTTGA
TTTCTAGCCTCCACAATAACTTTGACGGCGTCGACAAGTCTAACGGACACCAAGCAGCGAACCACCAGCGCCGAGCCAAGCGAAGCAGAC
GGCCGAGACGTTGACACCTTCGGCGCGGCATCTCTCGAGAGTTCCGCTCCGGCGCTCCACCTCCACCGCTGGCGGTTTCTTATTCCGTTC
CGTTCCGCCT

>SEQ ID NO: 187
AACTGCAGGGTCGAGTGAGGCCCGTA

>SEQ ID NO: 188
TTCTGCAGGGAACGGAACGGAATAAGAA

>SEQ ID NO: 189
GCCGTGGGTCGTTTAAGCTGCCGCTGTACCTGTGTCGTCTGGTGCCTTCTGGTGTACCTGGGAGGTTGTCGTCTATCAAGTATCTGTGGT
TGGTGTCATGAGTCAGTGAGTCCCAATACTGTTCGTGTCCTGTGTGCATTATACCCAAAACTGTTATGGGCAAATCATGAATAAGCTTGA
TGTTCGAACTTAAAAGTCTCTGCTCAATATGGTATTATGGTTGTTTTTGTTCGTCTCCT

>SEQ ID NO: 190
TAGGTACCGCCGTGGGTCGTTTAAGCT

>SEQ ID NO: 191
AAGGTACCAGGAGACGAACAAAAACAA

>SEQ ID NO: 192
AACGCGATCGTAATGGTCGAGTGAGGCCCGTATA

>SEQ ID NO: 193
ATGAAGAAACTGGTTCATCTTCAGTTTCTGTTTCTTGTCAAGATCTTTGCTACTCAATTCCTCACTCCTTCTTCATCATCTTTTGCTGCT
TCAAATCCTTCTATAGCTCCTGTTTATACCACCATGACTACTTTCTCTCCAGGAATTCAAATGGGAAGTGGTGAAGAACACAGATTAGAT
GCACATAAGAAACTCCTGATTGGTCTTATAATCAGTTCCTCTTCTCTTGGTATCGTAATCTTGATTTGCTTTGGCTTCTGGATGTACTGT
CGCAAGAAAGCTCCCAAACCCATCAAGATTCCGGATGCTGAGAGTGGGACTTCATCATTTTCAATGTTTGTGAGGCGGCTAAGCTCAATC
AAAACTCAGAGAACATCTAGCAATCAGGGTTATGTGCAGCGTTTCGATTCCAAGACGCTAGAGAAAGCGACAGGCGGTTTCAAAGACAGT
AATGTAATCGGACAGGGCGGTTTCGGATGCGTTTACAAGGCTTCTTTGGACAGCAACACTAAAGCAGCGGTTAAAAAGATCGAAAACGTT
AGCCAAGAAGCAAAACGAGAATTTCAGAATGAAGTTGAGCTGTTGAGCAAGATCCAGCACTCCAATATTATATCATTGTTGGGCTCTGCA
AGTGAAATCAACTCGAGTTTCGTCGTTTATGAGTTGATGGAGAAAGGATCCTTAGATGATCAGTTACATGGACCTTCGTGTGGATCCGCT
CTAACATGGCATATGCGTATGAAGATTGCTCTAGATACAGCTAGAGGATTAGAGTATCTCCATGAACATTGTCGTCCACCAGTTATCCAC
AGGGACCTGAAATCGTCTAATATACTTCTTGATTCTTCCTTCAATGCCAAGATTTCAGATTTTGGTCTGGCTGTATCGGTTGGAGTGCAT
GGGAGTAACAACATTAAACTCTCTGGGACACTTGGTTATGTTGCCCCGGAATATCTCCTAGACGGAAAGTTGACGGATAAGAGTGATGTC
TATGCATTTGGGGTGGTTCTTCTTGAACTTTTGTTGGGTAGAAGGCCGGTTGAGAAATTGAGTCCATCTCAGTGTCAATCTCTTGTGACT
TGGGCAATGCCACAACTTACCGATAGATCGAAACTCCCAAACATCGTGGATCCGGTTATAAAAGATACAATGGATCTTAAGCACTTATAC
CAGGTAGCAGCCATGGCTGTGTTGTGCGTTCAGCCAGAACCGAGTTACCGGCCGCTGATAACCGATGTTCTTCACTCACTTGTTCCATTG
GTTCCGGTCGAACTAGGAGGGACTCTCCGGTTAACCCGATGA

>SEQ ID NO: 194
MKKLVHLQFLFLVKIFATQFLTPSSSSFAASNPSIAPVYTTMTTFSPGIQMGSGEEHRLDAHKKLLIGLIISSSSLGIVILICFGFWMYC
RKKAPKPIKIPDAESGTSSFSMFVRRLSSIKTQRTSSNQGYVQRFDSKTLEKATGGFKDSNVIGQGGFGCVYKASLDSNTKAAVKKIENV
SQEAKREFQNEVELLSKIQHSNIISLLGSASEINSSFVVYELMEKGSLDDQLHGPSCGSALTWHMRMKIALDTARGLEYLHEHCRPPVIH
RDLKSSNILLDSSFNAKISDFGLAVSVGVHGSNNIKLSGTLGYVAPEYLLDGKLTDKSDVYAFGVVLLELLLGRRPVEKLSPSQCQSLVT
WAMPQLTDRSKLPNIVDPVIKDTMDLKHLYQVAAMAVLCVQPEPSYRPLITDVLHSLVPLVPVELGGTLRLTR

>SEQ ID NO: 195
AATCCAGCTCATTCTGGAATTCCTTCTCGCA

-continued

| Sequences |
|---|
| >SEQ ID NO: 196<br>TGAACTTGCTCAGGATTGGCACCAGTGTGATC |
| >SEQ ID NO: 197<br>MEIPAAPPPPLPVLCSYVVFLLLLSSCSLARGRIAVSSPGPSPVAAAVTANETASSSSSPVFPAAPPVVITVVRHHHYHRELVISAVLAC<br>VATAMILLSTLYAWTMWRRSRRTPHGGKGRGRRSGITLVPILSKFNSVKMSRKGGLVTMIEYPSLEAATGKFGESNVLGVGGFGCVYKAA<br>FDGGATAAVKRLEGGGPDCEKEFENELDLLGRIRHPNIVSLLGFCVHGGNHYIVYELMEKGSLETQLHGSSHGSALSWHVRMKIALDTAR<br>GLEYLHEHCNPPVIHRDLKPSNILLDSDFNAKIADFGLAVTGGNLNKGNLKLSGTLGYVAPEYLLDGKLTEKSDVYAFGVVLLELLMGRK<br>PVEKMSPSQCQSIVSWAMPQLTDRSKLPNIIDLVIKDTMDPKHLYQVAAVAVLCVQPEPSYRPLITDVLHSLVPLVPAELGGTLRVAEPP<br>SPSPDQRHYPC |
| >SEQ ID NO: 198<br>TATACCGGTAAAATGAGAGAGCTTCTTCTTCTTCTTCTTCATTTTCAGTC |
| >SEQ ID NO: 199<br>ATATACCGGTCTTGTTAACCGGAGAGTCCCTCCTAGCTC |
| >SEQ ID NO: 200<br>CGCTCCTCCCGTCGTGAT |

LITERATURE

1. Altschul S F, Gish W, Miller W, Myers E W, Lipman D J. (1990) Basic local alignment search tool. J. Mol. Biol. 215: 403-410.
2. Altschul S F, Madden T L, Schïffer A A, Zhang J, Zhang Z, Miller W, Lipman D J. (1997) Gapped BLAST and PSI-BLAST: a new generation of protein database search programs. Nucl. Acid Res. 25: 3389-3402.
3. An G, Mitra A, Choi H K, Costa M A, An K, Thornburg R W, Ryan C A. (1989) Functional analysis of the 3' control region of the potato wound-inducible proteinase inhibitor II gene. Plant Cell 1: 115-122.
4. Araus L J, Slafer G A, Reynolds M P, Royo C (2002) Plant Breeding and drought in C3 cereals: What should we breed for? Annals of Botany 89: 925-940.
5. Atanassvoa R, Chaubet N, Gigot C (1992) A 126 bp fragment of a plant histone gene promoter confers preferential expression in meristems of transgenic *Arabidopsis*. Plant Journal 2(3): 291-300.
6. Beetham P R, Kipp P B, Sawycky X L, Arntzen C J, May G D (1999) A tool for functional plant genomics: chimeric RNA/DNA oligonucleotides cause in vivo gene-specific mutations. Proceedings of the National Academy of Science USA, 96: 8774-8778.
7. Bevan M, Barnes W M, Chilton M D (1983) Structure and transcription of the nopaline synthase gene region of T-DNA. Nucl. Acids Res. 12: 369-385.
8. Bevan M, Barker R, Goldsbrough A, Jarvis M, Kavanagh T, Iturriaga G. (1986) The structure and transcription start site of a major potato tuber protein gene. Nucleic Acids Research 14: 4625-4636.
9. Christensen A H, Sharrock R A, Quail P H. (1992) Maize polyubiquitin genes: structure, thermal perturbation of expression and transcript splicing, and promoter activity following transfer to protoplasts by electroporation. Plant Mol. Biol. 18: 675-689.
10. Condon A G, Richards R A, Rebetzke G J, Farquhar G D (2002) Improving Intrinsic Water-Use Efficiency and crop yield. Crop Science 42:122-131.
11. Davies W J, Wilkinson S, Loveys B R (2002) Stomatal control by chemical signalling and the exploitation of this mechanism to increase water use efficiency in agriculture. New Phytol. 153: 449-460.
12. De Loose M, Gheysen G, Tiré C, Gielen J, Villarroel R, Genetello C, Van Montagu M, Depicker A, Inzé D (1991) The extensin signal peptide allows secretion of a heterologous protein from protoplasts. Gene 99: 95-100.
13. Dong C, Beetham P, Vincent K, Sharp P (2006) Oligonucleotide-directed gene repair in wheat using a transient plasmid gene repair assay system. Plant Cell Reports 25: 457-465.
14. Dratewka-Kos E, Rahman S, Grzelczak Z F, Kennedy T D, Murray R K, Lane B G (1989) Polypeptide structure of germin as deduced from cDNA sequencing. J. Biol. Chem. 264: 4896-4900.
15. Elomaa P, Mehto M, Kotilainen M, Helariutta Y, Nevalainen L, Teeri T H (1998) A bHLH transcription factor mediates organ, region and flower type specific signals on dihydroflavonol-4-reductase (dfr) gene expression in the inflorescence of *Gerbera hybrida* (Asteraceae). The Plant Journal 16(1): 93-99.
16. Farquhar G D and Sharky T D (1994) Photosynthesis and carbon assimilation (p187) in Physiology and Determination of Crop Yield, ASA, CSSA, SSSA, Madison Wis. USA.
17. Fraley R T, Rogers S G, Horsch R B, Sanders P R, Flick J S, Adams S P, Bittner M L, Brand L A, Fink C L, Fry J S, Galluppi G R, Goldberg S B, Hoffmann N L, Woo S C (1983) Expression of bacterial genes in plant cells. Proc Natl Acad Sci USA. 80(15): 4803-4807.
18. Goeddel, Gene Expression Technology: Methods in Enzymology 185, Academic Press, San Diego, Calif. (1990).
19. Goldberg R B (1986) Regulation of plant gene expression. Philos Trans R Soc London Ser B 314: 343-353.
20. Greene E A, Codomo C A, Taylor N E, Henikoff J G, Till B J, Reynolds S H, Enns L C, Burtner C, Johnson J E, Odden A R, Comai L, Henikoff S (2003) Spectrum of chemically induced mutations from a large-scale reverse-genetic screen in *Arabidopsis*. Genetics 164(2):731-740.
21. Gruber et al. "Vectors for Plant Transformation" in Methods in Plant Molecular Biology and Biotechnology, Glick B. R. and Thompson, J. E. Eds. (CRC Press, Inc., Boca Raton, 1993) pages 89-119.
22. Hardie D G (1999) PLANT PROTEIN SERINE/THREONINE KINASES: Classification and Functions. Annu Rev Plant Physiol Plant Mol Biol. 50:97-131.

23. Henikoff S, and Henikoff J G (1992) Amino acid substitution matrices from protein blocks. Proc. Natl. Acad. Sci. USA 89: 10915-10919.
24. Horsch R, Fry J E, Hoffmann N, Eichholtz D, Rogers S, Fraley R T (1985) A simple and general method for transferring genes into plants. Science 227:1229-1231.
25. Huang Y, Li H, Gupta R, Morris P C, Luan S, Kieber J J. (2000) ATMPK4, an *Arabidopsis* homolog of mitogen-activated protein kinase, is activated in vitro by AtMEK1 through threonine phosphorylation. Plant Physiol. 122(4): 1301-1310.
26. Kado C I, Hooykaas P J (1991) Molecular mechanisms of crown gall tumorigenesis. Crit. Rev. Plant Sci. 10: 1-32.
27. Karaba A, Dixit S, Greco R, Aharoni A, Trijatmiko K R, Marsch-Martinez N, Krishnan A, Nataraj a K N, Udayakumar M, Pereira A (2007) Improvement of water use efficiency in rice by expression of *HARDY*, an *Arabidopsis* drought and salt tolerant gene. Proc. Natl. Acad. Sci. USA 104: 15270-15272.
28. Keil M, Sanchez-Serrano J, Schell J, Willmitzer L (1986) Primary structure of a proteinase inhibitor II gene from potato (*Solanum tuberosum*). Nucl. Acids Res. 14: 5641-5650.
29. Laemmli, U K (1970) Cleavage of structural proteins during the assembly of the head of bacteriophage T4. Nature. 227(259): 680-685.
30. Last D I, Brettell R I, Chamberlain D A, Chaudhury A M, Larkin P J, Marsh E L, Peacock W J, Dennis E S (1991) pEmu: an improved promoter for gene expression in cereal cells Theor. Appl. Genet. 81: 581-588.
31. Lepetit M, Ehling M, Chaubet N, Gigot C (1992) A plant histone gene promoter can direct both replication-dependent and -independent gene expression in transgenic plants. Mol. Gen. Genet., 231: 276-285.
32. Lund P, Dunsmuir P (1992) A plant signal sequence enhances the secretion of bacterial ChiA in transgenic tobacco. Plant Mol. Biol. 18: 47-53.
33. McElroy D, Zhang W, Cao J, Wu R (1990) Isolation of an efficient actin promoter for use in rice transformation. Plant Cell 2(2): 163-171.
34. Mian M A R, Bailey M A, Ashley D A, Wells R, Carter T E Jr, Parrott W A, Boerma H R (1996) Molecular markers associated with water use efficiency and leaf ash in soybean. Crop Sci. 36: 1252-1257.
35. Martin B, Nienhuis J, King G, Schaefer A (1989) Restriction Fragment Length Polymorphisms Associated with Water Use Efficiency in Tomato. Science. 243(4899): 1725-1728.
36. Masle J, Gilmore S R, Farquhar G D (2005) The *ERECTA* gene regulates plant transpiration efficiency in *Arabidopsis*. Nature 436: 866-870
37. Matsuoka K, Nakamura K (1991) Propeptide of a precursor to a plant vacuolar protein required for vacuolar targeting. Proc. Nat'l Acad. Sci. USA 88: 834-838.
38. van der Meer I M, Spelt C E, Mol J N, Stuitje A R (1990) Promoter analysis of the chalcone synthase (chsA) gene of *Petunia hybrida*: a 67 bp promoter region directs flower-specific expression. Plant Molecular Biology 15(1): 95-109.
39. Mogen B D, MacDonald M H, Graybosch R, Hunt A G (1990) Upstream sequences other than AAUAAA are required for efficient messenger RNA 3'-end formation in plants. Plant Cell 2: 1261-1272.
40. Moloney M M, Walker J M, Sharma K K (1989) High efficiency transformation of *Brassica napus* using *Agrobacterium* vectors. Plant Cell Reports 8: 238-242.
41. Needleman S B, Wunsch C D (1970) A general method applicable to the search for similarities in the amino acid sequence of two proteins. J. Mol. Biol. 48: 443-453.
42. Odell J T, Nagy F, Chua N H (1985) Identification of DNA sequences required for activity of the cauliflower mosaic virus 35S promoter. Nature 313: 810-812.
43. Oleykowski C A, Bronson Mullins C R, Godwin A K, Yeung A T (1998) Mutation detection using a novel plant endonuclease. Nucleic Acids Res. 26(20): 4597-4602.
44. Sanford J C, Smith F D, Russell J A (1993) Optimizing the biolistic process for different biological applications. Methods Enzymol. 217: 483-509.
45. Klein T M, Arentzen R, Lewis P A, Fitzpatrick-McElligott S (1992) Transformation of microbes, plants and animals by particle bombardment. Biotechnology 10: 286-291.
46. Sambrook J, Fritsch E F, Maniatis T (1989) Molecular Cloning. A Laboratory Manual, $2^{nd}$ Ed., Cold Spring Harbor Laboratory Press, New York
47. Sinclair T R (1994) Limits to crop yield. in Physiology and Determination of Crop Yield, ASA, CSSA, SSSA, Madison Wis. USA.
48. Price A H, Cairns J E, Horton P, Jones H G, Griffiths H (2002) Linking drought-resistance mechanisms to drought avoidance in upland rice using a QTL approach: progress and new opportunities to integrate stomatal and mesophyll responses. Journal of Experimental Botany 53: 989-1004.
49. Schwab R, Ossowski S, Riester M, Warthmann N, Weigel D (2006) Highly specific gene silencing by artificial microRNAs in *Arabidopsis*. Plant Cell 18(5): 1121-1133.
50. Shiu S H, Bleecker A B (2001) Receptor-like kinases from *Arabidopsis* form a monophyletic gene family related to animal receptor kinases. Proc Natl Acad Sci USA. 98(19): 10763-10768.
51. Stockinger E J, Mulinix C A, Long C M, Brettin T S, Iezzoni A F (1996) A linkage map of sweet cherry based on RAPD analysis of a microspore-derived callus culture population. J. Heredity 87: 214-218.
52. Thumma B R, Naidu B P, Chandra A, Cameron D F, Bahnisch L M, Liu C (2001) Identification of causal relationship among traits related to drought resistance in *Stylosanthes scabra* using QTL analysis. Journal of Experimental Botany 52: 203-214.
53. Torii K U, Mitsukawa N, Oosumi T, Matsuura Y, Yokoyama R, Whittier R F, Komeda Y (1996) The *Arabidopsis ERECTA* gene encodes a putative receptor protein kinase with extracellular leucine-rich repeats. Plant Cell. 8(4): 735-746.
54. Velten J, Velten L, Hain R, Schell J (1984) Isolation of a dual plant promoter fragment from the Ti plasmid of *Agrobacterium tumefaciens*. EMBO J. 3: 2723-2730.
55. Verwoert I I, Linden K H, Nijkamp H J, Stuitje A R (1994) Developmental specific expression and organelle targeting of the *Escherichia coli* fabD gene, encoding malonyl coenzyme A-acyl carrier protein transacylase in transgenic rape and tobacco seeds. Plant Mol. Biol. 26: 189-202.
56. Visser R G, Stolte A, Jacobsen E (1991) Expression of a chimaeric granule-bound starch synthase-GUS gene in transgenic potato plants. Plant Molecular Biology 17: 691-699.
57. Walling L L, Chang Y C, Demmin D S, Holzer F M (1988) Isolation, characterization and evolutionary relatedness of three members from the soybean multigene family encoding chlorophyll a/b binding proteins. Nucl. Acids Res. 16: 10477-10492.

58. Weissbach A and Weissbach H Eds. (1988) Methods for plant molecular biology. Academic Press (San Diego).

59. Wilkins T A, Bednarek S Y, Raikhel N V (1990) Role of propeptide glycan in post-translational processing and transport of barley lectin to vacuoles in transgenic tobacco. Plant Cell 2: 301-313.

60. Yang B, Wen X, Kodali N S, Oleykowski C A, Miller C G, Kulinski J, Besack D, Yeung J A, Kowalski D, Yeung A T (2000) Purification, cloning, and characterization of the CEL I nuclease. Biochemistry. 39(13): 3533-3541.

We claim:

1. A vector comprising a promoter having the nucleic acid sequence of SEQ ID NO: 183.

2. The vector of claim 1, further comprising a terminator having the nucleic acid sequence of SEQ ID NO: 189.

3. The vector of claim 2, further comprising a gene of interest inserted between the promoter and the terminator.

4. The vector of claim 3, wherein the promoter is not endogenous to the gene of interest endogenously.

5. A method of producing a genetically modified plant, comprising introducing the vector of claim 1 into a plant, a plant tissue culture, or a plant cell.

6. A genetically modified plant produced by the method of claim 5.

7. A seed produced by the genetically modified plant of claim 6, wherein the seed comprises the vector.

* * * * *

SEQUENCE LISTING

```
<160> NUMBER OF SEQ ID NOS: 200

<210> SEQ ID NO 1
<211> LENGTH: 1299
<212> TYPE: DNA
<213> ORGANISM: ARABIDOPSIS THALIANA

<400> SEQUENCE: 1

atgagagagc ttcttcttct tcttcttctt cattttcagt ctctaattct tttgatgatc     60

ttcatcactg tctctgcttc ttctgcttca aatccttctt tagctcctgt ttactcttcc    120

atggctacat tctctcctcg aatccaaatg ggaagtggtg aagaagatag atttgatgct    180

cataagaaac ttctgattgg tctcataatc agtttctctt ctcttggcct tataatcttg    240

ttctgttttg gcttttgggt ttatcgcaag aaccaatctc caaaatccat caacaactca    300

gattctgaga gtgggaattc attttccttg ttaatgagac gacttggctc gattaaaact    360

cagagaagaa cttctatcca aaagggttac gtgcaatttt tcgatatcaa gaccctcgag    420

aaagcgacag gcggttttaa agaaagtagt gtaatcggac aaggcggttt cggatgcgtt    480

tacaagggtt gtttggacaa taacgttaaa gcagcggtca agaagatcga gaacgttagc    540

caagaagcaa aacgagaatt tcagaatgaa gttgacttgt tgagcaagat ccatcactcg    600

aacgttatat cattgttggg ctctgcaagc gaaatcaact cgagtttcat cgtttatgag    660

cttatggaga aggatcatt agatgaacag ttacatgggc cttctcgtgg atcagctcta    720

acatggcaca tgcgtatgaa gattgctctt gatacagcta gaggactaga gtatctccat    780

gagcattgtc gtccaccagt tatccacaga gatttgaaat cttcgaatat tcttcttgat    840

tcttccttca acgccaagat ttcagatttc ggtcttgctg tatcgctgga tgaacatggc    900

aagaacaaca ttaaactctc tgggacactt ggttatgttg ccccggaata cctccttgac    960

ggaaaactga cggataagag tgatgtttat gcatttgggg tagttctgct tgaactcttg   1020

ttgggtagac gaccagttga aaaattaact ccagctcaat gccaatctct tgtaacttgg   1080

gcaatgccac aacttaccga tagatccaag cttccaaaca ttgtggatgc cgttataaaa   1140

gatacaatgg atctcaaaca cttataccag gtagcagcca tggctgtgtt gtgcgtgcag   1200

ccagaaccaa gttaccggcc gttgataacc gatgttcttc actcacttgt tccactggtt   1260

ccggtagagc taggagggac tctccggtta acaagatga                          1299

<210> SEQ ID NO 2
<211> LENGTH: 432
<212> TYPE: PRT
<213> ORGANISM: ARABIDOPSIS THALIANA

<400> SEQUENCE: 2

Met Arg Glu Leu Leu Leu Leu Leu Leu Leu His Phe Gln Ser Leu Ile
1               5                   10                  15

Leu Leu Met Ile Phe Ile Thr Val Ser Ala Ser Ser Ala Ser Asn Pro
            20                  25                  30

Ser Leu Ala Pro Val Tyr Ser Ser Met Ala Thr Phe Ser Pro Arg Ile
        35                  40                  45
```

```
Gln Met Gly Ser Gly Glu Glu Asp Arg Phe Asp Ala His Lys Lys Leu
    50                  55                  60

Leu Ile Gly Leu Ile Ile Ser Phe Ser Ser Leu Gly Leu Ile Ile Leu
65                  70                  75                  80

Phe Cys Phe Gly Phe Trp Val Tyr Arg Lys Asn Gln Ser Pro Lys Ser
                85                  90                  95

Ile Asn Asn Ser Asp Ser Glu Ser Gly Asn Ser Phe Ser Leu Leu Met
            100                 105                 110

Arg Arg Leu Gly Ser Ile Lys Thr Gln Arg Arg Thr Ser Ile Gln Lys
        115                 120                 125

Gly Tyr Val Gln Phe Phe Asp Ile Lys Thr Leu Glu Lys Ala Thr Gly
    130                 135                 140

Gly Phe Lys Glu Ser Ser Val Ile Gly Gln Gly Gly Phe Gly Cys Val
145                 150                 155                 160

Tyr Lys Gly Cys Leu Asp Asn Asn Val Lys Ala Ala Val Lys Lys Ile
                165                 170                 175

Glu Asn Val Ser Gln Glu Ala Lys Arg Glu Phe Gln Asn Glu Val Asp
            180                 185                 190

Leu Leu Ser Lys Ile His His Ser Asn Val Ile Ser Leu Leu Gly Ser
        195                 200                 205

Ala Ser Glu Ile Asn Ser Ser Phe Ile Val Tyr Glu Leu Met Glu Lys
    210                 215                 220

Gly Ser Leu Asp Glu Gln Leu His Gly Pro Ser Arg Gly Ser Ala Leu
225                 230                 235                 240

Thr Trp His Met Arg Met Lys Ile Ala Leu Asp Thr Ala Arg Gly Leu
                245                 250                 255

Glu Tyr Leu His Glu His Cys Arg Pro Pro Val Ile His Arg Asp Leu
            260                 265                 270

Lys Ser Ser Asn Ile Leu Leu Asp Ser Ser Phe Asn Ala Lys Ile Ser
        275                 280                 285

Asp Phe Gly Leu Ala Val Ser Leu Asp Glu His Gly Lys Asn Asn Ile
    290                 295                 300

Lys Leu Ser Gly Thr Leu Gly Tyr Val Ala Pro Glu Tyr Leu Leu Asp
305                 310                 315                 320

Gly Lys Leu Thr Asp Lys Ser Asp Val Tyr Ala Phe Gly Val Val Leu
                325                 330                 335

Leu Glu Leu Leu Leu Gly Arg Arg Pro Val Glu Lys Leu Thr Pro Ala
            340                 345                 350

Gln Cys Gln Ser Leu Val Thr Trp Ala Met Pro Gln Leu Thr Asp Arg
        355                 360                 365

Ser Lys Leu Pro Asn Ile Val Asp Ala Val Ile Lys Asp Thr Met Asp
    370                 375                 380

Leu Lys His Leu Tyr Gln Val Ala Ala Met Ala Val Leu Cys Val Gln
385                 390                 395                 400

Pro Glu Pro Ser Tyr Arg Pro Leu Ile Thr Asp Val Leu His Ser Leu
                405                 410                 415

Val Pro Leu Val Pro Val Glu Leu Gly Gly Thr Leu Arg Leu Thr Arg
            420                 425                 430
```

<210> SEQ ID NO 3
<211> LENGTH: 1299
<212> TYPE: DNA
<213> ORGANISM: ARABIDOPSIS THALIANA

<400> SEQUENCE: 3

```
atgagagagc ttcttcttct tcttcttctt cattttcagt ctctaattct tttgatgatc     60

ttcatcactg tctctgcttc ttctgcttca aatccttctt tagctcctgt ttactcttcc    120

atggctacat tctctcctcg aatccaaatg ggaagtggtg aagaagatag atttgatgct    180

cataagaaac ttctgattgg tctcataatc agtttctctt ctcttggcct tataatcttg    240

ttctgttttg gcttttgggt ttatcgcaag aaccaatctc caaaatccat caacaactca    300

gattctgaga gtgggaattc attttccttg ttaatgagac gacttggctc gattaaaact    360

cagagaagaa cttctatcca aaagggttac gtgcaatttt tcgatatcaa gaccctcgag    420

aaagcgacag gcggttttaa agaaagtagt gtaatcggac aaggcggttt cggatgcgtt    480

tacaagggtt gtttggacaa taacgttaaa gcagcggtca agaagatcga gaacgttagc    540

caagaagcaa aacgagaatt tcagaatgaa gttgacttgt tgagcaagat ccatcactcg    600

aacgttatat cattgttggg ctctgcaagc gaaatcaact cgagtttcat cgtttatgag    660

cttatggaga aaggatcatt agatgaacag ttacatgggc cttctcgtgg atcagctcta    720

acatggcaca tgcgtatgaa gattgctctt gatacagcta gaggactaga gtatctccat    780

gagcattgtc gtccaccagt tatccacaga gatttgaaat cttcgaatat tcttcttgat    840

tcttccttca acgccaagat ttcagatttc ggttttgctg tatcgctgga tgaacatggc    900

aagaacaaca ttaaactctc tgggacactt ggttatgttg ccccggaata cctccttgac    960

ggaaaactga cggataagag tgatgtttat gcatttgggg tagttctgct tgaactcttg   1020

ttgggtagac gaccagttga aaaattaact ccagctcaat gccaatctct tgtaacttgg   1080

gcaatgccac aacttaccga tagatccaag cttccaaaca ttgtggatgc cgttataaaa   1140

gatacaatgg atctcaaaca cttataccag gtagcagcca tggctgtgtt gtgcgtgcag   1200

ccagaaccaa gttaccggcc gttgataacc gatgttcttc actcacttgt tccactggtt   1260

ccggtagagc taggagggac tctccggtta acaagatga                           1299
```

```
<210> SEQ ID NO 4
<211> LENGTH: 432
<212> TYPE: PRT
<213> ORGANISM: ARABIDOPSIS THALIANA

<400> SEQUENCE: 4

Met Arg Glu Leu Leu Leu Leu Leu Leu Leu His Phe Gln Ser Leu Ile
1               5                   10                  15

Leu Leu Met Ile Phe Ile Thr Val Ser Ala Ser Ser Ala Ser Asn Pro
            20                  25                  30

Ser Leu Ala Pro Val Tyr Ser Ser Met Ala Thr Phe Ser Pro Arg Ile
        35                  40                  45

Gln Met Gly Ser Gly Glu Glu Asp Arg Phe Asp Ala His Lys Lys Leu
    50                  55                  60

Leu Ile Gly Leu Ile Ile Ser Phe Ser Ser Leu Gly Leu Ile Ile Leu
65                  70                  75                  80

Phe Cys Phe Gly Phe Trp Val Tyr Arg Lys Asn Gln Ser Pro Lys Ser
                85                  90                  95

Ile Asn Asn Ser Asp Ser Glu Ser Gly Asn Ser Phe Ser Leu Leu Met
            100                 105                 110

Arg Arg Leu Gly Ser Ile Lys Thr Gln Arg Arg Thr Ser Ile Gln Lys
        115                 120                 125

Gly Tyr Val Gln Phe Phe Asp Ile Lys Thr Leu Glu Lys Ala Thr Gly
    130                 135                 140
```

```
Gly Phe Lys Glu Ser Ser Val Ile Gly Gln Gly Gly Phe Gly Cys Val
145                 150                 155                 160

Tyr Lys Gly Cys Leu Asp Asn Asn Val Lys Ala Ala Val Lys Lys Ile
                165                 170                 175

Glu Asn Val Ser Gln Glu Ala Lys Arg Glu Phe Gln Asn Glu Val Asp
            180                 185                 190

Leu Leu Ser Lys Ile His His Ser Asn Val Ile Ser Leu Leu Gly Ser
        195                 200                 205

Ala Ser Glu Ile Asn Ser Ser Phe Ile Val Tyr Glu Leu Met Glu Lys
    210                 215                 220

Gly Ser Leu Asp Glu Gln Leu His Gly Pro Ser Arg Gly Ser Ala Leu
225                 230                 235                 240

Thr Trp His Met Arg Met Lys Ile Ala Leu Asp Thr Ala Arg Gly Leu
                245                 250                 255

Glu Tyr Leu His Glu His Cys Arg Pro Pro Val Ile His Arg Asp Leu
            260                 265                 270

Lys Ser Ser Asn Ile Leu Leu Asp Ser Ser Phe Asn Ala Lys Ile Ser
        275                 280                 285

Asp Phe Gly Phe Ala Val Ser Leu Asp Glu His Gly Lys Asn Asn Ile
    290                 295                 300

Lys Leu Ser Gly Thr Leu Gly Tyr Val Ala Pro Glu Tyr Leu Leu Asp
305                 310                 315                 320

Gly Lys Leu Thr Asp Lys Ser Asp Val Tyr Ala Phe Gly Val Val Leu
                325                 330                 335

Leu Glu Leu Leu Leu Gly Arg Arg Pro Val Glu Lys Leu Thr Pro Ala
            340                 345                 350

Gln Cys Gln Ser Leu Val Thr Trp Ala Met Pro Gln Leu Thr Asp Arg
        355                 360                 365

Ser Lys Leu Pro Asn Ile Val Asp Ala Val Ile Lys Asp Thr Met Asp
    370                 375                 380

Leu Lys His Leu Tyr Gln Val Ala Ala Met Ala Val Leu Cys Val Gln
385                 390                 395                 400

Pro Glu Pro Ser Tyr Arg Pro Leu Ile Thr Asp Val Leu His Ser Leu
                405                 410                 415

Val Pro Leu Val Pro Val Glu Leu Gly Gly Thr Leu Arg Leu Thr Arg
            420                 425                 430
```

<210> SEQ ID NO 5
<211> LENGTH: 1160
<212> TYPE: DNA
<213> ORGANISM: ARABIDOPSIS THALIANA

<400> SEQUENCE: 5

```
atgggaagtg gtgaagaaga tagatttgat gctcataaga aacttctgat tggtctcata      60

atcagtttct cttctcttgg ccttataatc ttgttctgtt ttggcttttg ggtttatcgc     120

aagaaccaat ctccaaaatc catcaacaac tcagattctg agagtgggaa ttcattttcc     180

ttgttaatga gacgacttgg ctcgattaaa actcagagaa gaacttctat ccaaaagggt     240

tacgtgcaat ttttcgatat caagaccctc gagaaagcga caggcggttt taaagaaagt     300

agtgtaatcg gacaaggcgg tttcggatgc gtttacaagg gttgtttgga caataacgtt     360

aaagcagcgg tcaagaagat cgagaacgtt agccaagaag caaaacgaga atttcagaat     420

gaagttgact tgttgagcaa gatccatcac tcgaacgtta tatcattgtt gggctctgca     480
```

```
agcgaaatca actcgagttt catcgtttat gagcttatgg agaaaggatc attagatgaa    540

cagttacatg ggccttctcg tggatcagct ctaacatggc acatgcgtat gaagattgct    600

cttgatacag ctagaggact agagtatctc catgagcatt gtcgtccacc agttatccac    660

agagatttga aatcttcgaa tattcttctt gattcttcct tcaacgccaa gatttcagat    720

ttcggttttg ctgtatcgct ggatgaacat ggcaagaaca acattaaact ctctgggaca    780

cttggttatg ttgccccgga atacctcctt gacggaaaac tgacggataa gagtgatgtt    840

tatgcatttg ggtagttct gcttgaactc ttgttgggta gacgaccagt tgaaaaatta    900

actccagctc aatgccaatc tcttgtaact tgggcaatgc cacaacttac cgatagatcc    960

aagcttccaa acattgtgga tgccgttata aaagatacaa tggatctcaa acacttatac   1020

caggtagcag ccatggctgt gttgtgcgtg cagccagaac caagttaccg gccgttgata   1080

accgatgttc ttcactcact tgttccactg gttccggtag agctaggagg gactctccgg   1140

ttaacaagat gattcacaga                                               1160
```

```
<210> SEQ ID NO 6
<211> LENGTH: 383
<212> TYPE: PRT
<213> ORGANISM: ARABIDOPSIS THALIANA

<400> SEQUENCE: 6

Met Gly Ser Gly Glu Glu Asp Arg Phe Asp Ala His Lys Lys Leu Leu
1               5                   10                  15

Ile Gly Leu Ile Ile Ser Phe Ser Ser Leu Gly Leu Ile Ile Leu Phe
            20                  25                  30

Cys Phe Gly Phe Trp Val Tyr Arg Lys Asn Gln Ser Pro Lys Ser Ile
        35                  40                  45

Asn Asn Ser Asp Ser Glu Ser Gly Asn Ser Phe Ser Leu Leu Met Arg
    50                  55                  60

Arg Leu Gly Ser Ile Lys Thr Gln Arg Arg Thr Ser Ile Gln Lys Gly
65                  70                  75                  80

Tyr Val Gln Phe Phe Asp Ile Lys Thr Leu Glu Lys Ala Thr Gly Gly
                85                  90                  95

Phe Lys Glu Ser Ser Val Ile Gly Gln Gly Gly Phe Gly Cys Val Tyr
            100                 105                 110

Lys Gly Cys Leu Asp Asn Asn Val Lys Ala Ala Val Lys Lys Ile Glu
        115                 120                 125

Asn Val Ser Gln Glu Ala Lys Arg Glu Phe Gln Asn Glu Val Asp Leu
    130                 135                 140

Leu Ser Lys Ile His His Ser Asn Val Ile Ser Leu Leu Gly Ser Ala
145                 150                 155                 160

Ser Glu Ile Asn Ser Ser Phe Ile Val Tyr Glu Leu Met Glu Lys Gly
                165                 170                 175

Ser Leu Asp Glu Gln Leu His Gly Pro Ser Arg Gly Ser Ala Leu Thr
            180                 185                 190

Trp His Met Arg Met Lys Ile Ala Leu Asp Thr Ala Arg Gly Leu Glu
        195                 200                 205

Tyr Leu His Glu His Cys Arg Pro Pro Val Ile His Arg Asp Leu Lys
    210                 215                 220

Ser Ser Asn Ile Leu Leu Asp Ser Ser Phe Asn Ala Lys Ile Ser Asp
225                 230                 235                 240

Phe Gly Phe Ala Val Ser Leu Asp Glu His Gly Lys Asn Asn Ile Lys
                245                 250                 255
```

```
Leu Ser Gly Thr Leu Gly Tyr Val Ala Pro Glu Tyr Leu Leu Asp Gly
            260                 265                 270

Lys Leu Thr Asp Lys Ser Asp Val Tyr Ala Phe Gly Val Val Leu Leu
        275                 280                 285

Glu Leu Leu Leu Gly Arg Arg Pro Val Glu Lys Leu Thr Pro Ala Gln
    290                 295                 300

Cys Gln Ser Leu Val Thr Trp Ala Met Pro Gln Leu Thr Asp Arg Ser
305                 310                 315                 320

Lys Leu Pro Asn Ile Val Asp Ala Val Ile Lys Asp Thr Met Asp Leu
                325                 330                 335

Lys His Leu Tyr Gln Val Ala Ala Met Ala Val Leu Cys Val Gln Pro
            340                 345                 350

Glu Pro Ser Tyr Arg Pro Leu Ile Thr Asp Val Leu His Ser Leu Val
        355                 360                 365

Pro Leu Val Pro Val Glu Leu Gly Gly Thr Leu Arg Leu Thr Arg
    370                 375                 380


<210> SEQ ID NO 7
<211> LENGTH: 1160
<212> TYPE: DNA
<213> ORGANISM: ARABIDOPSIS THALIANA

<400> SEQUENCE: 7

atgggaagtg gtgaagaaga tagatttgat gctcataaga aacttctgat tggtctcata     60

atcagtttct cttctcttgg ccttataatc ttgttctgtt ttggcttttg ggtttatcgc    120

aagaaccaat ctccaaaatc catcaacaac tcagattctg agagtgggaa ttcattttcc    180

ttgttaatga gacgacttgg ctcgattaaa actcagagaa gaacttctat ccaaaagggt    240

tacgtgcaat ttttcgatat caagaccctc gagaaagcga caggcggttt taaagaaagt    300

agtgtaatcg gacaaggcgg tttcggatgc gtttacaagg gttgtttgga caataacgtt    360

aaagcagcgg tcaagaagat cgagaacgtt agccaagaag caaaacgaga atttcagaat    420

gaagttgact tgttgagcaa gatccatcac tcgaacgtta tatcattgtt gggctctgca    480

agcgaaatca actcgagttt catcgtttat gagcttatgg agaaaggatc attagatgaa    540

cagttacatg ggccttctcg tggatcagct ctaacatggc acatgcgtat gaagattgct    600

cttgatacag ctagaggact agagtatctc catgagcatt gtcgtccacc agttatccac    660

agagatttga aatcttcgaa tattcttctt gattcttcct tcaacgccaa gatttcagat    720

ttcggtcttg ctgtatcgct ggatgaacat ggcaagaaca acattaaact ctctgggaca    780

cttggttatg ttgccccgga atacctcctt gacggaaaac tgacggataa gagtgatgtt    840

tatgcatttg gggtagttct gcttgaactc ttgttgggta gacgaccagt tgaaaaatta    900

actccagctc aatgccaatc tcttgtaact tgggcaatgc cacaacttac cgatagatcc    960

aagcttccaa acattgtgga tgccgttata aaagatacaa tggatctcaa acacttatac   1020

caggtagcag ccatggctgt gttgtgcgtg cagccagaac caagttaccg gccgttgata   1080

accgatgttc ttcactcact tgttccactg gttccggtag agctaggagg gactctccgg   1140

ttaacaagat gattcacaga                                                1160


<210> SEQ ID NO 8
<211> LENGTH: 383
<212> TYPE: PRT
<213> ORGANISM: ARABIDOPSIS THALIANA
```

<400> SEQUENCE: 8

```
Met Gly Ser Gly Glu Glu Asp Arg Phe Asp Ala His Lys Lys Leu Leu
1               5                   10                  15

Ile Gly Leu Ile Ile Ser Phe Ser Ser Leu Gly Leu Ile Ile Leu Phe
            20                  25                  30

Cys Phe Gly Phe Trp Val Tyr Arg Lys Asn Gln Ser Pro Lys Ser Ile
        35                  40                  45

Asn Asn Ser Asp Ser Glu Ser Gly Asn Ser Phe Ser Leu Leu Met Arg
    50                  55                  60

Arg Leu Gly Ser Ile Lys Thr Gln Arg Arg Thr Ser Ile Gln Lys Gly
65                  70                  75                  80

Tyr Val Gln Phe Phe Asp Ile Lys Thr Leu Glu Lys Ala Thr Gly Gly
                85                  90                  95

Phe Lys Glu Ser Ser Val Ile Gly Gln Gly Gly Phe Gly Cys Val Tyr
            100                 105                 110

Lys Gly Cys Leu Asp Asn Asn Val Lys Ala Ala Val Lys Lys Ile Glu
        115                 120                 125

Asn Val Ser Gln Glu Ala Lys Arg Glu Phe Gln Asn Glu Val Asp Leu
    130                 135                 140

Leu Ser Lys Ile His His Ser Asn Val Ile Ser Leu Leu Gly Ser Ala
145                 150                 155                 160

Ser Glu Ile Asn Ser Ser Phe Ile Val Tyr Glu Leu Met Glu Lys Gly
                165                 170                 175

Ser Leu Asp Glu Gln Leu His Gly Pro Ser Arg Gly Ser Ala Leu Thr
            180                 185                 190

Trp His Met Arg Met Lys Ile Ala Leu Asp Thr Ala Arg Gly Leu Glu
        195                 200                 205

Tyr Leu His Glu His Cys Arg Pro Pro Val Ile His Arg Asp Leu Lys
    210                 215                 220

Ser Ser Asn Ile Leu Leu Asp Ser Ser Phe Asn Ala Lys Ile Ser Asp
225                 230                 235                 240

Phe Gly Leu Ala Val Ser Leu Asp Glu His Gly Lys Asn Asn Ile Lys
                245                 250                 255

Leu Ser Gly Thr Leu Gly Tyr Val Ala Pro Glu Tyr Leu Leu Asp Gly
            260                 265                 270

Lys Leu Thr Asp Lys Ser Asp Val Tyr Ala Phe Gly Val Val Leu Leu
        275                 280                 285

Glu Leu Leu Leu Gly Arg Arg Pro Val Glu Lys Leu Thr Pro Ala Gln
    290                 295                 300

Cys Gln Ser Leu Val Thr Trp Ala Met Pro Gln Leu Thr Asp Arg Ser
305                 310                 315                 320

Lys Leu Pro Asn Ile Val Asp Ala Val Ile Lys Asp Thr Met Asp Leu
                325                 330                 335

Lys His Leu Tyr Gln Val Ala Ala Met Ala Val Leu Cys Val Gln Pro
            340                 345                 350

Glu Pro Ser Tyr Arg Pro Leu Ile Thr Asp Val Leu His Ser Leu Val
        355                 360                 365

Pro Leu Val Pro Val Glu Leu Gly Gly Thr Leu Arg Leu Thr Arg
    370                 375                 380
```

<210> SEQ ID NO 9
<211> LENGTH: 1542
<212> TYPE: DNA
<213> ORGANISM: ARABIDOPSIS THALIANA

<400> SEQUENCE: 9

```
atcaaaaact tttcttttct tagcaaaaaa aacaaaaaaa tgagagagct tcttcttctt      60
cttcttcttc attttcagtc tctaattctt ttgatgatct tcatcactgt ctctgcttct     120
tctgcttcaa atccttcttt agctcctgtt tactcttcca tggctacatt ctctcctcga     180
atccaaatgg gaagtggtga agaagataga tttgatgctc ataagaaact tctgattggt     240
ctcataatca gtttctcttc tcttggcctt ataatcttgt tctgttttgg cttttgggtt     300
tatcgcaaga accaatctcc aaaatccatc aacaactcag attctgagag tgggaattca     360
ttttccttgt taatgagacg acttggctcg attaaaactc agagaagaac ttctatccaa     420
aagggttacg tgcaattttt cgatatcaag accctcgaga aagcgacagg cggttttaaa     480
gaaagtagtg taatcggaca aggcggtttc ggatgcgttt acaagggttg tttggacaat     540
aacgttaaag cagcggtcaa gaagatcgag aacgttagcc aagaagcaaa acgagaattt     600
cagaatgaag ttgacttgtt gagcaagatc catcactcga acgttatatc attgttgggc     660
tctgcaagcg aaatcaactc gagtttcatc gtttatgagc ttatggagaa aggatcatta     720
gatgaacagt tacatgggcc ttctcgtgga tcagctctaa catggcacat gcgtatgaag     780
attgctcttg atacagctag aggactagag tatctccatg agcattgtcg tccaccagtt     840
atccacagag atttgaaatc ttcgaatatt cttcttgatt cttccttcaa cgccaagatt     900
tcagatttcg gtcttgctgt atcgctggat gaacatggca agaacaacat taaactctct     960
gggacacttg gttatgttgc cccggaatac ctccttgacg gaaaactgac ggataagagt    1020
gatgtttatg catttggggt agttctgctt gaactcttgt tgggtagacg accagttgaa    1080
aaattaactc cagctcaatg ccaatctctt gtaacttggg caatgccaca acttaccgat    1140
agatccaagc ttccaaacat tgtggatgcc gttataaaag atacaatgga tctcaaacac    1200
ttataccagg tagcagccat ggctgtgttg tgcgtgcagc cagaaccaag ttaccggccg    1260
ttgataaccg atgttcttca ctcacttgtt ccactggttc cggtagagct aggagggact    1320
ctccggttaa caagatgatt cacagaaaca cgccaaaaga aatccaaagc catttagatg    1380
attttctttt atcctttgcc tttatatttt tttgtatagg gttatgatcc actcatctga    1440
aagtttgggg gtaagaatgt gagaatataa gttttcaggg ttgttgagtt ctatataatt    1500
atatttgttt ctttttattg tcaaatataa ttatattttt gt                       1542
```

<210> SEQ ID NO 10
<211> LENGTH: 1309
<212> TYPE: DNA
<213> ORGANISM: ARABIDOPSIS THALIANA

<400> SEQUENCE: 10

```
aaaatgagag agcttcttct tcttcttctt cttcattttc agtctctaat tcttttgatg      60
atcttcatca ctgtctctgc ttcttctgct tcaaatcctt ctttagctcc tgtttactct     120
tccatggcta cattctctcc tcgaatccaa atgggaagtg gtgaagaaga tagatttgat     180
gctcataaga aacttctgat tggtctcata atcagtttct cttctcttgg ccttataatc     240
ttgttctgtt ttggcttttg ggtttatcgc aagaaccaat ctccaaaatc catcaacaac     300
tcagattctg agagtgggaa ttcattttcc ttgttaatga gacgacttgg ctcgattaaa     360
actcagagaa gaacttctat ccaaaagggt tacgtgcaat tttcgatat caagaccctc     420
gagaaagcga caggcggttt taaagaaagt agtgtaatcg gacaaggcgg tttcggatgc     480
```

```
gtttacaagg gttgtttgga caataacgtt aaagcagcgg tcaagaagat cgagaacgtt    540

agccaagaag caaaacgaga atttcagaat gaagttgact tgttgagcaa gatccatcac    600

tcgaacgtta tatcattgtt gggctctgca agcgaaatca actcgagttt catcgtttat    660

gagcttatgg agaaaggatc attagatgaa cagttacatg ggccttctcg tggatcagct    720

ctaacatggc acatgcgtat gaagattgct cttgatacag ctagaggact agagtatctc    780

catgagcatt gtcgtccacc agttatccac agagatttga aatcttcgaa tattcttctt    840

gattcttcct tcaacgccaa gatttcagat ttcggtcttg ctgtatcgct ggatgaacat    900

ggcaagaaca acattaaact ctctgggaca cttggttatg ttgccccgga atacctcctt    960

gacggaaaac tgacggataa gagtgatgtt tatgcatttg ggtagttct gcttgaactc    1020

ttgttgggta gacgaccagt tgaaaaatta actccagctc aatgccaatc tcttgtaact   1080

tgggcaatgc cacaacttac cgatagatcc aagcttccaa acattgtgga tgccgttata   1140

aaagatacaa tggatctcaa acacttatac caggtagcag ccatggctgt gttgtgcgtg   1200

cagccagaac caagttaccg gccgttgata accgatgttc ttcactcact tgttccactg   1260

gttccggtag agctaggagg gactctccgg ttaacaagat gattcacag               1309
```

<210> SEQ ID NO 11
<211> LENGTH: 1177
<212> TYPE: DNA
<213> ORGANISM: ARABIDOPSIS THALIANA

<400> SEQUENCE: 11

```
tctgtgtcag gaatccaaat gggaagtggt gaagaagata gatttgatgc tcataagaaa     60

cttctgattg gtctcataat cagtttctct tctcttggcc ttataatctt gttctgtttt    120

ggcttttggg tttatcgcaa gaaccaatct ccaaaatcca tcaacaactc agattctgag    180

agtgggaatt cattttcctt gttaatgaga cgacttggct cgattaaaac tcagagaaga    240

acttctatcc aaaagggtta cgtgcaattt ttcgatatca agaccctcga gaaagcgaca    300

ggcggtttta aagaaagtag tgtaatcgga caaggcggtt tcggatgcgt ttacaagggt    360

tgtttggaca ataacgttaa agcagcggtc aagaagatcg agaacgttag ccaagaagca    420

aaacgagaat ttcagaatga agttgacttg ttgagcaaga tccatcactc gaacgttata    480

tcattgttgg gctctgcaag cgaaatcaac tcgagtttca tcgtttatga gcttatggag    540

aaaggatcat tagatgaaca gttacatggg ccttctcgtg gatcagctct aacatggcac    600

atgcgtatga agattgctct tgatacagct agaggactag agtatctcca tgagcattgt    660

cgtccaccag ttatccacag agatttgaaa tcttcgaata ttcttcttga ttcttccttc    720

aacgccaaga tttcagattt cggtcttgct gtatcgctgg atgaacatgg caagaacaac    780

attaaactct ctgggacact tggttatgtt gccccggaat acctccttga cggaaaactg    840

acggataaga gtgatgttta tgcatttggg gtagttctgc ttgaactctt gttgggtaga    900

cgaccagttg aaaaattaac tccagctcaa tgccaatctc ttgtaacttg ggcaatgcca    960

caacttaccg atagatccaa gcttccaaac attgtggatg ccgttataaa agatacaatg   1020

gatctcaaac acttatacca ggtagcagcc atggctgtgt tgtgcgtgca gccagaacca   1080

agttaccggc cgttgataac cgatgttctt cactcacttg ttccactggt tccggtagag   1140

ctaggaggga ctctccggtt aacaagatga ttcacag                            1177
```

<210> SEQ ID NO 12
<211> LENGTH: 154

<212> TYPE: DNA
<213> ORGANISM: ARABIDOPSIS THALIANA

<400> SEQUENCE: 12
tcgcaagaac caatctccaa aatccatcaa caactcagat tctgagagtg ggaattcatt 60
ttccttgtta atgagacgac ttggctcgat taaaactcag agaagaactt ctatccaaaa 120
gggttacgtg caatttttcg atatcaagac cctc 154

<210> SEQ ID NO 13
<211> LENGTH: 288
<212> TYPE: DNA
<213> ORGANISM: ARABIDOPSIS THALIANA

<400> SEQUENCE: 13
tctgtgtcag gaatccaaat gggaagtggt gaagaagata gatttgatgc tcataagaaa 60
cttctgattg gtctcataat cagtttctct tctcttggcc ttataatctt gttctgtttt 120
ggcttttggg tttatcgcaa gaaccaatct ccaaaatcca tcaacaactc agattctgag 180
agtgggaatt cattttcctt gttaatgaga cgacttggct cgattaaaac tcagagaaga 240
acttctatcc aaaagggtta cgtgcaattt ttcgatatca agaccctc 288

<210> SEQ ID NO 14
<211> LENGTH: 1510
<212> TYPE: DNA
<213> ORGANISM: ARABIDOPSIS THALIANA

<400> SEQUENCE: 14
tgttaaaagc gatttataat ttacaccgtt ttggtgtata tttctatcta tccttttaca 60
agacctatat atgttatgtt atggtggtgt actattttaa gtgagcgaca tagtattttc 120
ttcatatagc taattaatca acaacaattt cccaacttac aactatttgc gtactttaaa 180
cttatattga aagagaacta caaaattatt tttttgtaca agagaattat ggtcttcgga 240
tcaataattt ctctagatat aatatgtaaa gccaacccta taatttgtaa aatccatgat 300
ttgatataat tttcttttaa aattgtgaat tggcagacaa aaacaacatt acattttgat 360
ttaaattcat aactttgact tgctaaggaa acaccatgat tcattttttg tcatttgtta 420
catcatcact agaaatattt gatctaactt tattatgata atagactaca tactacatat 480
gcagttacga ttttaaatac tacatattta agcgtgttta aactgtaacc atatcatata 540
aaatgacata tctaaaagtg attttcaata ttttgatatg atatgtgttg tagcacggat 600
aatgatctaa tttttaagta ataagcttgt tcattacaaa agagaagaaa gtagtattgg 660
gccatgatta tgtaaggaca aaataggaag atgtggaaga agccattcga gggttttatt 720
acaaaaacag agtatataat tggtcataat gttttattca cttaatttaa cattattgca 780
ttatattttc atgaacacat atttctttaa ctaaaaatat acacatattt cttattgtag 840
atgaagtgaa aagaacaata tttgggttca catctatggg tgaatccttt taatcacccc 900
ctaaaataaa aaaggtgcca tatttctatt tttagagaaa gatatagagc accattggag 960
tggttttgct ccaaatatag agtttagaga aatatataat acaccattgg agatgctcta 1020
aaatgaattt atttatttat ttagatggaa gattctaatt ggttagaaaa agaggaagtg 1080
aataatagga ttcacctata agagtgaacc caagtatttt taagagataa tgtgtaaagt 1140
aaatagatgg tcattgtgtg aattatgaat agaaccatgg ttttccattt ttaattgctt 1200
aacatagggt aatcaacaat ggggtttaat atgtcaatag acaatagtaa agaaagtatt 1260

```
tgatctatcc caaatctttc ttcgttcgtt agttcatcac tttctttctt tttggttata   1320

ttaatggtag agaactaaaa attcaacttt ttattcaaaa gctccctttc tctttccctc   1380

ctttatttgc cataaaagtg atttcaagaa gacagcgaga gagaaagtga tagttcgttc   1440

actcttcgct ttctcaagaa tttcaaaaca ccaaaaaagt ctttagattg aatttcatca   1500

aaaacttttc                                                          1510
```

<210> SEQ ID NO 15
<211> LENGTH: 157
<212> TYPE: DNA
<213> ORGANISM: ARABIDOPSIS THALIANA

<400> SEQUENCE: 15

```
agacaagaaa aaaggaaaca aaattttatg aaagagatct ccattagaga aagagagagc     60

gagagagaga ttaatcttgg aagagcaatc tcacattctc acactgctct tagaaaatct    120

ctctttcacc attaaaaatc ccaaagagtc tggagaa                             157
```

<210> SEQ ID NO 16
<211> LENGTH: 1257
<212> TYPE: DNA
<213> ORGANISM: ARABIDOPSIS THALIANA

<400> SEQUENCE: 16

```
atgggaaaga ttcttcatct tcttcttctt cttcttaagg tctctgttct tgaattcatc     60

attagtgttt ctgcttttac ttcacctgct tcacagcctt ctctttctcc tgtttacact    120

tccatggctt ccttttctcc agggatccac atgggcaaag gccaagaaca caagttagat    180

gcacacaaga aacttctaat cgctctcata atcacctcat cttctctagg actaatactt    240

gtatcttgtt tatgcttttg ggtttattgg tctaagaaat ctcccaaaaa caccaagaac    300

tcaggtgaga gtaggatttc attatccaag aagggctttg tgcagtcctt cgattacaag    360

acactagaga aagcaacagg cggtttcaaa gacggtaatc ttataggacg aggcgggttc    420

ggagatgttt acaaggcctg tttaggcaac aacactctag cagcagtcaa aaagatcgaa    480

aacgttagtc aagaagcaaa acgagaattt cagaatgaag ttgatttgtt gagcaagatt    540

caccacccga acatcatctc attgtttgga tatggaaatg aactcagttc gagttttatc    600

gtctacgagc tgatggaaag cggatcattg gatacacagt tacacggacc ttctcgggga    660

tcggctttaa catggcacat gcggatgaag attgctcttg atacagcaag agctgttgag    720

tatctccacg agcgttgtcg tcctccggtt atccacagag atcttaaatc gtcaaatatt    780

ctccttgatt cttccttcaa cgccaagatt tcggattttg gtcttgcggt aatggtgggg    840

gctcacggca aaaacaacat taaactatca ggaacacttg gttatgttgc tccagaatat    900

ctcctagatg gaaaattgac ggataagagt gatgtttatg cgtttggtgt ggttttactt    960

gaactcttgt taggaagacg gccggttgag aaattgagtt cggttcagtg tcaatctctt   1020

gtcacttggg caatgcccca acttacggat agatcaaagc ttccgaaaat cgtggatccg   1080

gttatcaaag atacaatgga tcataagcac ttataccagg tggcagccgt ggcagtgctt   1140

tgtgtacaac cagaaccgag ttatcgaccg ttgataaccg atgttcttca ctcactagtt   1200

ccattggttc cggtagagct aggagggact ctccggttaa taccatcatc gtcttga      1257
```

<210> SEQ ID NO 17
<211> LENGTH: 418
<212> TYPE: PRT
<213> ORGANISM: ARABIDOPSIS THALIANA

<400> SEQUENCE: 17

```
Met Gly Lys Ile Leu His Leu Leu Leu Leu Leu Leu Lys Val Ser Val
1               5                   10                  15

Leu Glu Phe Ile Ile Ser Val Ser Ala Phe Thr Ser Pro Ala Ser Gln
            20                  25                  30

Pro Ser Leu Ser Pro Val Tyr Thr Ser Met Ala Ser Phe Ser Pro Gly
        35                  40                  45

Ile His Met Gly Lys Gly Gln Glu His Lys Leu Asp Ala His Lys Lys
    50                  55                  60

Leu Leu Ile Ala Leu Ile Ile Thr Ser Ser Ser Leu Gly Leu Ile Leu
65                  70                  75                  80

Val Ser Cys Leu Cys Phe Trp Val Tyr Trp Ser Lys Lys Ser Pro Lys
                85                  90                  95

Asn Thr Lys Asn Ser Gly Glu Ser Arg Ile Ser Leu Ser Lys Lys Gly
            100                 105                 110

Phe Val Gln Ser Phe Asp Tyr Lys Thr Leu Glu Lys Ala Thr Gly Gly
        115                 120                 125

Phe Lys Asp Gly Asn Leu Ile Gly Arg Gly Gly Phe Gly Asp Val Tyr
    130                 135                 140

Lys Ala Cys Leu Gly Asn Asn Thr Leu Ala Ala Val Lys Lys Ile Glu
145                 150                 155                 160

Asn Val Ser Gln Glu Ala Lys Arg Glu Phe Gln Asn Glu Val Asp Leu
                165                 170                 175

Leu Ser Lys Ile His His Pro Asn Ile Ile Ser Leu Phe Gly Tyr Gly
            180                 185                 190

Asn Glu Leu Ser Ser Ser Phe Ile Val Tyr Glu Leu Met Glu Ser Gly
        195                 200                 205

Ser Leu Asp Thr Gln Leu His Gly Pro Ser Arg Gly Ser Ala Leu Thr
    210                 215                 220

Trp His Met Arg Met Lys Ile Ala Leu Asp Thr Ala Arg Ala Val Glu
225                 230                 235                 240

Tyr Leu His Glu Arg Cys Arg Pro Pro Val Ile His Arg Asp Leu Lys
                245                 250                 255

Ser Ser Asn Ile Leu Leu Asp Ser Ser Phe Asn Ala Lys Ile Ser Asp
            260                 265                 270

Phe Gly Leu Ala Val Met Val Gly Ala His Gly Lys Asn Asn Ile Lys
        275                 280                 285

Leu Ser Gly Thr Leu Gly Tyr Val Ala Pro Glu Tyr Leu Leu Asp Gly
    290                 295                 300

Lys Leu Thr Asp Lys Ser Asp Val Tyr Ala Phe Gly Val Val Leu Leu
305                 310                 315                 320

Glu Leu Leu Leu Gly Arg Arg Pro Val Glu Lys Leu Ser Ser Val Gln
                325                 330                 335

Cys Gln Ser Leu Val Thr Trp Ala Met Pro Gln Leu Thr Asp Arg Ser
            340                 345                 350

Lys Leu Pro Lys Ile Val Asp Pro Val Ile Lys Asp Thr Met Asp His
        355                 360                 365

Lys His Leu Tyr Gln Val Ala Ala Val Ala Val Leu Cys Val Gln Pro
    370                 375                 380

Glu Pro Ser Tyr Arg Pro Leu Ile Thr Asp Val Leu His Ser Leu Val
385                 390                 395                 400

Pro Leu Val Pro Val Glu Leu Gly Gly Thr Leu Arg Leu Ile Pro Ser
```

405 410 415

Ser Ser

<210> SEQ ID NO 18
<211> LENGTH: 1302
<212> TYPE: DNA
<213> ORGANISM: ARABIDOPSIS THALIANA

<400> SEQUENCE: 18
atgaagcaaa ttgttataac agctcttgtt ttactacaag cttatgttct tcatcaatcc 60
acatgtgtta tgtcccttac tacacaagaa tctccttctc ctcaaccttc tgctttcact 120
cccgccttat ctcctgatta tcaacagaga gagaaggaat tgcataaaca agagagtaac 180
aacatgagac tggttatttc actagcagct acattttcct tagttggtat aatcttactt 240
tgctctctgc tttattggtt ttgccatagg agaagaaacc tcaagagctc aggttgtggg 300
tgtagtggaa tcacattctt gaatcggttt agtcgctcaa aaacattaga caagagaact 360
acaaagcagg gaacagtgtc attgatcgat tacaatatac tagaagaagg aactagtggt 420
ttcaaggaga gtaacatttt gggtcaaggt ggatttggat gtgtatattc tgccacatta 480
gagaacaaca tttcagctgc ggttaagaag ctagactgtg ccaatgaaga tgcagcaaag 540
gaatttaaga gtgaggttga gatattgagt aagctccagc acccgaatat aatatccctt 600
ttgggttata gcacgaatga tactgcgaga ttcattgtct atgagctgat gccaaacgtt 660
tctctggaat ctcatttaca cggatcttct cagggttcgg cgatcacatg gcctatgagg 720
atgaagattg ctcttgatgt aacaagggga ttagaatatt tgcatgaaca ttgtcatcca 780
gcaatcattc acagggactt gaaatcatcc aacatcttat tagatagcaa tttcaatgct 840
aagatttcag attttggtct agctgttgtt gatgggccaa agaacaagaa ccataaactt 900
tccgggacag ttggctacgt tgcaccagag tatcttctca acggccaatt gacagaaaag 960
agcgacgtgt atgcttttgg agtagtgtta ttagagcttt tactcgggaa aaaacctgtg 1020
gagaaactag ctcccggtga atgccaatcc atcatcactt gggcaatgcc ttatctcact 1080
gatagaacca agttaccaag cgtcatagat cctgcgatta aagatacgat ggacttgaaa 1140
cacctttacc aggtagcggc agtggcgatt ttgtgcgtgc agccagaacc gagttataga 1200
ccgttgatta cagacgtctt gcattctctt ataccttttgg ttccaatgga acttggtgga 1260
accttaaaaa ccatcaaatg tgcttcaatg gatcactgtt aa 1302

<210> SEQ ID NO 19
<211> LENGTH: 433
<212> TYPE: PRT
<213> ORGANISM: ARABIDOPSIS THALIANA

<400> SEQUENCE: 19

Met Lys Gln Ile Val Ile Thr Ala Leu Val Leu Leu Gln Ala Tyr Val
1 5 10 15

Leu His Gln Ser Thr Cys Val Met Ser Leu Thr Thr Gln Glu Ser Pro
20 25 30

Ser Pro Gln Pro Ser Ala Phe Thr Pro Ala Leu Ser Pro Asp Tyr Gln
35 40 45

Gln Arg Glu Lys Glu Leu His Lys Gln Glu Ser Asn Asn Met Arg Leu
50 55 60

Val Ile Ser Leu Ala Ala Thr Phe Ser Leu Val Gly Ile Ile Leu Leu
65 70 75 80

```
Cys Ser Leu Leu Tyr Trp Phe Cys His Arg Arg Arg Asn Leu Lys Ser
                85                  90                  95

Ser Gly Cys Gly Cys Ser Gly Ile Thr Phe Leu Asn Arg Phe Ser Arg
            100                 105                 110

Ser Lys Thr Leu Asp Lys Arg Thr Thr Lys Gln Gly Thr Val Ser Leu
        115                 120                 125

Ile Asp Tyr Asn Ile Leu Glu Glu Gly Thr Ser Gly Phe Lys Glu Ser
    130                 135                 140

Asn Ile Leu Gly Gln Gly Gly Phe Gly Cys Val Tyr Ser Ala Thr Leu
145                 150                 155                 160

Glu Asn Asn Ile Ser Ala Ala Val Lys Lys Leu Asp Cys Ala Asn Glu
                165                 170                 175

Asp Ala Ala Lys Glu Phe Lys Ser Glu Val Glu Ile Leu Ser Lys Leu
            180                 185                 190

Gln His Pro Asn Ile Ile Ser Leu Leu Gly Tyr Ser Thr Asn Asp Thr
        195                 200                 205

Ala Arg Phe Ile Val Tyr Glu Leu Met Pro Asn Val Ser Leu Glu Ser
    210                 215                 220

His Leu His Gly Ser Ser Gln Gly Ser Ala Ile Thr Trp Pro Met Arg
225                 230                 235                 240

Met Lys Ile Ala Leu Asp Val Thr Arg Gly Leu Glu Tyr Leu His Glu
                245                 250                 255

His Cys His Pro Ala Ile Ile His Arg Asp Leu Lys Ser Ser Asn Ile
            260                 265                 270

Leu Leu Asp Ser Asn Phe Asn Ala Lys Ile Ser Asp Phe Gly Leu Ala
        275                 280                 285

Val Val Asp Gly Pro Lys Asn Lys Asn His Lys Leu Ser Gly Thr Val
    290                 295                 300

Gly Tyr Val Ala Pro Glu Tyr Leu Leu Asn Gly Gln Leu Thr Glu Lys
305                 310                 315                 320

Ser Asp Val Tyr Ala Phe Gly Val Val Leu Leu Glu Leu Leu Leu Gly
                325                 330                 335

Lys Lys Pro Val Glu Lys Leu Ala Pro Gly Glu Cys Gln Ser Ile Ile
            340                 345                 350

Thr Trp Ala Met Pro Tyr Leu Thr Asp Arg Thr Lys Leu Pro Ser Val
        355                 360                 365

Ile Asp Pro Ala Ile Lys Asp Thr Met Asp Leu Lys His Leu Tyr Gln
    370                 375                 380

Val Ala Ala Val Ala Ile Leu Cys Val Gln Pro Glu Pro Ser Tyr Arg
385                 390                 395                 400

Pro Leu Ile Thr Asp Val Leu His Ser Leu Ile Pro Leu Val Pro Met
                405                 410                 415

Glu Leu Gly Gly Thr Leu Lys Thr Ile Lys Cys Ala Ser Met Asp His
            420                 425                 430

Cys
```

<210> SEQ ID NO 20
<211> LENGTH: 2016
<212> TYPE: DNA
<213> ORGANISM: ARABIDOPSIS THALIANA

<400> SEQUENCE: 20

```
atgaagacta tgtccaaatc gtctttgcgt ttgcattttc tctcgctact cttactttgt     60

tgtgtctccc cttcaagctt tgtcattata agattcatta cacataatca ttttgatggt    120
```

```
ctagtacgtt gtcatcccca caagtttcaa gcccttacgc agttcaagaa cgagtttgat    180
acccgccgtt gcaaccacag taactacttt aatggaatct ggtgtgataa ctccaaggtg    240
cggtcacaaa gctacgacta cgggactgtc tcagtggaac tctcaaatca aacagtagcc    300
tcttccagtt tcatcatctt cgctaccttg atctctctca caacaacttc acctcctctt    360
ccctcccttc cgagtttgtt tcccactttg cggaatctaa ccaagctcac agttttagac    420
ctttctcata atcacttctc cggaactttg aagcccaaca atagcctctt tgagttacac    480
caccttcgtt accttaatct cgaggtcaac aacttcagtt cctcactccc ttccgagttt    540
ggctatctca acaatttaca gcactgtggc ctcaaagagt tcccaaacat attcaagacc    600
cttaaaaaaa tggaggctat agacgtatcc aacaatagaa tcaacgggaa aatccctgag    660
tggttatgga gccttcctct tcttcattta gtgaatattt taaataattc ttttgacggt    720
ttcgaaggat caacggaagt tttagtaaat tcatcggttc ggatattact tttggagtca    780
aacaactttg aaggagcact tcctagtcta ccacactcta tcaacgcctt ctccgcgggt    840
cataacaatt tcactggaga gatacctctt tcaatctgca ccagaacctc acttggtgtc    900
cttgatctaa actacaacaa cctcattggt ccggtttctc aatgtttgag taatgtcacg    960
tttgtaaatc tccggaaaaa caatttggaa ggaactattc ctgagacttt cattgtcggt   1020
tcctcgataa ggacacttga tgttggatac aatcgactaa cgggaaagct tccaaggtct   1080
cttttgaact gctcatctct agagtttcta agcgttgaca acaacagaat caaagacaca   1140
tttcctttct ggctcaaggc tttaccaaag ttacaagtcc ttaccctaag ttcaaacaag   1200
ttttatggtc ctatatctcc tcctcatcaa ggtcctctcg ggtttccaga gctgagaata   1260
cttgagatat ctgataataa gtttactgga agcttgtcgt caagatactt tgagaattgg   1320
aaagcatcgt ccgccatgat gaatgaatat gtgggtttat atatggttta cgagaagaat   1380
ccttatggtg tagttgtcta taccttttg gatcgtatag atttgaaata caaaggtcta   1440
aacatggagc aagcgagggt tctcacttcc tacagcgcca ttgatttttc tagaaatcta   1500
cttgaaggaa atattcctga atccattgga cttttaaagg cattgattgc actaaactta   1560
tcgaacaacg cttttacagg ccatattcct cagtctttgg caaatcttaa ggagctccag   1620
tcactagaca tgtctaggaa ccaactctca gggactattc ctaatggact caagcaactc   1680
tcgtttttgg cttacataag tgtgtctcat aaccaactca agggtgaaat accacaagga   1740
acacaaatta ctgggcaatt gaaatcttcc tttgaaggga atgtaggact ttgtggtctt   1800
cctctcgagg aaaggtgctt cgacaatagt gcatctccaa cgcagcacca caagcaagac   1860
gaagaagaag aagaagaaca agtgttacac tggaaagcgg tggcaatggg gtatggacct   1920
ggattgttgg ttggatttgc aattgcatat gtcattgctt catacaagcc ggagtggcta   1980
accaagataa ttggtccgaa taagcgcaga aactag                              2016
```

<210> SEQ ID NO 21
<211> LENGTH: 671
<212> TYPE: PRT
<213> ORGANISM: ARABIDOPSIS THALIANA

<400> SEQUENCE: 21

```
Met Lys Thr Met Ser Lys Ser Ser Leu Arg Leu His Phe Leu Ser Leu
1               5                   10                  15

Leu Leu Leu Cys Cys Val Ser Pro Ser Ser Phe Val Ile Ile Arg Phe
            20                  25                  30
```

```
Ile Thr His Asn His Phe Asp Gly Leu Val Arg Cys His Pro His Lys
        35                  40                  45

Phe Gln Ala Leu Thr Gln Phe Lys Asn Glu Phe Asp Thr Arg Arg Cys
    50                  55                  60

Asn His Ser Asn Tyr Phe Asn Gly Ile Trp Cys Asp Asn Ser Lys Val
65                  70                  75                  80

Arg Ser Gln Ser Tyr Asp Tyr Gly Thr Val Ser Val Glu Leu Ser Asn
                85                  90                  95

Gln Thr Val Ala Ser Ser Ser Phe Ile Ile Phe Ala Thr Leu Ile Ser
            100                 105                 110

Leu Thr Thr Thr Ser Pro Pro Leu Pro Ser Leu Pro Ser Leu Phe Pro
        115                 120                 125

Thr Leu Arg Asn Leu Thr Lys Leu Thr Val Leu Asp Leu Ser His Asn
    130                 135                 140

His Phe Ser Gly Thr Leu Lys Pro Asn Asn Ser Leu Phe Glu Leu His
145                 150                 155                 160

His Leu Arg Tyr Leu Asn Leu Glu Val Asn Asn Phe Ser Ser Ser Leu
                165                 170                 175

Pro Ser Glu Phe Gly Tyr Leu Asn Asn Leu Gln His Cys Gly Leu Lys
            180                 185                 190

Glu Phe Pro Asn Ile Phe Lys Thr Leu Lys Lys Met Glu Ala Ile Asp
        195                 200                 205

Val Ser Asn Asn Arg Ile Asn Gly Lys Ile Pro Glu Trp Leu Trp Ser
    210                 215                 220

Leu Pro Leu Leu His Leu Val Asn Ile Leu Asn Asn Ser Phe Asp Gly
225                 230                 235                 240

Phe Glu Gly Ser Thr Glu Val Leu Val Asn Ser Ser Val Arg Ile Leu
                245                 250                 255

Leu Leu Glu Ser Asn Asn Phe Glu Gly Ala Leu Pro Ser Leu Pro His
            260                 265                 270

Ser Ile Asn Ala Phe Ser Ala Gly His Asn Asn Phe Thr Gly Glu Ile
        275                 280                 285

Pro Leu Ser Ile Cys Thr Arg Thr Ser Leu Gly Val Leu Asp Leu Asn
    290                 295                 300

Tyr Asn Asn Leu Ile Gly Pro Val Ser Gln Cys Leu Ser Asn Val Thr
305                 310                 315                 320

Phe Val Asn Leu Arg Lys Asn Asn Leu Glu Gly Thr Ile Pro Glu Thr
                325                 330                 335

Phe Ile Val Gly Ser Ser Ile Arg Thr Leu Asp Val Gly Tyr Asn Arg
            340                 345                 350

Leu Thr Gly Lys Leu Pro Arg Ser Leu Leu Asn Cys Ser Ser Leu Glu
        355                 360                 365

Phe Leu Ser Val Asp Asn Asn Arg Ile Lys Asp Thr Phe Pro Phe Trp
    370                 375                 380

Leu Lys Ala Leu Pro Lys Leu Gln Val Leu Thr Leu Ser Ser Asn Lys
385                 390                 395                 400

Phe Tyr Gly Pro Ile Ser Pro Pro His Gln Gly Pro Leu Gly Phe Pro
                405                 410                 415

Glu Leu Arg Ile Leu Glu Ile Ser Asp Asn Lys Phe Thr Gly Ser Leu
            420                 425                 430

Ser Ser Arg Tyr Phe Glu Asn Trp Lys Ala Ser Ser Ala Met Met Asn
        435                 440                 445

Glu Tyr Val Gly Leu Tyr Met Val Tyr Glu Lys Asn Pro Tyr Gly Val
```

```
    450                 455                 460

Val Val Tyr Thr Phe Leu Asp Arg Ile Asp Leu Lys Tyr Lys Gly Leu
465                 470                 475                 480

Asn Met Glu Gln Ala Arg Val Leu Thr Ser Tyr Ser Ala Ile Asp Phe
                485                 490                 495

Ser Arg Asn Leu Leu Glu Gly Asn Ile Pro Glu Ser Ile Gly Leu Leu
            500                 505                 510

Lys Ala Leu Ile Ala Leu Asn Leu Ser Asn Asn Ala Phe Thr Gly His
        515                 520                 525

Ile Pro Gln Ser Leu Ala Asn Leu Lys Glu Leu Gln Ser Leu Asp Met
    530                 535                 540

Ser Arg Asn Gln Leu Ser Gly Thr Ile Pro Asn Gly Leu Lys Gln Leu
545                 550                 555                 560

Ser Phe Leu Ala Tyr Ile Ser Val Ser His Asn Gln Leu Lys Gly Glu
                565                 570                 575

Ile Pro Gln Gly Thr Gln Ile Thr Gly Gln Leu Lys Ser Ser Phe Glu
            580                 585                 590

Gly Asn Val Gly Leu Cys Gly Leu Pro Leu Glu Glu Arg Cys Phe Asp
        595                 600                 605

Asn Ser Ala Ser Pro Thr Gln His His Lys Gln Asp Glu Glu Glu Glu
    610                 615                 620

Glu Glu Gln Val Leu His Trp Lys Ala Val Ala Met Gly Tyr Gly Pro
625                 630                 635                 640

Gly Leu Leu Val Gly Phe Ala Ile Ala Tyr Val Ile Ala Ser Tyr Lys
                645                 650                 655

Pro Glu Trp Leu Thr Lys Ile Ile Gly Pro Asn Lys Arg Arg Asn
            660                 665                 670
```

<210> SEQ ID NO 22
<211> LENGTH: 1662
<212> TYPE: DNA
<213> ORGANISM: ARABIDOPSIS THALIANA

<400> SEQUENCE: 22

```
atgacttcct ctcgccgtct tcttcttcct ctcggagcat cgctcactag aggaagattt     60

tcttccgatc aaatccgaaa tggatttcta agaaacttcc gtggattcgc caccgtaact    120

tcgtcggaac cggccttagc caatctggaa gcgaaatatg ccgtagcgtt gccagaatgt    180

tcaacagtag aggacgagat cacgaagatc cgtcatgaat tcgagttagc gaaacagagg    240

tttcttaata tccctgaagc tattaatagt atgccgaaga tgaatcctca agggatatat    300

gtgaataaga atctgagatt ggataatata caagtttatg gatttgatta tgattacact    360

ttggcacatt actcttctca cttacagagt ttgatctatg atcttgccaa gaaacatatg    420

gttaatgagt ttagatatcc tgatgtttgc actcagtttg agtatgatcc tacttttcca    480

atccgtgggt tgtactatga taaactaaaa ggatgcctca tgaaattgga tttcttcggt    540

tcaatcgagc cagatgggtg ttattttggt cgtcgtaagc ttagtaggaa ggaaatagaa    600

agcatgtatg gaacgcggca cataggtcgt gatcaagcga gaggtttggt gggattgatg    660

gatttcttct gttttagcga ggcgtgtctt atagcagaca tggtgcaata ttttgttgac    720

gccaaacttg agtttgatgc ctctaacatc tacaatgatg tcaatcgtgc tattcaacat    780

gtccatagaa gtggattggt tcatagagga attcttgctg atcccaacag atatttgcta    840

aaaaatggtc agcttctacg tttcctgaga atgctaaaag ataaaggaaa gaagcttttt    900
```

```
ttgctgacca actctccgta taattttgtt gatggcggaa tgcgctttct aatggaggaa    960

tcttttggct tcggagattc ctggcgagaa ctctttgatg ttgtgattgc taaagcaaat   1020

aaaccagaat tttacacatc tgagcaccct ttccgttgtt atgattcgga gagggataat   1080

ttggcattta caaaagtgga tgcatttgac ccaaagaaag tttattatca tggttgtctt   1140

aaatccttcc ttgaaatcac aaagtggcat ggccctgagg tgatttattt cggagatcac   1200

ttatttagtg atctaagagg gccttcaaaa gctggttggc gaactgctgc cataattcat   1260

gagctcgagc gagagataca gatacaaaat gatgatagct accggtttga gcaggccaag   1320

ttccatatta tccaagagtt actcggtaga tttcacgcga ctgtatcaaa caatcagaga   1380

agtgaagcat gccaatcact tttggatgag ctgaacaatg cgaggcagag agcaagagac   1440

acgatgaaac aaatgttcaa cagatcgttt ggagctacat ttgtcacaga cactggtcaa   1500

gaatcagcat tctcttatca catccaccaa tacgcagacg tttataccag taaacctgag   1560

aactttctgt tataccgacc tgaagcctgg cttcacgttc cttacgatat caagatcatg   1620

ccacatcatg tcaaggttgc ttcaaccctt ttcaaaacct ga                       1662
```

<210> SEQ ID NO 23
<211> LENGTH: 553
<212> TYPE: PRT
<213> ORGANISM: ARABIDOPSIS THALIANA

<400> SEQUENCE: 23

```
Met Thr Ser Ser Arg Arg Leu Leu Leu Pro Leu Gly Ala Ser Leu Thr
1               5                   10                  15

Arg Gly Arg Phe Ser Ser Asp Gln Ile Arg Asn Gly Phe Leu Arg Asn
            20                  25                  30

Phe Arg Gly Phe Ala Thr Val Thr Ser Ser Glu Pro Ala Leu Ala Asn
        35                  40                  45

Leu Glu Ala Lys Tyr Ala Val Ala Leu Pro Glu Cys Ser Thr Val Glu
    50                  55                  60

Asp Glu Ile Thr Lys Ile Arg His Glu Phe Glu Leu Ala Lys Gln Arg
65                  70                  75                  80

Phe Leu Asn Ile Pro Glu Ala Ile Asn Ser Met Pro Lys Met Asn Pro
                85                  90                  95

Gln Gly Ile Tyr Val Asn Lys Asn Leu Arg Leu Asp Asn Ile Gln Val
            100                 105                 110

Tyr Gly Phe Asp Tyr Asp Tyr Thr Leu Ala His Tyr Ser Ser His Leu
        115                 120                 125

Gln Ser Leu Ile Tyr Asp Leu Ala Lys Lys His Met Val Asn Glu Phe
    130                 135                 140

Arg Tyr Pro Asp Val Cys Thr Gln Phe Glu Tyr Asp Pro Thr Phe Pro
145                 150                 155                 160

Ile Arg Gly Leu Tyr Tyr Asp Lys Leu Lys Gly Cys Leu Met Lys Leu
                165                 170                 175

Asp Phe Phe Gly Ser Ile Glu Pro Asp Gly Cys Tyr Phe Gly Arg Arg
            180                 185                 190

Lys Leu Ser Arg Lys Glu Ile Glu Ser Met Tyr Gly Thr Arg His Ile
        195                 200                 205

Gly Arg Asp Gln Ala Arg Gly Leu Val Gly Leu Met Asp Phe Phe Cys
    210                 215                 220

Phe Ser Glu Ala Cys Leu Ile Ala Asp Met Val Gln Tyr Phe Val Asp
225                 230                 235                 240
```

```
Ala Lys Leu Glu Phe Asp Ala Ser Asn Ile Tyr Asn Asp Val Asn Arg
                245                 250                 255

Ala Ile Gln His Val His Arg Ser Gly Leu Val His Arg Gly Ile Leu
            260                 265                 270

Ala Asp Pro Asn Arg Tyr Leu Leu Lys Asn Gly Gln Leu Leu Arg Phe
        275                 280                 285

Leu Arg Met Leu Lys Asp Lys Gly Lys Lys Leu Phe Leu Leu Thr Asn
    290                 295                 300

Ser Pro Tyr Asn Phe Val Asp Gly Gly Met Arg Phe Leu Met Glu Glu
305                 310                 315                 320

Ser Phe Gly Phe Gly Asp Ser Trp Arg Glu Leu Phe Asp Val Val Ile
                325                 330                 335

Ala Lys Ala Asn Lys Pro Glu Phe Tyr Thr Ser Glu His Pro Phe Arg
            340                 345                 350

Cys Tyr Asp Ser Glu Arg Asp Asn Leu Ala Phe Thr Lys Val Asp Ala
        355                 360                 365

Phe Asp Pro Lys Lys Val Tyr Tyr His Gly Cys Leu Lys Ser Phe Leu
    370                 375                 380

Glu Ile Thr Lys Trp His Gly Pro Glu Val Ile Tyr Phe Gly Asp His
385                 390                 395                 400

Leu Phe Ser Asp Leu Arg Gly Pro Ser Lys Ala Gly Trp Arg Thr Ala
                405                 410                 415

Ala Ile Ile His Glu Leu Glu Arg Glu Ile Gln Ile Gln Asn Asp Asp
            420                 425                 430

Ser Tyr Arg Phe Glu Gln Ala Lys Phe His Ile Ile Gln Glu Leu Leu
        435                 440                 445

Gly Arg Phe His Ala Thr Val Ser Asn Asn Gln Arg Ser Glu Ala Cys
    450                 455                 460

Gln Ser Leu Leu Asp Glu Leu Asn Asn Ala Arg Gln Arg Ala Arg Asp
465                 470                 475                 480

Thr Met Lys Gln Met Phe Asn Arg Ser Phe Gly Ala Thr Phe Val Thr
                485                 490                 495

Asp Thr Gly Gln Glu Ser Ala Phe Ser Tyr His Ile His Gln Tyr Ala
            500                 505                 510

Asp Val Tyr Thr Ser Lys Pro Glu Asn Phe Leu Leu Tyr Arg Pro Glu
        515                 520                 525

Ala Trp Leu His Val Pro Tyr Asp Ile Lys Ile Met Pro His His Val
    530                 535                 540

Lys Val Ala Ser Thr Leu Phe Lys Thr
545                 550
```

<210> SEQ ID NO 24
<211> LENGTH: 1386
<212> TYPE: DNA
<213> ORGANISM: BRACHYPODIUM DISTACHYON

<400> SEQUENCE: 24

```
atggagattc cggcggcgcc gccgcctcca ttgccggtgc tgtgctcgta cgtcgtcttc     60

ttgctgctgc tgtcttcgtg ctcactggcc agagggagga tcgcggtttc ttccccgggc    120

ccgtcgcctg tggccgccgc cgttacagcc aatgagaccg cttcatcctc ttcttctccg    180

gtgtttccgg ccgctcctcc cgtcgtgatc acagtggtga ggcaccacca ttaccaccgg    240

gagctggtca tctccgctgt cctcgcctgc gtcgccaccg ccatgatcct cctctccaca    300

ctctacgcct ggacgatgtg gcggcggtct cgccggaccc cccacggcgg caagggccgc    360
```

```
ggccggagat cagggatcac actggtgcca atcctgagca agttcaattc agtgaagatg    420
agcaggaagg ggggccttgt gacgatgatc gagtacccgt cgctggaggc ggcgacaggc    480
aagttcggcg agagcaatgt gctcggtgtc ggcggcttcg gttgcgttta taaggcggcg    540
tttgatggcg gtgccaccgc cgccgtgaag aggcttgaag gcggcgggcc ggattgcgag    600
aaggaattcg agaatgagct ggatttgctt ggcaggatca ggcacccaaa catagtgtct    660
ctcctgggct tctgtgtcca tggtggcaat cactacattg tttatgagct catggagaag    720
ggatcattgg agacacagct gcatgggtct tcacatggat ctgctctgag ctggcacgtt    780
cggatgaaga tcgcgctcga tacggcgagg ggattagagt atcttcatga gcactgcaat    840
ccacctgtga tccataggga tctgaaacct tctaatatac ttttagattc agacttcaat    900
gctaagattg cagattttgg ccttgcggtc accggtggga atctcaacaa agggaacctg    960
aagctttccg ggaccttggg ttatgtagcc cctgagtact tattagatgg gaagttgact   1020
gagaagagcg atgtatacgc atttggagta gtgcttctag agctcctgat gggaaggaag   1080
cctgttgaga aaatgtcacc atctcagtgc caatcaattg tgtcatgggc tatgcctcag   1140
ctgaccgaca gatcgaagct ccccaacata attgacctgg tgatcaagga caccatggac   1200
ccaaaacact tgtaccaagt tgcagcagtg gctgttctat gtgtgcagcc cgaaccgagc   1260
tacagaccac tgataacaga tgttctccac tctcttgttc ctctagtgcc tgcggagctc   1320
ggaggaacac tcagggttgc agagccacct tcaccttctc cagaccaaag acattatcct   1380
tgttga                                                              1386
```

<210> SEQ ID NO 25
<211> LENGTH: 1302
<212> TYPE: DNA
<213> ORGANISM: BRASSICA NAPUS

<400> SEQUENCE: 25

```
atgaagaaac tggttcatct tcagtttttg tttcttgtca agatctttgc tactcaattc     60
ctcactcctt cttcatcatc ttttgctgct tcaaatcctt ctatagctcc tgtttacacc    120
tccatgacta ctttctctcc aggaattcaa atgggaagtg gtgaagaaca cagattagat    180
gcacataaga aactcctgat tggtcttata atcagttcct cttctcttgg tatcataatc    240
ttgatttgct ttggcttctg gatgtactgt cgcaagaaag ctcccaaacc catcaagatt    300
ccggatgccg agagtgggac ttcatcattt tcaatgtttg tgaggcggct aagctcaatt    360
aaaactcaca gaacatctag caatcagggt tatgtgcagc gtttcgattc caagacgcta    420
gagaaagcga caggcggttt caaagacagt aatgtaatcg gacagggcgg tttcggatgc    480
gtttacaagg cttctttgga cagcaacact aaagcagcgg ttaaaaagat cgaaaacgtt    540
acccaagaag caaaacgaga atttcagaat gaagttgagc tgttgagcaa gatccagcac    600
tccaatatta tatcattgtt gggctctgca agtgaaatca actcgagttt cgtcgtttat    660
gagttgatgg agaaaggatc cttagatgat cagttacatg gaccttcgtg tggatccgct    720
ctaacatggc atatgcgtat gaagattgct ctagatacag ctagaggact agagtatctc    780
catgaacatt gtcgtccacc agttatccac agggacctga aatcgtctaa tattcttctt    840
gattcttcct tcaatgccaa gatttcagat tttggtctgg ctgtatcggt tggagtgcat    900
gggagtaaca acattaaact ctctgggaca cttggttatg ttgccccgga atatctccta    960
gacggaaagt tgacggataa gagtgatgtc tatgcatttg ggtggttct tcttgaactt    1020
```

```
ttgttgggta ggcggccggt tgagaaattg agtccatctc agtgtcaatc tcttgtgact   1080

tgggcaatgc cacaacttac cgatagatcg aaactcccaa acatcgtgga tccggttata   1140

aaagatacaa tggatcttaa gcacttatac caagtagcag ccatggctgt gctgtgcgta   1200

cagccagaac cgagttaccg gccgctgata accgatgttc ttcattcact tgttccattg   1260

gttccggtag agctaggagg gactctccgg ttaacccgat ga                      1302


<210> SEQ ID NO 26
<211> LENGTH: 433
<212> TYPE: PRT
<213> ORGANISM: BRASSICA NAPUS

<400> SEQUENCE: 26

Met Lys Lys Leu Val His Leu Gln Phe Leu Phe Leu Val Lys Ile Phe
1               5                   10                  15

Ala Thr Gln Phe Leu Thr Pro Ser Ser Ser Ser Phe Ala Ala Ser Asn
            20                  25                  30

Pro Ser Ile Ala Pro Val Tyr Thr Ser Met Thr Thr Phe Ser Pro Gly
        35                  40                  45

Ile Gln Met Gly Ser Gly Glu Glu His Arg Leu Asp Ala His Lys Lys
    50                  55                  60

Leu Leu Ile Gly Leu Ile Ile Ser Ser Ser Ser Leu Gly Ile Ile Ile
65                  70                  75                  80

Leu Ile Cys Phe Gly Phe Trp Met Tyr Cys Arg Lys Lys Ala Pro Lys
                85                  90                  95

Pro Ile Lys Ile Pro Asp Ala Glu Ser Gly Thr Ser Ser Phe Ser Met
            100                 105                 110

Phe Val Arg Arg Leu Ser Ser Ile Lys Thr His Arg Thr Ser Ser Asn
        115                 120                 125

Gln Gly Tyr Val Gln Arg Phe Asp Ser Lys Thr Leu Glu Lys Ala Thr
    130                 135                 140

Gly Gly Phe Lys Asp Ser Asn Val Ile Gly Gln Gly Gly Phe Gly Cys
145                 150                 155                 160

Val Tyr Lys Ala Ser Leu Asp Ser Asn Thr Lys Ala Ala Val Lys Lys
                165                 170                 175

Ile Glu Asn Val Thr Gln Glu Ala Lys Arg Glu Phe Gln Asn Glu Val
            180                 185                 190

Glu Leu Leu Ser Lys Ile Gln His Ser Asn Ile Ile Ser Leu Leu Gly
        195                 200                 205

Ser Ala Ser Glu Ile Asn Ser Ser Phe Val Val Tyr Glu Leu Met Glu
    210                 215                 220

Lys Gly Ser Leu Asp Asp Gln Leu His Gly Pro Ser Cys Gly Ser Ala
225                 230                 235                 240

Leu Thr Trp His Met Arg Met Lys Ile Ala Leu Asp Thr Ala Arg Gly
                245                 250                 255

Leu Glu Tyr Leu His Glu His Cys Arg Pro Pro Val Ile His Arg Asp
            260                 265                 270

Leu Lys Ser Ser Asn Ile Leu Leu Asp Ser Ser Phe Asn Ala Lys Ile
        275                 280                 285

Ser Asp Phe Gly Leu Ala Val Ser Val Gly Val His Gly Ser Asn Asn
    290                 295                 300

Ile Lys Leu Ser Gly Thr Leu Gly Tyr Val Ala Pro Glu Tyr Leu Leu
305                 310                 315                 320

Asp Gly Lys Leu Thr Asp Lys Ser Asp Val Tyr Ala Phe Gly Val Val
```

```
                325                 330                 335

Leu Leu Glu Leu Leu Leu Gly Arg Arg Pro Val Glu Lys Leu Ser Pro
            340                 345                 350

Ser Gln Cys Gln Ser Leu Val Thr Trp Ala Met Pro Gln Leu Thr Asp
        355                 360                 365

Arg Ser Lys Leu Pro Asn Ile Val Asp Pro Val Ile Lys Asp Thr Met
    370                 375                 380

Asp Leu Lys His Leu Tyr Gln Val Ala Ala Met Ala Val Leu Cys Val
385                 390                 395                 400

Gln Pro Glu Pro Ser Tyr Arg Pro Leu Ile Thr Asp Val Leu His Ser
                405                 410                 415

Leu Val Pro Leu Val Pro Val Glu Leu Gly Gly Thr Leu Arg Leu Thr
            420                 425                 430

Arg


<210> SEQ ID NO 27
<211> LENGTH: 657
<212> TYPE: DNA
<213> ORGANISM: CICHORIUM ENDIVIA

<400> SEQUENCE: 27

atttttggtg ttgaaatgat gcacaacgga tctttggaat cccaattgca tggtccgtct      60

catggaactg gcttaagctg gcagcatcga atgaaaattg cacttgatat tgcacgagga     120

ctagagtatc ttcacgagcg ctgtaccccg cctgtgattc atagagatct gaaatcgtcc     180

aacattcttc taggttcgaa ctacaatgct aaactttctg atttcgggct cgcgattact     240

ggtgggattc agggcaagaa caacgtaaag ctttcgggaa cattaggtta tgtagctcca     300

gaatacctct tagatggtaa acttactgat aaaagtgatg tttatgcgtt tggagttgta     360

cttcttgaac ttttgatagg tagaaaacca gtggagaaaa tgtcaccatc tcaatgccaa     420

tctatcgtta catgggcaat gcctcaacta accgaccgat caaagcttcc taacatcgtt     480

gatcccgtga ttagagatac aatggacttg aagcacttgt atcaagttgc tgcggttgct     540

gtgctatgtg tacaaccgga accgagttac aggccattga taacagatgt tttgcattcg     600

ttcatcccac ttgtacctgt tgagcttgga gggtcgctaa gagttaccga atcttga        657


<210> SEQ ID NO 28
<211> LENGTH: 218
<212> TYPE: PRT
<213> ORGANISM: CICHORIUM ENDIVIA

<400> SEQUENCE: 28

Ile Phe Gly Val Glu Met Met His Asn Gly Ser Leu Glu Ser Gln Leu
1               5                   10                  15

His Gly Pro Ser His Gly Thr Gly Leu Ser Trp Gln His Arg Met Lys
            20                  25                  30

Ile Ala Leu Asp Ile Ala Arg Gly Leu Glu Tyr Leu His Glu Arg Cys
        35                  40                  45

Thr Pro Pro Val Ile His Arg Asp Leu Lys Ser Ser Asn Ile Leu Leu
    50                  55                  60

Gly Ser Asn Tyr Asn Ala Lys Leu Ser Asp Phe Gly Leu Ala Ile Thr
65                  70                  75                  80

Gly Gly Ile Gln Gly Lys Asn Asn Val Lys Leu Ser Gly Thr Leu Gly
                85                  90                  95

Tyr Val Ala Pro Glu Tyr Leu Leu Asp Gly Lys Leu Thr Asp Lys Ser
```

```
            100                 105                 110

Asp Val Tyr Ala Phe Gly Val Val Leu Leu Glu Leu Leu Ile Gly Arg
        115                 120                 125

Lys Pro Val Glu Lys Met Ser Pro Ser Gln Cys Gln Ser Ile Val Thr
    130                 135                 140

Trp Ala Met Pro Gln Leu Thr Asp Arg Ser Lys Leu Pro Asn Ile Val
145                 150                 155                 160

Asp Pro Val Ile Arg Asp Thr Met Asp Leu Lys His Leu Tyr Gln Val
                165                 170                 175

Ala Ala Val Ala Val Leu Cys Val Gln Pro Glu Pro Ser Tyr Arg Pro
            180                 185                 190

Leu Ile Thr Asp Val Leu His Ser Phe Ile Pro Leu Val Pro Val Glu
        195                 200                 205

Leu Gly Gly Ser Leu Arg Val Thr Glu Ser
    210                 215
```

<210> SEQ ID NO 29
<211> LENGTH: 474
<212> TYPE: DNA
<213> ORGANISM: CITRUS CLEMENTINA

<400> SEQUENCE: 29

```
aattcggcac gagggctgga ttccagtttt aatgcaaagc tttcagattt tggcctttct      60

gtgactgctg gaacccagag taggaatgtt aagatctctg gaactctggg ttatgttgcc     120

ccggagtacc tattagaagg aaaactaact gataaaagtg atgtatatgc tttcggagtt     180

gtattgctgg aacttttgat ggggagaagg cctgtggaaa agatgtcacc aactcaatgt     240

caatcaatgg tcacatgggc catgcctcag ctcaccgata gatcaaagct tccaaacatt     300

gtggatccag taattagaga cacaatggat ttaaagcact tataccaggt agccgctgtg     360

gcagtgctat gtatacaacc tgaaccaagt tataggccat tgataaccga cgttctgcat     420

tccctcattc ctcttgtacc taccgacctt ggagggtcac tccgagtgac ctaa           474
```

<210> SEQ ID NO 30
<211> LENGTH: 157
<212> TYPE: PRT
<213> ORGANISM: CITRUS CLEMENTINA

<400> SEQUENCE: 30

```
Asn Ser Ala Arg Gly Leu Asp Ser Ser Phe Asn Ala Lys Leu Ser Asp
1               5                   10                  15

Phe Gly Leu Ser Val Thr Ala Gly Thr Gln Ser Arg Asn Val Lys Ile
            20                  25                  30

Ser Gly Thr Leu Gly Tyr Val Ala Pro Glu Tyr Leu Leu Glu Gly Lys
        35                  40                  45

Leu Thr Asp Lys Ser Asp Val Tyr Ala Phe Gly Val Val Leu Leu Glu
    50                  55                  60

Leu Leu Met Gly Arg Arg Pro Val Glu Lys Met Ser Pro Thr Gln Cys
65                  70                  75                  80

Gln Ser Met Val Thr Trp Ala Met Pro Gln Leu Thr Asp Arg Ser Lys
                85                  90                  95

Leu Pro Asn Ile Val Asp Pro Val Ile Arg Asp Thr Met Asp Leu Lys
            100                 105                 110

His Leu Tyr Gln Val Ala Ala Val Ala Val Leu Cys Ile Gln Pro Glu
        115                 120                 125
```

-continued

```
Pro Ser Tyr Arg Pro Leu Ile Thr Asp Val Leu His Ser Leu Ile Pro
    130                 135                 140

Leu Val Pro Thr Asp Leu Gly Gly Ser Leu Arg Val Thr
145                 150                 155


<210> SEQ ID NO 31
<211> LENGTH: 770
<212> TYPE: DNA
<213> ORGANISM: CITRUS SINENSIS

<400> SEQUENCE: 31

ggattgtgtt tgtggcttta tcatttgaag tactccttca aatccagtaa caagaatgca      60

aagagcaaag attctgagaa tggagttgtg ttatcatcat ttttgggcaa attcacttct     120

gtgaggatgg ttagtaagaa gggatctgct atttcattta ttgagtataa gctgttagag     180

aaagccaccg acagttttca tgagagtaat atattgggtg agggtggatt tggatgtgtt     240

tacaaggcta aattggatga taacttgcac gtcgctgtca aaaaattaga ttgtgcaaca     300

caagatgccg gcagagaatt tgagaatgag gtggatttgc tgagtaatat tcaccaccca     360

aatgttgttt gtctgttggg ttatagtgct catgatgaca caaggtttat tgtttatgaa     420

ttgatggaaa atcggtccct tgatattcaa ttgcatggtc cttctcatgg atcagcattg     480

acttggcata tgcgaatgaa aattgctctt gataccgcta gaggattaga atatttacat     540

gagcactgca accctgcagt cattcataga gatctgaaat cctccaatat acttctagat     600

tccaagttta atgctaagct ctcagatttt ggtcttgcca taaccgatgg atcccaaaac     660

aagaacaatc ttaagctttc gggcactttg ggatatgtgg ctcccgagta tcttttagat     720

ggtaaattga cagacaagag tgatgtctat gcttttggag ttgtgcttct                770


<210> SEQ ID NO 32
<211> LENGTH: 257
<212> TYPE: PRT
<213> ORGANISM: CITRUS SINENSIS

<400> SEQUENCE: 32

Gly Leu Cys Leu Trp Leu Tyr His Leu Lys Tyr Ser Phe Lys Ser Ser
1               5                   10                  15

Asn Lys Asn Ala Lys Ser Lys Asp Ser Glu Asn Gly Val Val Leu Ser
            20                  25                  30

Ser Phe Leu Gly Lys Phe Thr Ser Val Arg Met Val Ser Lys Lys Gly
        35                  40                  45

Ser Ala Ile Ser Phe Ile Glu Tyr Lys Leu Leu Glu Lys Ala Thr Asp
    50                  55                  60

Ser Phe His Glu Ser Asn Ile Leu Gly Glu Gly Gly Phe Gly Cys Val
65                  70                  75                  80

Tyr Lys Ala Lys Leu Asp Asp Asn Leu His Val Ala Val Lys Lys Leu
                85                  90                  95

Asp Cys Ala Thr Gln Asp Ala Gly Arg Glu Phe Glu Asn Glu Val Asp
            100                 105                 110

Leu Leu Ser Asn Ile His His Pro Asn Val Val Cys Leu Leu Gly Tyr
        115                 120                 125

Ser Ala His Asp Asp Thr Arg Phe Ile Val Tyr Glu Leu Met Glu Asn
    130                 135                 140

Arg Ser Leu Asp Ile Gln Leu His Gly Pro Ser His Gly Ser Ala Leu
145                 150                 155                 160

Thr Trp His Met Arg Met Lys Ile Ala Leu Asp Thr Ala Arg Gly Leu
```

```
                165                 170                 175

Glu Tyr Leu His Glu His Cys Asn Pro Ala Val Ile His Arg Asp Leu
            180                 185                 190

Lys Ser Ser Asn Ile Leu Leu Asp Ser Lys Phe Asn Ala Lys Leu Ser
        195                 200                 205

Asp Phe Gly Leu Ala Ile Thr Asp Gly Ser Gln Asn Lys Asn Asn Leu
    210                 215                 220

Lys Leu Ser Gly Thr Leu Gly Tyr Val Ala Pro Glu Tyr Leu Leu Asp
225                 230                 235                 240

Gly Lys Leu Thr Asp Lys Ser Asp Val Tyr Ala Phe Gly Val Val Leu
                245                 250                 255

Leu


<210> SEQ ID NO 33
<211> LENGTH: 621
<212> TYPE: DNA
<213> ORGANISM: COFFEA CANEPHORA

<400> SEQUENCE: 33

gcattgacat ggcatcttag gatgaaaatt gcccttgatg tagctagagg attagaattt     60

ttgcatgagc actgccaccc agcagtgatc catagagatc tgaaatcatc taatatcctt    120

ctggattcaa atctcaatgc taagctatct gattttggtc ttgccattct tgatggggct    180

caaaataaga acaacatcaa gctttctgga accttgggct atgtagctcc agagtacctc    240

ttagatggta aattgactga caagagtgat gtttatgctt ttggagtggt gcttttggag    300

cttctcctga gaagaaagcc tgtggagaag ctggcaccag ctcaatgcca atctatagtc    360

acatgggcta tgcctcagct gacagataga tcaaagcttc caaacatcgt ggatcctgtg    420

attagaaatg ctatggatat aaagcactta ttccaggttg ctgcagtcgc tgtgctatgc    480

gtgcagcctg aaccaagcta tcgaccactg ataacagatg tgttgcattc ccttgttccc    540

cttgttccta tggagcttgg cgggacgctc agagttgaac gacctgcttc tgtgacctct    600

ctgttgattg attctacctg a                                              621


<210> SEQ ID NO 34
<211> LENGTH: 206
<212> TYPE: PRT
<213> ORGANISM: COFFEA CANEPHORA

<400> SEQUENCE: 34

Ala Leu Thr Trp His Leu Arg Met Lys Ile Ala Leu Asp Val Ala Arg
1               5                   10                  15

Gly Leu Glu Phe Leu His Glu His Cys His Pro Ala Val Ile His Arg
            20                  25                  30

Asp Leu Lys Ser Ser Asn Ile Leu Leu Asp Ser Asn Leu Asn Ala Lys
        35                  40                  45

Leu Ser Asp Phe Gly Leu Ala Ile Leu Asp Gly Ala Gln Asn Lys Asn
    50                  55                  60

Asn Ile Lys Leu Ser Gly Thr Leu Gly Tyr Val Ala Pro Glu Tyr Leu
65                  70                  75                  80

Leu Asp Gly Lys Leu Thr Asp Lys Ser Asp Val Tyr Ala Phe Gly Val
                85                  90                  95

Val Leu Leu Glu Leu Leu Leu Arg Arg Lys Pro Val Glu Lys Leu Ala
            100                 105                 110

Pro Ala Gln Cys Gln Ser Ile Val Thr Trp Ala Met Pro Gln Leu Thr
```

```
        115                 120                 125

Asp Arg Ser Lys Leu Pro Asn Ile Val Asp Pro Val Ile Arg Asn Ala
    130                 135                 140

Met Asp Ile Lys His Leu Phe Gln Val Ala Ala Val Ala Val Leu Cys
145                 150                 155                 160

Val Gln Pro Glu Pro Ser Tyr Arg Pro Leu Ile Thr Asp Val Leu His
                165                 170                 175

Ser Leu Val Pro Leu Val Pro Met Glu Leu Gly Gly Thr Leu Arg Val
            180                 185                 190

Glu Arg Pro Ala Ser Val Thr Ser Leu Leu Ile Asp Ser Thr
        195                 200                 205


<210> SEQ ID NO 35
<211> LENGTH: 411
<212> TYPE: DNA
<213> ORGANISM: EUCALYPTUS GUNNII

<400> SEQUENCE: 35

actgaggtga cccggaagaa aaacagggta aagctatcgg gcactttggg ttatgtagcc      60

ccagaatatg tcttggatgg taaattgact gataagagtg atgtctatgc ctttggagtt     120

gtgcttttgg agctcctttt gagaagaagg cctcttgaga tagtagcacc cactcagtgc     180

cagtctattg ttacatgggc catgcctcag ctgaccgacc gaactaagct tccagatatt     240

gtggatcctg taattagaga tgcgatggat gtcaagcact tataccaggc agctgctgtt     300

gctgttttgt gtctgcaacc agaaccgatc taccggccac tgataacgga tgtactccac     360

tctctcattc cacttgtacc cgttgaactt gggggaacgc tgaagaccta g              411


<210> SEQ ID NO 36
<211> LENGTH: 136
<212> TYPE: PRT
<213> ORGANISM: EUCALYPTUS GUNNII

<400> SEQUENCE: 36

Thr Glu Val Thr Arg Lys Lys Asn Arg Val Lys Leu Ser Gly Thr Leu
1               5                   10                  15

Gly Tyr Val Ala Pro Glu Tyr Val Leu Asp Gly Lys Leu Thr Asp Lys
            20                  25                  30

Ser Asp Val Tyr Ala Phe Gly Val Val Leu Leu Glu Leu Leu Leu Arg
        35                  40                  45

Arg Arg Pro Leu Glu Ile Val Ala Pro Thr Gln Cys Gln Ser Ile Val
    50                  55                  60

Thr Trp Ala Met Pro Gln Leu Thr Asp Arg Thr Lys Leu Pro Asp Ile
65                  70                  75                  80

Val Asp Pro Val Ile Arg Asp Ala Met Asp Val Lys His Leu Tyr Gln
                85                  90                  95

Ala Ala Ala Val Ala Val Leu Cys Leu Gln Pro Glu Pro Ile Tyr Arg
            100                 105                 110

Pro Leu Ile Thr Asp Val Leu His Ser Leu Ile Pro Leu Val Pro Val
        115                 120                 125

Glu Leu Gly Gly Thr Leu Lys Thr
    130                 135


<210> SEQ ID NO 37
<211> LENGTH: 522
<212> TYPE: DNA
<213> ORGANISM: FESTUCA ARUNDINACEA
```

<400> SEQUENCE: 37

```
acgaggcctc gtgccatact tttggattca gatttcaatg ccaagatttc ggatttcggt     60

cttgcagtgt caagtggaaa tcgcaccaaa ggtaatctga agctttccgg aactttgggc    120

tatgttgctc ctgagtactt attagacggg aagttgacag agaagagtga tgtatatgcg    180

ttcggagtag tacttcttga gcttttgtta ggaaggaggc caattgagaa gatggcccca    240

tctcaatgcc aatcaattgt tacatgggcc atgcctcagc taattgacag atcaaagctc    300

ccaaccataa ttgaccccgt gatcaggaac acgatggacc tgaagcactt gtaccaagtt    360

gctgcagtgg ctgtgctctg tgtgcagcca gaaccaagtt ataggccact aatcacagat    420

gtgctccact ctctgattcc cctggtgccc atggagctcg gagggtcact gagggctacc    480

ttggaatcgc ctcgcgtatc acaacatcgt tctccctgct ga                       522
```

<210> SEQ ID NO 38
<211> LENGTH: 173
<212> TYPE: PRT
<213> ORGANISM: FESTUCA ARUNDINACEA

<400> SEQUENCE: 38

```
Thr Arg Pro Arg Ala Ile Leu Leu Asp Ser Asp Phe Asn Ala Lys Ile
1               5                   10                  15

Ser Asp Phe Gly Leu Ala Val Ser Ser Gly Asn Arg Thr Lys Gly Asn
            20                  25                  30

Leu Lys Leu Ser Gly Thr Leu Gly Tyr Val Ala Pro Glu Tyr Leu Leu
        35                  40                  45

Asp Gly Lys Leu Thr Glu Lys Ser Asp Val Tyr Ala Phe Gly Val Val
    50                  55                  60

Leu Leu Glu Leu Leu Leu Gly Arg Arg Pro Ile Glu Lys Met Ala Pro
65                  70                  75                  80

Ser Gln Cys Gln Ser Ile Val Thr Trp Ala Met Pro Gln Leu Ile Asp
                85                  90                  95

Arg Ser Lys Leu Pro Thr Ile Ile Asp Pro Val Ile Arg Asn Thr Met
            100                 105                 110

Asp Leu Lys His Leu Tyr Gln Val Ala Ala Val Ala Val Leu Cys Val
        115                 120                 125

Gln Pro Glu Pro Ser Tyr Arg Pro Leu Ile Thr Asp Val Leu His Ser
    130                 135                 140

Leu Ile Pro Leu Val Pro Met Glu Leu Gly Gly Ser Leu Arg Ala Thr
145                 150                 155                 160

Leu Glu Ser Pro Arg Val Ser Gln His Arg Ser Pro Cys
                165                 170
```

<210> SEQ ID NO 39
<211> LENGTH: 740
<212> TYPE: DNA
<213> ORGANISM: GINKGO BILOBA

<400> SEQUENCE: 39

```
cctttattga atagattgaa ctccttccgt ggttctagga gaaagggatg tgcatatata     60

attgaatatt ctctgctgca agcagccaca aataatttta gtacaagtga catccttgga    120

gagggtggtt ttgggtgtgt atacagagct aggttagatg atgatttctt tgctgctgtg    180

aagaagttag atgagggcag caagcaggct gagtatgaat ttcagaatga agttgaacta    240

atgagcaaaa tcagacatcc aaatcttgtt tctttgctgg ggttctgcat tcatgggaag    300
```

```
actcggttgc tagtctacga gctcatgcaa aatggttctt tggaagacca attacatggg    360

ccatctcatg gatccgcact tacatggtac ctgcgcatga aaatagccct tgattcagca    420

aggggtctag aacacttgca cgagcactgc aatcctgctg tgattcatcg tgatttcaaa    480

tcatcaaata tccttctgga tgcaagcttc aatgccaagc tttcagattt tggtcttgca    540

gtaacagctg caggaggtat tggtaatgct aatgtcgagc tactgggcac tttgggatat    600

gtagctccag aatacctgct tgatggcaag ttgacggaga aaagtgatgt ctatggattt    660

ggagttgttc ttttggagct aattatggga agaaagccag ttgataaatc tgtggcaact    720

gaaagtcaat cgctagtttc                                                740


<210> SEQ ID NO 40
<211> LENGTH: 247
<212> TYPE: PRT
<213> ORGANISM: GINKGO BILOBA

<400> SEQUENCE: 40

Pro Leu Leu Asn Arg Leu Asn Ser Phe Arg Gly Ser Arg Arg Lys Gly
1               5                   10                  15

Cys Ala Tyr Ile Ile Glu Tyr Ser Leu Leu Gln Ala Ala Thr Asn Asn
            20                  25                  30

Phe Ser Thr Ser Asp Ile Leu Gly Glu Gly Gly Phe Gly Cys Val Tyr
        35                  40                  45

Arg Ala Arg Leu Asp Asp Asp Phe Phe Ala Ala Val Lys Lys Leu Asp
    50                  55                  60

Glu Gly Ser Lys Gln Ala Glu Tyr Glu Phe Gln Asn Glu Val Glu Leu
65                  70                  75                  80

Met Ser Lys Ile Arg His Pro Asn Leu Val Ser Leu Leu Gly Phe Cys
                85                  90                  95

Ile His Gly Lys Thr Arg Leu Leu Val Tyr Glu Leu Met Gln Asn Gly
            100                 105                 110

Ser Leu Glu Asp Gln Leu His Gly Pro Ser His Gly Ser Ala Leu Thr
        115                 120                 125

Trp Tyr Leu Arg Met Lys Ile Ala Leu Asp Ser Ala Arg Gly Leu Glu
    130                 135                 140

His Leu His Glu His Cys Asn Pro Ala Val Ile His Arg Asp Phe Lys
145                 150                 155                 160

Ser Ser Asn Ile Leu Leu Asp Ala Ser Phe Asn Ala Lys Leu Ser Asp
                165                 170                 175

Phe Gly Leu Ala Val Thr Ala Ala Gly Gly Ile Gly Asn Ala Asn Val
            180                 185                 190

Glu Leu Leu Gly Thr Leu Gly Tyr Val Ala Pro Glu Tyr Leu Leu Asp
        195                 200                 205

Gly Lys Leu Thr Glu Lys Ser Asp Val Tyr Gly Phe Gly Val Val Leu
    210                 215                 220

Leu Glu Leu Ile Met Gly Arg Lys Pro Val Asp Lys Ser Val Ala Thr
225                 230                 235                 240

Glu Ser Gln Ser Leu Val Ser
                245


<210> SEQ ID NO 41
<211> LENGTH: 1254
<212> TYPE: DNA
<213> ORGANISM: GLYCINE MAX
```

<400> SEQUENCE: 41

```
atgaaaatga agcttctcct catgcttctt cttcttgttc ttcttcttca ccaacccatt     60
tgggctgcag accctcctgc ttcttctcct gctttatctc caggggagga gcagcatcac    120
cggaataata aagtggtaat agctatcgtc gtagccacca ctgcacttgc tgcactcatt    180
ttcagtttct tatgcttctg ggtttatcat cataccaagt atccaacaaa atccaaattc    240
aaatccaaaa attttcgaag tccagatgca gagaagggga tcaccttagc accgtttgtg    300
agtaaattca gttccatcaa gattgttggc atggacgggt atgttccaat aattgactat    360
aagcaaatag aaaaaacgac caataatttt caagaaagta acatcttggg tgagggcggt    420
tttggacgtg tttacaaggc ttgtttggat cataacttgg atgttgcagt caaaaaacta    480
cattgtgaga ctcaacatgc tgagagagaa tttgagaacg aggtgaatat gttaagcaaa    540
attcagcatc cgaatataat atctttactg ggttgtagca tggatggtta cacgaggctc    600
gttgtctatg agctgatgca taatggatca ttggaagctc agttacatgg accttctcat    660
ggctcggcat tgacttggca catgaggatg aagattgctc ttgacacagc aagaggatta    720
gaatatctgc acgagcactg tcaccctgca gtgatccata gggatatgaa atcttctaat    780
attctcttag atgcaaactt caatgccaag ctgtctgatt ttggtcttgc cttaactgat    840
gggtcccaaa gcaagaagaa cattaaacta tcgggtacct tgggatacgt agcaccggag    900
tatcttctag atggtaaatt aagtgataaa agtgatgtct atgcttttgg ggttgtgcta    960
ttggagctcc tactaggaag gaagccagta gaaaaactgg taccagctca atgccaatct   1020
attgtcacat gggccatgcc acacctcacg gacagatcca agcttccaag cattgtggat   1080
ccagtgatta agaatacaat ggatcccaag cacttgtacc aggttgctgc tgtagctgtg   1140
ctgtgcgtgc aaccagaacc tagttaccgt ccactgatca ttgatgttct tcactcactc   1200
atccctcttg ttcccattga gcttggagga acactaagag tttcacaagt aatt         1254
```

<210> SEQ ID NO 42
<211> LENGTH: 418
<212> TYPE: PRT
<213> ORGANISM: GLYCINE MAX

<400> SEQUENCE: 42

```
Met Lys Met Lys Leu Leu Leu Met Leu Leu Leu Leu Val Leu Leu Leu
1               5                   10                  15

His Gln Pro Ile Trp Ala Ala Asp Pro Pro Ala Ser Ser Pro Ala Leu
            20                  25                  30

Ser Pro Gly Glu Glu Gln His His Arg Asn Asn Lys Val Val Ile Ala
        35                  40                  45

Ile Val Val Ala Thr Thr Ala Leu Ala Ala Leu Ile Phe Ser Phe Leu
    50                  55                  60

Cys Phe Trp Val Tyr His His Thr Lys Tyr Pro Thr Lys Ser Lys Phe
65                  70                  75                  80

Lys Ser Lys Asn Phe Arg Ser Pro Asp Ala Glu Lys Gly Ile Thr Leu
                85                  90                  95

Ala Pro Phe Val Ser Lys Phe Ser Ser Ile Lys Ile Val Gly Met Asp
            100                 105                 110

Gly Tyr Val Pro Ile Ile Asp Tyr Lys Gln Ile Glu Lys Thr Thr Asn
        115                 120                 125

Asn Phe Gln Glu Ser Asn Ile Leu Gly Glu Gly Gly Phe Gly Arg Val
    130                 135                 140
```

```
Tyr Lys Ala Cys Leu Asp His Asn Leu Asp Val Ala Val Lys Lys Leu
145                 150                 155                 160

His Cys Glu Thr Gln His Ala Glu Arg Glu Phe Glu Asn Glu Val Asn
                165                 170                 175

Met Leu Ser Lys Ile Gln His Pro Asn Ile Ile Ser Leu Leu Gly Cys
            180                 185                 190

Ser Met Asp Gly Tyr Thr Arg Leu Val Val Tyr Glu Leu Met His Asn
        195                 200                 205

Gly Ser Leu Glu Ala Gln Leu His Gly Pro Ser His Gly Ser Ala Leu
    210                 215                 220

Thr Trp His Met Arg Met Lys Ile Ala Leu Asp Thr Ala Arg Gly Leu
225                 230                 235                 240

Glu Tyr Leu His Glu His Cys His Pro Ala Val Ile His Arg Asp Met
                245                 250                 255

Lys Ser Ser Asn Ile Leu Leu Asp Ala Asn Phe Asn Ala Lys Leu Ser
            260                 265                 270

Asp Phe Gly Leu Ala Leu Thr Asp Gly Ser Gln Ser Lys Lys Asn Ile
        275                 280                 285

Lys Leu Ser Gly Thr Leu Gly Tyr Val Ala Pro Glu Tyr Leu Leu Asp
    290                 295                 300

Gly Lys Leu Ser Asp Lys Ser Asp Val Tyr Ala Phe Gly Val Val Leu
305                 310                 315                 320

Leu Glu Leu Leu Leu Gly Arg Lys Pro Val Glu Lys Leu Val Pro Ala
                325                 330                 335

Gln Cys Gln Ser Ile Val Thr Trp Ala Met Pro His Leu Thr Asp Arg
            340                 345                 350

Ser Lys Leu Pro Ser Ile Val Asp Pro Val Ile Lys Asn Thr Met Asp
        355                 360                 365

Pro Lys His Leu Tyr Gln Val Ala Ala Val Ala Val Leu Cys Val Gln
    370                 375                 380

Pro Glu Pro Ser Tyr Arg Pro Leu Ile Ile Asp Val Leu His Ser Leu
385                 390                 395                 400

Ile Pro Leu Val Pro Ile Glu Leu Gly Gly Thr Leu Arg Val Ser Gln
                405                 410                 415

Val Ile


<210> SEQ ID NO 43
<211> LENGTH: 702
<212> TYPE: DNA
<213> ORGANISM: HELIANTHUS ARGOPHYLLUS

<400> SEQUENCE: 43

actcaagcat caaaatattg taaatctttt gggtattgtg ttcatgatga cacaaggttt      60

ttggtctatg aaatgatgca tcaaggctct ttggactcac aattgcatgg accaactcat     120

ggaaccgcat taacctggca tcgaagaatg aaagtcgcac ttgatattgc tcgaggatta     180

gagtatcttc atgaacgatg caacccgcct gtgattcata gagatcttaa gtcatcgaac     240

attttgctag attccaattt caatgctaaa atttcgaatt ttgcacttgc taccactgag     300

ctccatgcga agaacaaagt taagctttcg gctacttctg gttatttggc tccggaatac     360

ctatcagaag gtaaacttac cgataaaagc gacgtatatg cattcggagt agtacttctt     420

gggcttttaa tcggtagaaa accagtggag aaaatgtcac catctttatt tcaatctatt     480

gtcacatggg caatgcctca gttaacagac cggtcaaagc ttccaaacat cgttgaccct     540
```

```
gtgattagag atacaatgga cctgaagcac ttatatcaag ttgctgctgt agccgtactt    600

tgcgtgcaac ccgaaccaag ttacagaccg ttgattacag acgtactaca ctcattcatt    660

ccactcgtac ccgttgatct tggagggtca ttaagagctt aa                       702


<210> SEQ ID NO 44
<211> LENGTH: 233
<212> TYPE: PRT
<213> ORGANISM: HELIANTHUS ARGOPHYLLUS

<400> SEQUENCE: 44

Thr Gln Ala Ser Lys Tyr Cys Lys Ser Phe Gly Tyr Cys Val His Asp
1               5                   10                  15

Asp Thr Arg Phe Leu Val Tyr Glu Met Met His Gln Gly Ser Leu Asp
            20                  25                  30

Ser Gln Leu His Gly Pro Thr His Gly Thr Ala Leu Thr Trp His Arg
        35                  40                  45

Arg Met Lys Val Ala Leu Asp Ile Ala Arg Gly Leu Glu Tyr Leu His
    50                  55                  60

Glu Arg Cys Asn Pro Pro Val Ile His Arg Asp Leu Lys Ser Ser Asn
65                  70                  75                  80

Ile Leu Leu Asp Ser Asn Phe Asn Ala Lys Ile Ser Asn Phe Ala Leu
                85                  90                  95

Ala Thr Thr Glu Leu His Ala Lys Asn Lys Val Lys Leu Ser Ala Thr
            100                 105                 110

Ser Gly Tyr Leu Ala Pro Glu Tyr Leu Ser Glu Gly Lys Leu Thr Asp
        115                 120                 125

Lys Ser Asp Val Tyr Ala Phe Gly Val Val Leu Leu Gly Leu Leu Ile
    130                 135                 140

Gly Arg Lys Pro Val Glu Lys Met Ser Pro Ser Leu Phe Gln Ser Ile
145                 150                 155                 160

Val Thr Trp Ala Met Pro Gln Leu Thr Asp Arg Ser Lys Leu Pro Asn
                165                 170                 175

Ile Val Asp Pro Val Ile Arg Asp Thr Met Asp Leu Lys His Leu Tyr
            180                 185                 190

Gln Val Ala Ala Val Ala Val Leu Cys Val Gln Pro Glu Pro Ser Tyr
        195                 200                 205

Arg Pro Leu Ile Thr Asp Val Leu His Ser Phe Ile Pro Leu Val Pro
    210                 215                 220

Val Asp Leu Gly Gly Ser Leu Arg Ala
225                 230


<210> SEQ ID NO 45
<211> LENGTH: 752
<212> TYPE: DNA
<213> ORGANISM: HELIANTHUS CILIARIS

<400> SEQUENCE: 45

cgatcatttc gttgcggctg taaaaaactc catggtccag aaccagatgc ccaaaaaggg     60

tttgagaatg aagtagattg gttaggtaaa ctcaagcatc aaaatattgt aaattttttg    120

ggttattgtg ttcatgatga cacaaggttt ttggtctatg aaatgatgca tcaaggctct    180

ttggactcac aattgcatgg accaactcat ggaaccgcat taacctggca tcgaagaatg    240

aaagtcgcac ttgatattgc tcgaggatta gagtatcttc atgaacgatg caacccgcct    300

gtgattcata gagatctcaa gtcatcgaac attttgctag attccaattt caatgctaaa    360
```

```
atttcgaatt ttgcacttgc taccactgag ctccatgcga agaacaaagt taagctttcg    420

ggtacttctg gttatttggc tccggaatac ctatccgaag gtaaacttac cgataaaagt    480

gatgtatatg cattcggagt agtacttctt gagcttttaa tcggtagaaa accagtggag    540

aaaatgtcac catctttatt tcaatctatt gtcacatggg caatgcctca gctaacagac    600

cggtcaaagc ttccaaacat tgttgaccct gtgattagag atacaatgga cctgaagcac    660

ttgtatcaag ttgctgctgt agccgtactt tgcgtgcaac ccgaaccaag ttacagaccg    720

ttgattacag acgtactaca ctcattcatt cc                                  752
```

<210> SEQ ID NO 46
<211> LENGTH: 251
<212> TYPE: PRT
<213> ORGANISM: HELIANTHUS CILIARIS

<400> SEQUENCE: 46

```
Arg Ser Phe Arg Cys Gly Cys Lys Lys Leu His Gly Pro Glu Pro Asp
1               5                   10                  15

Ala Gln Lys Gly Phe Glu Asn Glu Val Asp Trp Leu Gly Lys Leu Lys
            20                  25                  30

His Gln Asn Ile Val Asn Phe Leu Gly Tyr Cys Val His Asp Asp Thr
        35                  40                  45

Arg Phe Leu Val Tyr Glu Met Met His Gln Gly Ser Leu Asp Ser Gln
    50                  55                  60

Leu His Gly Pro Thr His Gly Thr Ala Leu Thr Trp His Arg Arg Met
65                  70                  75                  80

Lys Val Ala Leu Asp Ile Ala Arg Gly Leu Glu Tyr Leu His Glu Arg
                85                  90                  95

Cys Asn Pro Pro Val Ile His Arg Asp Leu Lys Ser Ser Asn Ile Leu
            100                 105                 110

Leu Asp Ser Asn Phe Asn Ala Lys Ile Ser Asn Phe Ala Leu Ala Thr
        115                 120                 125

Thr Glu Leu His Ala Lys Asn Lys Val Lys Leu Ser Gly Thr Ser Gly
    130                 135                 140

Tyr Leu Ala Pro Glu Tyr Leu Ser Glu Gly Lys Leu Thr Asp Lys Ser
145                 150                 155                 160

Asp Val Tyr Ala Phe Gly Val Val Leu Leu Glu Leu Leu Ile Gly Arg
                165                 170                 175

Lys Pro Val Glu Lys Met Ser Pro Ser Leu Phe Gln Ser Ile Val Thr
            180                 185                 190

Trp Ala Met Pro Gln Leu Thr Asp Arg Ser Lys Leu Pro Asn Ile Val
        195                 200                 205

Asp Pro Val Ile Arg Asp Thr Met Asp Leu Lys His Leu Tyr Gln Val
    210                 215                 220

Ala Ala Val Ala Val Leu Cys Val Gln Pro Glu Pro Ser Tyr Arg Pro
225                 230                 235                 240

Leu Ile Thr Asp Val Leu His Ser Phe Ile Pro
                245                 250
```

<210> SEQ ID NO 47
<211> LENGTH: 630
<212> TYPE: DNA
<213> ORGANISM: HELIANTHUS EXILIS

<400> SEQUENCE: 47

```
atgatgcatc aagactcttt ggactcacaa ttgcatggac caactcatgg aaccgcatta     60
```

```
acctggcatc gaagaatgaa agtcgcactt gatattgctc gaggattaga gtatcttcat    120

gaacgatgca acccgcctgt gattcataga gatctcaagt catcgaacat tttgctagat    180

tccaatttca atgctaaaat ttcgaatttt gcacttgcta ccactgagct ccatgcgaag    240

aacaaagtta agctttcggg tacttctggt tatttggctc cggaatacct atccgaaggt    300

aaacttaccg ataaaagtga tgtatatgca ttcggagtag tacttcttga gcttttaatc    360

ggtagaaaac cagtggagaa aatgtcacca tctttatttc aatctattgt cacatgggca    420

atgcctcagc taacagaccg gtcaaagctt ccaaacattg ttgaccctgt gattagagat    480

acaatggacc tgaagcactt gtatcaagtt gctgctgtag ccgtactttg cgtgcaaccc    540

gaaccaagtt acagaccgtt gattacagac gtactacact cattcattcc actcgtaccc    600

gttgatcttg gagggtcatt aagagcttaa                                     630
```

<210> SEQ ID NO 48
<211> LENGTH: 209
<212> TYPE: PRT
<213> ORGANISM: HELIANTHUS EXILIS

<400> SEQUENCE: 48

```
Met Met His Gln Asp Ser Leu Asp Ser Gln Leu His Gly Pro Thr His
1               5                   10                  15

Gly Thr Ala Leu Thr Trp His Arg Arg Met Lys Val Ala Leu Asp Ile
            20                  25                  30

Ala Arg Gly Leu Glu Tyr Leu His Glu Arg Cys Asn Pro Pro Val Ile
        35                  40                  45

His Arg Asp Leu Lys Ser Ser Asn Ile Leu Leu Asp Ser Asn Phe Asn
    50                  55                  60

Ala Lys Ile Ser Asn Phe Ala Leu Ala Thr Thr Glu Leu His Ala Lys
65                  70                  75                  80

Asn Lys Val Lys Leu Ser Gly Thr Ser Gly Tyr Leu Ala Pro Glu Tyr
                85                  90                  95

Leu Ser Glu Gly Lys Leu Thr Asp Lys Ser Asp Val Tyr Ala Phe Gly
            100                 105                 110

Val Val Leu Leu Glu Leu Leu Ile Gly Arg Lys Pro Val Glu Lys Met
        115                 120                 125

Ser Pro Ser Leu Phe Gln Ser Ile Val Thr Trp Ala Met Pro Gln Leu
    130                 135                 140

Thr Asp Arg Ser Lys Leu Pro Asn Ile Val Asp Pro Val Ile Arg Asp
145                 150                 155                 160

Thr Met Asp Leu Lys His Leu Tyr Gln Val Ala Ala Val Ala Val Leu
                165                 170                 175

Cys Val Gln Pro Glu Pro Ser Tyr Arg Pro Leu Ile Thr Asp Val Leu
            180                 185                 190

His Ser Phe Ile Pro Leu Val Pro Val Asp Leu Gly Gly Ser Leu Arg
        195                 200                 205

Ala
```

<210> SEQ ID NO 49
<211> LENGTH: 780
<212> TYPE: DNA
<213> ORGANISM: HORDEUM VULGARE

<400> SEQUENCE: 49

```
aatttgagag gtgagctgga tttgcttcag aggattcagc attcgaatat agtgtccctt     60
```

```
gtgggcttct gcattcatga ggagaaccgc ttcattgttt atgagctgat ggtgaatgga    120

tcacttgaaa cacagcttca tgggccatca catggatcag ctctgagttg gcacattcgg    180

atgaagattg ctcttgatac agcaagggga ttggagtatc ttcacgagca ctgcaatcca    240

ccaatcatcc atagggatct gaagtcgtct aacatacttt tgaattcaga ctttaatgca    300

aagatttcag attttggcct tgcagtgaca agtggaaatc gcagcaaagg gaatctgaag    360

ctttccggta ctttgggtta tgttgcccct gagtacttac tagatgggaa gttgactgag    420

aagagcgatg tatatgcatt tggagtagta cttcttgagc ttcttttggg aaggaggcca    480

gttgagaaga tggcaccatc tcagtgtcaa tcaattgtta catgggccat gccccagcta    540

attgacagat ccaagctccc taccataatc gaccccgtga tcagggacac gatggatcgg    600

aagcacttgt accaagttgc tgcagtggct gtgctctgcg tgcagccaga accaagctac    660

aggccactga tcacagatgt cctccactct ctgattcccc tggtgcccat ggaccttgga    720

gggacgctga ggatcaaccc ggaatcgcct tgcacgacac gaaatcaatc tccctgctga    780
```

```
<210> SEQ ID NO 50
<211> LENGTH: 259
<212> TYPE: PRT
<213> ORGANISM: HORDEUM VULGARE

<400> SEQUENCE: 50

Asn Leu Arg Gly Glu Leu Asp Leu Leu Gln Arg Ile Gln His Ser Asn
1               5                   10                  15

Ile Val Ser Leu Val Gly Phe Cys Ile His Glu Glu Asn Arg Phe Ile
            20                  25                  30

Val Tyr Glu Leu Met Val Asn Gly Ser Leu Glu Thr Gln Leu His Gly
        35                  40                  45

Pro Ser His Gly Ser Ala Leu Ser Trp His Ile Arg Met Lys Ile Ala
    50                  55                  60

Leu Asp Thr Ala Arg Gly Leu Glu Tyr Leu His Glu His Cys Asn Pro
65                  70                  75                  80

Pro Ile Ile His Arg Asp Leu Lys Ser Ser Asn Ile Leu Leu Asn Ser
                85                  90                  95

Asp Phe Asn Ala Lys Ile Ser Asp Phe Gly Leu Ala Val Thr Ser Gly
            100                 105                 110

Asn Arg Ser Lys Gly Asn Leu Lys Leu Ser Gly Thr Leu Gly Tyr Val
        115                 120                 125

Ala Pro Glu Tyr Leu Leu Asp Gly Lys Leu Thr Glu Lys Ser Asp Val
    130                 135                 140

Tyr Ala Phe Gly Val Val Leu Leu Glu Leu Leu Leu Gly Arg Arg Pro
145                 150                 155                 160

Val Glu Lys Met Ala Pro Ser Gln Cys Gln Ser Ile Val Thr Trp Ala
                165                 170                 175

Met Pro Gln Leu Ile Asp Arg Ser Lys Leu Pro Thr Ile Ile Asp Pro
            180                 185                 190

Val Ile Arg Asp Thr Met Asp Arg Lys His Leu Tyr Gln Val Ala Ala
        195                 200                 205

Val Ala Val Leu Cys Val Gln Pro Glu Pro Ser Tyr Arg Pro Leu Ile
    210                 215                 220

Thr Asp Val Leu His Ser Leu Ile Pro Leu Val Pro Met Asp Leu Gly
225                 230                 235                 240

Gly Thr Leu Arg Ile Asn Pro Glu Ser Pro Cys Thr Thr Arg Asn Gln
```

```
                245                 250                 255

Ser Pro Cys


<210> SEQ ID NO 51
<211> LENGTH: 816
<212> TYPE: DNA
<213> ORGANISM: IPOMOEA BATATAS

<400> SEQUENCE: 51

cgggggctct tatcactcat tgctgctgct actgcactgg gtacaagctt attgctcatg      60

ggttgcttct ggatttatca tagaaagaaa atccacaaat ctcatgacat tattcatagc     120

ccagatgtag ttaaaggtct tgcattatcc tcatatatta gcaaatacaa ctccttcaag     180

tcgaattgtg tgaaacgaca tgtctcgttg tgggagtaca atacactcga gtcggccaca     240

aatagttttc aagaaagcga gatcttgggt ggagggggt tcgggcttgt gtacaaggga      300

aaactagaag acaacttgta tgtagctgtg aagaggctgg aagttggaag acaaaacgca     360

attaaagaat tcgaggctga aatagaggta ttgggcacga ttcagcaccc gaatataatt     420

tcgttgttgg gatatagcat tcatgctgac acgaggctgc tagtttatga actgatgcag     480

aatggatctc tggagtatca actacatgga ccttcccatg gatcagcatt agcgtggcat     540

aatagattga aaatcgcact tgatacagca aggggattag aatatttaca tgaacattgc     600

aaaccaccag ttatccatag agatctgaaa tcctccaata ttcttctaga tgccaacttc     660

aatgccaaga tctcagattt tggtcttgct gtgcgcgatg gggctcaaaa caaaaataac     720

attaagctct cgggaaccgt tggctatgta gctccagaat acctattaga tggaatacta     780

acagataaaa gtgatgttta tggcttccga gttgta                                816


<210> SEQ ID NO 52
<211> LENGTH: 272
<212> TYPE: PRT
<213> ORGANISM: IPOMOEA BATATAS

<400> SEQUENCE: 52

Arg Gly Leu Leu Ser Leu Ile Ala Ala Ala Thr Ala Leu Gly Thr Ser
1               5                   10                  15

Leu Leu Leu Met Gly Cys Phe Trp Ile Tyr His Arg Lys Lys Ile His
            20                  25                  30

Lys Ser His Asp Ile Ile His Ser Pro Asp Val Val Lys Gly Leu Ala
        35                  40                  45

Leu Ser Ser Tyr Ile Ser Lys Tyr Asn Ser Phe Lys Ser Asn Cys Val
    50                  55                  60

Lys Arg His Val Ser Leu Trp Glu Tyr Asn Thr Leu Glu Ser Ala Thr
65                  70                  75                  80

Asn Ser Phe Gln Glu Ser Glu Ile Leu Gly Gly Gly Gly Phe Gly Leu
                85                  90                  95

Val Tyr Lys Gly Lys Leu Glu Asp Asn Leu Tyr Val Ala Val Lys Arg
            100                 105                 110

Leu Glu Val Gly Arg Gln Asn Ala Ile Lys Glu Phe Glu Ala Glu Ile
        115                 120                 125

Glu Val Leu Gly Thr Ile Gln His Pro Asn Ile Ile Ser Leu Leu Gly
    130                 135                 140

Tyr Ser Ile His Ala Asp Thr Arg Leu Leu Val Tyr Glu Leu Met Gln
145                 150                 155                 160

Asn Gly Ser Leu Glu Tyr Gln Leu His Gly Pro Ser His Gly Ser Ala
```

```
            165                 170                 175

Leu Ala Trp His Asn Arg Leu Lys Ile Ala Leu Asp Thr Ala Arg Gly
            180                 185                 190

Leu Glu Tyr Leu His Glu His Cys Lys Pro Pro Val Ile His Arg Asp
        195                 200                 205

Leu Lys Ser Ser Asn Ile Leu Leu Asp Ala Asn Phe Asn Ala Lys Ile
    210                 215                 220

Ser Asp Phe Gly Leu Ala Val Arg Asp Gly Ala Gln Asn Lys Asn Asn
225                 230                 235                 240

Ile Lys Leu Ser Gly Thr Val Gly Tyr Val Ala Pro Glu Tyr Leu Leu
                245                 250                 255

Asp Gly Ile Leu Thr Asp Lys Ser Asp Val Tyr Gly Phe Arg Val Val
            260                 265                 270


<210> SEQ ID NO 53
<211> LENGTH: 867
<212> TYPE: DNA
<213> ORGANISM: LACTUCA SATIVA

<400> SEQUENCE: 53

ggggatatac gtgtagaatc agcaacaaat aacttcggtg aaagcgagat attaggcgta      60

ggtggatttg gatgcgtgta taaagctcga ctcgatgata atttgcatgt agctgttaaa     120

agattagatg gtattagtca agacgccatt aaagaattcc agacggaggt ggatctattg     180

agtaaaattc atcatccgaa tatcatcacc ttattgggat attgtgttaa tgatgaaacc     240

aagcttcttg tttatgaact gatgcataat ggatctttag aaactcaatt acatgggcct     300

tccagtggat ccaatttaac atggcattgc aggatgaaga ttgctctaga tacagcaaga     360

ggattagaat atttgcatga gaactgcaaa ccatcggtga ttcatagaga tctgaaatca     420

tctaatatcc ttctggattc cagcttcaat gctaagcttt cagattttgg tcttgctata     480

atggatgggg cccagaacaa aaacaacatt aagctttcag ggacattggg ttatgtagct     540

cccgagtatc ttttagatgg aaaattgacg gataaaagtg acgtgtatgc gtttggagtt     600

gtgcttttag agcttttact tggaaggcga cctgtagaaa aattagcaga gtcgcaatgc     660

caatctattg tcacttgggc tatgccacaa ttaacagaca gatcaaagct tccgaatatt     720

gtagatcccg tgatcagata cacaatggat ctcaagcacc tgtaccaagt tgctgcggtg     780

gctgtgttat gtgtacaacc cggaccaagc taccggccat ttataaaccg acgtcttgca     840

ttctctgatc cctcttgttc cccgtga                                         867


<210> SEQ ID NO 54
<211> LENGTH: 288
<212> TYPE: PRT
<213> ORGANISM: LACTUCA SATIVA

<400> SEQUENCE: 54

Gly Asp Ile Arg Val Glu Ser Ala Thr Asn Asn Phe Gly Glu Ser Glu
1               5                   10                  15

Ile Leu Gly Val Gly Gly Phe Gly Cys Val Tyr Lys Ala Arg Leu Asp
            20                  25                  30

Asp Asn Leu His Val Ala Val Lys Arg Leu Asp Gly Ile Ser Gln Asp
        35                  40                  45

Ala Ile Lys Glu Phe Gln Thr Glu Val Asp Leu Leu Ser Lys Ile His
    50                  55                  60

His Pro Asn Ile Ile Thr Leu Leu Gly Tyr Cys Val Asn Asp Glu Thr
```

```
65                  70                  75                  80

Lys Leu Leu Val Tyr Glu Leu Met His Asn Gly Ser Leu Glu Thr Gln
                85                  90                  95

Leu His Gly Pro Ser Ser Gly Ser Asn Leu Thr Trp His Cys Arg Met
            100                 105                 110

Lys Ile Ala Leu Asp Thr Ala Arg Gly Leu Glu Tyr Leu His Glu Asn
        115                 120                 125

Cys Lys Pro Ser Val Ile His Arg Asp Leu Lys Ser Ser Asn Ile Leu
    130                 135                 140

Leu Asp Ser Ser Phe Asn Ala Lys Leu Ser Asp Phe Gly Leu Ala Ile
145                 150                 155                 160

Met Asp Gly Ala Gln Asn Lys Asn Asn Ile Lys Leu Ser Gly Thr Leu
                165                 170                 175

Gly Tyr Val Ala Pro Glu Tyr Leu Leu Asp Gly Lys Leu Thr Asp Lys
            180                 185                 190

Ser Asp Val Tyr Ala Phe Gly Val Val Leu Leu Glu Leu Leu Leu Gly
        195                 200                 205

Arg Arg Pro Val Glu Lys Leu Ala Glu Ser Gln Cys Gln Ser Ile Val
    210                 215                 220

Thr Trp Ala Met Pro Gln Leu Thr Asp Arg Ser Lys Leu Pro Asn Ile
225                 230                 235                 240

Val Asp Pro Val Ile Arg Tyr Thr Met Asp Leu Lys His Leu Tyr Gln
                245                 250                 255

Val Ala Ala Val Ala Val Leu Cys Val Gln Pro Gly Pro Ser Tyr Arg
            260                 265                 270

Pro Phe Ile Asn Arg Arg Leu Ala Phe Ser Asp Pro Ser Cys Ser Pro
        275                 280                 285
```

<210> SEQ ID NO 55
<211> LENGTH: 804
<212> TYPE: DNA
<213> ORGANISM: MEDICAGO TRUNCATULA

<400> SEQUENCE: 55

```
aagttgaact gtgaatgtca atatgctgag agagaatttg agaatgaggt ggatttgtta      60
agtaaaattc aacatccaaa tgtaatttct ctactgggct gtagcagtaa tgaggattca     120
aggtttattg tctatgagtt gatgcaaaat ggatcattgg aaactcaatt acatggacca     180
tctcatggct cagcattgac ttggcatatg aggatgaaga ttgctcttga cacagctaga     240
ggtttaaaat atctgcatga gcactgctac cctgcagtga tccatagaga tctgaaatct     300
tctaatattc ttttagatgc aaacttcaat gccaagcttt ctgattttgg tcttgcaata     360
actgatgggt cccaaaacaa gaataacatc aagctttcag gcacattggg gtatgttgcc     420
ccggagtatc ttttagatgg taaattgaca gataaaagtg atgtgtatgc ttttggagtt     480
gtgcttcttg agcttctatt aggaagaaag cctgtggaaa aacttacacc atctcaatgc     540
cagtctattg tcacatgggc catgccacag ctcacagaca gatccaagct tccaaacatt     600
gtggataatg tgattaagaa tacaatggat cctaagcact tataccaggt tgctgctgtg     660
gctgtattat gtgtgcaacc agagccgtgc taccgccctt tgattgcaga tgttctacac     720
tccctcatcc ctcttgtacc tgttgagctt ggaggaacac tcagagttgc acaagtgacg     780
cagcaaccta agaattctag ttaa                                            804
```

<210> SEQ ID NO 56

<211> LENGTH: 267
<212> TYPE: PRT
<213> ORGANISM: MEDICAGO TRUNCATULA

<400> SEQUENCE: 56

```
Lys Leu Asn Cys Glu Cys Gln Tyr Ala Glu Arg Glu Phe Glu Asn Glu
1               5                   10                  15

Val Asp Leu Leu Ser Lys Ile Gln His Pro Asn Val Ile Ser Leu Leu
            20                  25                  30

Gly Cys Ser Ser Asn Glu Asp Ser Arg Phe Ile Val Tyr Glu Leu Met
        35                  40                  45

Gln Asn Gly Ser Leu Glu Thr Gln Leu His Gly Pro Ser His Gly Ser
    50                  55                  60

Ala Leu Thr Trp His Met Arg Met Lys Ile Ala Leu Asp Thr Ala Arg
65                  70                  75                  80

Gly Leu Lys Tyr Leu His Glu His Cys Tyr Pro Ala Val Ile His Arg
                85                  90                  95

Asp Leu Lys Ser Ser Asn Ile Leu Leu Asp Ala Asn Phe Asn Ala Lys
            100                 105                 110

Leu Ser Asp Phe Gly Leu Ala Ile Thr Asp Gly Ser Gln Asn Lys Asn
        115                 120                 125

Asn Ile Lys Leu Ser Gly Thr Leu Gly Tyr Val Ala Pro Glu Tyr Leu
    130                 135                 140

Leu Asp Gly Lys Leu Thr Asp Lys Ser Asp Val Tyr Ala Phe Gly Val
145                 150                 155                 160

Val Leu Leu Glu Leu Leu Leu Gly Arg Lys Pro Val Glu Lys Leu Thr
                165                 170                 175

Pro Ser Gln Cys Gln Ser Ile Val Thr Trp Ala Met Pro Gln Leu Thr
            180                 185                 190

Asp Arg Ser Lys Leu Pro Asn Ile Val Asp Asn Val Ile Lys Asn Thr
        195                 200                 205

Met Asp Pro Lys His Leu Tyr Gln Val Ala Ala Val Ala Val Leu Cys
    210                 215                 220

Val Gln Pro Glu Pro Cys Tyr Arg Pro Leu Ile Ala Asp Val Leu His
225                 230                 235                 240

Ser Leu Ile Pro Leu Val Pro Val Glu Leu Gly Gly Thr Leu Arg Val
                245                 250                 255

Ala Gln Val Thr Gln Gln Pro Lys Asn Ser Ser
            260                 265
```

<210> SEQ ID NO 57
<211> LENGTH: 636
<212> TYPE: DNA
<213> ORGANISM: NICOTIANA TABACUM

<400> SEQUENCE: 57

```
cagttgcatg gacctcctcg tggatcagct ttgaattggc atcttcgcat ggaaattgca      60

ttggatgtgg ctaggggact agaatacctc catgagcgct gtaacccccc tgtaatccat     120

agagatctca aatcgtctaa tgttctattg gattcctact tcaatgcaaa gctttctgac     180

ttttggccta gctatagctg gatggaactt aaacaagagc accgtaaagt ctttcgggaa     240

ctctgggata tgtggctcca gagttacctc ttagatggga aattaactga taagagtgat     300

gtctatgctt tcggcattat acttctggag cttctaatgg ggagaagacc attggagaaa     360

ctagcaggag ctcagtgcca atctatcgtc acatgggcaa tgccacagct tactgacagg     420
```

```
tcaaagctcc caaatattgt tgatcctgtc atcagaaacg gaatgggcct caagcacttg    480

tatcaagttg ctgctgtagc cgtgctatgt gtacaaccag aaccaagtta ccgaccactg    540

ataacagatg tcctgcactc cttcattccc cttgtaccaa ttgagcttgg tgggtccttg    600

agagttgtgg attctgcatt atctgttaac gcataa                              636


<210> SEQ ID NO 58
<211> LENGTH: 211
<212> TYPE: PRT
<213> ORGANISM: NICOTIANA TABACUM

<400> SEQUENCE: 58

Gln Leu His Gly Pro Pro Arg Gly Ser Ala Leu Asn Trp His Leu Arg
1               5                   10                  15

Met Glu Ile Ala Leu Asp Val Ala Arg Gly Leu Glu Tyr Leu His Glu
            20                  25                  30

Arg Cys Asn Pro Pro Val Ile His Arg Asp Leu Lys Ser Ser Asn Val
        35                  40                  45

Leu Leu Asp Ser Tyr Phe Asn Ala Lys Leu Ser Asp Phe Trp Pro Ser
    50                  55                  60

Tyr Ser Trp Met Glu Leu Lys Gln Glu His Arg Lys Val Phe Arg Glu
65                  70                  75                  80

Leu Trp Asp Met Trp Leu Gln Ser Tyr Leu Leu Asp Gly Lys Leu Thr
                85                  90                  95

Asp Lys Ser Asp Val Tyr Ala Phe Gly Ile Ile Leu Leu Glu Leu Leu
            100                 105                 110

Met Gly Arg Arg Pro Leu Glu Lys Leu Ala Gly Ala Gln Cys Gln Ser
        115                 120                 125

Ile Val Thr Trp Ala Met Pro Gln Leu Thr Asp Arg Ser Lys Leu Pro
    130                 135                 140

Asn Ile Val Asp Pro Val Ile Arg Asn Gly Met Gly Leu Lys His Leu
145                 150                 155                 160

Tyr Gln Val Ala Ala Val Ala Val Leu Cys Val Gln Pro Glu Pro Ser
                165                 170                 175

Tyr Arg Pro Leu Ile Thr Asp Val Leu His Ser Phe Ile Pro Leu Val
            180                 185                 190

Pro Ile Glu Leu Gly Gly Ser Leu Arg Val Val Asp Ser Ala Leu Ser
        195                 200                 205

Val Asn Ala
    210


<210> SEQ ID NO 59
<211> LENGTH: 1437
<212> TYPE: DNA
<213> ORGANISM: ORYZA SATIVA

<400> SEQUENCE: 59

atggagatgg cgctaactcc attgccgctc ctgtgttcgt ccgtcttgtt cttggtgcta     60

tcttcgtgct cgttggccaa tgggagggat acgccttctt cttcttcttc ttcttcttct    120

tcttcttctt cttcttcttc ttcttcttct tcttcttctt ctccggcgac gtctactgtg    180

gccaccggca tttccgccgc cgccgccgcc gccgccaatg ggacggccgc cttgtcttcg    240

gcagttccgg cgcctccgcc tgttgtgatc gtagtgcacc accatttcca ccgcgagctg    300

gtcatcgccg ccgtcctcgc ctgcatcgcc accgtcacga tcttcctttc cacgctctac    360

gcttggacac tatggcggcg atctcgccgg agcaccggcg gcaaggtcac caggagctca    420
```

```
gacgcagcga aggggatcaa gctggtgccg atcttgagca ggttcaactc ggtgaagatg    480

agcaggaaga ggctggttgg gatgttcgag tacccgtcgc tggaggcagc gacagagaag    540

ttcagcgaga gcaacatgct cggtgtcggc gggtttggcc gcgtctacaa ggcggcgttc    600

gacgccggag ttaccgcggc ggtgaagcgg ctcgacggcg gcgggcccga ctgcgagaag    660

gaattcgaga atgagctgga tttgcttggc aggatcaggc accccaacat tgtgtccctc    720

ttgggcttct gtatccatga ggggaatcac tacattgttt atgagctgat ggagaaggga    780

tcactggaaa cacagcttca tgggtcttca catggatcaa ctctgagctg gcacatccgg    840

atgaagatcg cccttgacac ggccagggga ttagagtacc ttcatgagca ctgcagtcca    900

ccagtgatcc atagggatct gaaatcgtct aacatacttt tggattcaga cttcaatgct    960

aagattgcag attttggtct tgctgtgtct agtgggagtg tcaacaaagg gagtgtgaag   1020

ctctccggga ccttgggtta tgtagctcct gagtacttgt tggatgggaa gttgactgaa   1080

aagagcgatg tatacgcgtt cggagtagtg cttctagagc tccttatggg gaggaagcct   1140

gttgagaaga tgtcaccatc tcagtgccaa tcaattgtga catgggcaat gccacagttg   1200

accgacagat cgaagctccc cagcatagtt gacccagtga tcaaggacac catggatcca   1260

aaacacctgt accaagttgc agcagtggct gttctatgcg tgcaggctga accaagctac   1320

aggccactga tcacagatgt gctccactct cttgttcctc tagtgccgac ggagctcgga   1380

ggaacactaa gagctggaga gccaccttcc ccgaacctga ggaattctcc atgctga      1437
```

<210> SEQ ID NO 60
<211> LENGTH: 478
<212> TYPE: PRT
<213> ORGANISM: ORYZA SATIVA

<400> SEQUENCE: 60

```
Met Glu Met Ala Leu Thr Pro Leu Pro Leu Leu Cys Ser Ser Val Leu
1               5                   10                  15

Phe Leu Val Leu Ser Ser Cys Ser Leu Ala Asn Gly Arg Asp Thr Pro
            20                  25                  30

Ser Ser Ser Ser Ser Ser Ser Ser Ser Ser Ser Ser Ser Ser Ser Ser
        35                  40                  45

Ser Ser Ser Ser Ser Ser Pro Ala Thr Ser Thr Val Ala Thr Gly Ile
    50                  55                  60

Ser Ala Ala Ala Ala Ala Ala Ala Asn Gly Thr Ala Ala Leu Ser Ser
65                  70                  75                  80

Ala Val Pro Ala Pro Pro Pro Val Val Ile Val Val His His His Phe
                85                  90                  95

His Arg Glu Leu Val Ile Ala Ala Val Leu Ala Cys Ile Ala Thr Val
            100                 105                 110

Thr Ile Phe Leu Ser Thr Leu Tyr Ala Trp Thr Leu Trp Arg Arg Ser
        115                 120                 125

Arg Arg Ser Thr Gly Gly Lys Val Thr Arg Ser Ser Asp Ala Ala Lys
    130                 135                 140

Gly Ile Lys Leu Val Pro Ile Leu Ser Arg Phe Asn Ser Val Lys Met
145                 150                 155                 160

Ser Arg Lys Arg Leu Val Gly Met Phe Glu Tyr Pro Ser Leu Glu Ala
                165                 170                 175

Ala Thr Glu Lys Phe Ser Glu Ser Asn Met Leu Gly Val Gly Gly Phe
            180                 185                 190
```

```
Gly Arg Val Tyr Lys Ala Ala Phe Asp Ala Gly Val Thr Ala Ala Val
        195                 200                 205

Lys Arg Leu Asp Gly Gly Gly Pro Asp Cys Glu Lys Glu Phe Glu Asn
    210                 215                 220

Glu Leu Asp Leu Leu Gly Arg Ile Arg His Pro Asn Ile Val Ser Leu
225                 230                 235                 240

Leu Gly Phe Cys Ile His Glu Gly Asn His Tyr Ile Val Tyr Glu Leu
                245                 250                 255

Met Glu Lys Gly Ser Leu Glu Thr Gln Leu His Gly Ser Ser His Gly
            260                 265                 270

Ser Thr Leu Ser Trp His Ile Arg Met Lys Ile Ala Leu Asp Thr Ala
        275                 280                 285

Arg Gly Leu Glu Tyr Leu His Glu His Cys Ser Pro Pro Val Ile His
    290                 295                 300

Arg Asp Leu Lys Ser Ser Asn Ile Leu Leu Asp Ser Asp Phe Asn Ala
305                 310                 315                 320

Lys Ile Ala Asp Phe Gly Leu Ala Val Ser Ser Gly Ser Val Asn Lys
                325                 330                 335

Gly Ser Val Lys Leu Ser Gly Thr Leu Gly Tyr Val Ala Pro Glu Tyr
            340                 345                 350

Leu Leu Asp Gly Lys Leu Thr Glu Lys Ser Asp Val Tyr Ala Phe Gly
        355                 360                 365

Val Val Leu Leu Glu Leu Leu Met Gly Arg Lys Pro Val Glu Lys Met
    370                 375                 380

Ser Pro Ser Gln Cys Gln Ser Ile Val Thr Trp Ala Met Pro Gln Leu
385                 390                 395                 400

Thr Asp Arg Ser Lys Leu Pro Ser Ile Val Asp Pro Val Ile Lys Asp
                405                 410                 415

Thr Met Asp Pro Lys His Leu Tyr Gln Val Ala Ala Val Ala Val Leu
            420                 425                 430

Cys Val Gln Ala Glu Pro Ser Tyr Arg Pro Leu Ile Thr Asp Val Leu
        435                 440                 445

His Ser Leu Val Pro Leu Val Pro Thr Glu Leu Gly Gly Thr Leu Arg
    450                 455                 460

Ala Gly Glu Pro Pro Ser Pro Asn Leu Arg Asn Ser Pro Cys
465                 470                 475
```

<210> SEQ ID NO 61
<211> LENGTH: 891
<212> TYPE: DNA
<213> ORGANISM: PHYSCOMITRELLA

<400> SEQUENCE: 61

```
tactctcttt tacaaactgc tacgaacaac ttcagctcct ccaatttgct gggcgaggga     60

agtttcgggc atgtgtataa agcgagactc gattatgatg tctatgccgc tgtaaagaga    120

cttaccagcg taggaaaaca gccccaaaaa gaactccagg gagaggtgga tctgatgtgc    180

aagataagac atcccaactt ggtggctctc ctgggctatt caaatgacgg cccagagccc    240

ttggttgtgt acgagctcat gcagaatggt tcacttcatg atcagcttca tggcccctca    300

tgcgggagtg cactcacctg gtacctacga ctaaagattg ctcttgaagc tgccagcaga    360

ggactggagc acctgcatga aagctgcaag cctgcaataa tccacagaga cttcaaggca    420

tccaacatcc tcttggacgc cagcttcaat gcgaaggtgt ccgactttgg tatagcggta    480

gctctggagg aaggtggcgt ggtgaaagac gacgtacaag tgcaaggcac cttcgggtac    540
```

```
attgctcctg agtacctgat ggacgggaca ttgacagaga agagtgatgt ttacggattt    600

ggagtagtat tgcttgagct gctgacaggc agactgccca ttgatacgtc cttaccactc    660

ggatcgcaat ctctagtgac atgggtaaca cccatactaa ctaaccgagc aaagctgatg    720

gaagttatcg accccaccct tcaagatacg ctgaacgtga agcaacttca ccaggtggcc    780

gcagtggcag tcctttgcgt ccaagcggaa cccagctacc gccctctcat cgccgacgtg    840

gttcagtcac tggctccgct ggtgcctcaa gagctcggcg gcgcattgcg a             891
```

```
<210> SEQ ID NO 62
<211> LENGTH: 297
<212> TYPE: PRT
<213> ORGANISM: PHYSCOMITRELLA

<400> SEQUENCE: 62

Tyr Ser Leu Leu Gln Thr Ala Thr Asn Asn Phe Ser Ser Ser Asn Leu
1               5                   10                  15

Leu Gly Glu Gly Ser Phe Gly His Val Tyr Lys Ala Arg Leu Asp Tyr
            20                  25                  30

Asp Val Tyr Ala Ala Val Lys Arg Leu Thr Ser Val Gly Lys Gln Pro
        35                  40                  45

Gln Lys Glu Leu Gln Gly Glu Val Asp Leu Met Cys Lys Ile Arg His
    50                  55                  60

Pro Asn Leu Val Ala Leu Leu Gly Tyr Ser Asn Asp Gly Pro Glu Pro
65                  70                  75                  80

Leu Val Val Tyr Glu Leu Met Gln Asn Gly Ser Leu His Asp Gln Leu
                85                  90                  95

His Gly Pro Ser Cys Gly Ser Ala Leu Thr Trp Tyr Leu Arg Leu Lys
            100                 105                 110

Ile Ala Leu Glu Ala Ala Ser Arg Gly Leu Glu His Leu His Glu Ser
        115                 120                 125

Cys Lys Pro Ala Ile Ile His Arg Asp Phe Lys Ala Ser Asn Ile Leu
    130                 135                 140

Leu Asp Ala Ser Phe Asn Ala Lys Val Ser Asp Phe Gly Ile Ala Val
145                 150                 155                 160

Ala Leu Glu Glu Gly Gly Val Val Lys Asp Asp Val Gln Val Gln Gly
                165                 170                 175

Thr Phe Gly Tyr Ile Ala Pro Glu Tyr Leu Met Asp Gly Thr Leu Thr
            180                 185                 190

Glu Lys Ser Asp Val Tyr Gly Phe Gly Val Val Leu Leu Glu Leu Leu
        195                 200                 205

Thr Gly Arg Leu Pro Ile Asp Thr Ser Leu Pro Leu Gly Ser Gln Ser
    210                 215                 220

Leu Val Thr Trp Val Thr Pro Ile Leu Thr Asn Arg Ala Lys Leu Met
225                 230                 235                 240

Glu Val Ile Asp Pro Thr Leu Gln Asp Thr Leu Asn Val Lys Gln Leu
                245                 250                 255

His Gln Val Ala Ala Val Ala Val Leu Cys Val Gln Ala Glu Pro Ser
            260                 265                 270

Tyr Arg Pro Leu Ile Ala Asp Val Val Gln Ser Leu Ala Pro Leu Val
        275                 280                 285

Pro Gln Glu Leu Gly Gly Ala Leu Arg
    290                 295
```

<210> SEQ ID NO 63
<211> LENGTH: 1065
<212> TYPE: DNA
<213> ORGANISM: PICEA

<400> SEQUENCE: 63

```
acctcagatg cctatagggg tattccactc atgcctctcc tgaatcgttt gaactcccgt     60

atttccaaga agaagggatg tgcaactgca attgaatatt ctaagctgca agcagctaca    120

aataacttca gcagcaataa cattcttgga gagggtggat ttgcgtgtgt atacaaggcc    180

atgtttgatg atgattcctt tgctgctgtg aagaagctag atgagggtag cagacaggct    240

gagcatgaat ttcagaatga agtggagctg atgagcaaaa tccgacatcc aaaccttgtt    300

tctttgcttg ggttctgctc tcatgaaaat acacggttct tagtatatga tctgatgcag    360

aatggctctt tggaagacca attacatggg ccatctcacg gatctgcact tacatggttt    420

ttgcgcataa agatagcact tgattcagca aggggtctag aacacttgca tgagcactgc    480

aaccctgcag tgattcatcg agatttcaaa tcatcaaata ttcttcttga tgcaagcttc    540

aacgccaagc tttcagattt tggtcttgca gtaacaagtg caggatgtgc tggcaataca    600

aatattgatc tagtagggac attgggatat gtagctccag aatacctact tgatggtaaa    660

ttgacagaga aaagtgatgt ctatgcatat ggagttgttt tgttggagct actttttgga    720

agaaagccaa ttgataaatc tctaccaagt gaatgccaat ctctcatttc ttgggcaatg    780

ccacagctaa cagatagaga aaagctccca actatagtag accccatgat caaaggcaca    840

atgaacttga aacacctata tcaagtagca gctgttgcaa tgctatgtgt gcagccagaa    900

cccagttaca ggccattaat agctgacgtt gtgcactctc tcattcctct cgtaccaata    960

gaactcgggg gaactttaaa gctctctaat gcacgaccca ctgagatgaa gttatttact   1020

tcttcccaat gcagtgttga gattgcttcc aacccaaaat tgtga                   1065
```

<210> SEQ ID NO 64
<211> LENGTH: 354
<212> TYPE: PRT
<213> ORGANISM: PICEA

<400> SEQUENCE: 64

```
Thr Ser Asp Ala Tyr Arg Gly Ile Pro Leu Met Pro Leu Leu Asn Arg
1               5                   10                  15

Leu Asn Ser Arg Ile Ser Lys Lys Lys Gly Cys Ala Thr Ala Ile Glu
            20                  25                  30

Tyr Ser Lys Leu Gln Ala Ala Thr Asn Asn Phe Ser Ser Asn Asn Ile
        35                  40                  45

Leu Gly Glu Gly Gly Phe Ala Cys Val Tyr Lys Ala Met Phe Asp Asp
    50                  55                  60

Asp Ser Phe Ala Ala Val Lys Lys Leu Asp Glu Gly Ser Arg Gln Ala
65                  70                  75                  80

Glu His Glu Phe Gln Asn Glu Val Glu Leu Met Ser Lys Ile Arg His
                85                  90                  95

Pro Asn Leu Val Ser Leu Leu Gly Phe Cys Ser His Glu Asn Thr Arg
            100                 105                 110

Phe Leu Val Tyr Asp Leu Met Gln Asn Gly Ser Leu Glu Asp Gln Leu
        115                 120                 125

His Gly Pro Ser His Gly Ser Ala Leu Thr Trp Phe Leu Arg Ile Lys
    130                 135                 140

Ile Ala Leu Asp Ser Ala Arg Gly Leu Glu His Leu His Glu His Cys
```

```
145                 150                 155                 160

Asn Pro Ala Val Ile His Arg Asp Phe Lys Ser Ser Asn Ile Leu Leu
                165                 170                 175

Asp Ala Ser Phe Asn Ala Lys Leu Ser Asp Phe Gly Leu Ala Val Thr
            180                 185                 190

Ser Ala Gly Cys Ala Gly Asn Thr Asn Ile Asp Leu Val Gly Thr Leu
        195                 200                 205

Gly Tyr Val Ala Pro Glu Tyr Leu Leu Asp Gly Lys Leu Thr Glu Lys
    210                 215                 220

Ser Asp Val Tyr Ala Tyr Gly Val Val Leu Leu Glu Leu Leu Phe Gly
225                 230                 235                 240

Arg Lys Pro Ile Asp Lys Ser Leu Pro Ser Glu Cys Gln Ser Leu Ile
                245                 250                 255

Ser Trp Ala Met Pro Gln Leu Thr Asp Arg Glu Lys Leu Pro Thr Ile
            260                 265                 270

Val Asp Pro Met Ile Lys Gly Thr Met Asn Leu Lys His Leu Tyr Gln
        275                 280                 285

Val Ala Ala Val Ala Met Leu Cys Val Gln Pro Glu Pro Ser Tyr Arg
    290                 295                 300

Pro Leu Ile Ala Asp Val Val His Ser Leu Ile Pro Leu Val Pro Ile
305                 310                 315                 320

Glu Leu Gly Gly Thr Leu Lys Leu Ser Asn Ala Arg Pro Thr Glu Met
                325                 330                 335

Lys Leu Phe Thr Ser Ser Gln Cys Ser Val Glu Ile Ala Ser Asn Pro
            340                 345                 350

Lys Leu


<210> SEQ ID NO 65
<211> LENGTH: 596
<212> TYPE: DNA
<213> ORGANISM: PINUS

<400> SEQUENCE: 65

aattcggcac gaggagaaca cttgcacgag cactgcaacc ctgcagtgat tcaccgagat     60

ttcaaatcat caaatattct tcttgatgca agcttcaacg ccaagctttc agattttggt    120

cttgcagtaa aaagtgcagg atgtgctggt aacacaaata ttgatctagt agggacattg    180

ggatatgtag ctccagaata catgcttgat ggtaaattga cagagaaaag tgatgtctat    240

gcatatggag ttgttttgtt agagctactt tttggaagaa agccaattga taaatctcta    300

ccaagtgaat gccaatctct catttcttgg gcaatgccac agctaacaga tagagaaaag    360

ctcccgacta taatagatcc catgatcaaa ggcgcaatga acttgaaaca cctatatcaa    420

gtggcagctg ttgcagtgct atgtgtgcag ccagaaccca gttacaggcc attaatagct    480

gacgttgtgc actctctcat tcctctcgta ccagtagaac ttgggggaac attaaagtca    540

tcacccactg agatgaagtc atttgcttct tcccaatgca gtgcccacgt tgcttc        596


<210> SEQ ID NO 66
<211> LENGTH: 199
<212> TYPE: PRT
<213> ORGANISM: PINUS

<400> SEQUENCE: 66

Asn Ser Ala Arg Gly Glu His Leu His Glu His Cys Asn Pro Ala Val
1               5                   10                  15
```

```
Ile His Arg Asp Phe Lys Ser Ser Asn Ile Leu Leu Asp Ala Ser Phe
            20                  25                  30

Asn Ala Lys Leu Ser Asp Phe Gly Leu Ala Val Lys Ser Ala Gly Cys
        35                  40                  45

Ala Gly Asn Thr Asn Ile Asp Leu Val Gly Thr Leu Gly Tyr Val Ala
    50                  55                  60

Pro Glu Tyr Met Leu Asp Gly Lys Leu Thr Glu Lys Ser Asp Val Tyr
65                  70                  75                  80

Ala Tyr Gly Val Val Leu Leu Glu Leu Leu Phe Gly Arg Lys Pro Ile
                85                  90                  95

Asp Lys Ser Leu Pro Ser Glu Cys Gln Ser Leu Ile Ser Trp Ala Met
            100                 105                 110

Pro Gln Leu Thr Asp Arg Glu Lys Leu Pro Thr Ile Ile Asp Pro Met
        115                 120                 125

Ile Lys Gly Ala Met Asn Leu Lys His Leu Tyr Gln Val Ala Ala Val
    130                 135                 140

Ala Val Leu Cys Val Gln Pro Glu Pro Ser Tyr Arg Pro Leu Ile Ala
145                 150                 155                 160

Asp Val Val His Ser Leu Ile Pro Leu Val Pro Val Glu Leu Gly Gly
                165                 170                 175

Thr Leu Lys Ser Ser Pro Thr Glu Met Lys Ser Phe Ala Ser Ser Gln
            180                 185                 190

Cys Ser Ala His Val Ala Ser
        195
```

```
<210> SEQ ID NO 67
<211> LENGTH: 1377
<212> TYPE: DNA
<213> ORGANISM: POPULUS

<400> SEQUENCE: 67

atgttcttgt ttcctaaaac agttcctatt tggtttttc atctgtgtct agtagcagtt      60

catgccatac aagaagaccc acctgtccct tcaccatctc cctctctcat ttctcctatt    120

tcaacttcaa tggctgcctt ctctccaggg gttgaatcgg aaatgggaat caaagaccac    180

ccccagcatg atgacctcca caggaaaata atcttgttgc tcactgttgc ttgttgcata    240

cttgttatca tccttctttc tttgtgttct tgtttcattt actataagaa gtcctcacaa    300

aagaaaaaag ctactcggtg ttcagatgtg gagaaagggc tttcattggc accatttttg    360

ggcaaattca gttccttgaa aatggttagt aatagggat ctgtttcatt aattgagtat      420

aagatactag agaaaggaac aaacaatttt ggcgatgata aattgttggg aaagggagga    480

tttggacgtg tatataaggc tgtaatggaa gatgactcaa gtgctgcagt caagaaacta    540

gactgcgcaa ctgatgatgc gcagagagaa tttgagaatg aggtggattt gttaagcaaa    600

tttcaccatc caaatataat ttctattgtg ggttttagtg ttcatgagga gatggggttc    660

attatttatg agttaatgcc aaatgggtgc cttgaagatc tactgcatgg accttctcgt    720

ggatcttcac taaattggca tttaaggttg aaaattgctc ttgatacagc aagaggatta    780

gaatatctgc atgaattctg caagccagca gtgatccata gagatctgaa atcatcgaat    840

attcttttgg acgccaactt caatgccaag ctgtcagatt ttggtcttgc tgtagctgat    900

agctctcata acaagaaaaa gctcaagctt tcaggcactg tgggttatgt agccccagag    960

tatatgttag atggtgaatt gacggataag agtgatgtct atgcttttgg agttgtgctt   1020

ctagagcttc tattaggaag aaggcctgta gaaaaactga caccagctca ttgccaatct   1080
```

```
atagtaacat gggccatgcc tcagctcact aacagagctg tgcttccaac ccttgtggat   1140

cctgtgatca gagattcagt agatgagaag tacttgttcc aggttgcagc agtagccgtg   1200

ttgtgtattc aaccagagcc aagttaccgc cctctcataa cagatgttgt gcactctctc   1260

gtcccattag ttcctcttga gcttggaggg acactaagag ttccacagcc tacaactccc   1320

agaggtcaac gacaaggccc atcaaagaaa ctgtttttgg atggtgctgc ctctgct      1377


<210> SEQ ID NO 68
<211> LENGTH: 459
<212> TYPE: PRT
<213> ORGANISM: POPULUS

<400> SEQUENCE: 68

Met Phe Leu Phe Pro Lys Thr Val Pro Ile Trp Phe Phe His Leu Cys
1               5                   10                  15

Leu Val Ala Val His Ala Ile Gln Glu Asp Pro Pro Val Pro Ser Pro
            20                  25                  30

Ser Pro Ser Leu Ile Ser Pro Ile Ser Thr Ser Met Ala Ala Phe Ser
        35                  40                  45

Pro Gly Val Glu Ser Glu Met Gly Ile Lys Asp His Pro Gln His Asp
    50                  55                  60

Asp Leu His Arg Lys Ile Ile Leu Leu Leu Thr Val Ala Cys Cys Ile
65                  70                  75                  80

Leu Val Ile Ile Leu Leu Ser Leu Cys Ser Cys Phe Ile Tyr Tyr Lys
                85                  90                  95

Lys Ser Ser Gln Lys Lys Lys Ala Thr Arg Cys Ser Asp Val Glu Lys
            100                 105                 110

Gly Leu Ser Leu Ala Pro Phe Leu Gly Lys Phe Ser Ser Leu Lys Met
        115                 120                 125

Val Ser Asn Arg Gly Ser Val Ser Leu Ile Glu Tyr Lys Ile Leu Glu
    130                 135                 140

Lys Gly Thr Asn Asn Phe Gly Asp Asp Lys Leu Leu Gly Lys Gly Gly
145                 150                 155                 160

Phe Gly Arg Val Tyr Lys Ala Val Met Glu Asp Asp Ser Ser Ala Ala
                165                 170                 175

Val Lys Lys Leu Asp Cys Ala Thr Asp Asp Ala Gln Arg Glu Phe Glu
            180                 185                 190

Asn Glu Val Asp Leu Leu Ser Lys Phe His His Pro Asn Ile Ile Ser
        195                 200                 205

Ile Val Gly Phe Ser Val His Glu Glu Met Gly Phe Ile Ile Tyr Glu
    210                 215                 220

Leu Met Pro Asn Gly Cys Leu Glu Asp Leu Leu His Gly Pro Ser Arg
225                 230                 235                 240

Gly Ser Ser Leu Asn Trp His Leu Arg Leu Lys Ile Ala Leu Asp Thr
                245                 250                 255

Ala Arg Gly Leu Glu Tyr Leu His Glu Phe Cys Lys Pro Ala Val Ile
            260                 265                 270

His Arg Asp Leu Lys Ser Ser Asn Ile Leu Leu Asp Ala Asn Phe Asn
        275                 280                 285

Ala Lys Leu Ser Asp Phe Gly Leu Ala Val Ala Asp Ser Ser His Asn
    290                 295                 300

Lys Lys Lys Leu Lys Leu Ser Gly Thr Val Gly Tyr Val Ala Pro Glu
305                 310                 315                 320
```

```
Tyr Met Leu Asp Gly Glu Leu Thr Asp Lys Ser Asp Val Tyr Ala Phe
                325                 330                 335

Gly Val Val Leu Leu Glu Leu Leu Leu Gly Arg Arg Pro Val Glu Lys
            340                 345                 350

Leu Thr Pro Ala His Cys Gln Ser Ile Val Thr Trp Ala Met Pro Gln
        355                 360                 365

Leu Thr Asn Arg Ala Val Leu Pro Thr Leu Val Asp Pro Val Ile Arg
    370                 375                 380

Asp Ser Val Asp Glu Lys Tyr Leu Phe Gln Val Ala Ala Val Ala Val
385                 390                 395                 400

Leu Cys Ile Gln Pro Glu Pro Ser Tyr Arg Pro Leu Ile Thr Asp Val
                405                 410                 415

Val His Ser Leu Val Pro Leu Val Pro Leu Glu Leu Gly Gly Thr Leu
            420                 425                 430

Arg Val Pro Gln Pro Thr Thr Pro Arg Gly Gln Arg Gln Gly Pro Ser
        435                 440                 445

Lys Lys Leu Phe Leu Asp Gly Ala Ala Ser Ala
    450                 455
```

<210> SEQ ID NO 69
<211> LENGTH: 693
<212> TYPE: DNA
<213> ORGANISM: SACCHARUM OFFICINARUM

<400> SEQUENCE: 69

```
gctgctgcgg tgaagagatt ggatggtggg gctggggcac atgattgcga gaaggaattc     60

gagaatgagt tagatttgct tggaaagatt cggcatccga acattgtgtc ccttgtgggc    120

ttctgtattc atgaggagaa ccgtttcatt gtttatgagc tgatagagaa tgggtcgttg    180

gattcacaac ttcatgggcc atcacatggt tcagctctga gctggcatat tcggatgaag    240

attgctcttg acacggcaag ggattagag tacctgcatg agcactgcaa cccaccagtt    300

atccataggg atctgaagtc atctaacata cttttagatt cagacttcag tgctaagatt    360

tcagattttg gccttgcggt gattagtggg aatcacagca aagggaattt aaagctttct    420

gggactatgg gctatgtggc ccctgagtac ttattggatg ggaagttgac tgagaagagc    480

gatgtatatg cgtttggggt ggtacttcta gaacttctac tgggaaggaa acctgttgag    540

aagatggcac aatctcaatg ccaatcaatt gttacatggg ccatgcctca gctaactgat    600

agatccaaac tccctaacat aattgatccc atgatcaaga acacaatgga tctgaaacac    660

ttgtaccaag ttgctgcaat ggctgtgctc tga                                 693
```

<210> SEQ ID NO 70
<211> LENGTH: 230
<212> TYPE: PRT
<213> ORGANISM: SACCHARUM OFFICINARUM

<400> SEQUENCE: 70

```
Ala Ala Ala Val Lys Arg Leu Asp Gly Gly Ala Gly Ala His Asp Cys
1               5                   10                  15

Glu Lys Glu Phe Glu Asn Glu Leu Asp Leu Leu Gly Lys Ile Arg His
            20                  25                  30

Pro Asn Ile Val Ser Leu Val Gly Phe Cys Ile His Glu Glu Asn Arg
        35                  40                  45

Phe Ile Val Tyr Glu Leu Ile Glu Asn Gly Ser Leu Asp Ser Gln Leu
    50                  55                  60
```

```
His Gly Pro Ser His Gly Ser Ala Leu Ser Trp His Ile Arg Met Lys
65                  70                  75                  80

Ile Ala Leu Asp Thr Ala Arg Gly Leu Glu Tyr Leu His Glu His Cys
                85                  90                  95

Asn Pro Pro Val Ile His Arg Asp Leu Lys Ser Ser Asn Ile Leu Leu
            100                 105                 110

Asp Ser Asp Phe Ser Ala Lys Ile Ser Asp Phe Gly Leu Ala Val Ile
        115                 120                 125

Ser Gly Asn His Ser Lys Gly Asn Leu Lys Leu Ser Gly Thr Met Gly
    130                 135                 140

Tyr Val Ala Pro Glu Tyr Leu Leu Asp Gly Lys Leu Thr Glu Lys Ser
145                 150                 155                 160

Asp Val Tyr Ala Phe Gly Val Val Leu Leu Glu Leu Leu Leu Gly Arg
                165                 170                 175

Lys Pro Val Glu Lys Met Ala Gln Ser Gln Cys Gln Ser Ile Val Thr
            180                 185                 190

Trp Ala Met Pro Gln Leu Thr Asp Arg Ser Lys Leu Pro Asn Ile Ile
        195                 200                 205

Asp Pro Met Ile Lys Asn Thr Met Asp Leu Lys His Leu Tyr Gln Val
    210                 215                 220

Ala Ala Met Ala Val Leu
225                 230


<210> SEQ ID NO 71
<211> LENGTH: 414
<212> TYPE: DNA
<213> ORGANISM: TRIPHYSARIA VERSICOLOR

<400> SEQUENCE: 71

accctcggtt atgtagctcc tgagtatctg ttagatggta agttaacaga gaaaagcgat      60

gtgtatgggt ttggagtagt gttactcgag cttctgcttg ggaagaagcc tatggagaaa     120

gtggcaacaa cagcaactca gtgccagatg atagtcacat ggaccatgcc tcagctcact     180

gacagaacga aacttccgaa tatcgtggat ccggtgatca gaaactccat ggatttaaag     240

cacttgtacc aggttgctgc tgtggcagta ttgtgtgtgc agccagaacc gagttatcgg     300

ccattgataa ctgatatttt gcattctctt gtgccccttg tccctgttga gcttggtggg     360

acgctcagga actcgataac aatggctaca acaacaatat ctcctgaaag ctaa           414


<210> SEQ ID NO 72
<211> LENGTH: 137
<212> TYPE: PRT
<213> ORGANISM: TRIPHYSARIA VERSICOLOR

<400> SEQUENCE: 72

Thr Leu Gly Tyr Val Ala Pro Glu Tyr Leu Leu Asp Gly Lys Leu Thr
1               5                   10                  15

Glu Lys Ser Asp Val Tyr Gly Phe Gly Val Val Leu Leu Glu Leu Leu
            20                  25                  30

Leu Gly Lys Lys Pro Met Glu Lys Val Ala Thr Thr Ala Thr Gln Cys
        35                  40                  45

Gln Met Ile Val Thr Trp Thr Met Pro Gln Leu Thr Asp Arg Thr Lys
    50                  55                  60

Leu Pro Asn Ile Val Asp Pro Val Ile Arg Asn Ser Met Asp Leu Lys
65                  70                  75                  80

His Leu Tyr Gln Val Ala Ala Val Ala Val Leu Cys Val Gln Pro Glu
```

```
                85                  90                  95

Pro Ser Tyr Arg Pro Leu Ile Thr Asp Ile Leu His Ser Leu Val Pro
            100                 105                 110

Leu Val Pro Val Glu Leu Gly Gly Thr Leu Arg Asn Ser Ile Thr Met
        115                 120                 125

Ala Thr Thr Thr Ile Ser Pro Glu Ser
    130                 135
```

<210> SEQ ID NO 73
<211> LENGTH: 1140
<212> TYPE: DNA
<213> ORGANISM: TRITICUM AESTIVUM
<220> FEATURE:
<221> NAME/KEY: misc_feature
<222> LOCATION: (1000)..(1000)
<223> OTHER INFORMATION: n is a, c, g, or t
<220> FEATURE:
<221> NAME/KEY: misc_feature
<222> LOCATION: (1080)..(1080)
<223> OTHER INFORMATION: n is a, c, g, or t
<220> FEATURE:
<221> NAME/KEY: misc_feature
<222> LOCATION: (1088)..(1088)
<223> OTHER INFORMATION: n is a, c, g, or t

<400> SEQUENCE: 73

```
cggcacgagg ggctggtggc catgatcgag tacccgtcgc tggaggcggc gacgggcaag     60

ttcagcgaga gcaacgtgct cggcgtcggc gggttcggct gcgtctacaa ggcggcgttc    120

gacggcggcg ccaccgccgc cgtgaagagg ctcgaaggcg gcgagccgga ctgcgagaag    180

gagttcgaga atgagctgga cttgcttggc aggatcaggc acccaaacat agtgtccctc    240

ctgggcttct gcgtccatgg tggcaatcac tacattgttt atgagctcat ggagaaggga    300

tcattggaga cacaactgca tgggccttca catggatcgg ctatgagctg gcacgtccgg    360

atgaagatcg cgctcgacac ggcgagggga ttagagtatc ttcatgagca ctgcaatcca    420

ccagtcatcc atagggatct gaaatcgtct aatatactct tggattcaga cttcaatgct    480

aagattgcag attttggcct tgcagtgaca agtgggaatc ttgacaaagg gaacctgaag    540

atctctggga ccttgggata tgtagctccc gagtacttat tagatgggaa gttgaccgag    600

aagagcgacg tctacgcgtt tggagtagtg cttctagagc tcctgatggg gaggaagcct    660

gttgagaaga tgtcaccatc tcagtgccaa tcaattgtgt catgggccat gcctcagcta    720

accgacagat cgaagctacc caacatcatc gacccggtga tcaaggacac aatggaccca    780

aagcatttat accaagttgc ggcggtggcc gttctatgcg tgcagcccga accgagttac    840

agaccgctga taacagacgt tctccactcc cttgttcctc tggtacccgc ggatctcggg    900

gggaacgctc agagttacag agccgcattc tccacaccaa atgtaccatc cctcttgaga    960

agtgatccta caagtttcgt cgaagcgggg aaagcgaatn tatacggtcc agcggtagat   1020

ggctgttatt ttggtactta tatctcaccc tgtcctgctg cttatcttag gatgagtgan   1080

gagctccnac ctgctgcttt tgctggttgg gcagagagaa tacagttctg gttaggattg   1140
```

<210> SEQ ID NO 74
<211> LENGTH: 380
<212> TYPE: PRT
<213> ORGANISM: TRITICUM AESTIVUM
<220> FEATURE:
<221> NAME/KEY: misc_feature
<222> LOCATION: (334)..(334)
<223> OTHER INFORMATION: Xaa can be any naturally occurring amino acid
<220> FEATURE:

```
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (363)..(363)
<223> OTHER INFORMATION: Xaa can be any naturally occurring amino acid

<400> SEQUENCE: 74

Arg His Glu Gly Leu Val Ala Met Ile Glu Tyr Pro Ser Leu Glu Ala
1               5                   10                  15

Ala Thr Gly Lys Phe Ser Glu Ser Asn Val Leu Gly Val Gly Gly Phe
            20                  25                  30

Gly Cys Val Tyr Lys Ala Ala Phe Asp Gly Gly Ala Thr Ala Ala Val
        35                  40                  45

Lys Arg Leu Glu Gly Gly Glu Pro Asp Cys Glu Lys Glu Phe Glu Asn
    50                  55                  60

Glu Leu Asp Leu Leu Gly Arg Ile Arg His Pro Asn Ile Val Ser Leu
65                  70                  75                  80

Leu Gly Phe Cys Val His Gly Gly Asn His Tyr Ile Val Tyr Glu Leu
                85                  90                  95

Met Glu Lys Gly Ser Leu Glu Thr Gln Leu His Gly Pro Ser His Gly
            100                 105                 110

Ser Ala Met Ser Trp His Val Arg Met Lys Ile Ala Leu Asp Thr Ala
        115                 120                 125

Arg Gly Leu Glu Tyr Leu His Glu His Cys Asn Pro Pro Val Ile His
    130                 135                 140

Arg Asp Leu Lys Ser Ser Asn Ile Leu Leu Asp Ser Asp Phe Asn Ala
145                 150                 155                 160

Lys Ile Ala Asp Phe Gly Leu Ala Val Thr Ser Gly Asn Leu Asp Lys
                165                 170                 175

Gly Asn Leu Lys Ile Ser Gly Thr Leu Gly Tyr Val Ala Pro Glu Tyr
            180                 185                 190

Leu Leu Asp Gly Lys Leu Thr Glu Lys Ser Asp Val Tyr Ala Phe Gly
        195                 200                 205

Val Val Leu Leu Glu Leu Leu Met Gly Arg Lys Pro Val Glu Lys Met
    210                 215                 220

Ser Pro Ser Gln Cys Gln Ser Ile Val Ser Trp Ala Met Pro Gln Leu
225                 230                 235                 240

Thr Asp Arg Ser Lys Leu Pro Asn Ile Ile Asp Pro Val Ile Lys Asp
                245                 250                 255

Thr Met Asp Pro Lys His Leu Tyr Gln Val Ala Ala Val Ala Val Leu
            260                 265                 270

Cys Val Gln Pro Glu Pro Ser Tyr Arg Pro Leu Ile Thr Asp Val Leu
        275                 280                 285

His Ser Leu Val Pro Leu Val Pro Ala Asp Leu Gly Gly Asn Ala Gln
    290                 295                 300

Ser Tyr Arg Ala Ala Phe Ser Thr Pro Asn Val Pro Ser Leu Leu Arg
305                 310                 315                 320

Ser Asp Pro Thr Ser Phe Val Glu Ala Gly Lys Ala Asn Xaa Tyr Gly
                325                 330                 335

Pro Ala Val Asp Gly Cys Tyr Phe Gly Thr Tyr Ile Ser Pro Cys Pro
            340                 345                 350

Ala Ala Tyr Leu Arg Met Ser Xaa Glu Leu Xaa Pro Ala Ala Phe Ala
        355                 360                 365
```

```
Gly Trp Ala Glu Arg Ile Gln Phe Trp Leu Gly Leu
    370                 375                 380


<210> SEQ ID NO 75
<211> LENGTH: 978
<212> TYPE: DNA
<213> ORGANISM: VITIS VINIFERA

<400> SEQUENCE: 75

atgaaagtga ttgggagaaa gggttatgtc tcttttattg attataaggt actagaaact      60

gcaacaaaca attttcagga aagtaatatc ctgggtgagg gcgggtttgg ttgcgtctac     120

aaggcgcggt tggatgataa ctcccatgtg gctgtgaaga agatagatgg tagaggccag     180

gatgctgaga gagaatttga gaatgaggtg gatttgttga ctaaaattca gcacccaaat     240

ataatttctc tcctgggtta cagcagtcat gaggagtcaa agtttcttgt ctatgagctg     300

atgcagaatg gatctctgga aactgaattg cacggacctt ctcatggatc atctctaact     360

tggcatattc gaatgaaaat cgctctggat gcagcaagag gattagagta tctacatgag     420

cactgcaacc caccagtcat ccatagagat cttaaatcat ctaatattct tctggattca     480

aacttcaatg ccaagctttc ggattttggt ctagctgtaa ttgatgggcc tcaaaacaag     540

aacaacttga agctttcagg caccctgggt tatctagctc ctgagtatct tttagatggt     600

aaactgactg ataagagtga tgtgtatgca tttggagtgg tgcttctaga gctactactg     660

ggaagaaagc ctgtggaaaa actggcacca gctcaatgcc agtccattgt cacatgggcc     720

atgccacagc tgactgacag atcaaagctc ccaggcatcg ttgaccctgt ggtcagagac     780

acgatggatc taaagcattt ataccaagtt gctgctgtag ctgtgctatg tgtgcaacca     840

gaaccaagtt accggccatt gataacagat gttctgcact ccctcatccc actcgttcca     900

gttgagttgg gagggatgct aaaagttacc cagcaagcgc cgcctatcaa caccactgca     960

ccttctgctg gaggttga                                                   978


<210> SEQ ID NO 76
<211> LENGTH: 325
<212> TYPE: PRT
<213> ORGANISM: VITIS VINIFERA

<400> SEQUENCE: 76

Met Lys Val Ile Gly Arg Lys Gly Tyr Val Ser Phe Ile Asp Tyr Lys
1               5                   10                  15

Val Leu Glu Thr Ala Thr Asn Asn Phe Gln Glu Ser Asn Ile Leu Gly
            20                  25                  30

Glu Gly Gly Phe Gly Cys Val Tyr Lys Ala Arg Leu Asp Asp Asn Ser
        35                  40                  45

His Val Ala Val Lys Lys Ile Asp Gly Arg Gly Gln Asp Ala Glu Arg
    50                  55                  60

Glu Phe Glu Asn Glu Val Asp Leu Leu Thr Lys Ile Gln His Pro Asn
65                  70                  75                  80

Ile Ile Ser Leu Leu Gly Tyr Ser Ser His Glu Glu Ser Lys Phe Leu
                85                  90                  95

Val Tyr Glu Leu Met Gln Asn Gly Ser Leu Glu Thr Glu Leu His Gly
            100                 105                 110

Pro Ser His Gly Ser Ser Leu Thr Trp His Ile Arg Met Lys Ile Ala
        115                 120                 125

Leu Asp Ala Ala Arg Gly Leu Glu Tyr Leu His Glu His Cys Asn Pro
    130                 135                 140
```

```
Pro Val Ile His Arg Asp Leu Lys Ser Ser Asn Ile Leu Leu Asp Ser
145                 150                 155                 160

Asn Phe Asn Ala Lys Leu Ser Asp Phe Gly Leu Ala Val Ile Asp Gly
                165                 170                 175

Pro Gln Asn Lys Asn Asn Leu Lys Leu Ser Gly Thr Leu Gly Tyr Leu
            180                 185                 190

Ala Pro Glu Tyr Leu Leu Asp Gly Lys Leu Thr Asp Lys Ser Asp Val
        195                 200                 205

Tyr Ala Phe Gly Val Val Leu Leu Glu Leu Leu Leu Gly Arg Lys Pro
    210                 215                 220

Val Glu Lys Leu Ala Pro Ala Gln Cys Gln Ser Ile Val Thr Trp Ala
225                 230                 235                 240

Met Pro Gln Leu Thr Asp Arg Ser Lys Leu Pro Gly Ile Val Asp Pro
                245                 250                 255

Val Val Arg Asp Thr Met Asp Leu Lys His Leu Tyr Gln Val Ala Ala
            260                 265                 270

Val Ala Val Leu Cys Val Gln Pro Glu Pro Ser Tyr Arg Pro Leu Ile
        275                 280                 285

Thr Asp Val Leu His Ser Leu Ile Pro Leu Val Pro Val Glu Leu Gly
    290                 295                 300

Gly Met Leu Lys Val Thr Gln Gln Ala Pro Pro Ile Asn Thr Thr Ala
305                 310                 315                 320

Pro Ser Ala Gly Gly
                325
```

<210> SEQ ID NO 77
<211> LENGTH: 1377
<212> TYPE: DNA
<213> ORGANISM: ZEA MAYS

<400> SEQUENCE: 77

```
atgccgccgc catcgccgct cctccgttcc tccgccttcg tcgtcttgct gctcctggtg      60

tgtcgcccgt tgttggtcgc caatgggagg gccacgccgc cttctccggg atggccaccg     120

gcggctcagc ccgcgctgca gcctgcaccc accgccagcg gcggcgtggc ctccgtgctt     180

ccttcggccg tggcgcctcc tcccttaggt gtggttgtgg cggagaggca ccaccacctc     240

agcagggagc tcgtcgctgc cattatcctc tcatccgtcg ccagcgtcgt gatccccatt     300

gccgcgctgt atgccttctt gctgtggcga cgatcacggc gagccctggt ggattccaag     360

gacacccaga gcatagatac cgcaaggatt gcttttgcgc cgatgttgaa cagctttggc     420

tcgtacaaga ctaccaagaa gagtgccgcg gcgatgatgg attacacatc tttggaggca     480

gcgacagaaa acttcagtga gagcaatgtc cttggatttg gtgggtttgg gtctgtgtac     540

aaagccaatt ttgatgggag gtttgctgct gcggtgaaga gactggatgg tggggcacat     600

gattgcaaga aggaattcga gaatgagcta gacttgcttg ggaagattcg acatccgaac     660

atcgtgtccc ttgtgggctt ctgcattcat gaggagaacc gtttcgttgt ttatgagctg     720

atggagagtg ggtcgttgga ttcgcaactt catgggccat cacatggttc agctctgagc     780

tggcatattc ggatgaagat tgctctcgac acagcaaggg gattagagta cctgcatgag     840

cactgcaacc caccggttat ccatagggat cttaagtcat ctaacatact tttagattca     900

gacttcagcg ctaagatttc agactttggc ctggcagtga ctagtgggaa tcacagcaaa     960

gggaatttaa agctttctgg gactatgggc tatgtggctc ctgagtactt attagatggg    1020
```

```
aagctgactg agaagagcga tgtatacgcg tttggggtag tacttctaga actcctgctg   1080

ggaaggaaac ctgtcgagaa gatggcacaa tctcagtgcc gatcaatcgt tacatgggcc   1140

atgcctcagc taactgatag atccaagctc ccgaacataa ttgatcccat gatcaagaac   1200

acaatggatc tgaaacactt gtaccaagtt gctgcagtgg ccgtgctctg cgtgcagcca   1260

gagccgagtt acaggccact gatcaccgac gtgcttcact cactggtacc tctagtgccc   1320

acggagcttg gaggaacgct gaggatcggc ccggaatcgc cctacctacg ctactaa      1377
```

<210> SEQ ID NO 78
<211> LENGTH: 458
<212> TYPE: PRT
<213> ORGANISM: ZEA MAYS

<400> SEQUENCE: 78

```
Met Pro Pro Pro Ser Pro Leu Leu Arg Ser Ser Ala Phe Val Val Leu
1               5                   10                  15

Leu Leu Leu Val Cys Arg Pro Leu Leu Val Ala Asn Gly Arg Ala Thr
            20                  25                  30

Pro Pro Ser Pro Gly Trp Pro Pro Ala Ala Gln Pro Ala Leu Gln Pro
        35                  40                  45

Ala Pro Thr Ala Ser Gly Gly Val Ala Ser Val Leu Pro Ser Ala Val
    50                  55                  60

Ala Pro Pro Pro Leu Gly Val Val Val Ala Glu Arg His His His Leu
65                  70                  75                  80

Ser Arg Glu Leu Val Ala Ala Ile Ile Leu Ser Ser Val Ala Ser Val
                85                  90                  95

Val Ile Pro Ile Ala Ala Leu Tyr Ala Phe Leu Leu Trp Arg Arg Ser
            100                 105                 110

Arg Arg Ala Leu Val Asp Ser Lys Asp Thr Gln Ser Ile Asp Thr Ala
        115                 120                 125

Arg Ile Ala Phe Ala Pro Met Leu Asn Ser Phe Gly Ser Tyr Lys Thr
    130                 135                 140

Thr Lys Lys Ser Ala Ala Ala Met Met Asp Tyr Thr Ser Leu Glu Ala
145                 150                 155                 160

Ala Thr Glu Asn Phe Ser Glu Ser Asn Val Leu Gly Phe Gly Gly Phe
                165                 170                 175

Gly Ser Val Tyr Lys Ala Asn Phe Asp Gly Arg Phe Ala Ala Ala Val
            180                 185                 190

Lys Arg Leu Asp Gly Gly Ala His Asp Cys Lys Lys Glu Phe Glu Asn
        195                 200                 205

Glu Leu Asp Leu Leu Gly Lys Ile Arg His Pro Asn Ile Val Ser Leu
    210                 215                 220

Val Gly Phe Cys Ile His Glu Glu Asn Arg Phe Val Val Tyr Glu Leu
225                 230                 235                 240

Met Glu Ser Gly Ser Leu Asp Ser Gln Leu His Gly Pro Ser His Gly
                245                 250                 255

Ser Ala Leu Ser Trp His Ile Arg Met Lys Ile Ala Leu Asp Thr Ala
            260                 265                 270

Arg Gly Leu Glu Tyr Leu His Glu His Cys Asn Pro Pro Val Ile His
        275                 280                 285

Arg Asp Leu Lys Ser Ser Asn Ile Leu Leu Asp Ser Asp Phe Ser Ala
    290                 295                 300

Lys Ile Ser Asp Phe Gly Leu Ala Val Thr Ser Gly Asn His Ser Lys
305                 310                 315                 320
```

```
Gly Asn Leu Lys Leu Ser Gly Thr Met Gly Tyr Val Ala Pro Glu Tyr
                325                 330                 335

Leu Leu Asp Gly Lys Leu Thr Glu Lys Ser Asp Val Tyr Ala Phe Gly
            340                 345                 350

Val Val Leu Leu Glu Leu Leu Leu Gly Arg Lys Pro Val Glu Lys Met
        355                 360                 365

Ala Gln Ser Gln Cys Arg Ser Ile Val Thr Trp Ala Met Pro Gln Leu
    370                 375                 380

Thr Asp Arg Ser Lys Leu Pro Asn Ile Ile Asp Pro Met Ile Lys Asn
385                 390                 395                 400

Thr Met Asp Leu Lys His Leu Tyr Gln Val Ala Ala Val Ala Val Leu
                405                 410                 415

Cys Val Gln Pro Glu Pro Ser Tyr Arg Pro Leu Ile Thr Asp Val Leu
            420                 425                 430

His Ser Leu Val Pro Leu Val Pro Thr Glu Leu Gly Gly Thr Leu Arg
        435                 440                 445

Ile Gly Pro Glu Ser Pro Tyr Leu Arg Tyr
    450                 455
```

```
<210> SEQ ID NO 79
<211> LENGTH: 1188
<212> TYPE: DNA
<213> ORGANISM: ZEA MAYS

<400> SEQUENCE: 79

atgttgctcg cgtgtcctgc agtgatcatc gtggagcgcc accgtcattt ccaccgtgag     60

ctagtcatcg cctccatcct cgcctcaatc gccatggtcg cgattatcct ctccacgctg    120

tacgcgtgga tcccgcgcag gcggtcccgc cggctgcccc gcggcatgag cgcagacacc    180

gcgaggggga tcatgctggc gccgatcctg agcaagttca actcgctcaa gacgagcagg    240

aaggggctcg tggcgatgat cgagtacccg tcgctggagg cagcgacagg ggggttcagt    300

gagagcaacg tgctcggcgt aggcggcttc ggttgcgtct acaaggcagt cttcgatggc    360

ggcgttaccg cggcggtcaa gaggctggag ggaggtggcc ctgagtgcga gaaggaattc    420

gagaatgagc tggatctgct tggcaggatt cggcacccca acatcgtgtc cctgctgggc    480

ttttgtgttc acgaggggaa tcactacatt gtttatgagc tcatggagaa gggatccctg    540

gacacacagc tgcatggggc ctcacatgga tcagcgctga cctggcatat ccggatgaag    600

atcgcactcg acatggccag ggggattagaa tacctccatg agcactgcag tccaccagtg  660

atccataggg atctgaagtc atctaacata cttttagatt ctgacttcaa tgctaagatt    720

tcagattttg gtcttgcagt gaccagtggg aacattgaca agggaagcat gaagctttct    780

gggaccttgg gttatgtggc ccctgagtac ctattagatg ggaagctgac tgaaaagagt    840

gacgtatatg catttggagt ggtgcttctt gagctactaa tgggaaggaa gcctgtcgag    900

aagatgagtc aaactcagtg ccaatcaatt gtgacgtggg ccatgccgca gctgactgac    960

agaacaaaac ttcccaacat agttgaccca gtgatcaggg acaccatgga tccaaagcat   1020

ttgtaccaag tggcagcagt ggcagttcta tgtgtgcaac cagaaccaag ttacagaccg   1080

ctgattactg atgttctcca ctctcttgtc cctctagtcc ctgtggagct cggagggaca   1140

ctgagggttg tagagccacc ttccccaaac ctaaaacatt ctccttgt                1188

<210> SEQ ID NO 80
<211> LENGTH: 396
```

```
<212> TYPE: PRT
<213> ORGANISM: ZEA MAYS

<400> SEQUENCE: 80

Met Leu Leu Ala Cys Pro Ala Val Ile Ile Val Glu Arg His Arg His
1               5                   10                  15

Phe His Arg Glu Leu Val Ile Ala Ser Ile Leu Ala Ser Ile Ala Met
            20                  25                  30

Val Ala Ile Ile Leu Ser Thr Leu Tyr Ala Trp Ile Pro Arg Arg Arg
        35                  40                  45

Ser Arg Arg Leu Pro Arg Gly Met Ser Ala Asp Thr Ala Arg Gly Ile
    50                  55                  60

Met Leu Ala Pro Ile Leu Ser Lys Phe Asn Ser Leu Lys Thr Ser Arg
65                  70                  75                  80

Lys Gly Leu Val Ala Met Ile Glu Tyr Pro Ser Leu Glu Ala Ala Thr
                85                  90                  95

Gly Gly Phe Ser Glu Ser Asn Val Leu Gly Val Gly Gly Phe Gly Cys
            100                 105                 110

Val Tyr Lys Ala Val Phe Asp Gly Gly Val Thr Ala Ala Val Lys Arg
        115                 120                 125

Leu Glu Gly Gly Gly Pro Glu Cys Glu Lys Glu Phe Glu Asn Glu Leu
    130                 135                 140

Asp Leu Leu Gly Arg Ile Arg His Pro Asn Ile Val Ser Leu Leu Gly
145                 150                 155                 160

Phe Cys Val His Glu Gly Asn His Tyr Ile Val Tyr Glu Leu Met Glu
                165                 170                 175

Lys Gly Ser Leu Asp Thr Gln Leu His Gly Ala Ser His Gly Ser Ala
            180                 185                 190

Leu Thr Trp His Ile Arg Met Lys Ile Ala Leu Asp Met Ala Arg Gly
        195                 200                 205

Leu Glu Tyr Leu His Glu His Cys Ser Pro Pro Val Ile His Arg Asp
    210                 215                 220

Leu Lys Ser Ser Asn Ile Leu Leu Asp Ser Asp Phe Asn Ala Lys Ile
225                 230                 235                 240

Ser Asp Phe Gly Leu Ala Val Thr Ser Gly Asn Ile Asp Lys Gly Ser
                245                 250                 255

Met Lys Leu Ser Gly Thr Leu Gly Tyr Val Ala Pro Glu Tyr Leu Leu
            260                 265                 270

Asp Gly Lys Leu Thr Glu Lys Ser Asp Val Tyr Ala Phe Gly Val Val
        275                 280                 285

Leu Leu Glu Leu Leu Met Gly Arg Lys Pro Val Glu Lys Met Ser Gln
    290                 295                 300

Thr Gln Cys Gln Ser Ile Val Thr Trp Ala Met Pro Gln Leu Thr Asp
305                 310                 315                 320

Arg Thr Lys Leu Pro Asn Ile Val Asp Pro Val Ile Arg Asp Thr Met
                325                 330                 335

Asp Pro Lys His Leu Tyr Gln Val Ala Ala Val Ala Val Leu Cys Val
            340                 345                 350

Gln Pro Glu Pro Ser Tyr Arg Pro Leu Ile Thr Asp Val Leu His Ser
        355                 360                 365

Leu Val Pro Leu Val Pro Val Glu Leu Gly Gly Thr Leu Arg Val Val
    370                 375                 380

Glu Pro Pro Ser Pro Asn Leu Lys His Ser Pro Cys
385                 390                 395
```

<210> SEQ ID NO 81
<211> LENGTH: 1086
<212> TYPE: DNA
<213> ORGANISM: GOSSYPIUM

<400> SEQUENCE: 81

```
atgaagaaga agcttgtgct gcatctgctt cttttccttg tttgtgctct tgaaaacatt      60

gttttggccg tacaaggccc tgcttcatca cccatttcta ctcccatctc tgcttcaatg     120

gctgccttct ctccagctgg gattcaactt ggaggtgagg agcacaagaa aatggatcca     180

accaagaaaa tgttattagc tctcattctt gcttgctctt cattgggtgc aattatctct     240

tccttgttct gtttatggat ttattacagg aagaattcaa gcaaatcctc taaaaatggc     300

gctaagagct cagatggtga aaaagggaat ggtttggcac catatttggg taaattcaag     360

tctatgagga cggtttccaa agagggttat gcttcgttta tggactataa gatacttgaa     420

aaagctacaa acaagttcca tcatggtaac attctgggtg agggtggatt tggatgtgtt     480

tacaaggctc aattcaatga tggttcttat gctgctgtta agaagttgga ctgtgcaagc     540

caagatgctg aaaaagaata tgagaatgag gtgggtttgc tatgtagatt taagcattcc     600

aatataattt cactgttggg ttatagcagt gataacgata caaggtttat tgtttatgag     660

ttgatggaaa atggttcttt ggaaactcaa ttacatggac cttctcatgg ttcatcatta     720

acttggcata ggaggatgaa aattgctttg gatacagcaa gaggattaga atatctacat     780

gagcattgca atccaccagt catccataga gatctgaaat catctaatat acttttggat     840

ttggacttca atgcaaagct ttcagatttt ggtcttgcag taactgatgc ggcaacaaac     900

aagaataact tgaagctttc gggtacttta ggttatctag ctccagaata ccttttagat     960

ggtaaattaa cagataagag tgatgtttat gcattcggtg ttgtgctgct cgaacttcta    1020

ttgggacgaa aggctgttga aaaattatca caactcagtg ccaatcttag gtccatttgg    1080

gcatag                                                              1086
```

<210> SEQ ID NO 82
<211> LENGTH: 361
<212> TYPE: PRT
<213> ORGANISM: GOSSYPIUM

<400> SEQUENCE: 82

```
Met Lys Lys Lys Leu Val Leu His Leu Leu Leu Phe Leu Val Cys Ala
1               5                   10                  15

Leu Glu Asn Ile Val Leu Ala Val Gln Gly Pro Ala Ser Ser Pro Ile
            20                  25                  30

Ser Thr Pro Ile Ser Ala Ser Met Ala Ala Phe Ser Pro Ala Gly Ile
        35                  40                  45

Gln Leu Gly Gly Glu Glu His Lys Lys Met Asp Pro Thr Lys Lys Met
    50                  55                  60

Leu Leu Ala Leu Ile Leu Ala Cys Ser Ser Leu Gly Ala Ile Ile Ser
65                  70                  75                  80

Ser Leu Phe Cys Leu Trp Ile Tyr Tyr Arg Lys Asn Ser Ser Lys Ser
                85                  90                  95

Ser Lys Asn Gly Ala Lys Ser Ser Asp Gly Glu Lys Gly Asn Gly Leu
            100                 105                 110

Ala Pro Tyr Leu Gly Lys Phe Lys Ser Met Arg Thr Val Ser Lys Glu
        115                 120                 125
```

```
Gly Tyr Ala Ser Phe Met Asp Tyr Lys Ile Leu Glu Lys Ala Thr Asn
    130                 135                 140

Lys Phe His His Gly Asn Ile Leu Gly Glu Gly Gly Phe Gly Cys Val
145                 150                 155                 160

Tyr Lys Ala Gln Phe Asn Asp Gly Ser Tyr Ala Ala Val Lys Lys Leu
                165                 170                 175

Asp Cys Ala Ser Gln Asp Ala Glu Lys Glu Tyr Glu Asn Glu Val Gly
            180                 185                 190

Leu Leu Cys Arg Phe Lys His Ser Asn Ile Ile Ser Leu Leu Gly Tyr
        195                 200                 205

Ser Ser Asp Asn Asp Thr Arg Phe Ile Val Tyr Glu Leu Met Glu Asn
    210                 215                 220

Gly Ser Leu Glu Thr Gln Leu His Gly Pro Ser His Gly Ser Ser Leu
225                 230                 235                 240

Thr Trp His Arg Arg Met Lys Ile Ala Leu Asp Thr Ala Arg Gly Leu
                245                 250                 255

Glu Tyr Leu His Glu His Cys Asn Pro Pro Val Ile His Arg Asp Leu
            260                 265                 270

Lys Ser Ser Asn Ile Leu Leu Asp Leu Asp Phe Asn Ala Lys Leu Ser
        275                 280                 285

Asp Phe Gly Leu Ala Val Thr Asp Ala Ala Thr Asn Lys Asn Asn Leu
    290                 295                 300

Lys Leu Ser Gly Thr Leu Gly Tyr Leu Ala Pro Glu Tyr Leu Leu Asp
305                 310                 315                 320

Gly Lys Leu Thr Asp Lys Ser Asp Val Tyr Ala Phe Gly Val Val Leu
                325                 330                 335

Leu Glu Leu Leu Leu Gly Arg Lys Ala Val Glu Lys Leu Ser Gln Leu
            340                 345                 350

Ser Ala Asn Leu Arg Ser Ile Trp Ala
        355                 360
```

```
<210> SEQ ID NO 83
<211> LENGTH: 1089
<212> TYPE: DNA
<213> ORGANISM: SOLANUM LYCOPERSICUM
<220> FEATURE:
<221> NAME/KEY: misc_feature
<222> LOCATION: (1024)..(1024)
<223> OTHER INFORMATION: n is a, c, g, or t

<400> SEQUENCE: 83

ggagtgggaa ttgagaagca gccacccacc cacccaccct atggataaaa atagaaggct      60

gttgatagca ctcattgtag cttctactgc attaggacta atctttatct tcatcatttt     120

attctggatt tttcacaaaa gatttcacac ctcagatgtt gtgaagggaa tgagtaggaa     180

aacattggtt tctttaatgg actacaacat acttgaatca gccaccaaca aatttaaaga     240

aactgagatt ttaggtgagg ggggttttgg atgtgtgtac aaagctaaat tggaagacaa     300

tttttatgta gctgtcaaga aactaaccca aaattccatt aaagaatttg agactgagtt     360

agagttgttg agtcaaatgc aacatcccaa tattatttca ttgttgggat attgcatcca     420

cagtgaaaca agattgcttg tctatgaact catgcaaaat ggatcactag aaactcaatt     480

acatgggcct tcccgtggat cagcattaac ttggcatcgc aggataaaaa ttgcccttga     540

tgcagcaaga ggaatagaat atttacatga gcagcgccat ccccctgtaa ttcatagaga     600

tctgaaatca tctaatattc ttttagattc caacttcaat gcaaaggtaa aactttttat     660
```

```
gtagaaatta tactaggact agttttccct ctattaatct tgtgttgtga ttaattttag    720

ctgtcagatt ttggtcttgc tgtgttgagt ggggctcaaa acaaaaacaa tatcaagctt    780

tctggaacta taggttatgt agcgcctgaa tacatgttag atggaaaatt aagtgataaa    840

agtgatgttt atggttttgg agtagtactt ttggagctgt tattgggaag gcggcctgta    900

gaaaaggagg cagccactga atgtcagtct atagtgacat gggccatgcc tcagctgaca    960

gatagatcaa agcttccaaa cattgttgat cctgtcatac aaaacacaat ggatttaaag   1020

catntgtatc aggttgctgc aggtgctcta ttatgtgttc agccagagcc aagctatcgt   1080

cccgtataa                                                           1089
```

```
<210> SEQ ID NO 84
<211> LENGTH: 875
<212> TYPE: DNA
<213> ORGANISM: AQUILEGIA

<400> SEQUENCE: 84

gagtatcagt tattggaagc tgcaactgac aattttagtg agagtaatat tttgggagaa     60

ggtggatttg gatgtgttta caaagcatgt tttgataaca actttctcgc tgctgtcaag    120

agaatggatg ttggtgggca agatgcagaa agagaatttg agaaagaagt agatttgttg    180

aatagaattc agcatccgga tataatttcc ctgttgggtt attgtattca tgatgagaca    240

aggttcatca tttatgaact aatgcagaac ggatctttgg aaagacaatt acatggacct    300

tctcatggat cggctttaac ttggcatatc cggatgaaaa ttgcacttga tacagcaaga    360

gcattagaat atctccatga gaattgcaac cctcctgtga tccacagaga tctgaaatca    420

tccaatatac ttttggattc taatttcaag gccaagattt cagattttgg tcttgctgta    480

atttctggga gtcaaaacaa gaacaacatt aagctttcag gcactcttgg ttatgttgct    540

ccagaatatc tgttagatgg taaattgact gacaaaagtg atgtctatgc ttttggggtt    600

atccttctag aactcctaat gggaagaaaa cctgtagaga aaatgacacg aactcagtgt    660

caatctatcg ttacatgggc catgcctcaa ctcactgata gatcaaagct accaaacatt    720

gttgatcctg tgattaaaaa cacaatggat ttgaagcatt tgttccaagt tgctgctgta    780

gctgtactgt gtgtacaacc agaaccaagt taccggccat taatcacaga tgtccttcac    840

tccctcgtac cccttgttcc tgtcgatctt ggagg                               875
```

```
<210> SEQ ID NO 85
<211> LENGTH: 292
<212> TYPE: PRT
<213> ORGANISM: AQUILEGIA

<400> SEQUENCE: 85

Glu Tyr Gln Leu Leu Glu Ala Ala Thr Asp Asn Phe Ser Glu Ser Asn
1               5                   10                  15

Ile Leu Gly Glu Gly Gly Phe Gly Cys Val Tyr Lys Ala Cys Phe Asp
            20                  25                  30

Asn Asn Phe Leu Ala Ala Val Lys Arg Met Asp Val Gly Gly Gln Asp
        35                  40                  45

Ala Glu Arg Glu Phe Glu Lys Glu Val Asp Leu Leu Asn Arg Ile Gln
    50                  55                  60

His Pro Asp Ile Ile Ser Leu Leu Gly Tyr Cys Ile His Asp Glu Thr
65                  70                  75                  80

Arg Phe Ile Ile Tyr Glu Leu Met Gln Asn Gly Ser Leu Glu Arg Gln
                85                  90                  95
```

```
Leu His Gly Pro Ser His Gly Ser Ala Leu Thr Trp His Ile Arg Met
            100                 105                 110

Lys Ile Ala Leu Asp Thr Ala Arg Ala Leu Glu Tyr Leu His Glu Asn
        115                 120                 125

Cys Asn Pro Pro Val Ile His Arg Asp Leu Lys Ser Ser Asn Ile Leu
    130                 135                 140

Leu Asp Ser Asn Phe Lys Ala Lys Ile Ser Asp Phe Gly Leu Ala Val
145                 150                 155                 160

Ile Ser Gly Ser Gln Asn Lys Asn Asn Ile Lys Leu Ser Gly Thr Leu
                165                 170                 175

Gly Tyr Val Ala Pro Glu Tyr Leu Leu Asp Gly Lys Leu Thr Asp Lys
            180                 185                 190

Ser Asp Val Tyr Ala Phe Gly Val Ile Leu Leu Glu Leu Leu Met Gly
        195                 200                 205

Arg Lys Pro Val Glu Lys Met Thr Arg Thr Gln Cys Gln Ser Ile Val
    210                 215                 220

Thr Trp Ala Met Pro Gln Leu Thr Asp Arg Ser Lys Leu Pro Asn Ile
225                 230                 235                 240

Val Asp Pro Val Ile Lys Asn Thr Met Asp Leu Lys His Leu Phe Gln
                245                 250                 255

Val Ala Ala Val Ala Val Leu Cys Val Gln Pro Glu Pro Ser Tyr Arg
            260                 265                 270

Pro Leu Ile Thr Asp Val Leu His Ser Leu Val Pro Leu Val Pro Val
        275                 280                 285

Asp Leu Gly Gly
    290
```

<210> SEQ ID NO 86
<211> LENGTH: 696
<212> TYPE: DNA
<213> ORGANISM: CENTAUREA MACULOSA

<400> SEQUENCE: 86

```
tgtgctcatg atgagaccaa actacttgtt tacgaactta tgcacaatgg ttcgttagaa     60

actcaattac acggtccttc ttgtggatcc aatttaacat ggcattgtcg gatgaaaatt    120

gcgctagata tagcgagagg attggaatat ttacatgaac actgcaaacc atctgtgatt    180

catagagatt tgaagtcatc taacatcctt ttggattcaa aattcaatgc caagctttcg    240

gatttcggtc ttgctgtgat gaacggtgcc aataccaaaa acattaagct ttcggggacg    300

ttgggttacg tagctcccga gtatctttta aatgggaaat tgaccgataa aagtgacgtc    360

tacgcattcg gagttgtact tttagagctt ctactcaaaa ggcggcctgt cgaaaaacta    420

gcaccatccg agtgccagtc catcgtcact tgggctatgc cgcaactaac agacagaaca    480

aagcttccga gtgttataga tcccgtgatc agggacacga tggatcttaa acacttgtat    540

caagtggcgg ctgtggctgt gttgtgtgtt caaccggaac cgggataccg gccgttgata    600

accgacgtct tgcattctct ggttcctctc gtgccggttg aactcggagg gactctacga    660

gttgcggaaa caggttgcgg cacagttgac ttatga                               696
```

<210> SEQ ID NO 87
<211> LENGTH: 231
<212> TYPE: PRT
<213> ORGANISM: CENTAUREA MACULOSA

<400> SEQUENCE: 87

```
Cys Ala His Asp Glu Thr Lys Leu Leu Val Tyr Glu Leu Met His Asn
1               5                   10                  15

Gly Ser Leu Glu Thr Gln Leu His Gly Pro Ser Cys Gly Ser Asn Leu
            20                  25                  30

Thr Trp His Cys Arg Met Lys Ile Ala Leu Asp Ile Ala Arg Gly Leu
        35                  40                  45

Glu Tyr Leu His Glu His Cys Lys Pro Ser Val Ile His Arg Asp Leu
    50                  55                  60

Lys Ser Ser Asn Ile Leu Leu Asp Ser Lys Phe Asn Ala Lys Leu Ser
65                  70                  75                  80

Asp Phe Gly Leu Ala Val Met Asn Gly Ala Asn Thr Lys Asn Ile Lys
                85                  90                  95

Leu Ser Gly Thr Leu Gly Tyr Val Ala Pro Glu Tyr Leu Leu Asn Gly
            100                 105                 110

Lys Leu Thr Asp Lys Ser Asp Val Tyr Ala Phe Gly Val Val Leu Leu
        115                 120                 125

Glu Leu Leu Leu Lys Arg Arg Pro Val Glu Lys Leu Ala Pro Ser Glu
    130                 135                 140

Cys Gln Ser Ile Val Thr Trp Ala Met Pro Gln Leu Thr Asp Arg Thr
145                 150                 155                 160

Lys Leu Pro Ser Val Ile Asp Pro Val Ile Arg Asp Thr Met Asp Leu
                165                 170                 175

Lys His Leu Tyr Gln Val Ala Ala Val Ala Val Leu Cys Val Gln Pro
            180                 185                 190

Glu Pro Gly Tyr Arg Pro Leu Ile Thr Asp Val Leu His Ser Leu Val
        195                 200                 205

Pro Leu Val Pro Val Glu Leu Gly Gly Thr Leu Arg Val Ala Glu Thr
    210                 215                 220

Gly Cys Gly Thr Val Asp Leu
225                 230
```

<210> SEQ ID NO 88
<211> LENGTH: 842
<212> TYPE: DNA
<213> ORGANISM: CICHORIUM INTYBUS

<400> SEQUENCE: 88

```
tggatttgga tgcgtttaaa agctcaactc aatgataact tattagttgc ggtcaaacga     60

ctagacaata aaagtcaaaa ttccatcaaa gaattccaga cggaagtgaa tattttgagt    120

aaaattcaac atccaaatat aattagtttg ttgggatatt gcgatcatga tgaaagcaag    180

ctacttgttt acgaattgat gcaaaatggt tctttagaaa ctcagttaca tgggccttct    240

tgtggatcca atttaacatg gtattgccgg atgaaaattg ccctagatat agcaagagga    300

ttggaatatt tacatgaaca ctccaaacca tctgtgattc atagagatct caaatcatct    360

aatatacttc ttgattcaaa tttcaatgca aagctttcgg attttggtct tgcggtgatg    420

gaaggtgcaa atagcaaaaa cattaaactt tcggggacat tgggatacgt agcacccgaa    480

tatcttttag atgggaaatt aaccgataaa agtgacgtgt atgcatttgg agtcgtactt    540

tttgagcttt tactcagaag acgacacgtt gaaaaactag aatcatcaca atcccgccaa    600

tctattgtca cttgggcgat gccactacta atggacagat cgaagcttcc gagtgtgata    660

gatcctgtga ttagggatac aatggatctt aaacatcttt atcaagtggc tgcggtggcg    720

gtgttgtgtg ttcaatcgga accgagttac cgtccgttga taaccgatgt tttacattct    780
```

```
cttgttcctc ttgtcccggt tgaacttgga gggacactta gagttgtaga aaagagtgtt    840

gt                                                                   842


<210> SEQ ID NO 89
<211> LENGTH: 281
<212> TYPE: PRT
<213> ORGANISM: CICHORIUM INTYBUS

<400> SEQUENCE: 89

Trp Ile Trp Met Arg Leu Lys Ala Gln Leu Asn Asp Asn Leu Leu Val
1               5                   10                  15

Ala Val Lys Arg Leu Asp Asn Lys Ser Gln Asn Ser Ile Lys Glu Phe
            20                  25                  30

Gln Thr Glu Val Asn Ile Leu Ser Lys Ile Gln His Pro Asn Ile Ile
        35                  40                  45

Ser Leu Leu Gly Tyr Cys Asp His Asp Glu Ser Lys Leu Leu Val Tyr
    50                  55                  60

Glu Leu Met Gln Asn Gly Ser Leu Glu Thr Gln Leu His Gly Pro Ser
65                  70                  75                  80

Cys Gly Ser Asn Leu Thr Trp Tyr Cys Arg Met Lys Ile Ala Leu Asp
                85                  90                  95

Ile Ala Arg Gly Leu Glu Tyr Leu His Glu His Ser Lys Pro Ser Val
            100                 105                 110

Ile His Arg Asp Leu Lys Ser Ser Asn Ile Leu Leu Asp Ser Asn Phe
        115                 120                 125

Asn Ala Lys Leu Ser Asp Phe Gly Leu Ala Val Met Glu Gly Ala Asn
    130                 135                 140

Ser Lys Asn Ile Lys Leu Ser Gly Thr Leu Gly Tyr Val Ala Pro Glu
145                 150                 155                 160

Tyr Leu Leu Asp Gly Lys Leu Thr Asp Lys Ser Asp Val Tyr Ala Phe
                165                 170                 175

Gly Val Val Leu Phe Glu Leu Leu Leu Arg Arg Arg His Val Glu Lys
            180                 185                 190

Leu Glu Ser Ser Gln Ser Arg Gln Ser Ile Val Thr Trp Ala Met Pro
        195                 200                 205

Leu Leu Met Asp Arg Ser Lys Leu Pro Ser Val Ile Asp Pro Val Ile
    210                 215                 220

Arg Asp Thr Met Asp Leu Lys His Leu Tyr Gln Val Ala Ala Val Ala
225                 230                 235                 240

Val Leu Cys Val Gln Ser Glu Pro Ser Tyr Arg Pro Leu Ile Thr Asp
                245                 250                 255

Val Leu His Ser Leu Val Pro Leu Val Pro Val Glu Leu Gly Gly Thr
            260                 265                 270

Leu Arg Val Val Glu Lys Ser Val Val
        275                 280


<210> SEQ ID NO 90
<211> LENGTH: 495
<212> TYPE: DNA
<213> ORGANISM: CUCUMIS MELO

<400> SEQUENCE: 90

attcttttag atgcaaactt caatgccaag ctttctgatt ttggcttgtc tgtcattgtt     60

ggagcacaaa acaagaatga tataaagctt tccggaacga tgggttatgt tgctcctgaa    120
```

```
tatcttttag atggtaaatt gactgataaa agtgatgtct atgcttttgg agttgtgctt    180

ttggagcttc ttttaggaag aaggcctgtt gaaaaactgg caccatctca atgtcaatcc    240

attgtcacat gggctatgcc tcaactcact gatagatcaa agttacccga tatcgttgat    300

ccggtgatca gacacacaat ggaccctaaa catttatttc aggttgctgc tgtcgccgtg    360

ctgtgtgtgc aaccagaacc gagctatcgt cccctaataa cagatctttt gcactctctt    420

attcctcttg ttcctgttga gctaggaggt actcacagat catcaacatc acaagctcct    480

gtggctccag cttag                                                     495


<210> SEQ ID NO 91
<211> LENGTH: 164
<212> TYPE: PRT
<213> ORGANISM: CUCUMIS MELO

<400> SEQUENCE: 91

Ile Leu Leu Asp Ala Asn Phe Asn Ala Lys Leu Ser Asp Phe Gly Leu
1               5                   10                  15

Ser Val Ile Val Gly Ala Gln Asn Lys Asn Asp Ile Lys Leu Ser Gly
            20                  25                  30

Thr Met Gly Tyr Val Ala Pro Glu Tyr Leu Leu Asp Gly Lys Leu Thr
        35                  40                  45

Asp Lys Ser Asp Val Tyr Ala Phe Gly Val Val Leu Leu Glu Leu Leu
    50                  55                  60

Leu Gly Arg Arg Pro Val Glu Lys Leu Ala Pro Ser Gln Cys Gln Ser
65                  70                  75                  80

Ile Val Thr Trp Ala Met Pro Gln Leu Thr Asp Arg Ser Lys Leu Pro
                85                  90                  95

Asp Ile Val Asp Pro Val Ile Arg His Thr Met Asp Pro Lys His Leu
            100                 105                 110

Phe Gln Val Ala Ala Val Ala Val Leu Cys Val Gln Pro Glu Pro Ser
        115                 120                 125

Tyr Arg Pro Leu Ile Thr Asp Leu Leu His Ser Leu Ile Pro Leu Val
    130                 135                 140

Pro Val Glu Leu Gly Gly Thr His Arg Ser Ser Thr Ser Gln Ala Pro
145                 150                 155                 160

Val Ala Pro Ala


<210> SEQ ID NO 92
<211> LENGTH: 375
<212> TYPE: DNA
<213> ORGANISM: ERAGROSTIS CURVULA

<400> SEQUENCE: 92

gatgggaagc tcaccgagaa aagcgacgtg tacgcgtttg gcatagtgct tcttgagctg     60

ctaatgggaa ggaagcctgt tgagaagttg agtcaatctc agtgccaatc aattgtgact    120

tgggccatgc cccaactgac agacagatca aaacttccca acataattga cccagtgatc    180

agggacacaa tggatccaaa gcacttgtat caggttgcag cagtggctgt tctatgcgtg    240

caaccagaac cgagttacag accactgata acggatgttc tccactcttt agttcctcta    300

gtgcctgtgg agcttggtgg gacactaagg gttgcagagc caccgtcccc aaaccaaaat    360

cattctcctc gttga                                                     375


<210> SEQ ID NO 93
<211> LENGTH: 124
```

```
<212> TYPE: PRT
<213> ORGANISM: ERAGROSTIS CURVULA

<400> SEQUENCE: 93

Asp Gly Lys Leu Thr Glu Lys Ser Asp Val Tyr Ala Phe Gly Ile Val
1               5                   10                  15

Leu Leu Glu Leu Leu Met Gly Arg Lys Pro Val Glu Lys Leu Ser Gln
            20                  25                  30

Ser Gln Cys Gln Ser Ile Val Thr Trp Ala Met Pro Gln Leu Thr Asp
        35                  40                  45

Arg Ser Lys Leu Pro Asn Ile Ile Asp Pro Val Ile Arg Asp Thr Met
    50                  55                  60

Asp Pro Lys His Leu Tyr Gln Val Ala Ala Val Ala Val Leu Cys Val
65                  70                  75                  80

Gln Pro Glu Pro Ser Tyr Arg Pro Leu Ile Thr Asp Val Leu His Ser
                85                  90                  95

Leu Val Pro Leu Val Pro Val Glu Leu Gly Gly Thr Leu Arg Val Ala
            100                 105                 110

Glu Pro Pro Ser Pro Asn Gln Asn His Ser Pro Arg
        115                 120


<210> SEQ ID NO 94
<211> LENGTH: 414
<212> TYPE: DNA
<213> ORGANISM: GERBERA HYBRID

<400> SEQUENCE: 94

ggggttcatg gcaagaacaa tataaaactt tcaggaactt taggatatgt cgcgccggaa      60

taccttttag atggtaaact tactgataaa agtgacgttt atgcgtttgg agttgtgctt     120

ctcgagcttt tgataggacg aaaacccgtg gagaaaatgt caccatttca atgccaattt     180

atcgttacat gggcaatgcc tcagctaacg gacagatcga agcttcctaa tcttgtggat     240

cctgtgatta gagatactat ggacttgaag ccccttatatc aagttgcggc tgtaactgtg     300

ttatgtgtac aacccgaacc aagttaccgc ccattaataa cggatgtttt gcattcgttc     360

atcccacttg tacctgctga tcttggaggg tcgttaaaag ttgtcgactt ttaa           414


<210> SEQ ID NO 95
<211> LENGTH: 137
<212> TYPE: PRT
<213> ORGANISM: GERBERA HYBRID

<400> SEQUENCE: 95

Gly Val His Gly Lys Asn Asn Ile Lys Leu Ser Gly Thr Leu Gly Tyr
1               5                   10                  15

Val Ala Pro Glu Tyr Leu Leu Asp Gly Lys Leu Thr Asp Lys Ser Asp
            20                  25                  30

Val Tyr Ala Phe Gly Val Val Leu Leu Glu Leu Leu Ile Gly Arg Lys
        35                  40                  45

Pro Val Glu Lys Met Ser Pro Phe Gln Cys Gln Phe Ile Val Thr Trp
    50                  55                  60

Ala Met Pro Gln Leu Thr Asp Arg Ser Lys Leu Pro Asn Leu Val Asp
65                  70                  75                  80

Pro Val Ile Arg Asp Thr Met Asp Leu Lys Pro Leu Tyr Gln Val Ala
                85                  90                  95

Ala Val Thr Val Leu Cys Val Gln Pro Glu Pro Ser Tyr Arg Pro Leu
            100                 105                 110
```

```
Ile Thr Asp Val Leu His Ser Phe Ile Pro Leu Val Pro Ala Asp Leu
        115                 120                 125

Gly Gly Ser Leu Lys Val Val Asp Phe
    130                 135
```

<210> SEQ ID NO 96
<211> LENGTH: 498
<212> TYPE: DNA
<213> ORGANISM: HELIANTHUS PARADOXUS

<400> SEQUENCE: 96

```
atcgtgttcc attttggttg ttgtctaaag ctttcagatt ttggtcttgc tgtaatggat     60

ggagcccaga acaaaaacaa catcaagctt tcagggacat tgggttatgt agctccagag    120

tatcttttag atggaaaact gaccgacaaa agtgatgtat atgcatttgg agttgtactt    180

ttagagcttc tacttggaag acggcctgta gaaaaactgg ccgcatctca atgccaatct    240

atcgtcactt gggccatgcc acagctaaca gacagatcaa agctcccaaa tattgtcgat    300

cctgtaatca gatatacgat ggatctcaaa cacttgtacc aagttgctgc cgtggcagtg    360

ctgtgtgtgc aaccagagcc aagttaccgg ccattaataa ccgatgtttt gcattctctt    420

atccctcttg ttccggtgga gctcggggga actctaaaag ctccacaaac aaggtcttcg    480

gtaacaaatg acccgtga                                                  498
```

<210> SEQ ID NO 97
<211> LENGTH: 165
<212> TYPE: PRT
<213> ORGANISM: HELIANTHUS PARADOXUS

<400> SEQUENCE: 97

```
Ile Val Phe His Phe Gly Cys Cys Leu Lys Leu Ser Asp Phe Gly Leu
1               5                   10                  15

Ala Val Met Asp Gly Ala Gln Asn Lys Asn Asn Ile Lys Leu Ser Gly
            20                  25                  30

Thr Leu Gly Tyr Val Ala Pro Glu Tyr Leu Leu Asp Gly Lys Leu Thr
        35                  40                  45

Asp Lys Ser Asp Val Tyr Ala Phe Gly Val Val Leu Leu Glu Leu Leu
    50                  55                  60

Leu Gly Arg Arg Pro Val Glu Lys Leu Ala Ala Ser Gln Cys Gln Ser
65                  70                  75                  80

Ile Val Thr Trp Ala Met Pro Gln Leu Thr Asp Arg Ser Lys Leu Pro
                85                  90                  95

Asn Ile Val Asp Pro Val Ile Arg Tyr Thr Met Asp Leu Lys His Leu
            100                 105                 110

Tyr Gln Val Ala Ala Val Ala Val Leu Cys Val Gln Pro Glu Pro Ser
        115                 120                 125

Tyr Arg Pro Leu Ile Thr Asp Val Leu His Ser Leu Ile Pro Leu Val
    130                 135                 140

Pro Val Glu Leu Gly Gly Thr Leu Lys Ala Pro Gln Thr Arg Ser Ser
145                 150                 155                 160

Val Thr Asn Asp Pro
                165
```

<210> SEQ ID NO 98
<211> LENGTH: 612
<212> TYPE: DNA
<213> ORGANISM: IPOMOEA NIL

<400> SEQUENCE: 98

```
cgtggatcaa ctttaagttg gcctctccga atgaaaattg ctttggatat tgcaagagga     60
ttagaatacc ttcacgagcg ttgcaacccc cctgtgatcc ataggcatct caaatcgtct    120
aatattcttc ttgattccag cttcaacgca aagatttctg attttggcct ttctgtaact    180
ggcggaaacc taagcaagaa cataaccaag atttcgggat cactgggtta tcttgctcca    240
gagtatctct tagacggtaa actaactgat aagagtgatg tgtatggttt tggcattatt    300
cttctagagc ttttgatggg taaaaggcca gtggagaaag tgggagaaac taagtgccaa    360
tcaatagtta catgggctat gccccagctt acggaccgat caaagcttcc gaatattgtt    420
gaccctacga tcaggaacac aatggatgtt aagcatttat atcaggttgc ggctgtagct    480
gtgttatgtg tgcaaccgga gccaagctat aggccattga taactgatgt actacactcc    540
ttcattccac ttgtaccaaa tgaactcggg gggtcgctta gggtagtgga ttctactccc    600
cattgctcat ag                                                         612
```

<210> SEQ ID NO 99
<211> LENGTH: 203
<212> TYPE: PRT
<213> ORGANISM: IPOMOEA NIL

<400> SEQUENCE: 99

```
Arg Gly Ser Thr Leu Ser Trp Pro Leu Arg Met Lys Ile Ala Leu Asp
1               5                   10                  15

Ile Ala Arg Gly Leu Glu Tyr Leu His Glu Arg Cys Asn Pro Pro Val
            20                  25                  30

Ile His Arg His Leu Lys Ser Ser Asn Ile Leu Leu Asp Ser Ser Phe
        35                  40                  45

Asn Ala Lys Ile Ser Asp Phe Gly Leu Ser Val Thr Gly Gly Asn Leu
    50                  55                  60

Ser Lys Asn Ile Thr Lys Ile Ser Gly Ser Leu Gly Tyr Leu Ala Pro
65                  70                  75                  80

Glu Tyr Leu Leu Asp Gly Lys Leu Thr Asp Lys Ser Asp Val Tyr Gly
                85                  90                  95

Phe Gly Ile Ile Leu Leu Glu Leu Leu Met Gly Lys Arg Pro Val Glu
            100                 105                 110

Lys Val Gly Glu Thr Lys Cys Gln Ser Ile Val Thr Trp Ala Met Pro
        115                 120                 125

Gln Leu Thr Asp Arg Ser Lys Leu Pro Asn Ile Val Asp Pro Thr Ile
    130                 135                 140

Arg Asn Thr Met Asp Val Lys His Leu Tyr Gln Val Ala Ala Val Ala
145                 150                 155                 160

Val Leu Cys Val Gln Pro Glu Pro Ser Tyr Arg Pro Leu Ile Thr Asp
                165                 170                 175

Val Leu His Ser Phe Ile Pro Leu Val Pro Asn Glu Leu Gly Gly Ser
            180                 185                 190

Leu Arg Val Val Asp Ser Thr Pro His Cys Ser
        195                 200
```

<210> SEQ ID NO 100
<211> LENGTH: 708
<212> TYPE: DNA
<213> ORGANISM: NUPHAR ADVENA

<400> SEQUENCE: 100

```
ttagataatg gcggacccga ttgtcaacga gaattcgaga atgaggttga tttgatgagt     60

agaattaggc atccaaatgt ggtttcttta ttgggttatt gcattcatgg agaaaccagg    120

cttcttgtct atgaaatgat gcaaaacggg acgttggaat cgctattgca tggaccatca    180

catggatcct cactaacttg gcacattcgt atgaagatcg ccctcgacac agcaagaggc    240

ctcgagtatc tgcatgaaca ctgcgacccc tctgtgatcc accgtgacct gaagccttct    300

aacattcttt tggattccaa ctacaattcc aagctctcag actttggtct tgcagtcact    360

gttggaagcc agaatcaaac caacattaag attctaggga cactgggtta ccttgcacca    420

gagtacgttt tgaatggcaa attgacagag aaaagtgatg tgtttgcttt tggagttgtc    480

ctgttggagc ttctcatggg caagaaacca gtggagaaga tggcatcccc tccatgccaa    540

tccattgtca catgggcgat gcctcatctt actgacagaa ttaagcttcc aaatatcatt    600

gatcctgtta ttagaaacac catggatctg aaacacttgt accaggttgc agctgttgct    660

gttctctgcg tacaaccaga gccccagtta tcgtcctctg ataactga                 708
```

```
<210> SEQ ID NO 101
<211> LENGTH: 235
<212> TYPE: PRT
<213> ORGANISM: NUPHAR ADVENA

<400> SEQUENCE: 101

Leu Asp Asn Gly Gly Pro Asp Cys Gln Arg Glu Phe Glu Asn Glu Val
1               5                   10                  15

Asp Leu Met Ser Arg Ile Arg His Pro Asn Val Val Ser Leu Leu Gly
            20                  25                  30

Tyr Cys Ile His Gly Glu Thr Arg Leu Leu Val Tyr Glu Met Met Gln
        35                  40                  45

Asn Gly Thr Leu Glu Ser Leu Leu His Gly Pro Ser His Gly Ser Ser
    50                  55                  60

Leu Thr Trp His Ile Arg Met Lys Ile Ala Leu Asp Thr Ala Arg Gly
65                  70                  75                  80

Leu Glu Tyr Leu His Glu His Cys Asp Pro Ser Val Ile His Arg Asp
                85                  90                  95

Leu Lys Pro Ser Asn Ile Leu Leu Asp Ser Asn Tyr Asn Ser Lys Leu
            100                 105                 110

Ser Asp Phe Gly Leu Ala Val Thr Val Gly Ser Gln Asn Gln Thr Asn
        115                 120                 125

Ile Lys Ile Leu Gly Thr Leu Gly Tyr Leu Ala Pro Glu Tyr Val Leu
    130                 135                 140

Asn Gly Lys Leu Thr Glu Lys Ser Asp Val Phe Ala Phe Gly Val Val
145                 150                 155                 160

Leu Leu Glu Leu Leu Met Gly Lys Lys Pro Val Glu Lys Met Ala Ser
                165                 170                 175

Pro Pro Cys Gln Ser Ile Val Thr Trp Ala Met Pro His Leu Thr Asp
            180                 185                 190

Arg Ile Lys Leu Pro Asn Ile Ile Asp Pro Val Ile Arg Asn Thr Met
        195                 200                 205

Asp Leu Lys His Leu Tyr Gln Val Ala Ala Val Ala Val Leu Cys Val
    210                 215                 220

Gln Pro Glu Pro Gln Leu Ser Ser Ser Asp Asn
225                 230                 235
```

<210> SEQ ID NO 102
<211> LENGTH: 30
<212> TYPE: DNA
<213> ORGANISM: ARTIFICIAL SEQUENCE
<220> FEATURE:
<223> OTHER INFORMATION: Synthetic Primer

<400> SEQUENCE: 102
tcggctcggc ccagaacaag atcgcaagac 30

<210> SEQ ID NO 103
<211> LENGTH: 34
<212> TYPE: DNA
<213> ORGANISM: ARTIFICIAL SEQUENCE
<220> FEATURE:
<223> OTHER INFORMATION: Synthetic Primer

<400> SEQUENCE: 103
ctacattctc tcctcgtatt attcctcgtt gact 34

<210> SEQ ID NO 104
<211> LENGTH: 32
<212> TYPE: DNA
<213> ORGANISM: ARTIFICIAL SEQUENCE
<220> FEATURE:
<223> OTHER INFORMATION: Synthetic Primer

<400> SEQUENCE: 104
actttcagat gagtggatca taaccctata ca 32

<210> SEQ ID NO 105
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 105
agatacaatg gatctcaaac acttatacca g 31

<210> SEQ ID NO 106
<211> LENGTH: 42
<212> TYPE: DNA
<213> ORGANISM: ARTIFICIAL SEQUENCE
<220> FEATURE:
<223> OTHER INFORMATION: Synthetic Primer

<400> SEQUENCE: 106
aaaggatcca tgggaagtgg tgaagaagat agatttgatg ct 42

<210> SEQ ID NO 107
<211> LENGTH: 40
<212> TYPE: DNA
<213> ORGANISM: ARTIFICIAL SEQUENCE
<220> FEATURE:
<223> OTHER INFORMATION: Synthetic Primer

<400> SEQUENCE: 107
tttctgcagt ctgtgaatca tcttgttaac cggagagtcc 40

<210> SEQ ID NO 108
<211> LENGTH: 30
<212> TYPE: DNA
<213> ORGANISM: ARTIFICIAL SEQUENCE
<220> FEATURE:
<223> OTHER INFORMATION: Synthetic Primer

<400> SEQUENCE: 108
tctgagtttt aatcgagcca agtcgtctca 30

<210> SEQ ID NO 109
<211> LENGTH: 53
<212> TYPE: DNA
<213> ORGANISM: ARTIFICIAL SEQUENCE
<220> FEATURE:
<223> OTHER INFORMATION: Synthetic Primer

<400> SEQUENCE: 109
tatcccggga aaatgagaga gcttcttctt cttcttcttc ttcattttca gtc 53

<210> SEQ ID NO 110
<211> LENGTH: 38
<212> TYPE: DNA
<213> ORGANISM: ARTIFICIAL SEQUENCE
<220> FEATURE:
<223> OTHER INFORMATION: Synthetic Primer

<400> SEQUENCE: 110
tttggatcct gtgaatcatc ttgttaaccg gagagtcc 38

<210> SEQ ID NO 111
<211> LENGTH: 41
<212> TYPE: DNA
<213> ORGANISM: ARTIFICIAL SEQUENCE
<220> FEATURE:
<223> OTHER INFORMATION: Synthetic Primer

<400> SEQUENCE: 111
atacccgggt ctgtgtcagg aatccaaatg ggaagtggtg a 41

<210> SEQ ID NO 112
<211> LENGTH: 41
<212> TYPE: DNA
<213> ORGANISM: ARTIFICIAL SEQUENCE
<220> FEATURE:
<223> OTHER INFORMATION: Synthetic Primer

<400> SEQUENCE: 112
aaaggatcct ctgtgtcagg aatccaaatg ggaagtggtg a 41

<210> SEQ ID NO 113
<211> LENGTH: 39
<212> TYPE: DNA
<213> ORGANISM: ARTIFICIAL SEQUENCE
<220> FEATURE:
<223> OTHER INFORMATION: Synthetic Primer

<400> SEQUENCE: 113
aaatctagac tgtgaatcat cttgttaacc ggagagtcc 39

<210> SEQ ID NO 114
<211> LENGTH: 35
<212> TYPE: DNA
<213> ORGANISM: ARTIFICIAL SEQUENCE
<220> FEATURE:
<223> OTHER INFORMATION: Synthetic Primer

<400> SEQUENCE: 114
atagagctcg caagaaccaa tctccaaaat ccatc 35

<210> SEQ ID NO 115
<211> LENGTH: 37

<212> TYPE: DNA
<213> ORGANISM: ARTIFICIAL SEQUENCE
<220> FEATURE:
<223> OTHER INFORMATION: Synthetic Primer

<400> SEQUENCE: 115
atagagctcg agggtcttga tatcgaaaaa ttgcacg 37

<210> SEQ ID NO 116
<211> LENGTH: 37
<212> TYPE: DNA
<213> ORGANISM: ARTIFICIAL SEQUENCE
<220> FEATURE:
<223> OTHER INFORMATION: Synthetic Primer

<400> SEQUENCE: 116
ataggatcct cgcaagaacc aatctccaaa atccatc 37

<210> SEQ ID NO 117
<211> LENGTH: 40
<212> TYPE: DNA
<213> ORGANISM: ARTIFICIAL SEQUENCE
<220> FEATURE:
<223> OTHER INFORMATION: Synthetic Primer

<400> SEQUENCE: 117
atatctagac tcgagggtct tgatatcgaa aaattgcacg 40

<210> SEQ ID NO 118
<211> LENGTH: 52
<212> TYPE: DNA
<213> ORGANISM: ARTIFICIAL SEQUENCE
<220> FEATURE:
<223> OTHER INFORMATION: Synthetic Primer

<400> SEQUENCE: 118
atatctagaa aatgagagag cttcttcttc ttcttcttct tcattttcag tc 52

<210> SEQ ID NO 119
<211> LENGTH: 47
<212> TYPE: DNA
<213> ORGANISM: ARTIFICIAL SEQUENCE
<220> FEATURE:
<223> OTHER INFORMATION: Synthetic Primer

<400> SEQUENCE: 119
ataggatcct gttaaaagcg atttataatt tacaccgttt tggtgta 47

<210> SEQ ID NO 120
<211> LENGTH: 41
<212> TYPE: DNA
<213> ORGANISM: ARTIFICIAL SEQUENCE
<220> FEATURE:
<223> OTHER INFORMATION: Synthetic Primer

<400> SEQUENCE: 120
atacccggga aaagtttttg atgaaattca atctaaagac t 41

<210> SEQ ID NO 121
<211> LENGTH: 1309
<212> TYPE: DNA
<213> ORGANISM: ARABIDOPSIS THALIANA

<400> SEQUENCE: 121
aaaatgagag agcttcttct tcttcttctt cttcattttc agtctctaat tcttttgatg 60
atcttcatca ctgtctctgc ttcttctgct tcaaatcctt ctttagctcc tgtttactct 120
tccatggcta cattctctcc tcgaatccaa atgggaagtg gtgaagaaga tagatttgat 180
gctcataaga aacttctgat tggtctcata atcagtttct cttctcttgg ccttataatc 240
ttgttctgtt ttggcttttg ggtttatcgc aagaaccaat ctccaaaatc catcaacaac 300
tcagattctg agagtgggaa ttcattttcc ttgttaatga gacgacttgg ctcgattaaa 360
actcagagaa gaacttctat ccaaaagggt tacgtgcaat ttttcgatat caagaccctc 420
gagaaagcga caggcggttt taaagaaagt agtgtaatcg gacaaggcgg tttcggatgc 480
gtttacaagg gttgtttgga caataacgtt aaagcagcgg tcaagaagat cgagaacgtt 540
agccaagaag caaaacgaga atttcagaat gaagttgact tgttgagcaa gatccatcac 600
tcgaacgtta tatcattgtt gggctctgca agcgaaatca actcgagttt catcgtttat 660
gagcttatgg agaaaggatc attagatgaa cagttacatg ggccttctcg tggatcagct 720
ctaacatggc acatgcgtat gaagattgct cttgatacag ctagaggact agagtatctc 780
catgagcatt gtcgtccacc agttatccac agagatttga aatcttcgaa tattcttctt 840
gattcttcct tcaacgccaa gatttcagat ttcggttttg ctgtatcgct ggatgaacat 900
ggcaagaaca acattaaact ctctgggaca cttggttatg ttgccccgga atacctcctt 960
gacggaaaac tgacggataa gagtgatgtt tatgcatttg ggtagttct gcttgaactc 1020
ttgttgggta gacgaccagt tgaaaaatta actccagctc aatgccaatc tcttgtaact 1080
tgggcaatgc cacaacttac cgatagatcc aagcttccaa acattgtgga tgccgttata 1140
aaagatacaa tggatctcaa acacttatac caggtagcag ccatggctgt gttgtgcgtg 1200
cagccagaac caagttaccg gccgttgata accgatgttc ttcactcact tgttccactg 1260
gttccggtag agctaggagg gactctccgg ttaacaagat gattcacag 1309

<210> SEQ ID NO 122
<211> LENGTH: 25
<212> TYPE: DNA
<213> ORGANISM: ARTIFICIAL SEQUENCE
<220> FEATURE:
<223> OTHER INFORMATION: Synthetic Primer

<400> SEQUENCE: 122
tcggacaagg cggtttcgga tgcgt 25

<210> SEQ ID NO 123
<211> LENGTH: 32
<212> TYPE: DNA
<213> ORGANISM: ARTIFICIAL SEQUENCE
<220> FEATURE:
<223> OTHER INFORMATION: Synthetic Primer

<400> SEQUENCE: 123
tagtcctcta gctgtatcaa gagcaatctt ca 32

<210> SEQ ID NO 124
<211> LENGTH: 32
<212> TYPE: DNA
<213> ORGANISM: ARTIFICIAL SEQUENCE
<220> FEATURE:
<223> OTHER INFORMATION: Synthetic Primer

<400> SEQUENCE: 124
tatcattgtt gggctctgca agtgaaatca ac 32

<210> SEQ ID NO 125
<211> LENGTH: 32
<212> TYPE: DNA
<213> ORGANISM: ARTIFICIAL SEQUENCE
<220> FEATURE:
<223> OTHER INFORMATION: Synthetic Primer

<400> SEQUENCE: 125
tggagaaagg atccttagat gatcagttac at 32

<210> SEQ ID NO 126
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 126
tccatgtaac tgatcatcta aggatccttt c 31

<210> SEQ ID NO 127
<211> LENGTH: 37
<212> TYPE: DNA
<213> ORGANISM: ARTIFICIAL SEQUENCE
<220> FEATURE:
<223> OTHER INFORMATION: Synthetic Primer

<400> SEQUENCE: 127
ataaacgacg aaactcgagt tgatttcact tgcagag 37

<210> SEQ ID NO 128
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 128
aaaatgaaga aactggttca tcttcagt 28

<210> SEQ ID NO 129
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 129
tagacttcta ttctcacatt cttacac 27

<210> SEQ ID NO 130
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 130
tccaatgatc cattatgcat cagctca 27

<210> SEQ ID NO 131
<211> LENGTH: 29
<212> TYPE: DNA
<213> ORGANISM: ARTIFICIAL SEQUENCE
<220> FEATURE:
<223> OTHER INFORMATION: Synthetic Primer

<400> SEQUENCE: 131
tcgttctcaa attctctctc agcatgttg 29

<210> SEQ ID NO 132
<211> LENGTH: 29
<212> TYPE: DNA
<213> ORGANISM: ARTIFICIAL SEQUENCE
<220> FEATURE:
<223> OTHER INFORMATION: Synthetic Primer

<400> SEQUENCE: 132
tccggatatg ccaggtcagc gctgatcca 29

<210> SEQ ID NO 133
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 133
tccagggatc ccttctccat gagctcat 28

<210> SEQ ID NO 134
<211> LENGTH: 41
<212> TYPE: DNA
<213> ORGANISM: ARTIFICIAL SEQUENCE
<220> FEATURE:
<223> OTHER INFORMATION: Synthetic Primer

<400> SEQUENCE: 134
aaagagctct ctgtgtcagg aatccaaatg ggaagtggtg a 41

<210> SEQ ID NO 135
<211> LENGTH: 47
<212> TYPE: DNA
<213> ORGANISM: ARTIFICIAL SEQUENCE
<220> FEATURE:
<223> OTHER INFORMATION: Synthetic Primer

<400> SEQUENCE: 135
atagctagct gttaaaagcg atttataatt tacaccgttt tggtgta 47

<210> SEQ ID NO 136
<211> LENGTH: 43
<212> TYPE: DNA
<213> ORGANISM: ARTIFICIAL SEQUENCE
<220> FEATURE:
<223> OTHER INFORMATION: Synthetic Primer

<400> SEQUENCE: 136
atagctagca gaaaagtttt tgatgaaatt caatctaaag act 43

<210> SEQ ID NO 137
<211> LENGTH: 29
<212> TYPE: DNA
<213> ORGANISM: ARTIFICIAL SEQUENCE
<220> FEATURE:
<223> OTHER INFORMATION: Synthetic Primer

<400> SEQUENCE: 137
tctgggttta tcatcatacc aagtatcca 29

<210> SEQ ID NO 138
<211> LENGTH: 31

<212> TYPE: DNA
<213> ORGANISM: ARTIFICIAL SEQUENCE
<220> FEATURE:
<223> OTHER INFORMATION: Synthetic Primer

<400> SEQUENCE: 138
attcagttcc atcaagattg ttggcatgga c 31

<210> SEQ ID NO 139
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 139
tggagggagg tggccctgag tgcgagaagg a 31

<210> SEQ ID NO 140
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 140
gctggatctg cttggcagga ttcggca 27

<210> SEQ ID NO 141
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 141
atatctagat gctaggttat agatccatgc a 31

<210> SEQ ID NO 142
<211> LENGTH: 33
<212> TYPE: DNA
<213> ORGANISM: ARTIFICIAL SEQUENCE
<220> FEATURE:
<223> OTHER INFORMATION: Synthetic Primer

<400> SEQUENCE: 142
ataggatcca ccagaactat atatacgaag gca 33

<210> SEQ ID NO 143
<211> LENGTH: 40
<212> TYPE: DNA
<213> ORGANISM: ARTIFICIAL SEQUENCE
<220> FEATURE:
<223> OTHER INFORMATION: Synthetic Primer

<400> SEQUENCE: 143
aggacgactt ggctcgatta aaatcacagg tcgtgatatg 40

<210> SEQ ID NO 144
<211> LENGTH: 35
<212> TYPE: DNA
<213> ORGANISM: ARTIFICIAL SEQUENCE
<220> FEATURE:
<223> OTHER INFORMATION: Synthetic Primer

<400> SEQUENCE: 144

```
taatcgagcc aagtcgtcct acatatatat tccta                              35


<210> SEQ ID NO 145
<211> LENGTH: 35
<212> TYPE: DNA
<213> ORGANISM: ARTIFICIAL SEQUENCE
<220> FEATURE:
<223> OTHER INFORMATION: Synthetic Primer

<400> SEQUENCE: 145

taatcgagcc aagtcgtcct ctcttttgta ttcca                              35


<210> SEQ ID NO 146
<211> LENGTH: 42
<212> TYPE: DNA
<213> ORGANISM: ARTIFICIAL SEQUENCE
<220> FEATURE:
<223> OTHER INFORMATION: Synthetic Primer

<400> SEQUENCE: 146

aggacgactt ggctcgatta aaatcaaaga gaatcaatga tc                     42


<210> SEQ ID NO 147
<211> LENGTH: 21
<212> TYPE: DNA
<213> ORGANISM: ARTIFICIAL SEQUENCE
<220> FEATURE:
<223> OTHER INFORMATION: Synthesized gene fragment

<400> SEQUENCE: 147

gacgacttgg ctcgattaaa a                                             21


<210> SEQ ID NO 148
<211> LENGTH: 399
<212> TYPE: DNA
<213> ORGANISM: ARABIDOPSIS THALIANA

<400> SEQUENCE: 148

tgctaggtta tagatccatg caaatatgga gtagatgtac aaacacacgc tcggacgcat     60

attacacatg ttcatacact taatactcgc tgttttgaat tgatgtttta ggaatatata    120

tgtagagaga gcttccttga gtccattcac aggtcgtgat atgattcaat tagcttccga    180

ctcattcatc caaataccga gtcgccaaaa ttcaaactag actcgttaaa tgaatgaatg    240

atgcggtaga caaattggat cattgattct ctttgattgg actgaaggga gctccctctc    300

tcttttgtat tccaattttc ttgattaatc tttcctgcac aaaaacatgc ttgatccact    360

aagtgacata tatgctgcct tcgtatatat agttctggt                          399


<210> SEQ ID NO 149
<211> LENGTH: 399
<212> TYPE: DNA
<213> ORGANISM: ARTIFICIAL SEQUENCE
<220> FEATURE:
<223> OTHER INFORMATION: Artificial microRNA construct

<400> SEQUENCE: 149

tgctaggtta tagatccatg caaatatgga gtagatgtac aaacacacgc tcggacgcat     60

attacacatg ttcatacact taatactcgc tgttttgaat tgatgtttta ggaatatata    120

tgtaggacga cttggctcga ttaaaatcac aggtcgtgat atgattcaat tagcttccga    180

ctcattcatc caaataccga gtcgccaaaa ttcaaactag actcgttaaa tgaatgaatg    240

atgcggtaga caaattggat cattgattct ctttgatttt aatcgagcca agtcgtcctc    300
```

tcttttgtat tccaattttc ttgattaatc tttcctgcac aaaaacatgc ttgatccact 360
aagtgacata tatgctgcct tcgtatatat agttctggt 399

<210> SEQ ID NO 150
<211> LENGTH: 1475
<212> TYPE: DNA
<213> ORGANISM: ARABIDOPSIS THALIANA

<400> SEQUENCE: 150
cttagccaat ggatgaggat gacacgataa tgataatcaa agatcaacat ggcacgctca 60
agaccgcctt tagaagtcct ctctaaattc tttcttccga tctcctaaat atgttttgtt 120
ttggtcaaat aaattgatag gtaatactta gtgattatac tatttggttt ttgttttatc 180
attgactatt tcacttttat aaatcaaata cttatcaaaa ttgttctttc cgtatgtatt 240
catattttct aatattgtaa agatttgttt cacctaacat ctgtacccat ctttgatcat 300
tgacaaaata tatattagaa tggccttaga acgtgttagg catcttccta ctattatcat 360
attacctaat ccccaatttt attacatttt ttaatttcta aaagagcttg aatataatgt 420
catttcgaat atctctgttc atcttttttt ttttctgtgc gacttctgac ccaaagcctt 480
cgacgatttt ttccaatctg aaaacttttg aataaggaac ttagtcaatg gtcaacacct 540
tgctaattaa acaaagttcc attgatacaa taatgagatt tttgtacatt aacgctttca 600
tatagttttt gcgattcaac agataatctt aaaattaagg agtcctattg ataaagtctt 660
gttcaaacgt acaaactcaa tccacacaaa accttcataa aatacgatat aggaaataaa 720
gattgttttt gcgtgagaaa atactatatg aactcaaaag attttaaaac aatttgtatt 780
aatacataaa caattgttgt gatacacccg tgtaaaattt taagattgtt tttttctgaa 840
attcttcaag gaaacttata gcttaaaatc tacacttcaa atactctgtt ttaaaggcat 900
taaaaataac tgcgtttcag aaaaatattg aaattttagc tgatcttttg ctacaaattt 960
aaggaatctt ggcacctgca gaatctataa catgttcatt aagtaatgca atagttatac 1020
aattatacat tatttgcatc atacttatat tatagtgata ttaacaaacc catgttctca 1080
gcacactttt acgtagaaaa acataaaaac ccaaatagga agaagccact cataaggata 1140
atgggtttat ataattcaca gcaaagaaag ccatcgaact attcgattaa ttatccattc 1200 ttttttttt tagtttgaat gtataagaac aaagagttgt tacgcatcat gacaatgtct 1260
tagaaaacaa aagaaatgaa taaaaaagta aaacgaaaaa taaaaagtga ggatgaagtt 1320
gttgaatgag ttggcgaggc ggcgactttt tcatacattc catttactta attcctaaag 1380
tccttctcac atctctttgt tatataatga caccataacc atttcttctc ttcacaatct 1440
ttacaagaat atctctcttc tacagtaaac aaaaa 1475

<210> SEQ ID NO 151
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 151
acgtaagctt cttagccaat ggatgaggat g 31

<210> SEQ ID NO 152
<211> LENGTH: 31
<212> TYPE: DNA

<213> ORGANISM: ARTIFICIAL SEQUENCE
<220> FEATURE:
<223> OTHER INFORMATION: Synthetic Primer

<400> SEQUENCE: 152
acgttctaga tttttgttta ctgtagaaga g 31

<210> SEQ ID NO 153
<211> LENGTH: 338
<212> TYPE: DNA
<213> ORGANISM: BRASSICA NAPUS

<400> SEQUENCE: 153
tgctgcttca aatccttcta tagctcctgt ttataccacc atgactactt tctctccagg 60
aattcaaatg ggaagtggtg aagaacacag attagatgca cataagaaac tcctgattgg 120
tcttataatc agttcctctt ctcttggtat cgtaatcttg atttgctttg gcttctggat 180
gtactgtcgc aagaaagctc ccaaacccat caagattccg gatgctgaga gtgggacttc 240
atcattttca atgtttgtga ggcggctaag ctcaatcaaa actcagagaa catctagcaa 300
tcagggttat gtgcagcgtt tcgattccaa gacgctag 338

<210> SEQ ID NO 154
<211> LENGTH: 38
<212> TYPE: DNA
<213> ORGANISM: ARTIFICIAL SEQUENCE
<220> FEATURE:
<223> OTHER INFORMATION: Synthetic Primer

<400> SEQUENCE: 154
tatggatcct gctgcttcaa atccttctat agctcctg 38

<210> SEQ ID NO 155
<211> LENGTH: 37
<212> TYPE: DNA
<213> ORGANISM: ARTIFICIAL SEQUENCE
<220> FEATURE:
<223> OTHER INFORMATION: Synthetic Primer

<400> SEQUENCE: 155
tattctagac tagcgtcttg gaatcgaaac gctgcac 37

<210> SEQ ID NO 156
<211> LENGTH: 38
<212> TYPE: DNA
<213> ORGANISM: ARTIFICIAL SEQUENCE
<220> FEATURE:
<223> OTHER INFORMATION: Synthetic Primer

<400> SEQUENCE: 156
tatgagctct gctgcttcaa atccttctat agctcctg 38

<210> SEQ ID NO 157
<211> LENGTH: 37
<212> TYPE: DNA
<213> ORGANISM: ARTIFICIAL SEQUENCE
<220> FEATURE:
<223> OTHER INFORMATION: Synthetic Primer

<400> SEQUENCE: 157
tatgagctcc tagcgtcttg gaatcgaaac gctgcac 37

<210> SEQ ID NO 158
<211> LENGTH: 24

<212> TYPE: DNA
<213> ORGANISM: ARTIFICIAL SEQUENCE
<220> FEATURE:
<223> OTHER INFORMATION: Synthetic Primer

<400> SEQUENCE: 158
gcagatcgct cctcccgtcg tgat 24

<210> SEQ ID NO 159
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 159
cgcctaggag cgacgggtac tcgatcat 28

<210> SEQ ID NO 160
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 160
cctagctaag cgacgggtac tcgatcat 28

<210> SEQ ID NO 161
<211> LENGTH: 272
<212> TYPE: DNA
<213> ORGANISM: BRACHYPODIUM DISTACHYON

<400> SEQUENCE: 161
gctcctcccg tcgtgatcac agtggtgagg caccaccatt accaccggga gctggtcatc 60
tccgctgtcc tcgcctgcgt cgccaccgcc atgatcctcc tctccacact ctacgcctgg 120
acgatgtggc ggcggtctcg ccggaccccc cacggcggca agggccgcgg ccggagatca 180
gggatcacac tggtgccaat cctgagcaag ttcaattcag tgaagatgag caggaagggg 240
ggccttgtga cgatgatcga gtacccgtcg ct 272

<210> SEQ ID NO 162
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 162
cgggatcccg gcataacaaa ctcgtgcatc c 31

<210> SEQ ID NO 163
<211> LENGTH: 30
<212> TYPE: DNA
<213> ORGANISM: ARTIFICIAL SEQUENCE
<220> FEATURE:
<223> OTHER INFORMATION: Synthetic Primer

<400> SEQUENCE: 163
ccatcgatgg cgccaaacac aatagctcaa 30

<210> SEQ ID NO 164
<211> LENGTH: 1174
<212> TYPE: DNA

<213> ORGANISM: BRACHYPODIUM DISTACHYON

<400> SEQUENCE: 164
gtaagtaatt tcaagtttaa gtttcataag cataacaaac tcgtgcatcc aatttgaacc 60
attttactgt cctggcatcc tctaaatatt tccttgatta tcagcttatc ttcatcccat 120
tgaatcagaa aattaccaac ccttgtttta gctttaatca ttgttatttg ttgtctgagg 180
ggctacactg tttctttata ttggtgaagg agttaccagg caaaaattcc cacctcctga 240
tattagcaga gaccccccttt tttgtgcctg tatgcatact aacaaataat acagatggaa 300
atatgtatat ttgttatatc atggattgat gctttatgtt tagcaagtcc atgcaatggt 360
agtcaaaaga tgtaaacttt tgaatgatat attggggctt tagattagcc atttttaccc 420
tcacttgaaa atgacaattt tgcccttccg atctactttc tcttgtcacc tcaggcaggc 480
tcttgaaagt tcttatccct gaattccgtg gaagtttatt attctaatgt tatagtttac 540
ttaaagtgtc gcataatcta ctagagccta atggaagtac tgatggactt tgttttgcta 600
caatcactgc ttgcaagaat gactactttg gggcatttct aatatattat tgatatttct 660
atgatgtatt gttgtccatg tacttcagtc cttacagcga ctagtcctat ttctgcattg 720
ataaattgtt cactgtcaga ccatcttgag tggcaagaat gagtataaca tgtcttgttt 780
ttctgtgatt tcaaggtaag cgcacatgcg cacagtgtac accgtcacca catgtgagta 840
cacccccctag tacacatgta aaaaaagcac agtccagtta ttaaatggac cattggcatt 900
gattgtcgtg tttataggag taaagataca tgtaaacact aattcattgg gagatataaa 960
tttatactac cattgaatgt gacataggct ctaaggtttt tagttcagca tttcgaaaga 1020
gctttgtttg gttggcttgg gatggaatca ggtgacaaca tttttgggtt gcagcaaatt 1080
taatattgat tgaggaggca tacaacgaaa tcattgagct attgtgtttg gcgttacatc 1140
tatggaattt cttctaatct gattattgtt tgta 1174

<210> SEQ ID NO 165
<211> LENGTH: 22
<212> TYPE: DNA
<213> ORGANISM: ARTIFICIAL SEQUENCE
<220> FEATURE:
<223> OTHER INFORMATION: Synthetic Primer

<400> SEQUENCE: 165
gatccgctcc tcccgtcgtg at 22

<210> SEQ ID NO 166
<211> LENGTH: 30
<212> TYPE: DNA
<213> ORGANISM: ARTIFICIAL SEQUENCE
<220> FEATURE:
<223> OTHER INFORMATION: Synthetic Primer

<400> SEQUENCE: 166
aacgcgatcg cttgcatgcc tgcagtagac 30

<210> SEQ ID NO 167
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 167
gacttaatta agaattcgag ctcgggta 28

<210> SEQ ID NO 168
<211> LENGTH: 251
<212> TYPE: DNA
<213> ORGANISM: PANICUM VIRGATUM

<400> SEQUENCE: 168
tcgtagtgca ccaccatttc caccgcgagc tggtcatcgc cgccgtcctc gcctgcatcg 60
ccaccgtcac gatcttcctt tccacgctct acgcttggac actatggcgg cgatctcgcc 120
ggagcaccgg cggcaaggtc accaggagct cagacgcagc gaaggggatc aagctggtgc 180
cgatcttgag caggttcaac tcggtgaaga tgagcaggaa gaggctggtt gggatgttcg 240
agtacccgtc g 251

<210> SEQ ID NO 169
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 169
gcagatctcg tagtgcacca ccatttc 27

<210> SEQ ID NO 170
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 170
cgcctaggcg acgggtactc gaacatc 27

<210> SEQ ID NO 171
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 171
cctagctacg acgggtactc gaacatc 27

<210> SEQ ID NO 172
<211> LENGTH: 25
<212> TYPE: DNA
<213> ORGANISM: ARTIFICIAL SEQUENCE
<220> FEATURE:
<223> OTHER INFORMATION: Synthetic Primer

<400> SEQUENCE: 172
gatcctcgta gtgcaccacc atttc 25

<210> SEQ ID NO 173
<211> LENGTH: 21
<212> TYPE: DNA
<213> ORGANISM: ARTIFICIAL SEQUENCE
<220> FEATURE:
<223> OTHER INFORMATION: Synthetic Primer

<400> SEQUENCE: 173
ctcgtagtgc accaccattt c 21

<210> SEQ ID NO 174
<211> LENGTH: 261
<212> TYPE: DNA
<213> ORGANISM: SORGHUM BICOLOR

<400> SEQUENCE: 174
aatgggaccg cctccgttgc tccggcggtg ccggcgccgc ctcccgtcgt gatcatcgtg 60
gagcggcgcc atcatttcca ccgcgagcta gtcatcgcct ccgttctcgc ctccatcgcc 120
atcgtcgcga ttatcctctc cacgctctat gcgtggatcc tgtggcggcg gtctcgccgg 180
ctgcccagcg gcaagggcgc caggagcgca gacaccgcga ggggaatcat gctggtgccg 240
atcctgagca agttccactc a 261

<210> SEQ ID NO 175
<211> LENGTH: 26
<212> TYPE: DNA
<213> ORGANISM: ARTIFICIAL SEQUENCE
<220> FEATURE:
<223> OTHER INFORMATION: Synthetic Primer

<400> SEQUENCE: 175
gcagatcaat gggaccgcct ccgttg 26

<210> SEQ ID NO 176
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 176
cgcctaggtg agtggaactt gctcagga 28

<210> SEQ ID NO 177
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 177
cctagctatg agtggaactt gctcagga 28

<210> SEQ ID NO 178
<211> LENGTH: 273
<212> TYPE: DNA
<213> ORGANISM: SORGHUM BICOLOR

<400> SEQUENCE: 178
gtaagtattc ttgcaacaca ttactatttt caataaccac aagtttaaaa gcttgagtcc 60
atttcgcaaa ccagttgttc ataaccaaat tcttaggtaa ttaggtccaa ttgagaaaat 120
ctgatcattg aacactagca ggaaataact cagacatagt ttctgcatac tataatgatg 180
cttaatatat ttgttctctt ttgagattgt attgcataga catttctgtg taaaataatg 240
ttttacatca tgtatatata tcacttttta tag 273

<210> SEQ ID NO 179
<211> LENGTH: 30
<212> TYPE: DNA
<213> ORGANISM: ARTIFICIAL SEQUENCE
<220> FEATURE:
<223> OTHER INFORMATION: Synthetic Primer

<400> SEQUENCE: 179
cgggatcctt cttgcaacac attactattt 30

<210> SEQ ID NO 180
<211> LENGTH: 34
<212> TYPE: DNA
<213> ORGANISM: ARTIFICIAL SEQUENCE
<220> FEATURE:
<223> OTHER INFORMATION: Synthetic Primer

<400> SEQUENCE: 180
ccatcgatga aatgtctatg caatacaatc tcaa 34

<210> SEQ ID NO 181
<211> LENGTH: 24
<212> TYPE: DNA
<213> ORGANISM: ARTIFICIAL SEQUENCE
<220> FEATURE:
<223> OTHER INFORMATION: Synthetic Primer

<400> SEQUENCE: 181
gatccaatgg gaccgcctcc gttg 24

<210> SEQ ID NO 182
<211> LENGTH: 21
<212> TYPE: DNA
<213> ORGANISM: ARTIFICIAL SEQUENCE
<220> FEATURE:
<223> OTHER INFORMATION: Synthetic Primer

<400> SEQUENCE: 182
caatgggacc gcctccgttg a 21

<210> SEQ ID NO 183
<211> LENGTH: 1000
<212> TYPE: DNA
<213> ORGANISM: SORGHUM BICOLOR

<400> SEQUENCE: 183
ggccccggcc gcgcgcgtct ccgtgtcctc cgcgactgtg cacgtttcgt cgggagcggc 60
gtgcccacgc ccaccccccg tccaccagcc agcaaccgac ggcactggtg acacgcggct 120
ggtccgctcg gtccgccccg cggctccaga tcacggcaag cgcgcccgcc gcccgctgct 180
gcgctgcgct gcacgtcccg ccctgacgcc acgccacgcc aagcgcgaca cgacacgaca 240
cgacacgacc cgaccccCgc caacgaaacg ccgaaacgcg gcaacgcgtg acgggcgcgc 300
atggtcgatg ctctacccgc gcgtccgccc cacgccaatc tcccggcggg tccctcgtgg 360
gacggggaac gcgatgcggc tgcaggctgc gaccgcgacc gcgaccgcga ccgcgcccac 420
gtgaaggcag gcaggcagcc ccggagcggg cgcggcggtg ggccaacgac gcgttgccgt 480
cgcgaatctt cttctggcca cggccaaggg ccaatcgccc gctccgctcc gctccgcact 540
ccgcctccgc tagggaatat ggaacccgat cccacggccc tctgggtctg gtcgacgggt 600
cctctcgccg tggcagctgc ttcccggacc ggaggatcgc tgagcgcgga cgccactgcc 660
attgccgtcc gactatagtt gttaattacc ataaaataat ttgttaacga taaaacccgt 720
gtcaggcacc gtcgtctgga cgctgctatg ggataaccat tcgcgtacgt cggttgtatg 780
ggtgggatcc tctgcggcac gccattctgg tgctgctagt ggaatagaca aaaaaagggc 840
cgacggtgtt tgctcgtggc aggccacaca gagtgacaac cagagtggtt gccgcaaaaa 900
caaccaatca cacaaaaagt gttgtaccgg tggaggacag ccattaatca gcaggccggc 960
ttcgcggcca aaagaaacgg agaagaggaa aaaggggggc 1000

<210> SEQ ID NO 184
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 184
tcccaagctt gcgcgtctcc gtgtcctc 28

<210> SEQ ID NO 185
<211> LENGTH: 30
<212> TYPE: DNA
<213> ORGANISM: ARTIFICIAL SEQUENCE
<220> FEATURE:
<223> OTHER INFORMATION: Synthetic Primer

<400> SEQUENCE: 185
agtaaagctt ccccctttt cctcttctcc 30

<210> SEQ ID NO 186
<211> LENGTH: 1000
<212> TYPE: DNA
<213> ORGANISM: SORGHUM BICOLOR

<400> SEQUENCE: 186
taatggtcga gtgaggcccg tatagatgta gttaaatagc taaaattttt ggagaaataa 60
gcattttttt ggaagaatat atttaaacat gggcttgtaa aacttggctg taaagatttg 120
gaatttagga tcttggagcc ccaaaactgt ataaacttgc ttagggaccc gtgtcttgtg 180
tgttgcagac caaaaaattt agaaagcatc taaacaccta tttgaatgta aagtttacag 240
ccaaaagttt taggatgtaa agatttggga tctaaaagta gtcattagga aataacacgt 300
tagagagaga gagtagatct tcttattggt ttctcatgca ctaatcgaac caatcactgg 360
accacttgaa ccaaacttta tcacattgaa ctttgtcagt tcagttcgaa cgcaggactg 420
gagctgccct taaggccaat tgctcaagat tcattcaaca attgaaacat ctcccatgat 480
taaatcagta taaggttgct atggtcttgc ttgacaaagt tttttttttg agggaatttc 540
aactaaattt ttgagtgaaa ctatcaaata ctgattttaa aaattttta taaaaggaag 600 cgcagagata aaaggccatc tatgctacaa aagtacccaa aaatgtaatc ctaaagtatg 660
aattgcattt tttttgtttg gacgaaagga aaggagtatt accacaagaa tgatatcatc 720
ttcatattta gatctttttt gggtaaagct tgagattctc taaatataga gaaatcagaa 780
gaaaaaaaaa ccgtgttttg gtggttttga tttctagcct ccacaataac tttgacggcg 840
tcgacaagtc taacggacac caagcagcga accaccagcg ccgagccaag cgaagcagac 900
ggccgagacg ttgacacctt cggcgcggca tctctcgaga gttccgctcc ggcgctccac 960
ctccaccgct ggcggtttct tattccgttc cgttccgcct 1000

<210> SEQ ID NO 187
<211> LENGTH: 26
<212> TYPE: DNA
<213> ORGANISM: ARTIFICIAL SEQUENCE
<220> FEATURE:
<223> OTHER INFORMATION: Synthetic Primer

<400> SEQUENCE: 187
aactgcaggg tcgagtgagg cccgta 26

<210> SEQ ID NO 188
<211> LENGTH: 28
<212> TYPE: DNA
<213> ORGANISM: ARTIFICIAL SEQUENCE
<220> FEATURE:
<223> OTHER INFORMATION: Synthetic Primer

<400> SEQUENCE: 188
ttctgcaggg aacggaacgg aataagaa 28

<210> SEQ ID NO 189
<211> LENGTH: 239
<212> TYPE: DNA
<213> ORGANISM: SORGHUM BICOLOR

<400> SEQUENCE: 189
gccgtgggtc gtttaagctg ccgctgtacc tgtgtcgtct ggtgccttct ggtgtacctg 60
ggaggttgtc gtctatcaag tatctgtggt tggtgtcatg agtcagtgag tcccaatact 120
gttcgtgtcc tgtgtgcatt atacccaaaa ctgttatggg caaatcatga ataagcttga 180
tgttcgaact taaaagtctc tgctcaatat ggtattatgg ttgtttttgt tcgtctcct 239

<210> SEQ ID NO 190
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 190
taggtaccgc cgtgggtcgt ttaagct 27

<210> SEQ ID NO 191
<211> LENGTH: 27
<212> TYPE: DNA
<213> ORGANISM: ARTIFICIAL SEQUENCE
<220> FEATURE:
<223> OTHER INFORMATION: Synthetic Primer

<400> SEQUENCE: 191
aaggtaccag gagacgaaca aaaacaa 27

<210> SEQ ID NO 192
<211> LENGTH: 34
<212> TYPE: DNA
<213> ORGANISM: ARTIFICIAL SEQUENCE
<220> FEATURE:
<223> OTHER INFORMATION: Synthetic Primer

<400> SEQUENCE: 192
aacgcgatcg taatggtcga gtgaggcccg tata 34

<210> SEQ ID NO 193
<211> LENGTH: 1302
<212> TYPE: DNA
<213> ORGANISM: BRASSICA NAPUS

<400> SEQUENCE: 193
atgaagaaac tggttcatct tcagtttctg tttcttgtca agatctttgc tactcaattc 60
ctcactcctt cttcatcatc ttttgctgct tcaaatcctt ctatagctcc tgtttatacc 120

```
accatgacta ctttctctcc aggaattcaa atgggaagtg gtgaagaaca cagattagat    180

gcacataaga aactcctgat tggtcttata atcagttcct cttctcttgg tatcgtaatc    240

ttgatttgct ttggcttctg gatgtactgt cgcaagaaag ctcccaaacc catcaagatt    300

ccggatgctg agagtgggac ttcatcattt tcaatgtttg tgaggcggct aagctcaatc    360

aaaactcaga gaacatctag caatcagggt tatgtgcagc gtttcgattc caagacgcta    420

gagaaagcga caggcggttt caaagacagt aatgtaatcg gacagggcgg tttcggatgc    480

gtttacaagg cttctttgga cagcaacact aaagcagcgg ttaaaaagat cgaaaacgtt    540

agccaagaag caaaacgaga atttcagaat gaagttgagc tgttgagcaa gatccagcac    600

tccaatatta tatcattgtt gggctctgca agtgaaatca actcgagttt cgtcgtttat    660

gagttgatgg agaaaggatc cttagatgat cagttacatg gaccttcgtg tggatccgct    720

ctaacatggc atatgcgtat gaagattgct ctagatacag ctagaggatt agagtatctc    780

catgaacatt gtcgtccacc agttatccac agggacctga aatcgtctaa tatacttctt    840

gattcttcct tcaatgccaa gatttcagat tttggtctgg ctgtatcggt tggagtgcat    900

gggagtaaca acattaaact ctctgggaca cttggttatg ttgccccgga atatctccta    960

gacggaaagt tgacggataa gagtgatgtc tatgcatttg ggtggttct tcttgaactt   1020

ttgttgggta gaaggccggt tgagaaattg agtccatctc agtgtcaatc tcttgtgact   1080

tgggcaatgc cacaacttac cgatagatcg aaactcccaa acatcgtgga tccggttata   1140

aaagatacaa tggatcttaa gcacttatac caggtagcag ccatggctgt gttgtgcgtt   1200

cagccagaac cgagttaccg gccgctgata accgatgttc ttcactcact tgttccattg   1260

gttccggtcg aactaggagg gactctccgg ttaacccgat ga                      1302
```

<210> SEQ ID NO 194
<211> LENGTH: 433
<212> TYPE: PRT
<213> ORGANISM: BRASSICA NAPUS

<400> SEQUENCE: 194

```
Met Lys Lys Leu Val His Leu Gln Phe Leu Phe Leu Val Lys Ile Phe
1               5                   10                  15

Ala Thr Gln Phe Leu Thr Pro Ser Ser Ser Ser Phe Ala Ala Ser Asn
            20                  25                  30

Pro Ser Ile Ala Pro Val Tyr Thr Thr Met Thr Thr Phe Ser Pro Gly
        35                  40                  45

Ile Gln Met Gly Ser Gly Glu Glu His Arg Leu Asp Ala His Lys Lys
    50                  55                  60

Leu Leu Ile Gly Leu Ile Ile Ser Ser Ser Ser Leu Gly Ile Val Ile
65                  70                  75                  80

Leu Ile Cys Phe Gly Phe Trp Met Tyr Cys Arg Lys Lys Ala Pro Lys
                85                  90                  95

Pro Ile Lys Ile Pro Asp Ala Glu Ser Gly Thr Ser Ser Phe Ser Met
            100                 105                 110

Phe Val Arg Arg Leu Ser Ser Ile Lys Thr Gln Arg Thr Ser Ser Asn
        115                 120                 125

Gln Gly Tyr Val Gln Arg Phe Asp Ser Lys Thr Leu Glu Lys Ala Thr
    130                 135                 140

Gly Gly Phe Lys Asp Ser Asn Val Ile Gly Gln Gly Gly Phe Gly Cys
145                 150                 155                 160

Val Tyr Lys Ala Ser Leu Asp Ser Asn Thr Lys Ala Ala Val Lys Lys
```

```
                165                 170                 175

Ile Glu Asn Val Ser Gln Glu Ala Lys Arg Glu Phe Gln Asn Glu Val
            180                 185                 190

Glu Leu Leu Ser Lys Ile Gln His Ser Asn Ile Ile Ser Leu Leu Gly
        195                 200                 205

Ser Ala Ser Glu Ile Asn Ser Ser Phe Val Val Tyr Glu Leu Met Glu
    210                 215                 220

Lys Gly Ser Leu Asp Asp Gln Leu His Gly Pro Ser Cys Gly Ser Ala
225                 230                 235                 240

Leu Thr Trp His Met Arg Met Lys Ile Ala Leu Asp Thr Ala Arg Gly
                245                 250                 255

Leu Glu Tyr Leu His Glu His Cys Arg Pro Pro Val Ile His Arg Asp
            260                 265                 270

Leu Lys Ser Ser Asn Ile Leu Leu Asp Ser Ser Phe Asn Ala Lys Ile
        275                 280                 285

Ser Asp Phe Gly Leu Ala Val Ser Val Gly Val His Gly Ser Asn Asn
    290                 295                 300

Ile Lys Leu Ser Gly Thr Leu Gly Tyr Val Ala Pro Glu Tyr Leu Leu
305                 310                 315                 320

Asp Gly Lys Leu Thr Asp Lys Ser Asp Val Tyr Ala Phe Gly Val Val
                325                 330                 335

Leu Leu Glu Leu Leu Leu Gly Arg Arg Pro Val Glu Lys Leu Ser Pro
            340                 345                 350

Ser Gln Cys Gln Ser Leu Val Thr Trp Ala Met Pro Gln Leu Thr Asp
        355                 360                 365

Arg Ser Lys Leu Pro Asn Ile Val Asp Pro Val Ile Lys Asp Thr Met
    370                 375                 380

Asp Leu Lys His Leu Tyr Gln Val Ala Ala Met Ala Val Leu Cys Val
385                 390                 395                 400

Gln Pro Glu Pro Ser Tyr Arg Pro Leu Ile Thr Asp Val Leu His Ser
                405                 410                 415

Leu Val Pro Leu Val Pro Val Glu Leu Gly Gly Thr Leu Arg Leu Thr
            420                 425                 430

Arg


<210> SEQ ID NO 195
<211> LENGTH: 31
<212> TYPE: DNA
<213> ORGANISM: ARTIFICIAL SEQUENCE
<220> FEATURE:
<223> OTHER INFORMATION: Synthetic Primer

<400> SEQUENCE: 195

aatccagctc attctggaat tccttctcgc a                                  31


<210> SEQ ID NO 196
<211> LENGTH: 32
<212> TYPE: DNA
<213> ORGANISM: ARTIFICIAL SEQUENCE
<220> FEATURE:
<223> OTHER INFORMATION: Synthetic Primer

<400> SEQUENCE: 196

tgaacttgct caggattggc accagtgtga tc                                 32


<210> SEQ ID NO 197
<211> LENGTH: 461
```

```
<212> TYPE: PRT
<213> ORGANISM: BRACHYPODIUM DISTACHYON

<400> SEQUENCE: 197

Met Glu Ile Pro Ala Ala Pro Pro Pro Pro Leu Pro Val Leu Cys Ser
1               5                   10                  15

Tyr Val Val Phe Leu Leu Leu Leu Ser Ser Cys Ser Leu Ala Arg Gly
            20                  25                  30

Arg Ile Ala Val Ser Ser Pro Gly Pro Ser Pro Val Ala Ala Ala Val
        35                  40                  45

Thr Ala Asn Glu Thr Ala Ser Ser Ser Ser Ser Pro Val Phe Pro Ala
    50                  55                  60

Ala Pro Pro Val Val Ile Thr Val Val Arg His His His Tyr His Arg
65                  70                  75                  80

Glu Leu Val Ile Ser Ala Val Leu Ala Cys Val Ala Thr Ala Met Ile
                85                  90                  95

Leu Leu Ser Thr Leu Tyr Ala Trp Thr Met Trp Arg Arg Ser Arg Arg
            100                 105                 110

Thr Pro His Gly Gly Lys Gly Arg Gly Arg Arg Ser Gly Ile Thr Leu
        115                 120                 125

Val Pro Ile Leu Ser Lys Phe Asn Ser Val Lys Met Ser Arg Lys Gly
    130                 135                 140

Gly Leu Val Thr Met Ile Glu Tyr Pro Ser Leu Glu Ala Ala Thr Gly
145                 150                 155                 160

Lys Phe Gly Glu Ser Asn Val Leu Gly Val Gly Gly Phe Gly Cys Val
                165                 170                 175

Tyr Lys Ala Ala Phe Asp Gly Gly Ala Thr Ala Ala Val Lys Arg Leu
            180                 185                 190

Glu Gly Gly Gly Pro Asp Cys Glu Lys Glu Phe Glu Asn Glu Leu Asp
        195                 200                 205

Leu Leu Gly Arg Ile Arg His Pro Asn Ile Val Ser Leu Leu Gly Phe
    210                 215                 220

Cys Val His Gly Gly Asn His Tyr Ile Val Tyr Glu Leu Met Glu Lys
225                 230                 235                 240

Gly Ser Leu Glu Thr Gln Leu His Gly Ser Ser His Gly Ser Ala Leu
                245                 250                 255

Ser Trp His Val Arg Met Lys Ile Ala Leu Asp Thr Ala Arg Gly Leu
            260                 265                 270

Glu Tyr Leu His Glu His Cys Asn Pro Pro Val Ile His Arg Asp Leu
        275                 280                 285

Lys Pro Ser Asn Ile Leu Leu Asp Ser Asp Phe Asn Ala Lys Ile Ala
    290                 295                 300

Asp Phe Gly Leu Ala Val Thr Gly Gly Asn Leu Asn Lys Gly Asn Leu
305                 310                 315                 320

Lys Leu Ser Gly Thr Leu Gly Tyr Val Ala Pro Glu Tyr Leu Leu Asp
                325                 330                 335

Gly Lys Leu Thr Glu Lys Ser Asp Val Tyr Ala Phe Gly Val Val Leu
            340                 345                 350

Leu Glu Leu Leu Met Gly Arg Lys Pro Val Glu Lys Met Ser Pro Ser
        355                 360                 365

Gln Cys Gln Ser Ile Val Ser Trp Ala Met Pro Gln Leu Thr Asp Arg
    370                 375                 380

Ser Lys Leu Pro Asn Ile Ile Asp Leu Val Ile Lys Asp Thr Met Asp
385                 390                 395                 400
```

```
Pro Lys His Leu Tyr Gln Val Ala Ala Val Ala Val Leu Cys Val Gln
                405                 410                 415

Pro Glu Pro Ser Tyr Arg Pro Leu Ile Thr Asp Val Leu His Ser Leu
            420                 425                 430

Val Pro Leu Val Pro Ala Glu Leu Gly Gly Thr Leu Arg Val Ala Glu
        435                 440                 445

Pro Pro Ser Pro Ser Pro Asp Gln Arg His Tyr Pro Cys
    450                 455                 460


<210> SEQ ID NO 198
<211> LENGTH: 53
<212> TYPE: DNA
<213> ORGANISM: ARTIFICIAL SEQUENCE
<220> FEATURE:
<223> OTHER INFORMATION: Synthetic Primer

<400> SEQUENCE: 198

tataccggta aaatgagaga gcttcttctt cttcttcttc ttcattttca gtc           53


<210> SEQ ID NO 199
<211> LENGTH: 39
<212> TYPE: DNA
<213> ORGANISM: ARTIFICIAL SEQUENCE
<220> FEATURE:
<223> OTHER INFORMATION: Synthetic Primer

<400> SEQUENCE: 199

atataccggt cttgttaacc ggagagtccc tcctagctc                           39


<210> SEQ ID NO 200
<211> LENGTH: 18
<212> TYPE: DNA
<213> ORGANISM: ARTIFICIAL SEQUENCE
<220> FEATURE:
<223> OTHER INFORMATION: Synthetic Primer

<400> SEQUENCE: 200

cgctcctccc gtcgtgat                                                  18
```